(12) United States Patent
Frendéus et al.

(10) Patent No.: US 12,344,673 B2
(45) Date of Patent: Jul. 1, 2025

(54) MEDICAMENTS, USES AND METHODS

(71) Applicant: BIOINVENT INTERNATIONAL AB, Lund (SE)

(72) Inventors: Björn Frendéus, Landskrona (SE); Ingrid Teige, Lund (SE); Linda Mårtensson, Bjärred (SE); Mark Cragg, Southampton (GB); Ali Roghanian, Southampton (GB)

(73) Assignee: BIOINVENT INTERNATIONAL AB, Lund (SE)

( * ) Notice: Subject to any disclaimer, the term of this patent is extended or adjusted under 35 U.S.C. 154(b) by 0 days.

(21) Appl. No.: 15/311,016

(22) PCT Filed: May 15, 2015

(86) PCT No.: PCT/EP2015/060744
§ 371 (c)(1),
(2) Date: Nov. 14, 2016

(87) PCT Pub. No.: WO2015/173384
PCT Pub. Date: Nov. 19, 2015

(65) Prior Publication Data
US 2017/0107293 A1  Apr. 20, 2017

(30) Foreign Application Priority Data
May 15, 2014 (GB) .................................... 1408673

(51) Int. Cl.
| C07K 16/28 | (2006.01) |
| --- | --- |
| A61K 9/00 | (2006.01) |
| A61K 9/02 | (2006.01) |
| A61K 9/20 | (2006.01) |
| A61K 9/48 | (2006.01) |
| A61K 47/02 | (2006.01) |
| A61K 47/10 | (2017.01) |
| A61K 47/12 | (2006.01) |
| A61K 47/26 | (2006.01) |
| A61K 47/38 | (2006.01) |
| C07K 16/30 | (2006.01) |
| A61K 39/00 | (2006.01) |

(52) U.S. Cl.
CPC ........ *C07K 16/2887* (2013.01); *A61K 9/0034* (2013.01); *A61K 9/0048* (2013.01); *A61K 9/0095* (2013.01); *A61K 9/02* (2013.01); *A61K 9/2018* (2013.01); *A61K 9/2027* (2013.01); *A61K 9/2054* (2013.01); *A61K 9/2059* (2013.01); *A61K 9/4858* (2013.01); *A61K 9/4866* (2013.01); *A61K 47/02* (2013.01); *A61K 47/10* (2013.01); *A61K 47/12* (2013.01); *A61K 47/26* (2013.01); *A61K 47/38* (2013.01); *C07K 16/283* (2013.01); *C07K 16/2893* (2013.01); *C07K 16/30* (2013.01); *A61K 2039/507* (2013.01); *A61K 2039/55* (2013.01); *C07K 2317/21* (2013.01); *C07K 2317/33* (2013.01); *C07K 2317/56* (2013.01); *C07K 2317/565* (2013.01); *C07K 2317/73* (2013.01); *C07K 2317/732* (2013.01); *C07K 2317/75* (2013.01); *C07K 2317/76* (2013.01); *C07K 2317/77* (2013.01); *C07K 2317/92* (2013.01); *C07K 2317/94* (2013.01)

(58) Field of Classification Search
CPC .............. C07K 16/2887; C07K 16/283; C07K 16/2893; C07K 16/30; C07K 2317/56; C07K 2317/565; C07K 2317/76; A61K 9/4858; A61K 2039/507; A61K 39/395; A61P 35/00; A61P 37/04; A61P 43/00
See application file for complete search history.

(56) References Cited

U.S. PATENT DOCUMENTS

| 2006/0134709 A1 | 6/2006 | Stavenhagen et al. |
| --- | --- | --- |
| 2009/0017023 A1 | 1/2009 | Koenig et al. |
| 2009/0191195 A1 * | 7/2009 | Tuaillon ............... C07K 16/283 424/133.1 |

FOREIGN PATENT DOCUMENTS

| KR | 10-2014-0005866 A | 1/2014 |
| --- | --- | --- |
| WO | 2005/018669 A1 | 3/2005 |
| WO | 2008/002933 A2 | 1/2008 |
| WO | 2008/140603 A2 | 11/2008 |
| WO | 2012/022985 A1 | 8/2011 |

OTHER PUBLICATIONS

Cragg et al. (Blood, 123(5): 669-677, 2014).*
Mariuzza (Annu. Rev. Biophys. Biophys. Chem., 16: 139-159, 1987).*
Stancovski et al. (PNAS, 88: 8691-8695, 1991).*
Jiang et al. (J. Biol. Chem., 280: 4656-4662, 2005).*
Lim et al., "Fc gamma receptor IIb on target B cells promotes rituximab internatlization and reduces clinical efficacy", Blood, 118:2530-2540 (Sep. 1, 2011).
Vaughan et al., "Inhibitory FcγRIIb (CD32b) becomes activated by therapeutic mAb in both cis and trans and drives Internalization according to antibody specificity", Blood, 123(5):669-677 (2014).
Williams et al., "Overcoming Resistance to Therapeutic Antibodies by Targeting Fc Receptors", Resistance to Immunotherapeutic Antibodies in Cancer, pp. 49-71 (2013).

(Continued)

Primary Examiner — Nelson B Moseley, II
(74) Attorney, Agent, or Firm — BOOTH UDALL FULLER; Rodney J Fuller

(57) ABSTRACT

Description of a composition comprising an antibody molecule and an agent for use in the treatment of refractory cancer and/or relapsed cancer, and of a method of treating refractory cancer and/or relapsed cancer comprising administering an antibody molecule and an agent. There are also described kits comprising the antibody molecule and agents.

Figure 1:
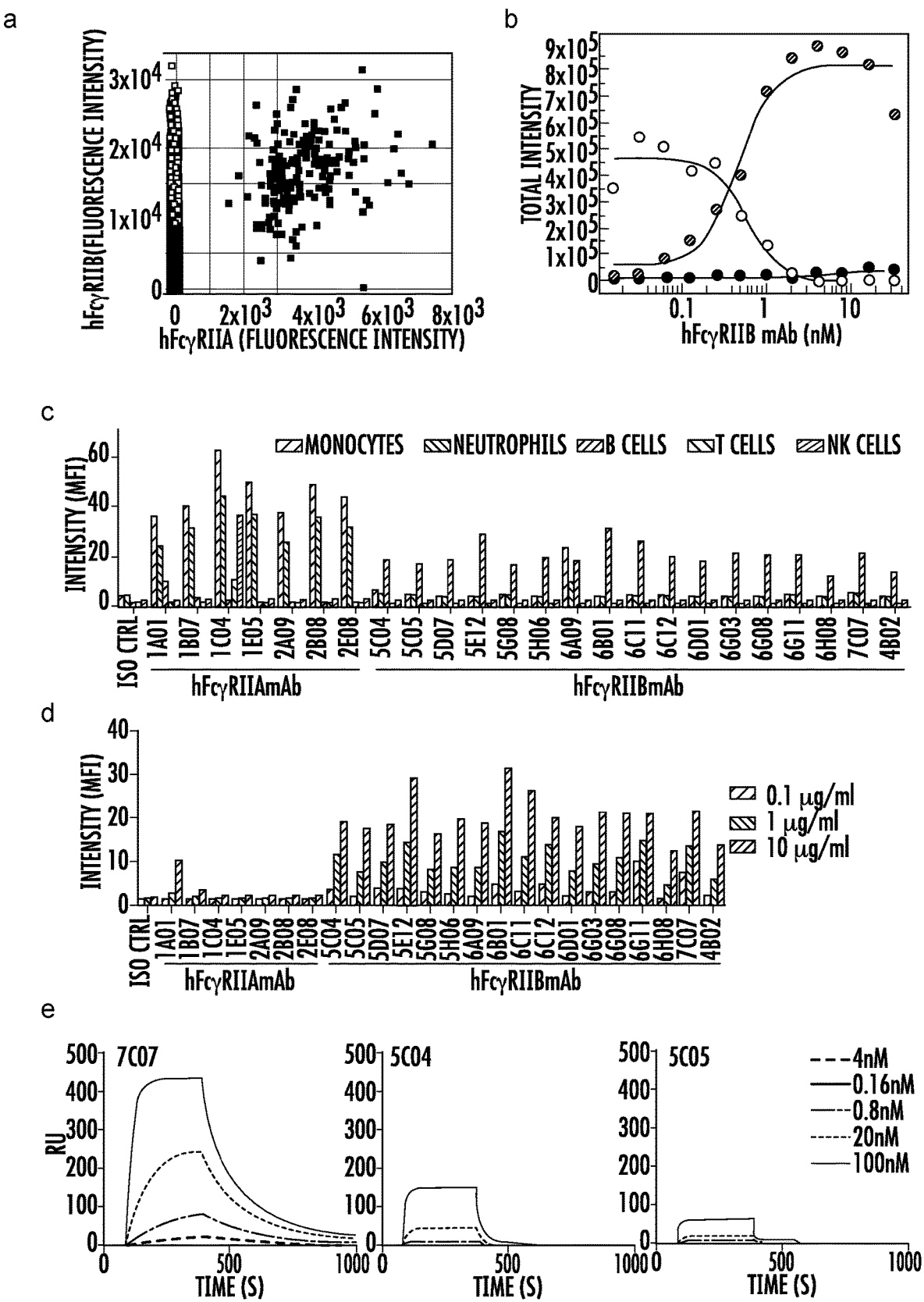

14 Claims, 27 Drawing Sheets
Specification includes a Sequence Listing.

(56) References Cited

OTHER PUBLICATIONS

Roghanian et al., "Antagonistic Human FcγRIIB (CD32B) Antibodies Have Anti-tumor Activity and Overcome Resistance to Antibody Therapy In Vivo", Cancer Cell, 27:473-488 (Apr. 13, 2015).
Agency for Healthcare Research and Quality Guideline Summary NGC-9278 (2012).
Antibodies: A Laboratory Manual, Harlow & Lane (pp. 567 to 569, 574 to 576, 583 and 590 to 612, CSHL, NY, ISBN 0-87969-314-2) (1988).
Beers et al., "CD20 as a Target for Therapeutic Type I and II Monoclonal Antibodies", Seminars in Haematology, 47 (2):107-114 (2010).
Beers et al., "Antigenic modulation limits the efficacy of anti-CD20 antibodies: implications for antibody selection", Blood, 115:5191-5201 (2010).
Beers et al., "Type II (tositumomab) anti-CD20 monoclonal antibody out performs type I (rituximab-like) reagents in B-cell depletion regardless of complement activation", Blood, 112(10):4170-4177 (2008).
Biburger et al., "Monocyte Subsets Responsible for Immunoglobulin G-Dependent Effector Functions In Vivo", Immunity, 35:932-944 (Dec. 23, 2011).
Binyamin et al., "Blocking NK Cell Inhibitory Self-Recognition Promotes Antibody-Dependent Cellular Cytotoxicity in a Model of Anti-Lymphoma Therapy", J. Immunol., 180(9):6392-6401 (May 1, 2008).
Busillo et al., "Regulation of CXCR4 Signaling", Biochim Biophys Acta., 1768(4):952-963 (Apr. 2007).
Bradley et al., "Roles and regulation of Thy-1, a context dependent modulator of cell phenotype", Biofactors, 35(3):258-265 (2009).
Byrd et al., "Targeting BTK with Ibrutinib in Relapsed Chronic Lymphocytic Leukemia", N. Engl. J. Med., 369(1):32-42 (Jul. 4, 2013).
Cartron et al., "Therapeutic activity of humanized anti-CD20 monoclonal antibody and polymorphism in IgG Fc receptor FcγRIIIa gene", Blood, 99:754-758 (2002).
Chan et al., "CD20-induced Lymphoma Cell Death is Independent of Both Caspases and Its Redistribution into Triton X-100 Insoluble Membrane Rafts", Cancer Res., 63:5480-5489 (2003).
Chao et al., "Anti-CD47 antibody synergizes with rituximab to promote phagocytosisand eradicate non-Hodgkin Lymphoma", Cell, 142(5):699-713 (Sep. 3, 2010).
Cheson et al., "Monoclonal Antibody Therapy for B-Cell Non-Hodgkin's Lymphoma", The New England Journal of Medicine, 359(6):613-626 (2008).
Park et al., "Unraveling the Biologic and Clinical Complexities of HER2", Clinical Breast Cancer, 8(5):392-401 (Oct. 2008).
Clynes et al., "Inhibitory Fc receptors modulate in vivo cytoxicity against tumor targets", Nature Medicine, 6(4):443-446 (2000).
Coiffier et al., "Safety and efficacy of otatumumab, a fully human monoclonal anti-CD20 antibody, in patients with relapsed or refractory B-cell chronic lymphocytic leukemia: a phase 1-2 study", Blood, 111(3):1094-1100 (2008).
Coiffier et al., "Significant Correlation between Survival Endpoints and Exposure of Ofatumumab (HuMax-CD20) in Chronic Lymphocytic Leukemia", ASH Annual Meeting Abstracts, 108:2842 (2006).
Corbin et al., "Analysis of the Structural Basis of Specificity of Inhibition of the Abl Kinase by STI571", The Journal of Biological Chemistry, 277(35):32214-32219 (Aug. 30, 2002).
Cragg et al., "Antibody specificity controls in vivo effector mechanisms of anti-CD20 reagents", Blood, 103:2738-2743 (2004).
Cragg et al.,, "Opposing Properties of CD20 mAb in Leukocyte Typing VII", Oxford University Press, Oxford (2002).
Cragg et al., "Complement-mediated lysis by anti-CD20 mAb correlates with segregation into lipid rafts", Blood, 101:1045-1052 (2003).
Cragg et al., "Unleashing the power of inhibitors of oncogenic kinases through BH3 mimetics", Nat. Rev. Cancer, 9:321-326 (2009).
Dyer et al., "Effects of CAMPATH-1 Antibodies In Vivo in Patients with Lymphoid Malignancies: Influence of Antibody sotype", Blood, 73(6): 1431-1439 (1989).
Engelman et al., "MET Amplification Leads to Gefitinib Resistance in Lung Cancer by Activating ERBB3 Signaling", Science, 316:1039-1043 (May 18, 2007).
Mitsudomi et al., "Epidermal growth factor receptor in relation to tumor development: EGFR gene and cancer", FEBS Journal, 277:301-308 (2009).
Gao et al., "Molecular Cloning of a Proteolytic Antibody Light Chain", The Journal of Biological Chemistry, 269(51):32389-32393 (Dec. 23, 1994).
Glennie et al., "Preparation and Performance of Bispecific f(ab'y)2 Antibody Containing Thioether-Linked Fab'y' Fragments", The Journal of Immunology, 139(7):2367-2375 (Oct. 1, 1987).
Greenman et al., "Characterization of a New Monoclonal Anti-Fcγ' RII Antibody, AT10, and its Incorporation into a Bispecific F(ab')2 Derivative for Recruitment of Cytotoxic Effectors", Molecular Immunology, 28(11):1243-1254 (1991).
Gul et al., "Macrophages eliminate circulating tumor cells after monoclonal antibody therapy", The Journal of Clinical Investigation, 124(2):812-823 (Feb. 2014).
Hallborn et al., "Automated Screening Procedure for High-Throughput Generation of Antibody Fragments", Bio Techniques, 33:S30-S37 (Dec. 2002).
Hallek et al., "Guidelines for the diagnosis and treatment of chronic lymphocytic leukemia: a report from the International Workshop on Chronic Lymphocytic Leukemia updating the National Cancer Institute—Working Group 1996 guidelines", Blood, 111(12):5446-5456 (Jun. 15, 2008).
Hamaguchi et al., "Antibody isotype-specific engagement of FCY receptors regulates B lymphocyte depletion during CD20 immunotherapy", The Journal of Experimental Medicine, 203(3):743-753 (Mar. 20, 2006).
Hanahan et al., "Hallmarks of Cancer: The Next Generation", Cell, 144:646-674 (2011).
Heap et al., "Analysis of a 17-amino acid residue, virus-neutralizing microantibody", Journal of General Virology, 86:1791-1800 (2005).
Hiu et al., "Treatment of CD20-specific antibody prevents and reverses autoimmune diabetes in mice", The Journal of Clinical Investigation, 117(12):3857-3867 (2007).
Hussain et al., "Upregulation of FCγRIIb on monocytes is necessary to promote the superagonist activity of TGN1412", Blood, 125(1):102-110 (2015).
Bricarello et al., "Ganglioside embedded in reconstituted lipoprotein binds cholera toxin with elevated affinity", Journal of Lipid Research, 51(9):2731-2738 (Sep. 2010).
Kabat et al., "Sequences of Proteins of Immunological Interest", Fifth Edition, NIH Publication No. 91-3242, pp. xv-xvii (1991).
Ee et al., "New HLA Nomenclature (2010) and Its Clinical Application in Koreans", Korean J Lab Med, 30(3):203-217 (Jun. 2010).
Ladner, Robert Charles, "Antibodies cut down to size", Nature Biotechnology, 25(8):875-877 (2007).
Laune et al., "Protein Chemistry and Structure: Systemic Exploration of the Antigen Binding Activity of Synthetic Peptides Isolated from the Variable Regions of Immunoglobulins", The Journal of Biological Chemistry, 272(49):30937-30944 (Dec. 5, 1997).
Lee et al., "Expression of Inhibitory Fc Receptor (FCγRIIB) is a Marker of Poor Response to Rituximab Monotherapy in Follicular Lymphoma (FL)", ASH abstract 50396 (2012).
Lim et al., "Anti-CD20 monoclonal antibodies: historical and future perspectives", Haematologica, 95:135-143 (2010).
McKay et al., "Guidelines for the investigation and management of mantle cell lymphoma", British Journal of Haematology, 159:405-426 (2012).
Minard-Colin et al., "Lymphoma depletion during CD20 immunotherapy in mice is mediated by macrophage FcγRI, FcγRIII, and FcγRIV", Blood, 112(4):1206-1213 (Aug. 15, 2008).

(56) References Cited

OTHER PUBLICATIONS

Roghanian et al., "Parallel Session: Cancer Therapy Through Immune Modulation", Oral Abstracts BSI Congress 2013, Abstract No. 280, Immunology, 140(Suppl. 1):19-38 (2013).
Ni et al., "Cloning and characterization of a human LYPD7, a new member of the Ly-6 superfamily", Mol. Biol. Rep. 36:697-703 (2009).
Kimberley et al., "Alternative roles for CD59", Molecular Immunology, 44:73-81 (2007).
Monnet et al., "Synthetic Peptides Derived from the Variable Regions of an Anti-CD4 Monoclonal Antibody Bind to CD4 and Inhibit HIV-1 Promoter Activation in Virus-infected Cells", The Journal of Biological Chemistry, 274 (6):3789-3796 (Feb. 5, 1999).
Montalvao et al., "The mechanism of anti-CD20-mediated B cell depletion revealed by intravital imaging", The Journal of Clinical Investigation, 123(12):5098-5103 (Dec. 2013).
NCCN Guidelines on Non-Hodgkin's Lymphomas Version 1. (Nov. 19, 2013).
Neubig et al., "International Union of Pharmacology Committee on Receptor Nomenclature and Drug Classification. XXXVIII. Update on Terms and Symbols in Quantitative Pharmacology", Pharmacology Reviews, 55(4):597-606 (2003).
Nicaise et al., "Affinity transfer by CDR grafting on a nonimmunoglobulin scaffold", Protein Science, 13:1882-1891 (2004).
Niederfellner et al., "Epitope characterization and crystal structure of GA101 provide insights into the molecular basis for type I/II distinction of CD20 antibodies", Blood, 118(2):358-367 (2011).
Nimmerjahn et al., Fcγ' receptors as regulators of immune responses, Nature Reviews, 8:34-47 (2008).
Nimmerjahn et al., "FcyRs in Health and Disease", Curr Top Microbiol Immunol 350, 105-125 (2011).
Nishimura et al., "Characterization of the human FcyRIIB gene promoter: human zinc-finger proteins (ZNF140 and ZNF91) that bind to different regions function as transcription repressors", International Immunology, 13(8):1075-1084 (2001).
O'Brien et al., "Rituximab Dose-Esclation Trial in Chronic Lymphocytic Leukemia", Journal of Clinical Oncology, 19 (8):2165-2170 (Apr. 15, 2001).
Olsson et al., "Proteomic Analysis and Discovery Using Affinity Proteomics and Mass Spectrometry", Mol Cell Proteomics, 10, M110 003962 (2011).
Pallasch et al., "Sensitizing Protective Tumor Microenvironments to Antibody-Mediated Therapy", Cell, 156:590-602 (Jan. 30, 2014).
Pao et al., "Acquired Resistance of Lung Adenocarcinomas to Gefitinib or Erlotinib is Associated with a Second Mutation in the EGFR Kinase Domain", PLos Medicine, 2(3):e73 (Mar. 2005).
Pessi et al., "A designed metal-binding protein with a novel fold", Nature, 362:367-369 (Mar. 25, 1993).
Qui et al., "Small antibody mimetics comprising two complementarity-determining regions and a framework region for tumor targeting", Nature Biotechnology, 25(8):921-929 (Aug. 2007).
Quiocho, F. A., "Making of the minibody", Nature, 362:293-294 (Mar. 25, 1993).
Rankin et al., "CD32B, the human inhibitory Fc-γ' receptor IIB, as a target for monoclonal antibody therapy of B-cell lymphoma", Blood, 108(7):2384-2391 (Oct. 1, 2006).
Reichert et al., "Foundation review: The future of antibodies as cancer drugs", Drug Discovery Today, 17 (17/18):954-963 (2012).
Roghanian et al., "Filament-associaed TSGA10 protein is expressed in professional antigen presenting cells and Interacts with vimentin", Cellular Immunology, 265:120-126 (2010).
Romer et al., "Preculture of PBMCs at high cell density increases sensitivity of T-cell responses, revealing cytokine release by CD28 superagonist TGN1412", Blood, 118(26):6772-6782 (Dec. 22, 2011).
Rossi et al., "Clinical impact of small TP53 mutated subclones in chronic lymphocytic leukemia", Blood, 123(14):2139-2147 (Apr. 3, 2014).

Shah et al., "Multiple BCR-ABL kinase domain mutations confer polyclonal resistance to the tyrosine kinase inhibitor imatinib (STI571) in chronic phase and blast crisis chronic myeloid leukemia", Cancer Cell, 2:117-125 (Aug. 2002).
Rose et al., "A novel Ly6C/Ly6G-based strategy to analyze the mouse splenic myeloid compartment", Cytometry Part A, 81(4)343-350 (2012).
Tao et al., "Studies of aglycosylated chimeric mouse-human IgG. Role of carbohydrate in the structure and effector functions mediated by the human IgG constant region", J. Immunol., 143:2595-2601 (1989).
Tutt et al., "Monoclonal Antibody Therapy of B Cell Lymphoma: Signaling Activity on Tumor Cells Appears More Important Than Recruitment of Effectors", J. Imunol., 161:3176-3185 (1998).
Veri et al., "Monoclonal antibodies capable of discriminating the human inhibitory Fcγ'-receptor IIb (CD32B) from the activating Fcγ'-receptor IIA (CD32A): biochemical, biological and functional characterization", Immunology, 121:392-404 (2007).
Walshe et al., "Induction of Cytosolic Calcium Flux by CD20 is Dependent upon B Cell Antigen Receptor Signaling", The Journal of Biological Chemistry, 283(25):16971-16984 (Jun. 20, 2008).
Wang et al., "Targeting BTK with Ibrutinib in Relapsed or Refractory Mantle-Cell Lymphoma", The New England Journal of Medicine, 369(6):507-516 (Aug. 8, 2013).
Weng et al., "Genetic polymorphism of the inhibitory IgG Fc receptor FcγRIIb is not associated with clinical outcome in patients with follicular lymphoma treated with rituximab", Leuk Lymphoma, 50(5):723-727 (May 2009).
Weng et al., "Two Immunoglobulin G Fragment C Receptor Polymorphisms Independently Predict Response to Rituximab in Patients with Follicular Lymphoma", Journal of Clinical Oncology, 21(21):3940-3947 (Nov. 1, 2003).
Williams et al., "Development and characterisation of monoclonal antibodies specific for the murine inhibitory FcγRIIB (CD32B)", Eur. J. Immunol., 42:2109-2120 (2012).
Williams et al., "Immunotherapy Targeting Inhibitory Fcγ' Receptor IIB (CD32b) in the Mouse is Limited by Monoclonal Antibody Consumption and Receptor Internalization", J. Immunol., 191:4130-4140 (2013).
Williams et al., "Overcoming Resistance to Therapeutic Antibodies by Targeting Fc Receptors", Resistance to Immunotherapeutic Antibodies in Cancer: Strategies to Overcome Resistance (2013).
Yun et al., "The T790M mutation in EGFR kinase causes drug resistance by increasing the affinity for ATP", PNAS, 105(6):2070-2075 (Feb. 12, 2008).
Zhang et al., "Targeting cancer with small molecule kinase inhbitors", Nat Rev Cancer, 9:28-39 (2009).
Kalbasi e al., "CD40 Expression by Human Melanocytic Lesions and Melanoma Cell Lines and Direct CD40 Targeting with the Therapeutic Anti-CD40 Antibody CP-870,893", J. Immunother, 33(8):810-816 (Oct. 2010).
Cassard et al., "Selective expression of inhibitory Fcγ' receptor by metastatic melanoma impairs tumor susceptibility to IgG-dependent cellular response", Int. J. Cancer, 123:2832-2839 (2008).
Welcome! to the IMGT Home page, retrieved from http://www.imgt.org/, retrieved on Aug. 2, 2017 (4 pages).
Kharkevich, D.A., Farmakologiya (Pharmacology), Textbook, 10th Edition, pp. 72-82 (2010). See English translation of Russian Search Report.
Yakubke, Kh.-D, Amino Acids, peptides, proteins/M:Mir, pp. 92-94 (1985). See English translation of Russian Search Report.
English translation of Russian Search Report for PCT/EP2015/060744 dated Dec. 26, 2018.
Tobinai, K. et al., "Phase I study of LY2469298, an Fc-engineered humanized anti-CD20 antibody, in patients with relapsed or refractory follicular lymphoma", Cancer Science, 102(2):432-438 (Feb. 2011).
English translation of Office Action for corresponding Japanese patent application No. 2016-567851 dated Jun. 10, 2019.
Latest Medicine, 69(3):379-385 (2014)—English translation not available. See English translation of Office Action for Japanese patent application No. 2016-567851 dated Jun. 10, 2019.

(56) References Cited

OTHER PUBLICATIONS

Yasuyoshi, 229(10): 1033-1038 (2009)—English translation not available. See English translation of Office Action for Japanese patent application No. 2016-567851 dated Jun. 10, 2019.
Clinical Blood, 52(8):618-626 (2011)—English translation not available. See English translation of Office Action for Japanese patent application No. 2016-567851 dated Jun. 10, 2019.
Roghanian, Ali et al., Supplemental Information "Antagonistic Human FcyRIIB (CD32B) Antibodies Have Anti-Tumor Activity and Overcome Resistance to Antibody Therapy In Vivo", Cancer Cell, vol. 27, pp. 1-36 (2015).
Declaration of Dr. Björn Frendéus dated Mar. 9, 2020 (8 pages).
Pandzic, Tatjana et al., "Transposon Mutagenesis Reveals Fludarabine Resistance Mechanisms in Chronic Lymphocytic Leukemia", Clinical Cancer Research, 22(24):6217-6227 (Mar. 8, 2016) <DOI: 10.1158/1078-0432.CCR-15-2903>.
Gross, E., et al., "B-chronic lymphocytic leukemia chemoresistance involves innate and acquired leukemic side population cells", Leukemia, 24(11):1885-1892 (Sep. 9, 2010) <DOI: 10.1038/leu. 2010. 176>.
Lorkova, Lucie, et al., "Detailed Functional and Proteomic Characterization of Fludarabine Resistance in Mantle Cell Lymphoma Cells", PLOS One, 10(8):e0135314 (Aug. 18, 2015) <DOI: 10.1371/journal.pone.0135314>.
Andersson, Borje S., et al. "Mechanisms of Cyclophosphamide Resistance in a Human Myeloid Leukemia Cell Line", Acta Oncologica., 34(2):247-251 (Jan. 1, 1995) <DOI: 10.3109/02841869509093963>.
Kath, R. et al., "Bendamustine monotherapy in advanced and refractory chronic lymphocytic leukemia", Journal of Cancer Research and Clinical Oncology, 127(1):48-54 (Jan. 1, 2001) <DOI: 10.1007/S004320000180>.
Cheson, Bruce D., et al., "Bendamustine: mechanism of action and clinical data", Clinical Advances in Hematology & Oncology, vol. 9, No. 8 Suppl 19, pp. 1-11 (Aug. 1, 2011).
Schnaiter, Andrea et al., "Refractory chronic lymphocytic leukemia—new therapeutic strategies", Oncotarget, 1(7):472-482 (Nov. 30, 2010) <DOI: 10.18632/oncotarget.184>.
Rezvani, Andrew R., et al., "Rituximab resistance", Best Practice & Research Clinical Haematology, 24(2):203-216 (Jun. 1, 2011) <DOI: 10.1016/j.beha.2011.02.009>.
Haidar, JH et al., "Loss of CD20 expression in relapsed lymphomas after rituximab therapy", European Journal of Haematology, Munskgaard, Copenhagen, DK, 70(5):330-332 (May 1, 2003) <DOI: 10.1034/J.1600-0609.2003.00007.X>.
Bonavida, Benjamin, "Postulated Mechanisms of Resistance of B-Cell Non-Hodgkin Lymphoma to Rituximab Treatment Regimens: Strategies to Overcome Resistance", Seminars in Oncology, 41(5):667-677 (Oct. 1, 2014) <DOI: 10.1053/j.seminoncol.2014. 08.006>.
Smith, Mitchell R., "Rituximab (monoclonal anti-CD20 antibody): mechanisms of action and resistance", Oncogene, 22:7359-7368 (2003).
Jurczak et al., "Rituximab biosimilars for lymphoma in Europe", Exp. Opin. Biol. Ther., 19(10):1045-1056 (2019).
Otremba et al., "Real-world use and acceptance of rituximab biosimilars in non-Hodgkin lymphoma in an oncologist network in Germany", Future Oncol., 16(15):1001-1012, (2020).
Urru et al., "Safety of switching between rituximab biosimilars in onco-hematology", Scientific Reports, vol. 11:5956 (pp. 1-5) (2021).
Visser et al., "Physicochemical and Functional Comparability Between the Proposed Biosimilar Rituximab GP2013 and Originator Rituximab", BioDrugs, 27:495-507 (2013).
Kaplanov et al., "Key Results of International Randomized Open-Label Clinical Study of BCD-020 (rituximab biosimilar candidate) in Patients with B-Cell Non-Hodgkin's Lymphoma", Blood, 124(21):5467 (pp. 1-6) (2014).
Nowicka et al., "Prognostic significance of FCGR2B expression for the response of DLBCL patients to rituximab or obinutuzumab treatment", Blood adv, 5(15):2945-2957 (2021).
Golay et al., "Effect of alemtuzumab on neoplastic B cells", Haematologica, 89(12):1476-1483 (2004).

\* cited by examiner

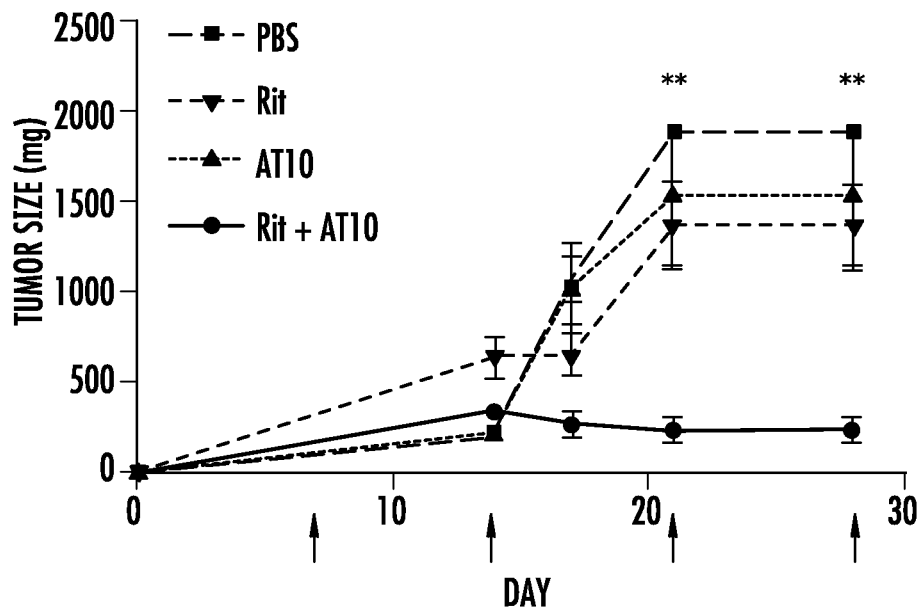
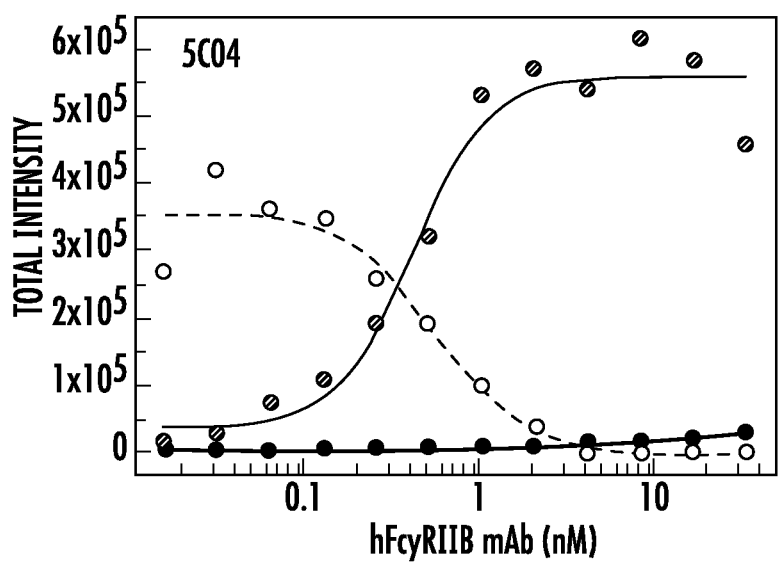
Figure 1 (continued)

Figure 3 (1/2)
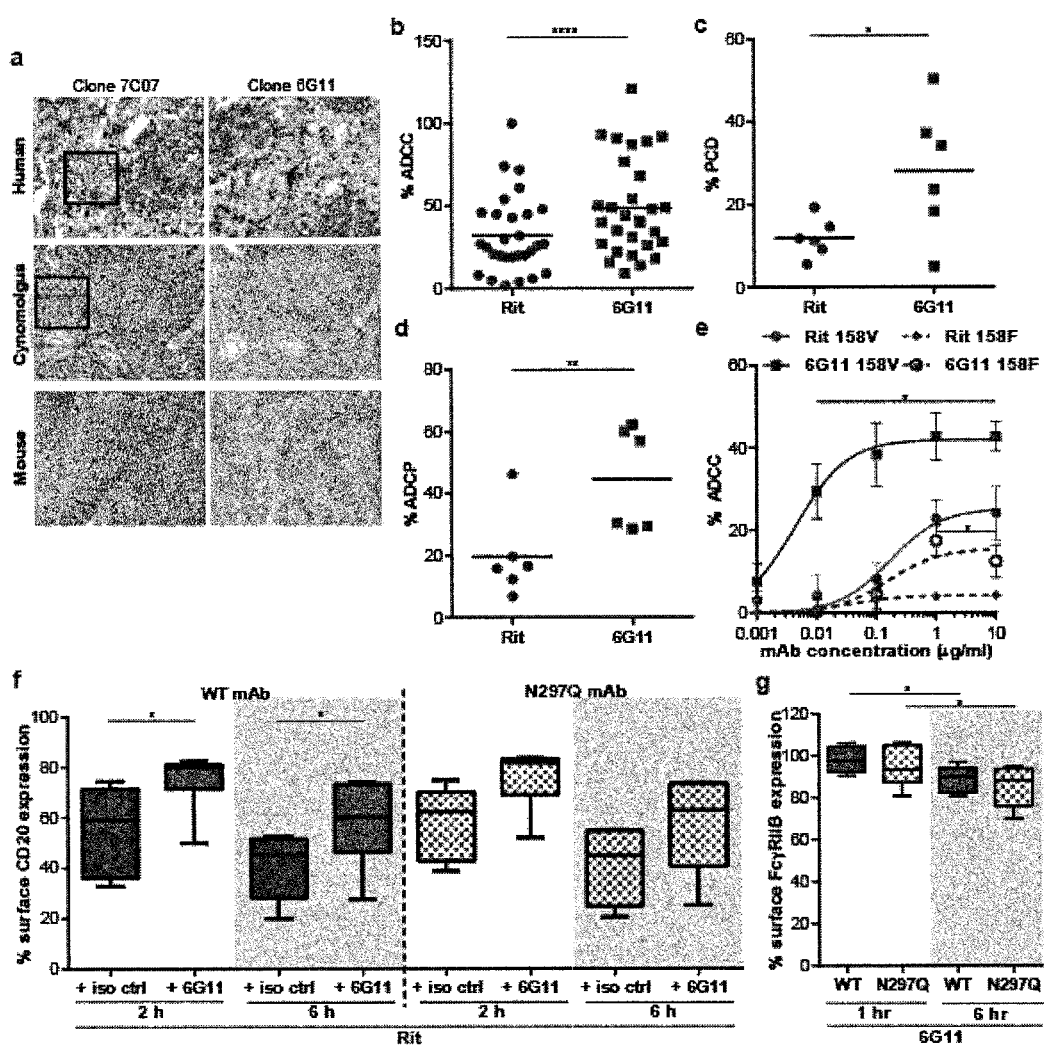

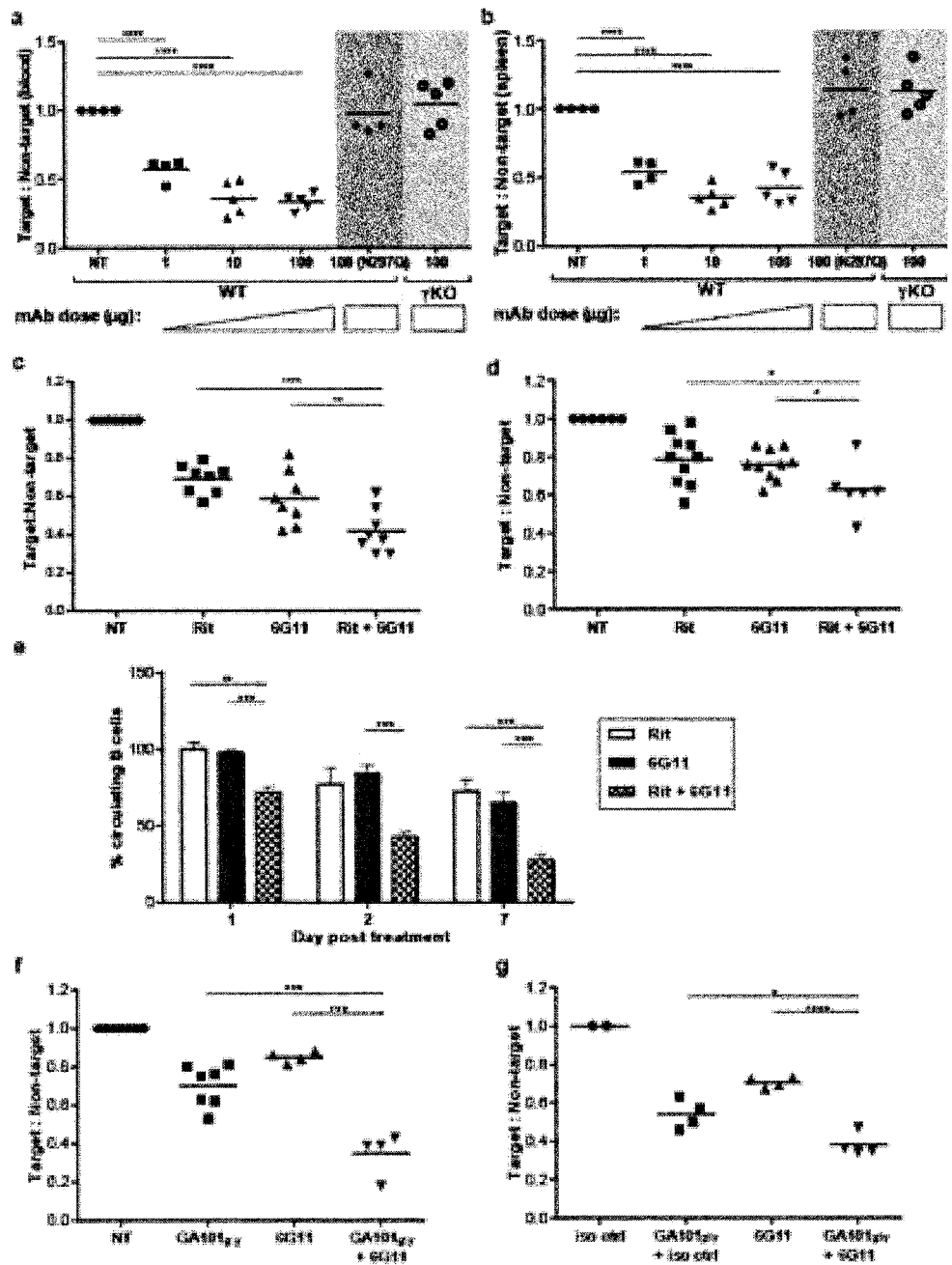

Figure 5:
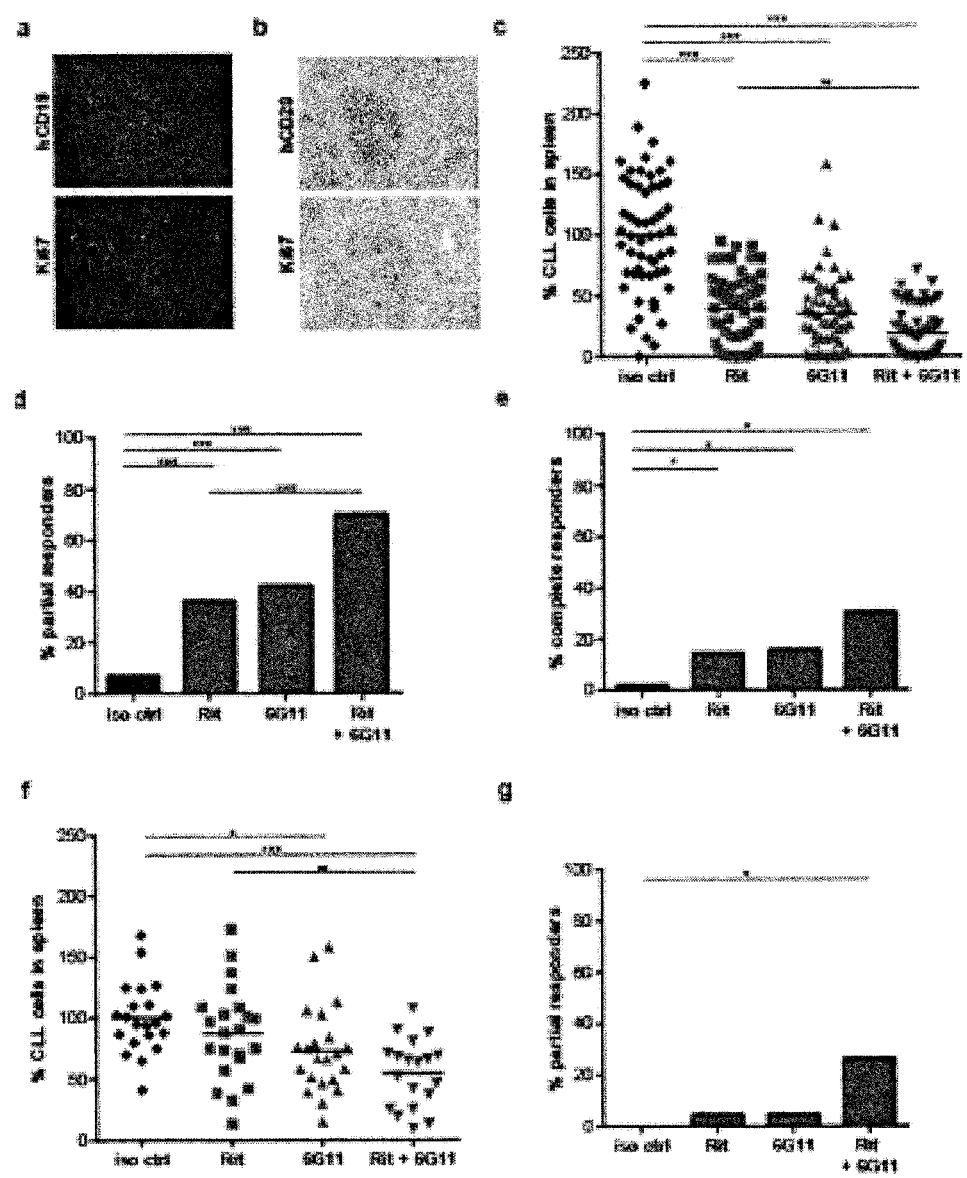

Figure 5 (2/2)
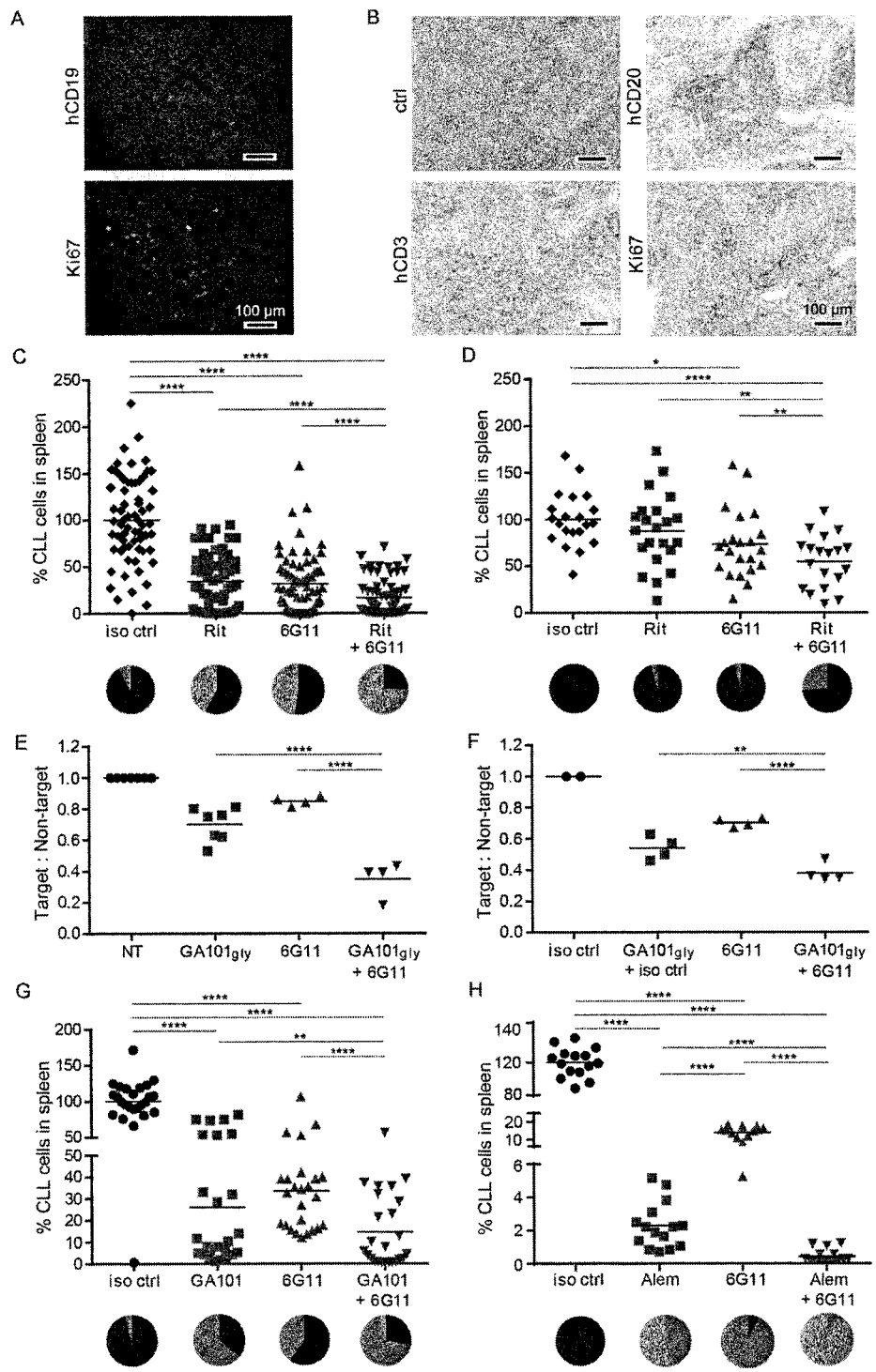

a
```
          10              20          30            40          50
hFcγRIIA APPKAVLKLEPPWINVLQEDSVTLTGQGARSPESDSIQWFHNGNLIPTHTQPSYR
hFcγRIIB APPKAVLKLEPQWINVLQEDSVTLTGRGTHSPESDSIQWFHNGNLIPTHTQPSYR
          60          70          80          90          100       110
FKANNDSGEYTCQTGQTSLSDPVHLTVLSEWLVLQTPHLEFQEGETIMLRCHSW
FKANNDSGEYTCQTGQTSLSDPVHLTVLSEWLVLQTPHLEFQEGETIVLRCHSW
          120         130         140         150         160
KDKPLVKVTFFQNGKSQKFSRLDPTFGIPQANMSMSGDTMGTGNIGYTLFSSKPV
KDKPLVKVTFFQNGKSKKFSRSDPNFBIPQANHSHSGDYHGTGNIGYTLYSSKPV
          170         180
TITVQVPSMGSSSPMGII    IgG BINDING SITE
TITVQAP...SSSPMGII
```

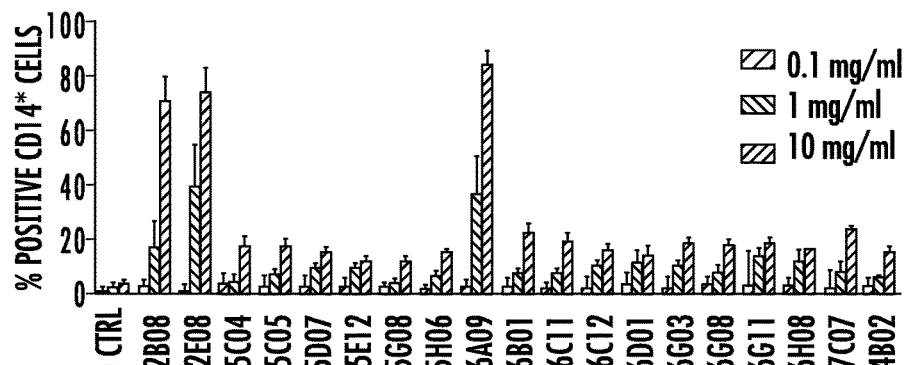

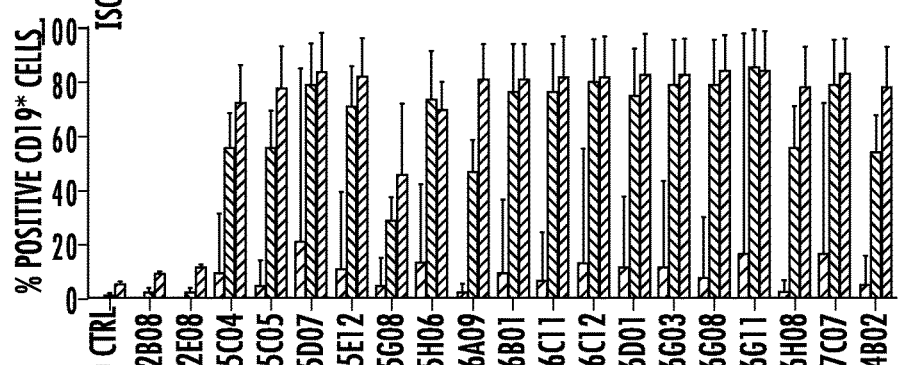

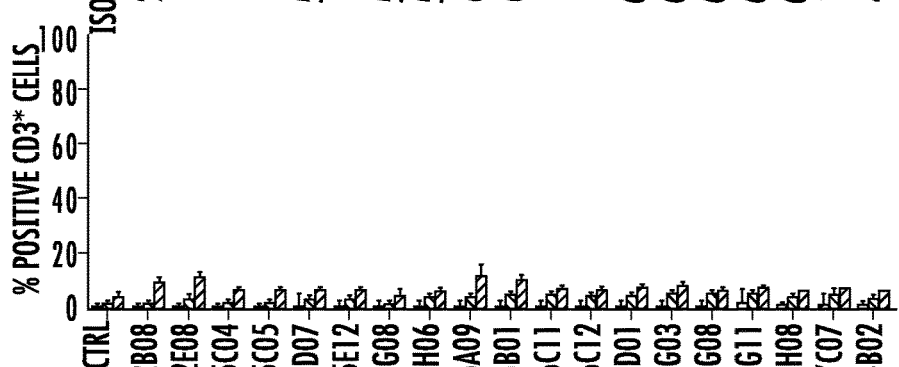

Figure 8

Figures 14A, 14B, 14C:
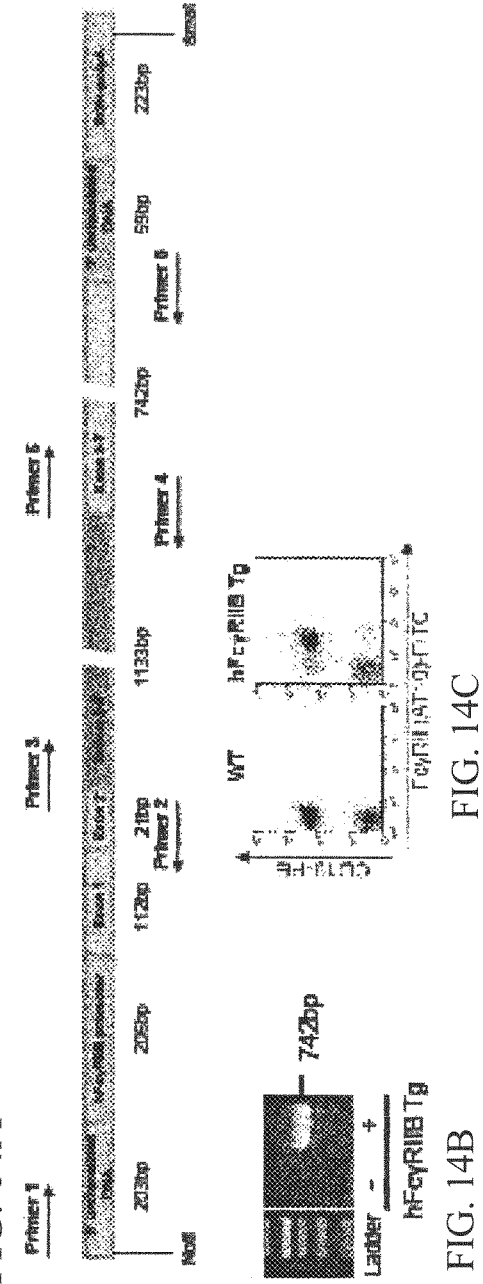
Figure 14E:
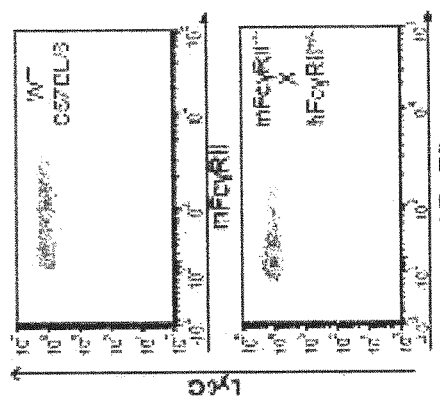
Figure 14D:
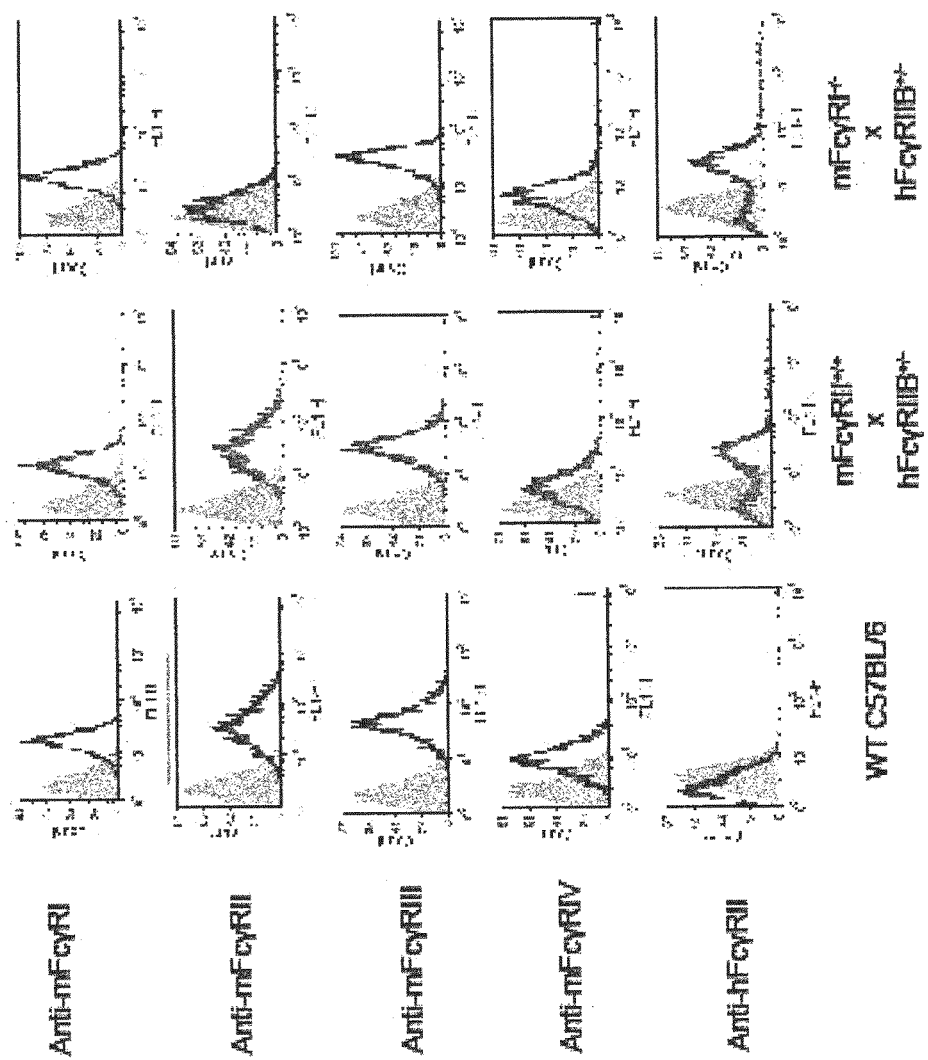
Figure 14F:
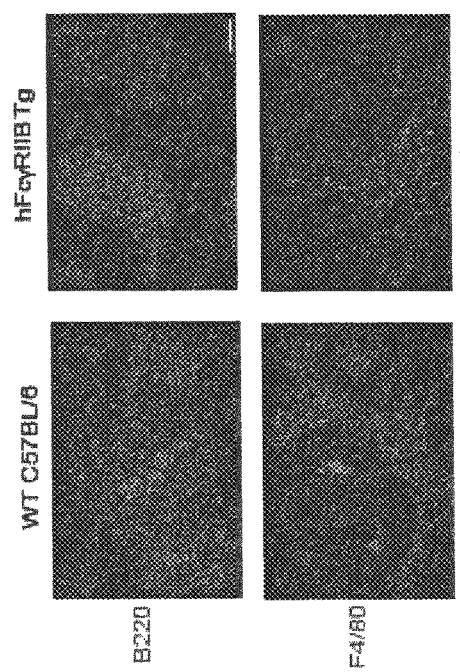
Figure 14:
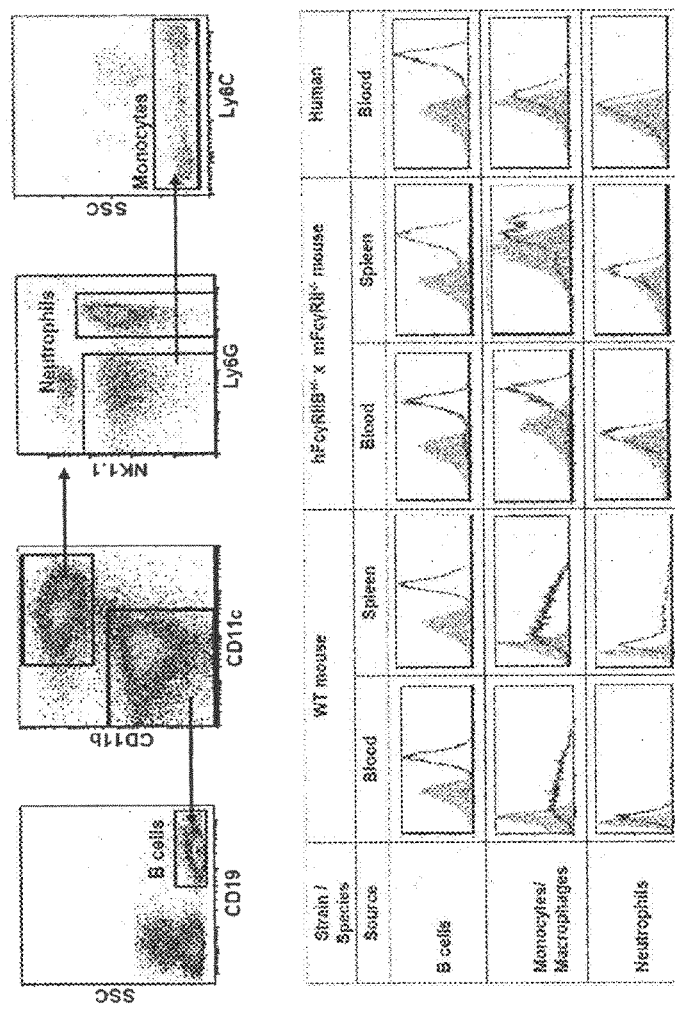

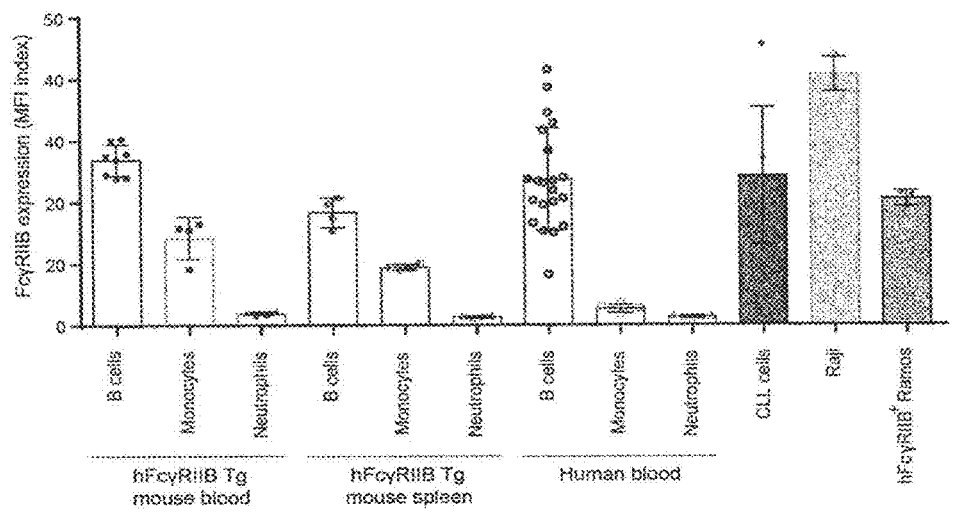
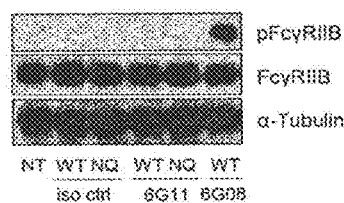
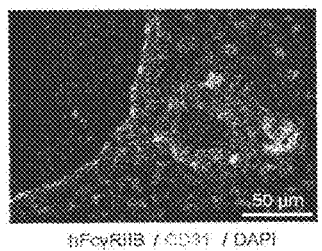
FIG. 14
(continued)

SEQUENCE LISTING

<160> NUMBER OF SEQ ID NOS: 196

<210> SEQ ID NO 1
<211> LENGTH: 330
<212> TYPE: PRT
<213> ORGANISM: Homo sapiens
<220> FEATURE:
<223> OTHER INFORMATION: IgG constant region heavy (CH)

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 105
<212> TYPE: PRT
<213> ORGANISM: Homo sapiens
<220> FEATURE:
<223> OTHER INFORMATION: IgG constant region light (CL)

<400> SEQUENCE: 2

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
                 20                  25                  30

Tyr Pro Gly Ala Val Thr Val Ala Trp Lys Ala Asp Ser Ser Pro Val
                 35                  40                  45

Lys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
```

```
                 65                  70                  75                  80
His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 3
<211> LENGTH: 118
<212> TYPE: PRT
<213> ORGANISM: Artificial Sequence
<220> FEATURE:
<223> OTHER INFORMATION: Antibody clone 1A01-VH: variable region heavy
      (VH)

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Thr Pro Gly Lys Gly Leu Glu Trp Val
        35                  40                  45

Ser Leu Ile Gly Trp Asp Gly Ser Thr Tyr Tyr Ala Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Ser Gly Tyr Glu Leu Asp Tyr Trp Gly Gln Gly Thr
            100                 105                 110

Leu Val Thr Val Ser Ser
        115

<210> SEQ ID NO 4
<211> LENGTH: 117
<212> TYPE: PRT
<213> ORGANISM: Artificial Sequence
<220> FEATURE:
<223> OTHER INFORMATION: Antibody clone 1B07: variable region heavy (VH)

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Thr Arg Tyr Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Ile Asp Ala Phe Asp Val Trp Gly Gln Gly Thr Leu
            100                 105                 110

Val Thr Val Ser Ser
        115

<210> SEQ ID NO 5
```

-continued

<211> LENGTH: 122
<212> TYPE: PRT
<213> ORGANISM: Artificial Sequence
<220> FEATURE:
<223> OTHER INFORMATION: Antibody clone 1C04: variable region heavy (VH)

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Asp Ser Gly Ala Gly Arg Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr His Asp Ser Gly Glu Leu Leu Asp Ala Phe Asp Ile Trp
            100                 105                 110

Gly Gln Gly Thr Leu Val Thr Val Ser Ser
        115                 120
```

<210> SEQ ID NO 6
<211> LENGTH: 124
<212> TYPE: PRT
<213> ORGANISM: Artificial Sequence
<220> FEATURE:
<223> OTHER INFORMATION: Antibody clone 1E05: variable region heavy (VH)

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Val Pro Gly Lys Gly Leu Glu Trp Val
        35                  40                  45

Ala Val Ile Ser Tyr Asp Gly Ser Asn Lys Asn Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Phe Asp Asn Ser Gly Tyr Ala Ile Pro Asp Ala Phe Asp
            100                 105                 110

Ile Trp Gly Gln Gly Thr Leu Val Thr Val Ser Ser
        115                 120
```

<210> SEQ ID NO 7
<211> LENGTH: 121
<212> TYPE: PRT
<213> ORGANISM: Artificial Sequence
<220> FEATURE:
<223> OTHER INFORMATION: Antibody clone 2A09 : variable region heavy (VH)

<400> SEQUENCE: 7

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ala Tyr Ile Ser Arg Asp Ala Asp Ile Thr His Tyr Pro Ala Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Thr Thr Gly Phe Asp Tyr Ala Gly Asp Asp Ala Phe Asp Ile Trp Gly
            100                 105                 110

Gln Gly Thr Leu Val Thr Val Ser Ser
        115                 120

<210> SEQ ID NO 8
<211> LENGTH: 119
<212> TYPE: PRT
<213> ORGANISM: Artificial Sequence
<220> FEATURE:
<223> OTHER INFORMATION: Antibody clone 2B08: variable region heavy (VH)

<400> SEQUENCE: 8

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ala Leu Ile Gly His Asp Gly Asn Asn Lys Tyr Tyr Leu Asp Ser Leu
    50                  55                  60

Glu Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Ala Thr Asp Ser Gly Tyr Asp Leu Leu Tyr Trp Gly Gln Gly
            100                 105                 110

Thr Leu Val Thr Val Ser Ser
        115

<210> SEQ ID NO 9
<211> LENGTH: 117
<212> TYPE: PRT
<213> ORGANISM: Artificial Sequence
<220> FEATURE:
<223> OTHER INFORMATION: Antibody clone 2E08: variable region heavy (VH)

<400> SEQUENCE: 9

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Ala Ile Gly Phe Ser Asp Asp Asn Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Gly Gly Asp Gly Ser Gly Trp Ser Phe Trp Gly Gln Gly Thr Leu
                100                 105                 110

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: Antibody clone 5C04: variable region heavy (VH)

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Glu Trp Arg Asp Ala Phe Asp Ile Trp Gly Gln Gly Thr Leu
                100                 105                 110

Val Thr Val Ser Ser
        115

<210> SEQ ID NO 11
<211> LENGTH: 117
<212> TYPE: PRT
<213> ORGANISM: Artificial Sequence
<220> FEATURE:
<223> OTHER INFORMATION: Antibody clone 5C05: variable region heavy (VH)

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Glu Asn Phe Asp Ala Phe Asp Val Trp Gly Gln Gly Thr Leu
                100                 105                 110

Val Thr Val Ser Ser
        115
```

<210> SEQ ID NO 12
<211> LENGTH: 117
<212> TYPE: PRT
<213> ORGANISM: Artificial Sequence
<220> FEATURE:
<223> OTHER INFORMATION: Antibody clone 5D07: variable region heavy (VH)

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ala Tyr Asp Gly Ser Lys Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Arg Asp Ala Phe Asp Ile Trp Gly Gln Gly Thr Leu
            100                 105                 110

Val Thr Val Ser Ser
        115

<210> SEQ ID NO 13
<211> LENGTH: 117
<212> TYPE: PRT
<213> ORGANISM: Artificial Sequence
<220> FEATURE:
<223> OTHER INFORMATION: Antibody clone 5E12: variable region heavy (VH)

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ile Asn Lys Asp Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Lys Asp Ala Phe Asp Ile Trp Gly Gln Gly Thr Leu
            100                 105                 110

Val Thr Val Ser Ser
        115

<210> SEQ ID NO 14
<211> LENGTH: 117
<212> TYPE: PRT
<213> ORGANISM: Artificial Sequence
<220> FEATURE:
<223> OTHER INFORMATION: Antibody clone 5G08: variable region heavy (VH)

<400> SEQUENCE: 14

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Thr Phe Asn Asn Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Arg Tyr Tyr Ala Asp Ser Val
        50                  55                  60

Lys Gly Arg Phe Thr Met Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Asp Arg Trp Asn Gly Met Asp Val Trp Gly Gln Gly Thr Leu
            100                 105                 110

Val Thr Val Ser Ser
        115
```

<210> SEQ ID NO 15
<211> LENGTH: 119
<212> TYPE: PRT
<213> ORGANISM: Artificial Sequence
<220> FEATURE:
<223> OTHER INFORMATION: Antibody clone 5H06: variable region heavy (VH)

<400> SEQUENCE: 15

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asp Thr Ala Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Asp His Ser Val Ile Gly Ala Phe Asp Ile Trp Gly Gln Gly
            100                 105                 110

Thr Leu Val Thr Val Ser Ser
        115
```

<210> SEQ ID NO 16
<211> LENGTH: 119
<212> TYPE: PRT
<213> ORGANISM: Artificial Sequence
<220> FEATURE:
<223> OTHER INFORMATION: Antibody clone 6A09: variable region heavy (VH)

<400> SEQUENCE: 16

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Thr Ser Tyr Asp Gly Asn Thr Lys Tyr Tyr Ala Asn Ser Val
        50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Cys Gly Gly Asp Cys Phe Asp Tyr Trp Gly Gln Gly
            100                 105                 110

Thr Leu Val Thr Val Ser Ser
            115
```

<210> SEQ ID NO 17
<211> LENGTH: 118
<212> TYPE: PRT
<213> ORGANISM: Artificial Sequence
<220> FEATURE:
<223> OTHER INFORMATION: Antibody clone 6B01: variable region heavy (VH)

<400> SEQUENCE: 17

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Leu Gly Glu Ala Phe Asp Ile Trp Gly Gln Gly Thr
            100                 105                 110

Leu Val Thr Val Ser Ser
            115
```

<210> SEQ ID NO 18
<211> LENGTH: 117
<212> TYPE: PRT
<213> ORGANISM: Artificial Sequence
<220> FEATURE:
<223> OTHER INFORMATION: Antibody clone 6C11: variable region heavy (VH)

<400> SEQUENCE: 18

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
                 20                  25                  30

Gly Met Ser Trp Val Arg Gln Ala Pro Gly Lys Gly Leu Glu Trp Val
             35                  40                  45

Ser Ala Ile Ser Gly Ser Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Gly Asp Ile Asp Tyr Phe Asp Tyr Trp Gly Gln Gly Thr Leu
            100                 105                 110

Val Thr Val Ser Ser
            115
```

```
<210> SEQ ID NO 19
<211> LENGTH: 117
<212> TYPE: PRT
<213> ORGANISM: Artificial Sequence
<220> FEATURE:
<223> OTHER INFORMATION: Antibody clone 6C12: variable region heavy (VH)

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Arg Asp Ala Phe Asp Ile Trp Gly Gln Gly Thr Leu
            100                 105                 110

Val Thr Val Ser Ser
        115

<210> SEQ ID NO 20
<211> LENGTH: 119
<212> TYPE: PRT
<213> ORGANISM: Artificial Sequence
<220> FEATURE:
<223> OTHER INFORMATION: Antibody clone 6D01: variable region heavy (VH)

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp His Ser Ala Ala Gly Tyr Phe Asp Tyr Trp Gly Gln Gly
            100                 105                 110

Thr Leu Val Thr Val Ser Ser
        115

<210> SEQ ID NO 21
<211> LENGTH: 119
<212> TYPE: PRT
<213> ORGANISM: Artificial Sequence
<220> FEATURE:
<223> OTHER INFORMATION: Antibody clone 6G03: variable region heavy (VH)

<400> SEQUENCE: 21
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ser Gly Ile Ser Trp Asp Ser Ala Ile Ile Asp Tyr Ala Gly Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Glu Ala Ala Ala Gly Ala Phe Asp Ile Trp Gly Gln Gly
        100                 105                 110

Thr Leu Val Thr Val Ser Ser
        115

<210> SEQ ID NO 22
<211> LENGTH: 121
<212> TYPE: PRT
<213> ORGANISM: Artificial Sequence
<220> FEATURE:
<223> OTHER INFORMATION: Antibody clone 6G08: variable region heavy (VH)

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Gly Ile Ser Trp Val Arg Gln Ala Pro Gly Lys Gly Leu Glu Trp Val
        35                  40                  45

Ser Gly Ile Ser Gly Ser Gly Gly Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Ser Val Gly Ala Tyr Ser Asn Asp Ala Phe Asp Ile Trp Gly
        100                 105                 110

Gln Gly Thr Leu Val Thr Val Ser Ser
        115                 120

<210> SEQ ID NO 23
<211> LENGTH: 117
<212> TYPE: PRT
<213> ORGANISM: Artificial Sequence
<220> FEATURE:
<223> OTHER INFORMATION: Antibody clone 6G11: variable region heavy (VH)

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Val Ile Ser Tyr Asp Gly Ser Asn Lys Tyr Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Tyr Asp Ala Phe Asp Ile Trp Gly Gln Gly Thr Leu
            100                 105                 110

Val Thr Val Ser Ser
            115

<210> SEQ ID NO 24
<211> LENGTH: 117
<212> TYPE: PRT
<213> ORGANISM: Artificial Sequence
<220> FEATURE:
<223> OTHER INFORMATION: Antibody clone 6H08: variable region heavy (VH)

<400> SEQUENCE: 24

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
         50                  55                  60

Lys Gly Arg Phe Thr Ile Ser Lys Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Tyr Lys Asp Ala Phe Asp Ile Trp Gly Gln Gly Thr Leu
            100                 105                 110

Val Thr Val Ser Ser
            115

<210> SEQ ID NO 25
<211> LENGTH: 118
<212> TYPE: PRT
<213> ORGANISM: Artificial Sequence
<220> FEATURE:
<223> OTHER INFORMATION: Antibody clone 7C07: variable region heavy (VH)

<400> SEQUENCE: 25

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Gln Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Phe Gly Tyr Ile Ile Leu Asp Tyr Trp Gly Gln Gly Thr
            100                 105                 110

Leu Val Thr Val Ser Ser
```

```
<210> SEQ ID NO 26
<211> LENGTH: 117
<212> TYPE: PRT
<213> ORGANISM: Artificial Sequence
<220> FEATURE:
<223> OTHER INFORMATION: Antibody clone 4B02: variable region heavy (VH)

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Gly Met His Trp Val Arg Gln Ala Pro Gly Lys Gly Leu Glu Trp Val
        35                  40                  45

Ala Val Ile Ser Tyr Asp Gly Thr Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asp Ala Phe Asp Val Trp Gly Gln Gly Thr Leu
            100                 105                 110

Val Thr Val Ser Ser
            115

<210> SEQ ID NO 27
<211> LENGTH: 111
<212> TYPE: PRT
<213> ORGANISM: Artificial Sequence
<220> FEATURE:
<223> OTHER INFORMATION: Antibody clone 1A01: variable region light (VL)

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Ala Ser Ile Phe Gly Gly Gly Thr Lys Leu Thr Val Leu Gly
            100                 105                 110

<210> SEQ ID NO 28
<211> LENGTH: 111
<212> TYPE: PRT
<213> ORGANISM: Artificial Sequence
<220> FEATURE:
<223> OTHER INFORMATION: Antibody clone 1B07: variable region light (VL)

<400> SEQUENCE: 28

Gln Ser Val Leu Thr Gln Pro Pro Ser Ala Ser Gly Thr Pro Gly Gln
1               5                   10                  15
```

```
Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Asp Asn Gln Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Glu Ala Trp Asp Asp Arg Leu
                85                  90                  95

Phe Gly Pro Val Phe Gly Gly Gly Thr Lys Leu Thr Val Leu Gly
            100                 105                 110

<210> SEQ ID NO 29
<211> LENGTH: 111
<212> TYPE: PRT
<213> ORGANISM: Artificial Sequence
<220> FEATURE:
<223> OTHER INFORMATION: Antibody clone 1C04: variable region light (VL)

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

His Val Leu Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Antibody clone 1E05: variable region light (VL)

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Ser Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Gly Gly Pro Val Phe Gly Gly Gly Thr Lys Leu Thr Val Leu Gly
```

<210> SEQ ID NO 31
<211> LENGTH: 112
<212> TYPE: PRT
<213> ORGANISM: Artificial Sequence
<220> FEATURE:
<223> OTHER INFORMATION: Antibody clone 2A09: variable region light (VL)

<400> SEQUENCE: 31

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Gly Asn Ser Asp Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Arg Trp Val Phe Gly Gly Gly Thr Lys Leu Thr Val Leu Gly
            100                 105                 110
```

<210> SEQ ID NO 32
<211> LENGTH: 111
<212> TYPE: PRT
<213> ORGANISM: Artificial Sequence
<220> FEATURE:
<223> OTHER INFORMATION: Antibody clone 2B08: variable region light (VL)

<400> SEQUENCE: 32

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Tyr Asp Asp Leu Leu Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Thr Thr Trp Asp Asp Ser Leu
                85                  90                  95

Ser Gly Val Val Phe Gly Gly Gly Thr Lys Leu Thr Val Leu Gly
            100                 105                 110
```

<210> SEQ ID NO 33
<211> LENGTH: 111
<212> TYPE: PRT
<213> ORGANISM: Artificial Sequence
<220> FEATURE:
<223> OTHER INFORMATION: Antibody clone 2E08: variable region light (VL)

<400> SEQUENCE: 33

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30
```

Ala Val Asn Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Arg Gly Trp Val Phe Gly Gly Gly Thr Lys Leu Thr Val Leu Gly
            100                 105                 110

<210> SEQ ID NO 34
<211> LENGTH: 113
<212> TYPE: PRT
<213> ORGANISM: Artificial Sequence
<220> FEATURE:
<223> OTHER INFORMATION: Antibody clone 5C04: variable region light (VL)

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Ser Asp Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Ser Trp Val Phe Gly Gly Gly Thr Lys Leu Thr Val Leu
            100                 105                 110

Gly

<210> SEQ ID NO 35
<211> LENGTH: 113
<212> TYPE: PRT
<213> ORGANISM: Artificial Sequence
<220> FEATURE:
<223> OTHER INFORMATION: Antibody clone 5C05: variable region light (VL)

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Ser Asn Ser Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Gln Val Val Phe Gly Gly Gly Thr Lys Leu Thr Val Leu
            100                 105                 110

```
<210> SEQ ID NO 36
<211> LENGTH: 112
<212> TYPE: PRT
<213> ORGANISM: Artificial Sequence
<220> FEATURE:
<223> OTHER INFORMATION: Antibody clone 5D07: variable region light (VL)

<400> SEQUENCE: 36

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Thr Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Val Ser Gly Trp Met Phe Gly Gly Gly Thr Lys Leu Thr Val Leu Gly
            100                 105                 110

<210> SEQ ID NO 37
<211> LENGTH: 112
<212> TYPE: PRT
<213> ORGANISM: Artificial Sequence
<220> FEATURE:
<223> OTHER INFORMATION: Antibody clone 5E12: variable region light (VL)

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Ser Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Thr Trp Asp Asp Ser
                85                  90                  95

Leu Asn Gly Leu Val Phe Gly Gly Gly Thr Lys Leu Thr Val Leu Gly
            100                 105                 110

<210> SEQ ID NO 38
<211> LENGTH: 113
<212> TYPE: PRT
<213> ORGANISM: Artificial Sequence
<220> FEATURE:
<223> OTHER INFORMATION: Antibody clone 5G08: variable region light (VL)

<400> SEQUENCE: 38

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ala Gly
```

```
                20                  25                  30
Tyr Asp Val His Trp Tyr Gln Gln Leu Pro Gly Thr Ala Pro Lys Leu
            35                  40                  45

Leu Ile Tyr Ala Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Pro Trp Val Phe Gly Gly Gly Thr Lys Leu Thr Val Leu
            100                 105                 110

Gly

<210> SEQ ID NO 39
<211> LENGTH: 110
<212> TYPE: PRT
<213> ORGANISM: Artificial Sequence
<220> FEATURE:
<223> OTHER INFORMATION: Antibody clone 5H06: variable region light (VL)

<400> SEQUENCE: 39

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Ala Gly Ser Asn
                85                  90                  95

Asn Val Val Phe Gly Gly Gly Thr Lys Leu Thr Val Leu Gly
            100                 105                 110

<210> SEQ ID NO 40
<211> LENGTH: 112
<212> TYPE: PRT
<213> ORGANISM: Artificial Sequence
<220> FEATURE:
<223> OTHER INFORMATION: Antibody clone 6A09: variable region light (VL)

<400> SEQUENCE: 40

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Glu Gly Val Phe Gly Gly Gly Thr Lys Leu Thr Val Leu Gly
```

-continued

```
                100                 105                 110

<210> SEQ ID NO 41
<211> LENGTH: 112
<212> TYPE: PRT
<213> ORGANISM: Artificial Sequence
<220> FEATURE:
<223> OTHER INFORMATION: Antibody clone 6B01: variable region light (VL)

<400> SEQUENCE: 41

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Thr Trp Asp Asp Ser
                85                  90                  95

Leu Ser Gly Pro Val Phe Gly Gly Gly Thr Lys Leu Thr Val Leu Gly
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Antibody clone 6C11: variable region light (VL)

<400> SEQUENCE: 42

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Phe Gly Ala Gly
            20                  25                  30

Tyr Asp Val His Trp Tyr Gln Gln Leu Pro Gly Thr Ala Pro Lys Leu
        35                  40                  45

Leu Ile Tyr Glu Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Pro Val Phe Gly Gly Gly Thr Lys Leu Thr Val Leu Gly
            100                 105                 110

<210> SEQ ID NO 43
<211> LENGTH: 110
<212> TYPE: PRT
<213> ORGANISM: Artificial Sequence
<220> FEATURE:
<223> OTHER INFORMATION: Antibody clone 6C12: variable region light (VL)

<400> SEQUENCE: 43

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30
```

Tyr Asp Val His Trp Tyr Gln Gln Leu Pro Gly Thr Ala Pro Lys Leu
        35                  40                  45

Leu Ile Tyr Ser Asp Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Thr Trp Asp Ser Asp
                85                  90                  95

Thr Pro Val Phe Gly Gly Gly Thr Lys Leu Thr Val Leu Gly
            100                 105                 110

<210> SEQ ID NO 44
<211> LENGTH: 111
<212> TYPE: PRT
<213> ORGANISM: Artificial Sequence
<220> FEATURE:
<223> OTHER INFORMATION: Antibody clone 6D01: variable region light (VL)

<400> SEQUENCE: 44

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Ile Arg Pro Ser Gly Gly Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ser Pro Val Phe Gly Gly Gly Thr Lys Leu Thr Val Leu Gly
            100                 105                 110

<210> SEQ ID NO 45
<211> LENGTH: 113
<212> TYPE: PRT
<213> ORGANISM: Artificial Sequence
<220> FEATURE:
<223> OTHER INFORMATION: Antibody clone 6G03: variable region light (VL)

<400> SEQUENCE: 45

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Thr Asp Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Pro Val Val Phe Gly Gly Gly Thr Lys Leu Thr Val Leu
            100                 105                 110

Gly

<210> SEQ ID NO 46
<211> LENGTH: 112
<212> TYPE: PRT
<213> ORGANISM: Artificial Sequence
<220> FEATURE:
<223> OTHER INFORMATION: Antibody clone 6G08: variable region light (VL)

<400> SEQUENCE: 46

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Thr Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Pro Val Phe Gly Gly Gly Thr Lys Leu Thr Val Leu Gly
            100                 105                 110

<210> SEQ ID NO 47
<211> LENGTH: 112
<212> TYPE: PRT
<213> ORGANISM: Artificial Sequence
<220> FEATURE:
<223> OTHER INFORMATION: Antibody clone 6G11: variable region light (VL)

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asp Asp His Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ser Trp Asp Asp Ser
                85                  90                  95

Gln Arg Ala Val Ile Phe Gly Gly Gly Thr Lys Leu Thr Val Leu Gly
            100                 105                 110

<210> SEQ ID NO 48
<211> LENGTH: 109
<212> TYPE: PRT
<213> ORGANISM: Artificial Sequence
<220> FEATURE:
<223> OTHER INFORMATION: Antibody clone 6H08: variable region light (VL)

<400> SEQUENCE: 48

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

```
Thr Val Asn Trp Tyr Gln Gln Leu Pro Gly Thr Ala Pro Lys Leu Leu
         35                  40                  45

Ile Tyr Asp Asn Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ala Trp Gly Thr Gly Ile
                 85                  90                  95

Arg Val Phe Gly Gly Gly Thr Lys Leu Thr Val Leu Gly
                100                 105

<210> SEQ ID NO 49
<211> LENGTH: 111
<212> TYPE: PRT
<213> ORGANISM: Artificial Sequence
<220> FEATURE:
<223> OTHER INFORMATION: Antibody clone 7C07: variable region light (VL)

<400> SEQUENCE: 49

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Thr Val Asn Trp Tyr Gln Gln Leu Pro Gly Thr Ala Pro Lys Leu Leu
         35                  40                  45

Ile Tyr Arg Asp Tyr Glu Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Met Ala Trp Asp Asp Ser Leu
                 85                  90                  95

Ser Gly Val Val Phe Gly Gly Gly Thr Lys Leu Thr Val Leu Gly
                100                 105                 110

<210> SEQ ID NO 50
<211> LENGTH: 109
<212> TYPE: PRT
<213> ORGANISM: Artificial Sequence
<220> FEATURE:
<223> OTHER INFORMATION: Antibody clone 4B02: variable region light (VL)

<400> SEQUENCE: 50

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Asn Ala Asn Trp Tyr Gln Gln Leu Pro Gly Thr Ala Pro Lys Leu Leu
         35                  40                  45

Ile Tyr Asp Asn Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ala Trp Asp Ser Ser Thr
                 85                  90                  95

Val Val Phe Gly Gly Gly Thr Lys Leu Thr Val Leu Gly
                100                 105

<210> SEQ ID NO 51
```

```
<211> LENGTH: 5
<212> TYPE: PRT
<213> ORGANISM: Artificial Sequence
<220> FEATURE:
<223> OTHER INFORMATION: Antibody clone 1A01: CDRH1

<400> SEQUENCE: 51

Asp Tyr Tyr Met Asn
1               5

<210> SEQ ID NO 52
<211> LENGTH: 17
<212> TYPE: PRT
<213> ORGANISM: Artificial Sequence
<220> FEATURE:
<223> OTHER INFORMATION: Antibody clone 1A01: CDRH2

<400> SEQUENCE: 52

Leu Ile Gly Trp Asp Gly Gly Ser Thr Tyr Tyr Ala Asp Ser Val Lys
1               5                   10                  15

Gly

<210> SEQ ID NO 53
<211> LENGTH: 9
<212> TYPE: PRT
<213> ORGANISM: Artificial Sequence
<220> FEATURE:
<223> OTHER INFORMATION: Antibody clone 1A01: CDRH3

<400> SEQUENCE: 53

Ala Tyr Ser Gly Tyr Glu Leu Asp Tyr
1               5

<210> SEQ ID NO 54
<211> LENGTH: 13
<212> TYPE: PRT
<213> ORGANISM: Artificial Sequence
<220> FEATURE:
<223> OTHER INFORMATION: Antibody clone 1A01: CDRL1

<400> SEQUENCE: 54

Ser Gly Ser Ser Ser Asn Ile Gly Asn Asn Ala Val Asn
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Antibody clone 1A01: CDRL2

<400> SEQUENCE: 55

Asp Asn Asn Asn Arg Pro Ser
1               5

<210> SEQ ID NO 56
<211> LENGTH: 11
<212> TYPE: PRT
<213> ORGANISM: Artificial Sequence
<220> FEATURE:
<223> OTHER INFORMATION: Antibody clone 1A01: CDRL3

<400> SEQUENCE: 56

Ala Ala Trp Asp Asp Ser Leu Asn Ala Ser Ile
1               5                   10
```

```
<210> SEQ ID NO 57
<211> LENGTH: 5
<212> TYPE: PRT
<213> ORGANISM: Artificial Sequence
<220> FEATURE:
<223> OTHER INFORMATION: Antibody clone 1B07: CDRH1

<400> SEQUENCE: 57

Ser Tyr Gly Met His
1               5

<210> SEQ ID NO 58
<211> LENGTH: 17
<212> TYPE: PRT
<213> ORGANISM: Artificial Sequence
<220> FEATURE:
<223> OTHER INFORMATION: Antibody clone 1B07: CDRH2

<400> SEQUENCE: 58

Phe Thr Arg Tyr Asp Gly Ser Asn Lys Tyr Tyr Ala Asp Ser Val Arg
1               5                   10                  15

Gly

<210> SEQ ID NO 59
<211> LENGTH: 8
<212> TYPE: PRT
<213> ORGANISM: Artificial Sequence
<220> FEATURE:
<223> OTHER INFORMATION: Antibody clone 1B07: CDRH3

<400> SEQUENCE: 59

Glu Asn Ile Asp Ala Phe Asp Val
1               5

<210> SEQ ID NO 60
<211> LENGTH: 13
<212> TYPE: PRT
<213> ORGANISM: Artificial Sequence
<220> FEATURE:
<223> OTHER INFORMATION: Antibody clone 1B07: CDRL1

<400> SEQUENCE: 60

Ser Gly Ser Ser Ser Asn Ile Gly Asn Asn Ala Val Asn
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Antibody clone 1B07: CDRL2

<400> SEQUENCE: 61

Asp Asn Gln Gln Arg Pro Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Antibody clone 1B07: CDRL3

<400> SEQUENCE: 62

Trp Asp Asp Arg Leu Phe Gly Pro Val
1               5
```

```
<210> SEQ ID NO 63
<211> LENGTH: 5
<212> TYPE: PRT
<213> ORGANISM: Artificial Sequence
<220> FEATURE:
<223> OTHER INFORMATION: Antibody clone 1C04: CDRH1

<400> SEQUENCE: 63

Ser Tyr Ala Met Ser
1               5

<210> SEQ ID NO 64
<211> LENGTH: 17
<212> TYPE: PRT
<213> ORGANISM: Artificial Sequence
<220> FEATURE:
<223> OTHER INFORMATION: Antibody clone 1C04: CDRH2

<400> SEQUENCE: 64

Ser Ile Ser Asp Ser Gly Ala Gly Arg Tyr Tyr Ala Asp Ser Val Glu
1               5                   10                  15

Gly

<210> SEQ ID NO 65
<211> LENGTH: 13
<212> TYPE: PRT
<213> ORGANISM: Artificial Sequence
<220> FEATURE:
<223> OTHER INFORMATION: Antibody clone 1C04: CDRH3

<400> SEQUENCE: 65

Thr His Asp Ser Gly Glu Leu Leu Asp Ala Phe Asp Ile
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Antibody clone 1C04: CDRL1

<400> SEQUENCE: 66

Ser Gly Ser Ser Ser Asn Ile Gly Ser Asn His Val Leu
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Antibody clone 1C04: CDRL2

<400> SEQUENCE: 67

Gly Asn Ser Asn Arg Pro Ser
1               5

<210> SEQ ID NO 68
<211> LENGTH: 11
<212> TYPE: PRT
<213> ORGANISM: Artificial Sequence
<220> FEATURE:
<223> OTHER INFORMATION: Antibody clone 1C04: CDRL3

<400> SEQUENCE: 68

Ala Ala Trp Asp Asp Ser Leu Asn Gly Trp Val
1               5                   10
```

<210> SEQ ID NO 69
<211> LENGTH: 5
<212> TYPE: PRT
<213> ORGANISM: Artificial Sequence
<220> FEATURE:
<223> OTHER INFORMATION: Antibody clone 1E05: CDRH1

<400> SEQUENCE: 69

Thr Tyr Ala Met Asn
1               5

<210> SEQ ID NO 70
<211> LENGTH: 17
<212> TYPE: PRT
<213> ORGANISM: Artificial Sequence
<220> FEATURE:
<223> OTHER INFORMATION: Antibody clone 1E05: CDRH2

<400> SEQUENCE: 70

Val Ile Ser Tyr Asp Gly Ser Asn Lys Asn Tyr Val Asp Ser Val Lys
1               5                   10                  15

Gly

<210> SEQ ID NO 71
<211> LENGTH: 15
<212> TYPE: PRT
<213> ORGANISM: Artificial Sequence
<220> FEATURE:
<223> OTHER INFORMATION: Antibody clone 1E05: CDRH3

<400> SEQUENCE: 71

Asn Phe Asp Asn Ser Gly Tyr Ala Ile Pro Asp Ala Phe Asp Ile
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: Antibody clone 1E05: CDRL1

<400> SEQUENCE: 72

Thr Gly Ser Ser Ser Asn Ile Gly Ala Gly Tyr Asp Val His
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Antibody clone 1E05: CDRL2

<400> SEQUENCE: 73

Asp Asn Asn Ser Arg Pro Ser
1               5

<210> SEQ ID NO 74
<211> LENGTH: 11
<212> TYPE: PRT
<213> ORGANISM: Artificial Sequence
<220> FEATURE:
<223> OTHER INFORMATION: Antibody clone 1E05: CDRL3

<400> SEQUENCE: 74

Ala Ala Trp Asp Asp Ser Leu Gly Gly Pro Val

<210> SEQ ID NO 75
<211> LENGTH: 5
<212> TYPE: PRT
<213> ORGANISM: Artificial Sequence
<220> FEATURE:
<223> OTHER INFORMATION: Antibody clone 2A09: CDRH1

<400> SEQUENCE: 75

Asn Ala Trp Met Ser
1               5

<210> SEQ ID NO 76
<211> LENGTH: 17
<212> TYPE: PRT
<213> ORGANISM: Artificial Sequence
<220> FEATURE:
<223> OTHER INFORMATION: Antibody clone 2A09: CDRH2

<400> SEQUENCE: 76

Tyr Ile Ser Arg Asp Ala Asp Ile Thr His Tyr Pro Ala Ser Val Lys
1               5                   10                  15

Gly

<210> SEQ ID NO 77
<211> LENGTH: 12
<212> TYPE: PRT
<213> ORGANISM: Artificial Sequence
<220> FEATURE:
<223> OTHER INFORMATION: Antibody clone 2A09: CDRH3

<400> SEQUENCE: 77

Gly Phe Asp Tyr Ala Gly Asp Asp Ala Phe Asp Ile
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Antibody clone 2A09: CDRL1

<400> SEQUENCE: 78

Ser Gly Ser Ser Ser Asn Ile Gly Ser Asn Ala Val Asn
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Antibody clone 2A09: CDRL2

<400> SEQUENCE: 79

Gly Asn Ser Asp Arg Pro Ser
1               5

<210> SEQ ID NO 80
<211> LENGTH: 12
<212> TYPE: PRT
<213> ORGANISM: Artificial Sequence
<220> FEATURE:
<223> OTHER INFORMATION: Antibody clone 2A09: CDRL3

<400> SEQUENCE: 80

```
Ala Ala Trp Asp Asp Ser Leu Asn Gly Arg Trp Val
1               5                   10
```

<210> SEQ ID NO 81
<211> LENGTH: 5
<212> TYPE: PRT
<213> ORGANISM: Artificial Sequence
<220> FEATURE:
<223> OTHER INFORMATION: Antibody clone 2B08: CDRH1

<400> SEQUENCE: 81

```
Asp Tyr Tyr Met Ser
1               5
```

<210> SEQ ID NO 82
<211> LENGTH: 17
<212> TYPE: PRT
<213> ORGANISM: Artificial Sequence
<220> FEATURE:
<223> OTHER INFORMATION: Antibody clone 2B08: CDRH2

<400> SEQUENCE: 82

```
Leu Ile Gly His Asp Gly Asn Asn Lys Tyr Tyr Leu Asp Ser Leu Glu
1               5                   10                  15

Gly
```

<210> SEQ ID NO 83
<211> LENGTH: 10
<212> TYPE: PRT
<213> ORGANISM: Artificial Sequence
<220> FEATURE:
<223> OTHER INFORMATION: Antibody clone 2B08: CDRH3

<400> SEQUENCE: 83

```
Ala Thr Asp Ser Gly Tyr Asp Leu Leu Tyr
1               5                   10
```

<210> SEQ ID NO 84
<211> LENGTH: 13
<212> TYPE: PRT
<213> ORGANISM: Artificial Sequence
<220> FEATURE:
<223> OTHER INFORMATION: Antibody clone 2B08: CDRL1

<400> SEQUENCE: 84

```
Ser Gly Ser Ser Ser Asn Ile Gly Asn Asn Ala Val Asn
1               5                   10
```

<210> SEQ ID NO 85
<211> LENGTH: 7
<212> TYPE: PRT
<213> ORGANISM: Artificial Sequence
<220> FEATURE:
<223> OTHER INFORMATION: Antibody clone 2B08: CDRL2

<400> SEQUENCE: 85

```
Tyr Asp Asp Leu Leu Pro Ser
1               5
```

<210> SEQ ID NO 86
<211> LENGTH: 11
<212> TYPE: PRT
<213> ORGANISM: Artificial Sequence
<220> FEATURE:
<223> OTHER INFORMATION: Antibody clone 2B08: CDRL3

<400> SEQUENCE: 86

```
Thr Thr Trp Asp Asp Ser Leu Ser Gly Val Val
1               5                   10

<210> SEQ ID NO 87
<211> LENGTH: 5
<212> TYPE: PRT
<213> ORGANISM: Artificial Sequence
<220> FEATURE:
<223> OTHER INFORMATION: Antibody clone 2E08: CDRH1

<400> SEQUENCE: 87

Asp Tyr Tyr Met Ser
1               5

<210> SEQ ID NO 88
<211> LENGTH: 17
<212> TYPE: PRT
<213> ORGANISM: Artificial Sequence
<220> FEATURE:
<223> OTHER INFORMATION: Antibody clone 2E08: CDRH2

<400> SEQUENCE: 88

Ala Ile Gly Phe Ser Asp Asp Asn Thr Tyr Tyr Ala Asp Ser Val Lys
1               5                   10                  15

Gly

<210> SEQ ID NO 89
<211> LENGTH: 8
<212> TYPE: PRT
<213> ORGANISM: Artificial Sequence
<220> FEATURE:
<223> OTHER INFORMATION: Antibody clone 2E08: CDRH3

<400> SEQUENCE: 89

Gly Asp Gly Ser Gly Trp Ser Phe
1               5

<210> SEQ ID NO 90
<211> LENGTH: 13
<212> TYPE: PRT
<213> ORGANISM: Artificial Sequence
<220> FEATURE:
<223> OTHER INFORMATION: Antibody clone 2E08: CDRL1

<400> SEQUENCE: 90

Ser Gly Ser Ser Ser Asn Ile Gly Asn Asn Ala Val Asn
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Antibody clone 2E08: CDRL2

<400> SEQUENCE: 91

Asp Asn Asn Lys Arg Pro Ser
1               5

<210> SEQ ID NO 92
<211> LENGTH: 11
<212> TYPE: PRT
<213> ORGANISM: Artificial Sequence
<220> FEATURE:
<223> OTHER INFORMATION: Antibody clone 2E08: CDRL3
```

```
<400> SEQUENCE: 92

Ala Thr Trp Asp Asp Ser Leu Arg Gly Trp Val
1               5                   10

<210> SEQ ID NO 93
<211> LENGTH: 5
<212> TYPE: PRT
<213> ORGANISM: Artificial Sequence
<220> FEATURE:
<223> OTHER INFORMATION: Antibody clone 5C04: CDRH1

<400> SEQUENCE: 93

Asn Tyr Gly Met His
1               5

<210> SEQ ID NO 94
<211> LENGTH: 17
<212> TYPE: PRT
<213> ORGANISM: Artificial Sequence
<220> FEATURE:
<223> OTHER INFORMATION: Antibody clone 5C04: CDRH2

<400> SEQUENCE: 94

Val Ile Ser Tyr Asp Gly Ser Asn Lys Tyr Tyr Ala Asp Ser Val Lys
1               5                   10                  15

Gly

<210> SEQ ID NO 95
<211> LENGTH: 7
<212> TYPE: PRT
<213> ORGANISM: Artificial Sequence
<220> FEATURE:
<223> OTHER INFORMATION: Antibody clone 5C04: CDRH2

<400> SEQUENCE: 95

Trp Arg Asp Ala Phe Asp Ile
1               5

<210> SEQ ID NO 96
<211> LENGTH: 14
<212> TYPE: PRT
<213> ORGANISM: Artificial Sequence
<220> FEATURE:
<223> OTHER INFORMATION: Antibody clone 5C04: CDRL1

<400> SEQUENCE: 96

Thr Gly Ser Ser Ser Asn Ile Gly Ala Gly Tyr Asp Val His
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Antibody clone 5C04: CDRL2

<400> SEQUENCE: 97

Ser Asp Asn Gln Arg Pro Ser
1               5

<210> SEQ ID NO 98
<211> LENGTH: 12
<212> TYPE: PRT
<213> ORGANISM: Artificial Sequence
<220> FEATURE:
<223> OTHER INFORMATION: Antibody clone 5C04: CDRL3
```

```
<400> SEQUENCE: 98

Ala Ala Trp Asp Asp Ser Leu Ser Gly Ser Trp Val
1               5                   10

<210> SEQ ID NO 99
<211> LENGTH: 5
<212> TYPE: PRT
<213> ORGANISM: Artificial Sequence
<220> FEATURE:
<223> OTHER INFORMATION: Antibody clone 5C05: CDRH1

<400> SEQUENCE: 99

Thr Tyr Gly Met His
1               5

<210> SEQ ID NO 100
<211> LENGTH: 17
<212> TYPE: PRT
<213> ORGANISM: Artificial Sequence
<220> FEATURE:
<223> OTHER INFORMATION: Antibody clone 5C05: CDRH2

<400> SEQUENCE: 100

Val Ile Ser Tyr Asp Gly Ser Asn Lys Tyr Tyr Ala Asp Ser Val Lys
1               5                   10                  15
Gly

<210> SEQ ID NO 101
<211> LENGTH: 8
<212> TYPE: PRT
<213> ORGANISM: Artificial Sequence
<220> FEATURE:
<223> OTHER INFORMATION: Antibody clone 5C05: CDRH3

<400> SEQUENCE: 101

Glu Asn Phe Asp Ala Phe Asp Val
1               5

<210> SEQ ID NO 102
<211> LENGTH: 14
<212> TYPE: PRT
<213> ORGANISM: Artificial Sequence
<220> FEATURE:
<223> OTHER INFORMATION: Antibody clone 5C05: CDRL1

<400> SEQUENCE: 102

Thr Gly Ser Ser Ser Asn Ile Gly Ala Gly Tyr Asp Val His
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Antibody clone 5C05: CDRL2

<400> SEQUENCE: 103

Ser Asn Ser Gln Arg Pro Ser
1               5

<210> SEQ ID NO 104
<211> LENGTH: 12
<212> TYPE: PRT
<213> ORGANISM: Artificial Sequence
<220> FEATURE:
```

```
<223> OTHER INFORMATION: Antibody clone 5C05: CDRL3

<400> SEQUENCE: 104

Ala Ala Trp Asp Asp Ser Leu Asn Gly Gln Val Val
1               5                   10

<210> SEQ ID NO 105
<211> LENGTH: 5
<212> TYPE: PRT
<213> ORGANISM: Artificial Sequence
<220> FEATURE:
<223> OTHER INFORMATION: Antibody clone 5D07: CDRH1

<400> SEQUENCE: 105

Thr Tyr Gly Met His
1               5

<210> SEQ ID NO 106
<211> LENGTH: 17
<212> TYPE: PRT
<213> ORGANISM: Artificial Sequence
<220> FEATURE:
<223> OTHER INFORMATION: Antibody clone 5D07: CDRH2

<400> SEQUENCE: 106

Val Ile Ala Tyr Asp Gly Ser Lys Lys Asp Tyr Ala Asp Ser Val Lys
1               5                   10                  15

Gly

<210> SEQ ID NO 107
<211> LENGTH: 8
<212> TYPE: PRT
<213> ORGANISM: Artificial Sequence
<220> FEATURE:
<223> OTHER INFORMATION: Antibody clone 5D07: CDRH3

<400> SEQUENCE: 107

Glu Tyr Arg Asp Ala Phe Asp Ile
1               5

<210> SEQ ID NO 108
<211> LENGTH: 14
<212> TYPE: PRT
<213> ORGANISM: Artificial Sequence
<220> FEATURE:
<223> OTHER INFORMATION: Antibody clone 5D07: CDRL1

<400> SEQUENCE: 108

Thr Gly Ser Ser Ser Asn Ile Gly Ala Gly Tyr Asp Val His
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Antibody clone 5D07: CDRL2

<400> SEQUENCE: 109

Gly Asn Ser Asn Arg Pro Ser
1               5

<210> SEQ ID NO 110
<211> LENGTH: 11
<212> TYPE: PRT
<213> ORGANISM: Artificial Sequence
```

```
<220> FEATURE:
<223> OTHER INFORMATION: Antibody clone 5D07: CDRL3

<400> SEQUENCE: 110

Ala Ala Trp Asp Asp Ser Val Ser Gly Trp Met
1               5                   10

<210> SEQ ID NO 111
<211> LENGTH: 5
<212> TYPE: PRT
<213> ORGANISM: Artificial Sequence
<220> FEATURE:
<223> OTHER INFORMATION: Antibody clone 5E12: CDRH1

<400> SEQUENCE: 111

Ser Tyr Gly Met His
1               5

<210> SEQ ID NO 112
<211> LENGTH: 17
<212> TYPE: PRT
<213> ORGANISM: Artificial Sequence
<220> FEATURE:
<223> OTHER INFORMATION: Antibody clone 5E12: CDRH2

<400> SEQUENCE: 112

Val Ile Ser Tyr Asp Gly Ile Asn Lys Asp Tyr Ala Asp Ser Met Lys
1               5                   10                  15

Gly

<210> SEQ ID NO 113
<211> LENGTH: 8
<212> TYPE: PRT
<213> ORGANISM: Artificial Sequence
<220> FEATURE:
<223> OTHER INFORMATION: Antibody clone 5E12: CDRH3

<400> SEQUENCE: 113

Glu Arg Lys Asp Ala Phe Asp Ile
1               5

<210> SEQ ID NO 114
<211> LENGTH: 14
<212> TYPE: PRT
<213> ORGANISM: Artificial Sequence
<220> FEATURE:
<223> OTHER INFORMATION: Antibody clone 5E12: CDRL1

<400> SEQUENCE: 114

Thr Gly Ser Ser Ser Asn Ile Gly Ala Gly Tyr Asp Val His
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Antibody clone 5E12: CDRL2

<400> SEQUENCE: 115

Ser Asn Asn Gln Arg Pro Ser
1               5

<210> SEQ ID NO 116
<211> LENGTH: 11
<212> TYPE: PRT
```

```
<213> ORGANISM: Artificial Sequence
<220> FEATURE:
<223> OTHER INFORMATION: Antibody clone 5E12: CDRL3

<400> SEQUENCE: 116

Ala Thr Trp Asp Asp Ser Leu Asn Gly Leu Val
1               5                   10

<210> SEQ ID NO 117
<211> LENGTH: 5
<212> TYPE: PRT
<213> ORGANISM: Artificial Sequence
<220> FEATURE:
<223> OTHER INFORMATION: Antibody clone 5G08: CDRH1

<400> SEQUENCE: 117

Asn Tyr Gly Met His
1               5

<210> SEQ ID NO 118
<211> LENGTH: 17
<212> TYPE: PRT
<213> ORGANISM: Artificial Sequence
<220> FEATURE:
<223> OTHER INFORMATION: Antibody clone 5G08: CDRH2

<400> SEQUENCE: 118

Val Ile Ser Tyr Asp Gly Ser Asn Arg Tyr Tyr Ala Asp Ser Val Lys
1               5                   10                  15

Gly

<210> SEQ ID NO 119
<211> LENGTH: 8
<212> TYPE: PRT
<213> ORGANISM: Artificial Sequence
<220> FEATURE:
<223> OTHER INFORMATION: Antibody clone 5G08: CDRH3

<400> SEQUENCE: 119

Asp Arg Trp Asn Gly Met Asp Val
1               5

<210> SEQ ID NO 120
<211> LENGTH: 14
<212> TYPE: PRT
<213> ORGANISM: Artificial Sequence
<220> FEATURE:
<223> OTHER INFORMATION: Antibody clone 5G08: CDRL1

<400> SEQUENCE: 120

Ser Gly Ser Ser Ser Asn Ile Gly Ala Gly Tyr Asp Val His
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Antibody clone 5G08: CDRL2

<400> SEQUENCE: 121

Ala Asn Asn Gln Arg Pro Ser
1               5

<210> SEQ ID NO 122
<211> LENGTH: 12
```

```
<212> TYPE: PRT
<213> ORGANISM: Artificial Sequence
<220> FEATURE:
<223> OTHER INFORMATION: Antibody clone 5G08: CDRL3

<400> SEQUENCE: 122

Ala Ala Trp Asp Asp Ser Leu Asn Gly Pro Trp Val
1               5                   10

<210> SEQ ID NO 123
<211> LENGTH: 5
<212> TYPE: PRT
<213> ORGANISM: Artificial Sequence
<220> FEATURE:
<223> OTHER INFORMATION: Antibody clone 5H06: CDRH1

<400> SEQUENCE: 123

Ser Tyr Gly Met His
1               5

<210> SEQ ID NO 124
<211> LENGTH: 17
<212> TYPE: PRT
<213> ORGANISM: Artificial Sequence
<220> FEATURE:
<223> OTHER INFORMATION: Antibody clone 5H06: CDRH2

<400> SEQUENCE: 124

Val Ile Ser Tyr Asp Gly Ser Asp Thr Ala Tyr Ala Asp Ser Val Lys
1               5                   10                  15

Gly

<210> SEQ ID NO 125
<211> LENGTH: 10
<212> TYPE: PRT
<213> ORGANISM: Artificial Sequence
<220> FEATURE:
<223> OTHER INFORMATION: Antibody clone 5H06: CDRH3

<400> SEQUENCE: 125

Asp His Ser Val Ile Gly Ala Phe Asp Ile
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Antibody clone 5H06: CDRL1

<400> SEQUENCE: 126

Ser Gly Ser Ser Ser Asn Ile Gly Ser Asn Thr Val Asn
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Antibody clone 5H06: CDRL2

<400> SEQUENCE: 127

Asp Asn Asn Lys Arg Pro Ser
1               5

<210> SEQ ID NO 128
```

```
<211> LENGTH: 10
<212> TYPE: PRT
<213> ORGANISM: Artificial Sequence
<220> FEATURE:
<223> OTHER INFORMATION: Antibody clone 5H06: CDRL3

<400> SEQUENCE: 128

Ser Ser Tyr Ala Gly Ser Asn Asn Val Val
1               5                   10

<210> SEQ ID NO 129
<211> LENGTH: 5
<212> TYPE: PRT
<213> ORGANISM: Artificial Sequence
<220> FEATURE:
<223> OTHER INFORMATION: Antibody clone 6A09: CDRH1

<400> SEQUENCE: 129

Ser Tyr Gly Met His
1               5

<210> SEQ ID NO 130
<211> LENGTH: 17
<212> TYPE: PRT
<213> ORGANISM: Artificial Sequence
<220> FEATURE:
<223> OTHER INFORMATION: Antibody clone 6A09: CDRH2

<400> SEQUENCE: 130

Val Thr Ser Tyr Asp Gly Asn Thr Lys Tyr Tyr Ala Asn Ser Val Lys
1               5                   10                  15
Gly

<210> SEQ ID NO 131
<211> LENGTH: 10
<212> TYPE: PRT
<213> ORGANISM: Artificial Sequence
<220> FEATURE:
<223> OTHER INFORMATION: Antibody clone 6A09: CDRH3

<400> SEQUENCE: 131

Glu Asp Cys Gly Gly Asp Cys Phe Asp Tyr
1               5                   10

<210> SEQ ID NO 132
<211> LENGTH: 14
<212> TYPE: PRT
<213> ORGANISM: Artificial Sequence
<220> FEATURE:
<223> OTHER INFORMATION: Antibody clone 6A09: CDRL1

<400> SEQUENCE: 132

Thr Gly Ser Ser Ser Asn Ile Gly Ala Gly Tyr Asp Val His
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Antibody clone 6A09: CDRL2

<400> SEQUENCE: 133

Gly Asn Ser Asn Arg Pro Ser
1               5
```

```
<210> SEQ ID NO 134
<211> LENGTH: 11
<212> TYPE: PRT
<213> ORGANISM: Artificial Sequence
<220> FEATURE:
<223> OTHER INFORMATION: Antibody clone 6A09: CDRL3

<400> SEQUENCE: 134

Ala Ala Trp Asp Asp Ser Leu Asn Glu Gly Val
1               5                   10

<210> SEQ ID NO 135
<211> LENGTH: 5
<212> TYPE: PRT
<213> ORGANISM: Artificial Sequence
<220> FEATURE:
<223> OTHER INFORMATION: Antibody clone 6B01: CDRH1

<400> SEQUENCE: 135

Asn Tyr Gly Met His
1               5

<210> SEQ ID NO 136
<211> LENGTH: 17
<212> TYPE: PRT
<213> ORGANISM: Artificial Sequence
<220> FEATURE:
<223> OTHER INFORMATION: Antibody clone 6B01: CDRH2

<400> SEQUENCE: 136

Val Ile Ser Tyr Asp Gly Ser Asn Lys Tyr Tyr Ala Asp Ser Val Lys
1               5                   10                  15

Gly

<210> SEQ ID NO 137
<211> LENGTH: 9
<212> TYPE: PRT
<213> ORGANISM: Artificial Sequence
<220> FEATURE:
<223> OTHER INFORMATION: Antibody clone 6B01: CDRH3

<400> SEQUENCE: 137

Asp Gln Leu Gly Glu Ala Phe Asp Ile
1               5

<210> SEQ ID NO 138
<211> LENGTH: 14
<212> TYPE: PRT
<213> ORGANISM: Artificial Sequence
<220> FEATURE:
<223> OTHER INFORMATION: Antibody clone 6B01: CDRL1

<400> SEQUENCE: 138

Thr Gly Ser Ser Ser Asn Ile Gly Ala Gly Tyr Asp Val His
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Antibody clone 6B01: CDRL2

<400> SEQUENCE: 139

Asp Asn Asn Lys Arg Pro Ser
1               5
```

```
<210> SEQ ID NO 140
<211> LENGTH: 11
<212> TYPE: PRT
<213> ORGANISM: Artificial Sequence
<220> FEATURE:
<223> OTHER INFORMATION: Antibody clone 6B01: CDRL3

<400> SEQUENCE: 140

Ala Thr Trp Asp Asp Ser Leu Ser Gly Pro Val
1               5                   10

<210> SEQ ID NO 141
<211> LENGTH: 5
<212> TYPE: PRT
<213> ORGANISM: Artificial Sequence
<220> FEATURE:
<223> OTHER INFORMATION: Antibody clone 6C11: CDRH1

<400> SEQUENCE: 141

Asp Tyr Gly Met Ser
1               5

<210> SEQ ID NO 142
<211> LENGTH: 17
<212> TYPE: PRT
<213> ORGANISM: Artificial Sequence
<220> FEATURE:
<223> OTHER INFORMATION: Antibody clone 6C11: CDRH2

<400> SEQUENCE: 142

Ala Ile Ser Gly Ser Gly Ser Ser Thr Tyr Tyr Ala Asp Ser Val Lys
1               5                   10                  15

Gly

<210> SEQ ID NO 143
<211> LENGTH: 8
<212> TYPE: PRT
<213> ORGANISM: Artificial Sequence
<220> FEATURE:
<223> OTHER INFORMATION: Antibody clone 6C11: CDRH3

<400> SEQUENCE: 143

Gly Asp Ile Asp Tyr Phe Asp Tyr
1               5

<210> SEQ ID NO 144
<211> LENGTH: 14
<212> TYPE: PRT
<213> ORGANISM: Artificial Sequence
<220> FEATURE:
<223> OTHER INFORMATION: Antibody clone 6C11: CDRL1

<400> SEQUENCE: 144

Thr Gly Ser Ser Ser Asn Phe Gly Ala Gly Tyr Asp Val His
1               5                   10

<210> SEQ ID NO 145
<211> LENGTH: 7
<212> TYPE: PRT
<213> ORGANISM: Artificial Sequence
<220> FEATURE:
<223> OTHER INFORMATION: Antibody clone 6C11: CDRL3

<400> SEQUENCE: 145

Glu Asn Asn Lys Arg Pro Ser
1               5
```

<210> SEQ ID NO 146
<211> LENGTH: 11
<212> TYPE: PRT
<213> ORGANISM: Artificial Sequence
<220> FEATURE:
<223> OTHER INFORMATION: Antibody clone 6C11: CDRL3

<400> SEQUENCE: 146

Ala Ala Trp Asp Asp Ser Leu Asn Gly Pro Val
1               5                   10

<210> SEQ ID NO 147
<211> LENGTH: 5
<212> TYPE: PRT
<213> ORGANISM: Artificial Sequence
<220> FEATURE:
<223> OTHER INFORMATION: Antibody clone 6C12: CDRH1

<400> SEQUENCE: 147

Ser Tyr Gly Met His
1               5

<210> SEQ ID NO 148
<211> LENGTH: 17
<212> TYPE: PRT
<213> ORGANISM: Artificial Sequence
<220> FEATURE:
<223> OTHER INFORMATION: Antibody clone 6C12: CDRH2

<400> SEQUENCE: 148

Val Ile Ser Tyr Asp Gly Ser Asn Lys Tyr Tyr Ala Asp Ser Val Lys
1               5                   10                  15

Gly

<210> SEQ ID NO 149
<211> LENGTH: 8
<212> TYPE: PRT
<213> ORGANISM: Artificial Sequence
<220> FEATURE:
<223> OTHER INFORMATION: Antibody clone 6C12: CDRH3

<400> SEQUENCE: 149

Glu Arg Arg Asp Ala Phe Asp Ile
1               5

<210> SEQ ID NO 150
<211> LENGTH: 14
<212> TYPE: PRT
<213> ORGANISM: Artificial Sequence
<220> FEATURE:
<223> OTHER INFORMATION: Antibody clone 6C12: CDRL1

<400> SEQUENCE: 150

Thr Gly Ser Ser Ser Asn Ile Gly Ala Gly Tyr Asp Val His
1               5                   10

<210> SEQ ID NO 151
<211> LENGTH: 7
<212> TYPE: PRT
<213> ORGANISM: Artificial Sequence
<220> FEATURE:
<223> OTHER INFORMATION: Antibody clone 6C12: CDRL2

<400> SEQUENCE: 151

Ser Asp Asn Gln Arg Pro Ser

<210> SEQ ID NO 152
<211> LENGTH: 9
<212> TYPE: PRT
<213> ORGANISM: Artificial Sequence
<220> FEATURE:
<223> OTHER INFORMATION: Antibody clone 6C12: CDRL3

<400> SEQUENCE: 152

Ala Thr Trp Asp Ser Asp Thr Pro Val
1               5

<210> SEQ ID NO 153
<211> LENGTH: 5
<212> TYPE: PRT
<213> ORGANISM: Artificial Sequence
<220> FEATURE:
<223> OTHER INFORMATION: Antibody clone 6D01: CDRH1

<400> SEQUENCE: 153

Ser Tyr Gly Met His
1               5

<210> SEQ ID NO 154
<211> LENGTH: 17
<212> TYPE: PRT
<213> ORGANISM: Artificial Sequence
<220> FEATURE:
<223> OTHER INFORMATION: Antibody clone 6D01: CDRH2

<400> SEQUENCE: 154

Val Ile Ser Tyr Asp Gly Ser Asn Lys Tyr Tyr Ala Asp Ser Val Lys
1               5                   10                  15
Gly

<210> SEQ ID NO 155
<211> LENGTH: 10
<212> TYPE: PRT
<213> ORGANISM: Artificial Sequence
<220> FEATURE:
<223> OTHER INFORMATION: Antibody clone 6D01: CDRH3

<400> SEQUENCE: 155

Asp His Ser Ala Ala Gly Tyr Phe Asp Tyr
1               5                   10

<210> SEQ ID NO 156
<211> LENGTH: 13
<212> TYPE: PRT
<213> ORGANISM: Artificial Sequence
<220> FEATURE:
<223> OTHER INFORMATION: Antibody clone 6D01: CDRL1

<400> SEQUENCE: 156

Ser Gly Ser Ser Ser Asn Ile Gly Ser Asn Thr Val Asn
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Antibody clone 6D01: CDRL2

<400> SEQUENCE: 157

Gly Asn Ser Ile Arg Pro Ser
1               5

<210> SEQ ID NO 158
<211> LENGTH: 11
<212> TYPE: PRT
<213> ORGANISM: Artificial Sequence
<220> FEATURE:
<223> OTHER INFORMATION: Antibody clone 6D01: CDRL3

<400> SEQUENCE: 158

Ala Ser Trp Asp Asp Ser Leu Ser Ser Pro Val
1               5                   10

<210> SEQ ID NO 159
<211> LENGTH: 5
<212> TYPE: PRT
<213> ORGANISM: Artificial Sequence
<220> FEATURE:
<223> OTHER INFORMATION: Antibody clone 6G03: CDRH1

<400> SEQUENCE: 159

Ser Tyr Gly Met His
1               5

<210> SEQ ID NO 160
<211> LENGTH: 17
<212> TYPE: PRT
<213> ORGANISM: Artificial Sequence
<220> FEATURE:
<223> OTHER INFORMATION: Antibody clone 6G03: CDRH2

<400> SEQUENCE: 160

Gly Ile Ser Trp Asp Ser Ala Ile Ile Asp Tyr Ala Gly Ser Val Lys
1               5                   10                  15

Gly

<210> SEQ ID NO 161
<211> LENGTH: 10
<212> TYPE: PRT
<213> ORGANISM: Artificial Sequence
<220> FEATURE:
<223> OTHER INFORMATION: Antibody clone 6G03: CDRH3

<400> SEQUENCE: 161

Asp Glu Ala Ala Ala Gly Ala Phe Asp Ile
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Antibody clone 6G03: CDRL1

<400> SEQUENCE: 162

Thr Gly Ser Ser Ser Asn Ile Gly Ala Gly Tyr Asp Val His
1               5                   10

<210> SEQ ID NO 163
<211> LENGTH: 7
<212> TYPE: PRT
<213> ORGANISM: Artificial Sequence
<220> FEATURE:
<223> OTHER INFORMATION: Antibody clone 6G03: CDRL2

<400> SEQUENCE: 163

```
Gly Asn Thr Asp Arg Pro Ser
1               5
```

<210> SEQ ID NO 164
<211> LENGTH: 12
<212> TYPE: PRT
<213> ORGANISM: Artificial Sequence
<220> FEATURE:
<223> OTHER INFORMATION: Antibody clone 6G03: CDRL3

<400> SEQUENCE: 164

```
Ala Ala Trp Asp Asp Ser Leu Ser Gly Pro Val Val
1               5                   10
```

<210> SEQ ID NO 165
<211> LENGTH: 5
<212> TYPE: PRT
<213> ORGANISM: Artificial Sequence
<220> FEATURE:
<223> OTHER INFORMATION: Antibody clone 6G08: CDRH1

<400> SEQUENCE: 165

```
Ser Tyr Gly Ile Ser
1               5
```

<210> SEQ ID NO 166
<211> LENGTH: 17
<212> TYPE: PRT
<213> ORGANISM: Artificial Sequence
<220> FEATURE:
<223> OTHER INFORMATION: Antibody clone 6G08: CDRH2

<400> SEQUENCE: 166

```
Gly Ile Ser Gly Ser Gly Gly Asn Thr Tyr Tyr Ala Asp Ser Val Lys
1               5                   10                  15

Gly
```

<210> SEQ ID NO 167
<211> LENGTH: 12
<212> TYPE: PRT
<213> ORGANISM: Artificial Sequence
<220> FEATURE:
<223> OTHER INFORMATION: Antibody clone 6G08: CDRH3

<400> SEQUENCE: 167

```
Ser Val Gly Ala Tyr Ala Asn Asp Ala Phe Asp Ile
1               5                   10
```

<210> SEQ ID NO 168
<211> LENGTH: 14
<212> TYPE: PRT
<213> ORGANISM: Artificial Sequence
<220> FEATURE:
<223> OTHER INFORMATION: Antibody clone 6G08: CDRL1

<400> SEQUENCE: 168

```
Thr Gly Ser Ser Ser Asn Ile Gly Ala Gly Tyr Asp Val His
1               5                   10
```

<210> SEQ ID NO 169
<211> LENGTH: 7
<212> TYPE: PRT
<213> ORGANISM: Artificial Sequence
<220> FEATURE:
<223> OTHER INFORMATION: Antibody clone 6G08: CDRL2

```
<400> SEQUENCE: 169

Gly Asp Thr Asn Arg Pro Ser
1               5

<210> SEQ ID NO 170
<211> LENGTH: 11
<212> TYPE: PRT
<213> ORGANISM: Artificial Sequence
<220> FEATURE:
<223> OTHER INFORMATION: Antibody clone 6G08: CDRL3

<400> SEQUENCE: 170

Ala Ala Trp Asp Asp Ser Leu Asn Gly Pro Val
1               5                   10

<210> SEQ ID NO 171
<211> LENGTH: 5
<212> TYPE: PRT
<213> ORGANISM: Artificial Sequence
<220> FEATURE:
<223> OTHER INFORMATION: Antibody clone 6G11: CDRH1

<400> SEQUENCE: 171

Ser Tyr Gly Met His
1               5

<210> SEQ ID NO 172
<211> LENGTH: 17
<212> TYPE: PRT
<213> ORGANISM: Artificial Sequence
<220> FEATURE:
<223> OTHER INFORMATION: Antibody clone 6G11: CDRH2

<400> SEQUENCE: 172

Val Ile Ser Tyr Asp Gly Ser Asn Lys Tyr Tyr Ala Asp Ser Val Lys
1               5                   10                  15

Gly

<210> SEQ ID NO 173
<211> LENGTH: 8
<212> TYPE: PRT
<213> ORGANISM: Artificial Sequence
<220> FEATURE:
<223> OTHER INFORMATION: Antibody clone 6G11: CDRH3

<400> SEQUENCE: 173

Glu Leu Tyr Asp Ala Phe Asp Ile
1               5

<210> SEQ ID NO 174
<211> LENGTH: 14
<212> TYPE: PRT
<213> ORGANISM: Artificial Sequence
<220> FEATURE:
<223> OTHER INFORMATION: Antibody clone 6G11: CDRL1

<400> SEQUENCE: 174

Thr Gly Ser Ser Ser Asn Ile Gly Ala Gly Tyr Asp Val His
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Antibody clone 6G11: CDRL2
```

<400> SEQUENCE: 175

Ala Asp Asp His Arg Pro Ser
1               5

<210> SEQ ID NO 176
<211> LENGTH: 11
<212> TYPE: PRT
<213> ORGANISM: Artificial Sequence
<220> FEATURE:
<223> OTHER INFORMATION: Antibody clone 6G11: CDRL3

<400> SEQUENCE: 176

Ala Ser Trp Asp Asp Ser Gln Arg Ala Val Ile
1               5                   10

<210> SEQ ID NO 177
<211> LENGTH: 5
<212> TYPE: PRT
<213> ORGANISM: Artificial Sequence
<220> FEATURE:
<223> OTHER INFORMATION: Antibody clone 6H08: CDRH1

<400> SEQUENCE: 177

Asn Tyr Gly Met His
1               5

<210> SEQ ID NO 178
<211> LENGTH: 17
<212> TYPE: PRT
<213> ORGANISM: Artificial Sequence
<220> FEATURE:
<223> OTHER INFORMATION: Antibody clone 6H08: CDRH2

<400> SEQUENCE: 178

Val Ile Ser Tyr Asp Gly Ser Asn Lys Tyr Tyr Ala Asp Ser Val Lys
1               5                   10                  15
Gly

<210> SEQ ID NO 179
<211> LENGTH: 8
<212> TYPE: PRT
<213> ORGANISM: Artificial Sequence
<220> FEATURE:
<223> OTHER INFORMATION: Antibody clone 6H08: CDRH3

<400> SEQUENCE: 179

Glu Tyr Lys Asp Ala Phe Asp Ile
1               5

<210> SEQ ID NO 180
<211> LENGTH: 13
<212> TYPE: PRT
<213> ORGANISM: Artificial Sequence
<220> FEATURE:
<223> OTHER INFORMATION: Antibody clone 6H08: CDRL1

<400> SEQUENCE: 180

Thr Gly Ser Ser Ser Asn Ile Gly Ser Asn Thr Val Asn
1               5                   10

<210> SEQ ID NO 181
<211> LENGTH: 7
<212> TYPE: PRT
<213> ORGANISM: Artificial Sequence
<220> FEATURE:

```
<223> OTHER INFORMATION: Antibody clone 6H08: CDRL2

<400> SEQUENCE: 181

Asp Asn Asn Lys Arg Pro Ser
1               5

<210> SEQ ID NO 182
<211> LENGTH: 9
<212> TYPE: PRT
<213> ORGANISM: Artificial Sequence
<220> FEATURE:
<223> OTHER INFORMATION: Antibody clone 6H08: CDRL3

<400> SEQUENCE: 182

Gln Ala Trp Gly Thr Gly Ile Arg Val
1               5

<210> SEQ ID NO 183
<211> LENGTH: 5
<212> TYPE: PRT
<213> ORGANISM: Artificial Sequence
<220> FEATURE:
<223> OTHER INFORMATION: Antibody clone 7C07: CDRH1

<400> SEQUENCE: 183

Ser Tyr Gly Met His
1               5

<210> SEQ ID NO 184
<211> LENGTH: 17
<212> TYPE: PRT
<213> ORGANISM: Artificial Sequence
<220> FEATURE:
<223> OTHER INFORMATION: Antibody clone 7C07: CDRH2

<400> SEQUENCE: 184

Val Ile Ser Tyr Asp Gly Ser Asn Lys Tyr Tyr Ala Asp Ser Val Lys
1               5                   10                  15

Gly

<210> SEQ ID NO 185
<211> LENGTH: 9
<212> TYPE: PRT
<213> ORGANISM: Artificial Sequence
<220> FEATURE:
<223> OTHER INFORMATION: Antibody clone 7C07: CDRH3

<400> SEQUENCE: 185

Glu Phe Gly Tyr Ile Ile Leu Asp Tyr
1               5

<210> SEQ ID NO 186
<211> LENGTH: 13
<212> TYPE: PRT
<213> ORGANISM: Artificial Sequence
<220> FEATURE:
<223> OTHER INFORMATION: Antibody clone 7C07: CDRL1

<400> SEQUENCE: 186

Ser Gly Ser Ser Ser Asn Ile Gly Ser Asn Thr Val Asn
1               5                   10

<210> SEQ ID NO 187
<211> LENGTH: 7
<212> TYPE: PRT
<213> ORGANISM: Artificial Sequence
```

```
<220> FEATURE:
<223> OTHER INFORMATION: Antibody clone 7C07: CDRL2

<400> SEQUENCE: 187

Arg Asp Tyr Glu Arg Pro Ser
1               5

<210> SEQ ID NO 188
<211> LENGTH: 11
<212> TYPE: PRT
<213> ORGANISM: Artificial Sequence
<220> FEATURE:
<223> OTHER INFORMATION: Antibody clone 7C07: CDRL1

<400> SEQUENCE: 188

Met Ala Trp Asp Asp Ser Leu Ser Gly Val Val
1               5                   10

<210> SEQ ID NO 189
<211> LENGTH: 5
<212> TYPE: PRT
<213> ORGANISM: Artificial Sequence
<220> FEATURE:
<223> OTHER INFORMATION: Antibody clone 4B02: CDRH1

<400> SEQUENCE: 189

Asn His Gly Met His
1               5

<210> SEQ ID NO 190
<211> LENGTH: 17
<212> TYPE: PRT
<213> ORGANISM: Artificial Sequence
<220> FEATURE:
<223> OTHER INFORMATION: Antibody clone 4B02: CDRH2

<400> SEQUENCE: 190

Val Ile Ser Tyr Asp Gly Thr Asn Lys Tyr Tyr Ala Asp Ser Val Arg
1               5                   10                  15

Gly

<210> SEQ ID NO 191
<211> LENGTH: 8
<212> TYPE: PRT
<213> ORGANISM: Artificial Sequence
<220> FEATURE:
<223> OTHER INFORMATION: Antibody clone 4B02: CDRH3

<400> SEQUENCE: 191

Glu Thr Trp Asp Ala Phe Asp Val
1               5

<210> SEQ ID NO 192
<211> LENGTH: 13
<212> TYPE: PRT
<213> ORGANISM: Artificial Sequence
<220> FEATURE:
<223> OTHER INFORMATION: Antibody clone 4B02: CDRL1

<400> SEQUENCE: 192

Ser Gly Ser Ser Ser Asn Ile Gly Ser Asn Asn Ala Asn
1               5                   10

<210> SEQ ID NO 193
<211> LENGTH: 7
<212> TYPE: PRT
```

```
<213> ORGANISM: Artificial Sequence
<220> FEATURE:
<223> OTHER INFORMATION: Antibody clone 4B02: CDRL2

<400> SEQUENCE: 193

Asp Asn Asn Lys Arg Pro Ser
1               5

<210> SEQ ID NO 194
<211> LENGTH: 9
<212> TYPE: PRT
<213> ORGANISM: Artificial Sequence
<220> FEATURE:
<223> OTHER INFORMATION: Antibody clone 4B02: CDRL3

<400> SEQUENCE: 194

Gln Ala Trp Asp Ser Ser Thr Val Val
1               5

<210> SEQ ID NO 195
<211> LENGTH: 183
<212> TYPE: PRT
<213> ORGANISM: Homo sapiens
<220> FEATURE:
<223> OTHER INFORMATION: Human FCGAMMARIIA protein sequence (ACCESSION:
      P12318) - amino acids 37-219

<400> SEQUENCE: 195

Ala Pro Pro Lys Ala Val Leu Lys Leu Glu Pro Pro Trp Ile Asn Val
1               5                   10                  15

Leu Gln Glu Asp Ser Val Thr Leu Thr Cys Gln Gly Ala Arg Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Met Leu Arg Cys His Ser Trp Lys Asp
            100                 105                 110

Lys Pro Leu Val Lys Val Thr Phe Phe Gln Asn Gly Lys Ser Gln Lys
        115                 120                 125

Phe Ser His Leu Asp Pro Thr Phe Ser Ile Pro Gln Ala Asn His Ser
    130                 135                 140

His Ser Gly Asp Tyr His Cys Thr Gly Asn Ile Gly Tyr Thr Leu Phe
145                 150                 155                 160

Ser Ser Lys Pro Val Thr Ile Thr Val Gln Val Pro Ser Met Gly Ser
                165                 170                 175

Ser Ser Pro Met Gly Ile Ile
            180

<210> SEQ ID NO 196
<211> LENGTH: 180
<212> TYPE: PRT
<213> ORGANISM: Homo sapiens
<220> FEATURE:
<223> OTHER INFORMATION: Human FCGAMMARIIB protein sequence (ACCESSION:
      P31994) - amino acids 46-225

<400> SEQUENCE: 196
```

```
Ala Pro Pro Lys Ala Val Leu Lys Leu Glu Pro Gln Trp Ile Asn Val
1               5                   10                  15

Leu Gln Glu Asp Ser Val Thr Leu Thr Cys Arg Gly Thr His Ser Pro
                20                  25                  30

Glu Ser Asp Ser Ile Gln Trp Phe His Asn Gly Asn Leu Ile Pro Thr
            35                  40                  45

His Thr Gln Pro Ser Tyr Arg Phe Lys Ala Asn Asn Asn Asp Ser Gly
        50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
            115                 120                 125

Phe Ser Arg Ser Asp Pro Asn Phe Ser Ile Pro Gln Ala Asn His Ser
        130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln Ala Pro Ser Ser Ser Pro
                165                 170                 175

Met Gly Ile Ile
            180
```

MEDICAMENTS, USES AND METHODS

CROSS-REFERENCE TO RELATED APPLICATIONS

This application is the U.S. National Stage of International Application No. PCT/EP2015/060744, filed May 15, 2015, which claims the benefit of and priority to Great Britain Patent Application No. 1408673.0, filed May 15, 2014, the contents of each of which are incorporated by reference in their entireties for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 89,176 byte ASCII (text) file named "Seq_List" created on Nov. 2, 2016.

The present invention relates to a composition comprising an antibody molecule and an agent for use in the treatment of refractory cancer and/or relapsed cancer. The invention also relates to a method of treating refractory cancer and/or relapsed cancer comprising administering an antibody molecule and an agent. There are also described kits comprising the antibody molecule and agents.

Therapeutic antibodies have transformed cancer therapy, unlocking new mechanisms of action by engaging the immune system. For example, a mechanism by which antibodies can exert therapeutic effects is by stimulating the removal of cancer and other unwanted cells through recruiting natural effector systems such as cytotoxic cells (e.g. macrophages) and enzymes (e.g. complement) which then target the cell to which the antibody molecule is bound.

The CD20 specific monoclonal antibody (mAb) rituximab was the first antibody to be approved for cancer immunotherapy, and as such has been widely administered to patients with CD20 expressing B cell cancers including follicular lymphoma (FL), diffuse large cell B cell lymphoma (DLBCL), chronic lymphocytic leukaemia (CLL), and mantle cell lymphoma (MCL) (reviewed in Lim, S. H., et al., Anti-CD20 monoclonal antibodies: historical and future perspectives. Haematologica 95, 135-143 (2010).

Although antibody therapies are effective, in some cases a patient will acquire a resistance to the antibody therapy, which will lead to the treatment becoming ineffective and the cancer worsening. In other cases, the cancer may not respond to the cancer therapy at all.

Unfortunately, effective therapeutic antibody treatments are still lacking for relapsed cancers and/or refractory cancers. With an increasing number of antibody therapies being developed for treatment of several types of cancer, there is an emerging need to understand cancer cell resistance to these therapies, and develop drugs to overcome such resistance.

For example, within rituximab responsive lymphomas some individuals show resistance on first treatment or become resistant to rituximab-containing combination therapy. In addition to rituximab, lymphomas can also display resistance to other antibody therapies; for example, the antibody molecules ofatumumab (which binds to CD20) or alemtuzumab (which binds to CD52).

Against that background, the present inventors have surprisingly identified that a treatment comprising an antibody and an agent that prevents or reduces FcγRIIb binding to the Fc domain of the antibody molecule can be used to treat relapsed cancer and/or refractory cancer.

It has previously been shown that inhibiting the interactions between FcγRIIb and the therapeutic antibody rituximab can reduce the recycling of the antibody, and improve the efficacy of rituximab in the treatment of chronic lymphocytic leukaemia and mantle cell lymphoma (Lim, S. H., et al. Fc gamma receptor IIb on target B cells promotes rituximab internalization and reduces clinical efficacy. *Blood* (2011) and WO 2012/022985).

It is further known that activity of therapeutic antibodies is governed partially by their interaction with Fc gamma receptors (FcγR). Specifically, it is the relative expression level, affinity and activity of the FcγR which explains much of the therapeutic activity of IgG (reviewed in Nimmerjahn, F. & Ravetch, J. V. FcgammaRs in health and disease. Curr Top Microbiol Immunol 350, 105-125 (2011), and Nimmerjahn, F. & Ravetch, J. V. Fcgamma receptors as regulators of immune responses. Nature reviews 8, 34-47 (2008)).

However, the inventors of the present invention have now surprisingly demonstrated that a combination therapy comprising an antibody and an agent that prevents or reduces FcγRIIb binding to the Fc domain of the antibody molecule can be used to treat relapsed cancer and/or refractory cancer. Thus, the present invention provides methods and uses for treating a sub-group of patients that have relapsed cancer and/or refractory cancer.

In other words, the inventors of the present invention have demonstrated that a combination therapy comprising an antibody to which a cancer in a subject does not respond to (i.e. is resistant to), in combination with an agent that prevents or reduces FcγRIIb binding to the Fc domain of the antibody molecule, can be used to treat relapsed cancer and/or refractory cancer by reducing and/or overcoming the resistance of the cancer to the antibody.

In a first aspect, the invention provides a composition comprising:
(i) an antibody molecule that specifically binds a cell surface antigen of a target cell, which antibody molecule has a Fc domain capable of binding FcγRIIb; in combination with
(ii) an agent that prevents or reduces FcγRIIb binding to the Fc domain of the antibody molecule;
characterized in that the composition is for use in the treatment of relapsed cancer and/or refractory cancer in a subject, and in that the subject has target cells that express FcγRIIb.

In a second aspect, the invention provides the use of a composition comprising:
(i) an antibody molecule that specifically binds a cell surface antigen of a target cell, which antibody molecule has a Fc domain capable of binding FcγRIIb; in combination with
(ii) an agent that prevents or reduces FcγRIIb binding to the Fc domain of the antibody molecule;
characterized in that the use is in the manufacture of a medicament for use in the treatment of relapsed cancer and/or refractory cancer in a subject, and in that the subject has target cells that express FcγRIIb.

In a third aspect, the invention provides a method of treating relapsed cancer and/or refractory cancer in a subject, the method comprising administering:
(i) an antibody molecule that specifically binds a cell surface antigen of the target cell, which antibody molecule has an Fc domain capable of binding FcγRIIb; in combination with (ii) an agent that prevents or reduces FcγRIIb binding to the Fc domain of the antibody molecule.

characterized in that the subject is selected on the basis that it has relapsed cancer and/or refractory cancer, and in that the subject has target cells that express FcγRIIb.

In a fourth aspect, the invention provides a kit for use in the treatment of relapsed cancer and/or refractory cancer in a subject comprising:

(i) an antibody molecule that specifically binds a cell surface antigen of a target cell, which antibody molecule has a Fc domain capable of binding FcγRIIb;

(ii) an agent that prevents or reduces FcγRIIb binding to the Fc domain of the antibody molecule;

(iii) one or more substance selected from the group consisting of: rituximab; a rituximab biosimilar; ofatumumab; obinutuzumab; alemtuzumab; galiximab; tositumomab; radioactively conjugated tositumomab; ibritumomab; radioactively conjugated ibritumomab; an anti-CD40 antibody; an anti-CD19 antibody; an anti-CD37 antibody; a therapeutic antibody used to treat a B cell cancer;

characterized in that the use is for the treatment of relapsed cancer and/or refractory cancer in a subject, and that the subject has target cells that express FcγRIIb.

In a preferred embodiment of the fourth aspect of the invention, the one or more substance comprises or consists of: rituximab (or a rituximab biosimilar) and ofatumumab; or rituximab (or a rituximab biosimilar) and obinutuzumab.

In an alternative preferred embodiment of the fourth aspect of the invention, the one or more substance comprises or consists of: alemtuzumab and an anti-CD40 antibody; alemtuzumab and an anti-CD19 antibody; alemtuzumab and an anti-CD37 antibody; or alemtuzumab and an anti-CD40 antibody and an anti-CD19 antibody and an anti-CD37 antibody.

In an alternative preferred embodiment of the fourth aspect of the invention, the one or more substance comprises or consists of: a therapeutic antibody used to treat a B cell cancer, such as galiximab.

Antibody molecules are well known to those skilled in the art of immunology and molecular biology. An antibody molecule is a component of the humoral immune system, and is a protein that is produced by effector B cells to identify and neutralize objects foreign to the body, such as bacteria and viruses.

Typically, an antibody molecule comprises two heavy chains and two light chains. The antibody molecule heavy chain comprises one variable domain and three constant domains, and the antibody molecule light chain comprises one variable domain and one constant domain. The variable domains (sometimes collectively referred to as the $F_v$ region) bind to the antibody's target, and each variable domain comprises three loops, referred to as complementary determining regions (CDRs), which are responsible for target binding.

Accordingly, by the term "antibody molecule" we include all types and classes of antibody molecule and functional fragments thereof, including: monoclonal antibodies, or polyclonal antibodies, or synthetic antibodies, or recombinantly produced antibodies, or multi-specific antibodies, or bi-specific antibodies, or human antibodies, or humanized antibodies, or chimeric antibodies, or camelized antibodies, or single-chain Fvs (scFv), or single chain antibodies, or Fab fragments, or F(ab') fragments, or disulfide-linked Fvs (sdFv), or intrabodies, or antibody heavy chains, or antibody light chains, or homo-dimers or heterodimers of antibody heavy and/or light chains, or antigen binding functional fragments or derivatives of the same, or IgG, or IgG1, or IgG2, or IgG3, or IgG4, or IgA, or IgM, or IgD, or IgE.

It is known that an antibody molecule specifically binds a defined target molecule. That is to say, the antibody molecule preferentially and selectively binds its target and not a molecule which is a non-target.

Methods of assessing protein binding are known to the person skilled in biochemistry and immunology. It would be appreciated by the skilled person that those methods could be used to assess binding of an antibody molecule to a target and/or binding of the Fc domain of an antibody to an Fc receptor; as well as the relative strength, or the specificity, or the inhibition, or prevention, or reduction in those interactions. Examples of methods that may be used to assess protein binding are, for example, immunoassays, BIAcore, western blots, radioimmunoassay (RIA) and enzyme-linked immunosorbent assays (ELISAs) (See Fundamental Immunology Second Edition, Raven Press, New York at pages 332-336 (1989) for a discussion regarding antibody specificity).

Accordingly, by "antibody molecule that specifically binds" we include that the antibody molecule specifically binds a target but does not bind to non-target, or binds to a non-target more weakly (such as with a lower affinity) than the target.

We also include the meaning that the antibody molecule specifically binds to the target at least two-fold more strongly, or at least five-fold more strongly, or at least 10-fold more strongly, or at least 20-fold more strongly, or at least 50-fold more strongly, or at least 100-fold more strongly, or at least 200-fold more strongly, or at least 500-fold more strongly, or at least than about 1000-fold more strongly than to a non-target.

Additionally, we include the meaning that the antibody molecule specifically binds to the target if it binds to the target with a $K_d$ of at least about $10^{-1}$ $K_d$, or at least about $10^{-2}$ $K_d$, or at least about $10^{-3}$ $K_d$, or at least about $10^{-4}$ $K_d$, or at least about $10^{-5}$ $K_d$, or at least about $10^{-6}$ $K_d$, or at least about $10^{-7}$ $K_d$, or at least about $10^{-8}$ $K_d$, or at least about $10^{-9}$ $K_d$, or at least about $10^{-10}$ $K_d$, or at least about $10^{-11}$ $K_d$, or at least about $10^{-12}$ $K_d$, or at least about $10^{-13}$ $K_d$, or at least about $10^{-14}$ $K_d$, or at least about $10^{-15}$ $K_d$.

Another notable part of an antibody molecule is the Fc domain (otherwise known as the fragment crystallizable domain), which comprises two of the constant domains of each of the antibody molecule heavy chains. The Fc domain is responsible for interactions between the antibody molecule and Fc receptor.

Fc receptors are membrane proteins which are often found on the cell surface of cells of the immune system (i.e. Fc receptors are found on the target cell membrane—otherwise known as the plasma membrane or cytoplasmic membrane). The role of Fc receptors is to bind antibodies via the Fc domain, and to internalize the antibody into the cell. In the immune system, this can result in antibody-mediated phagocytosis and antibody-dependent cell-mediated cytotoxicity.

An example of an Fc receptor included in the present invention is FcγRIIb (otherwise known as CD32, CD32B, CD32B1, CD32B2, FcRII, FcγRII or FcRIIB), which is an inhibitory Fc receptor that is responsible for binding to and recycling antibodies.

Accordingly, by "Fc domain capable of binding FcγRIIb" we include that the Fc domain of the antibody molecule of the invention is capable of binding FcγRIIb and preferably that binding is at least two-fold more strongly, or at least five-fold more strongly, or at least 10-fold more strongly, or at least than about 20-fold more strongly, or at least 50-fold more strongly, or at least 100-fold more strongly, or at least 200-fold more strongly, or at least 500-fold more strongly, or at least 1000-fold more strongly than that antibody molecule binding to another protein, or peptide, or polypeptide, or Fc receptor.

The agent of the invention prevents or reduces FcγRIIb binding to the Fc domain of the antibody molecule, which prevents or reduces the internalization of the antibody molecule into the cell.

It would be readily apparent to those skilled in molecular biology what could constitute an agent of the invention, and how an agent of the invention could be identified. For example, agents of the invention could be identified by screening for agents that block stimulation or signalling of FcγRIIb, as indicated by phosphorylation of tyrosine-293 in the intracellular immunoreceptor tyrosine-based inhibitory (ITIM) motif as detected by Western blotting. For example, Raji cells may be cultured with an antibody molecule to a cell surface antigen, e.g. the anti-CD20 rituximab, in the presence or absence of the anti-FcγRIIb test agent before immunoblotting for phosphorylated FcγRIIb (WO 2012/022985).

Neubig et al (2003) Pharmacol. Rev. 55, 597-606, incorporated herein by reference, describes various classes of molecule which may be screened to identify agents that prevent or reduce FcγRIIb binding to an Fc domain of an antibody molecule.

The agent of the invention may be a small organic moiety, or a small inorganic moiety, or a peptide, or a polypeptide, or a peptidomimetic, or a nucleic acid, or a peptide nucleic acid (PNA), or an aptamer, or a lipid, or a carbohydrate, or an antibody molecule.

By "agent that prevent or reduces FcγRIIb binding", we include that the agent completely blocks the binding of FcγRIIb to the Fc domain of the antibody molecule, or partially blocks the binding of FcγRIIb to the Fc domain of the antibody molecule.

By "completely blocks", we include that there is no detectable binding between FcγRIIb and the Fc domain of the antibody molecule. By "partially blocks", we include that the detectable binding between FcγRIIb and the Fc domain of the antibody molecule is lower in the presence of the agent than the detectable binding between FcγRIIb and the Fc domain of the antibody molecule is in the absence of the agent.

The agent may prevent or reduce FcγRIIb binding by steric hindrance, and/or by binding to the antibody molecule, and/or by binding to the Fc domain, and/or binding to FcγRIIb, and/or by binding to the antibody molecule and blocking contact with FcγRIIb, and/or by binding to the Fc domain and blocking contact with FcγRIIb, and/or by binding the FcγRIIb and blocking contact with the Fc domain.

We also include that an agent reduces FcγRIIb binding to the Fc domain of the antibody molecule if in the presence of the agent the binding is less than about 90%, or less than about 80%, or less than about 70%, or about less than about 60%, or less than about 50%, or less than about 40%, or less than about 30%, or less than about 20%, or less than about 10%, or less than about 5%, or less than about 1% that of the FcγRIIb binding to the Fc domain of the antibody molecule in the absence of the agent.

We further include that an agent reduces FcγRIIb binding to the Fc domain of the antibody molecule if in the presence of the agent the binding is at least two-fold more weakly, or at least five-fold more weakly, or at least 10-fold more weakly, or at least 20-fold more weakly, or at least 50-fold more weakly, or at least 100-fold more weakly, or at least 200-fold more weakly, or at least 500-fold more weakly, or at least 1000-fold more weakly that of the FcγRIIb binding to the Fc domain of the antibody molecule in the absence of the agent.

We include that an agent prevents FcγRIIb binding to the Fc domain of the antibody molecule if in the presence of the agent the binding is not detectable, or if binding is detectable then the detectable binding is negligible.

An example of an antibody molecule target which is included in the invention is a cell surface antigen, which would be an epitope (otherwise known in this context as a cell surface epitope) for the antibody molecule. Cell surface antigen and epitope are terms that would be readily understood by one skilled in immunology or cell biology.

By "cell surface antigen", we include that the cell surface antigen is exposed on the extracellular side of the cell membrane, but may only be transiently exposed on the extracellular side of the cell membrane. By "transiently exposed", we include that the cell surface antigen may be internalized into the cell, or released from the extracellular side of the cell membrane into the extracellular space. The cell surface antigen may be released from the extracellular side of the cell membrane by cleavage, which may be mediated by a protease.

We also include that the cell surface antigen may be connected to the cell membrane, but may only be transiently associated with the cell membrane. By "transiently associated", we include that the cell surface antigen may be released from the extracellular side of the cell membrane into the extracellular space. The cell surface antigen may be released from the extracellular side of the cell membrane by cleavage, which may be mediated by a protease.

We further include that the cell surface antigen may be a peptide, or a polypeptide, or a carbohydrate, or an oligosaccharide chain, or a lipid; and/or an epitope that is present on a protein, or a glycoprotein, or a lipoprotein.

The disease to be treated by the present invention is relapsed cancer and/or refractory cancer.

A relapsed cancer is a cancer that has previously been treated and, as a result of that treatment, the subject made a complete or partial recovery (i.e. the subject is said to be in remission), but that after the cessation of the treatment the cancer returned or worsened. Put another way, a relapsed cancer is one that has become resistant to a treatment, after a period in which it was effective and the subject made a complete or partial recovery.

It will be appreciated that a cancer may be a relapsed cancer, or a relapsed cancer and a refractory cancer, due to an acquired resistance. By "acquired resistance", we include that the cancer and/or the subject and/or the target cell was not resistant to a particular treatment prior to the first time it was administered, but became resistant after or during at least the first time it was administered—for example: after the second time; after the third time; after the fourth time; after the fifth time; after the sixth time; after the seventh time; after the eighth time; after the ninth time; after the tenth time; after the eleventh time; after the twelfth time the treatment was administered.

Within the context of the present invention, it is preferred that the relapsed cancer has previously been treated with an antibody, and has become resistant to that antibody. As discussed herein, the present invention provides a means for treating a sub-group of patients that have such a relapsed cancer—that is, the invention provides a means for treating a subject having a relapsed cancer which is resistant to treatment with an antibody.

Within the context of the present invention, it is further preferred that the relapsed cancer has previously been treated with an antibody molecule as defined herein, and has become resistant to that antibody molecule. As discussed herein, the present invention provides a means for treating a sub-group of patients that have such a relapsed cancer—that is, the invention provides a means for treating a subject having a relapsed cancer which is resistant to an antibody molecule as defined herein.

It will be appreciated that the present invention therefore provides a means for treating a cancer in a subject using the same antibody molecule to which the cancer has become resistant.

A refractory cancer is a cancer that has been treated but which has not responded to that treatment, and/or has been treated but which has progressed during treatment. Put another way, a refractory cancer is one that is resistant to a treatment.

It will be appreciated that a cancer may be a refractory cancer due to an intrinsic resistance. By "intrinsic resistance", we include the meaning that the cancer and/or the subject and/or the target cell is resistant to a particular treatment from the first time at which it is administered.

Within the context of the present invention, it is preferred that the refractory cancer has previously been treated with an antibody but was resistant to that antibody. As discussed herein, the present invention provides a means for treating a sub-group of patients that have such a refractory cancer—that is, the invention provides a means for treating a subject having a refractory cancer which is resistant to treatment with an antibody.

Within the context of the present invention, it is further preferred that the refractory cancer has previously been treated with an antibody molecule as defined herein, but was resistant to that antibody molecule. As discussed herein, the present invention provides a means for treating a sub-group of patients that have such a refractory cancer—that is, the invention provides a means for treating a subject having a refractory cancer which is resistant to an antibody molecule as defined herein.

It will be appreciated that the present invention therefore provides a means for treating a cancer in a subject using the same antibody molecule to which the cancer is resistant.

A relapsed cancer and/or refractory cancer would be readily diagnosed by one skilled in the art of medicine, and is discussed further herein.

The inventors have now unexpectedly shown that treatment with an antibody molecule and an agent that blocks FcγRIIB binding to the antibody molecule can be used to treat relapsed cancer and/or refractory cancer. As demonstrated in the accompanying Examples, the antibody molecule and agent of the invention are particularly effective for the treatment of refractory chronic lymphocytic leukaemia and/or relapsed chronic lymphocytic leukaemia.

The inventors believe that treatment with the antibody molecule and agent of the invention functions because FcγRIIB reduces the effectiveness of therapeutic antibody molecules in treating relapsed cancer and/or refractory cancer by internalizing those antibody molecules. In light of their findings, the inventors believe that such antibody molecules and agents of the invention will be effective in treating any relapsed cancer and/or refractory cancer that can treated by a therapeutic antibody molecule and for which the target cells of the subject express FcγRIIB.

It is appreciated that a number of B cell cancers express FcγRIIB, albeit at different levels. FcγRIIB expression is most pronounced in chronic lymphocytic leukaemia and mantle cell lymphomas, moderately so in diffuse large B cell lymphoma and least pronounced in follicular lymphomas. However, in some cases subjects with cancers that generally express low levels of FcγRIIB (e.g. follicular lymphomas) may have very high levels of FcγRIIB expression. The expression level of FcγRIIB in different types of B cell cancer (and, in particular, those mentioned above) correlates with rate of internalization of the antibody molecule Rituximab. Therefore, the expression of FcγRIIB and the associated internalization of antibody molecules is believed to be a common mechanism that is shared by B cell cancers (Lim et al., 2011). The FcγRIIB-dependent initialization of an antibody molecule can be blocked by herein disclosed antibodies to FcγRIIB (Examples, particularly FIG. 3).

Accordingly, the antibody molecule and agent of the invention may be used in treating B cell cancers, and, in particular, relapsed mantle cell lymphoma and/or refractory mantle cell lymphoma, and/or relapsed follicular lymphoma and/or refractory follicular lymphoma, and/or relapsed diffuse large B cell lymphoma and/or refractory diffuse large B cell lymphoma.

For the invention to treat a subject with relapsed cancer and/or refractory cancer, the subject should have target cells that express FcγRIIb. It will be appreciated that FcγRIIb is a cell surface receptor, and will therefore be present on the surface of the target cells. It would be understood by the skilled person that different biological markers could be used to assess the presence of FcγRIIb; for example, FcγRIIb protein and/or FcγRIIb mRNA.

The skilled person would appreciate that there are methods known in the art for measuring FcγRIIb protein; for example, immunohistochemistry, western blotting, Bradford protein assays, flow cytometry and detection using the AT-10 antibody. The skilled person would appreciate that there are methods known in the art for measuring FcγRIIb mRNA; for example, northern blotting, RNA sequencing, quantitative PCR, and microarray hybridization.

The skilled person would appreciate that in order to assess the presence of FcγRIIb it may be necessary to compare the level of the FcγRIIb biological marker in the target cell with the level of an FcγRIIb biological marker in a control cell which does not express FcγRIIb. That control cell could be a control cell from an individual which does not express FcγRIIb, or a control cell which does not express FcγRIIb from an individual, or a control cell which does not express FcγRIIb from the subject, or a cell that has been genetically engineered not to express FcγRIIb.

By "target cells that express FcγRIIb", we include that the target cell express FcγRIIb protein and/or FcγRIIb mRNA. We also include that the target cell could be defined as expressing FcγRIIb if the FcγRIIb protein and/or the FcγRIIb mRNA is more than two-fold higher, or more than five-fold higher, or more than 10-fold higher, or more than 20-fold higher, or more than 50-fold higher, or more than 100-fold higher, or more than 200-fold higher, or more than 500-fold higher, or more than 1000 higher in the target cell than the control cell.

It would be known to the person skilled in medicine, that medicines can be modified with different additives, for example to change the rate in which the medicine is absorbed by the body; and can be modified in different forms, for example to allow for a particular administration route to the body.

Accordingly, we include that the composition, and/or antibody, and/or agent, and/or medicament of the invention may be combined with an excipient and/or a pharmaceutically acceptable carrier and/or a pharmaceutically acceptable diluent and/or an adjuvant.

We also include that the composition, and/or antibody, and/or agent, and/or medicament of the invention may be suitable for parenteral administration including aqueous and/or non-aqueous sterile injection solutions which may contain anti-oxidants, and/or buffers, and/or bacteriostats, and/or solutes which render the formulation isotonic with the blood of the intended recipient; and/or aqueous and/or non-aqueous sterile suspensions which may include suspending agents and/or thickening agents. The composition, and/or antibody, and/or agent, and/or medicament of the invention may be presented in unit-dose or multi-dose containers, for example sealed ampoules and vials, and may be stored in a freeze-dried (i.e. lyophilised) condition requiring only the addition of the sterile liquid carrier, for example water for injections, immediately prior to use.

Extemporaneous injection solutions and suspensions may be prepared from sterile powders, and/or granules, and/or tablets of the kind previously described.

For parenteral administration to human patients, the daily dosage level of the composition, and/or antibody, and/or agent, and/or medicament of the invention will usually be from 1 pg to 10 mg per adult per day administered in single or divided doses. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. Typically, the composition and/or medicament of the invention will contain the antibody and/or agent of the invention at a concentration of between approximately 2 mg/ml and 150 mg/ml or between approximately 2 mg/ml and 200 mg/ml. In a preferred embodiment, the medicaments and/or compositions of the invention will contain the antibody and/or agent of the invention at a concentration of 10 mg/ml.

Generally, in humans, oral or parenteral administration of the composition, and/or antibody, and/or agent, and/or medicament of the invention is the preferred route, being the most convenient. For veterinary use, the composition, and/or antibody, and/or agent and/or medicament of the invention are administered as a suitably acceptable formulation in accordance with normal veterinary practice and the veterinary surgeon will determine the dosing regimen and route of administration which will be most appropriate for a particular animal. Thus, the present invention provides a pharmaceutical formulation comprising an amount of an antibody and/or agent of the invention effective to treat various conditions (as described above and further below). Preferably, the composition, and/or antibody, and/or agent, and/or medicament is adapted for delivery by a route selected from the group comprising: intravenous; intramuscular; subcutaneous.

The present invention also includes composition, and/or antibody, and/or agent, and/or medicament comprising pharmaceutically acceptable acid or base addition salts of the polypeptide binding moieties of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others. Pharmaceutically acceptable base addition salts may also be used to produce pharmaceutically acceptable salt forms of the agents according to the present invention. The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others. The agents and/or polypeptide binding moieties of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) polypeptide binding moiety loses no more than about 20%, or no more than about 25%, or no more than about 30%, or no more than about 35%, or no more than about 40%, or no more than about 45%, or no more than about 50% of its activity (prior to lyophilisation) when re-hydrated.

We include that the subject could be mammalian or non-mammalian. Preferably, the mammalian subject is a human or is a non-mammalian, such as a horse, or a cow, or a sheep, or a pig, or a camel, or a dog, or a cat. Most preferably, the mammalian subject is a human.

Preferably, the invention provides a composition, or a use, or a method, or a kit, wherein the relapsed cancer and/or refractory cancer is resistant to an antibody treatment.

Preferably, the invention provides a composition, or a use, or a method, or a kit, wherein the relapsed cancer and/or refractory cancer is resistant to the antibody molecule as defined in (i).

Preferably, the invention provides a composition, or a use, or a method, or a kit, wherein the agent prevents or reduces FcγRIIb present on the target cell from binding to the Fc domain of the antibody molecule.

As outlined above, Fc receptors (including FcγRIIb) are membrane proteins which are present on cells. The skilled person would understand that there methods known in the art for detecting whether a protein is present on a cell; for example, immunohistochemistry, and visualizing proteins tagged with a detectable label.

By "FcγRIIb present on the target cell", we include that FcγRIIb is an FcγRIIb protein, and/or the FcγRIIb is present on the target cell membrane, and/or the FcγRIIb is present in the target cell membrane.

Preferably, the invention provides a composition, or a use, or a method, or a kit, wherein the antibody molecule that specifically binds a cell surface antigen of a target cell, which antibody molecule has an Fc domain capable of binding FcγRIIb, is capable of being internalized into the target cell in an FcγRIIb-dependent manner.

As outlined above, Fc receptors (including FcγRIIb) mediate the internalization of an antibody molecule into the cell, which can lead to the destruction of the antibody molecule. The manner in which FcγRIIb mediates the internalization of the antibody molecule into the cell would be known to the person skilled in cell biology.

By "internalized into the target cell", we include that the antibody molecule is removed from the cell membrane into the target cell, and/or that the antibody molecule is recycled into the target cell, and/or the antibody molecule is internalized into the target cell and destroyed, and/or the antibody molecule is encapsulated in an endosome of the target cell, and/or the antibody molecule is internalized into the target cell and so is no longer therapeutically effective, and/or the antibody molecule is endocytosed by the target cell.

It will be appreciated that an antibody molecule could be internalized into a cell in a number of different processes. As discussed above, the teaching of the invention is that the antibody molecule may be internalized through the binding of the Fc domain of the antibody molecule to FcγRIIb. However, it would be appreciated that an antibody molecule could be internalized via another process, such as pinocytosis—a process in which extracellular molecules can be passively up-taken into a cell. Other processes by which an antibody molecule could be up-taken into a cell would be known to the person skilled in cellular biology.

By "FcγRIIb-dependent manner", we include that the antibody molecule is internalized in a manner which requires FcγRIIb activity.

Preferably, the invention provides a composition, or a use, or a method, or a kit, wherein the agent that prevents or reduces FcγRIIb binding to the Fc domain of the antibody molecule additionally prevents or reduces internalization of the antibody molecule into the target cell.

Preferably, the invention provides a composition, or a use, or a method, or a kit, wherein the refractory cancer is characterized as being a refractory cancer if the subject has received cancer treatment and not responded, and/or the subject has received cancer treatment, but the cancer progressed in the subject during said treatment.

By "the subject has received cancer treatment", we include that the subject has previously been treated with a therapeutic agent or is currently being treated with a therapeutic agent.

We also include that if the subject previously been treated with a therapeutic agent that that treatment occurred about one day, or about two days, or about three days, or about four days, or about five days, or about six days, or more than about one week, or more than about two weeks, or more than about three weeks, or more than about one month, or more than about two months, or more than about three months, or more than about four months, or more than about five months, or more than about six months, or more than about seven months, or more than about eight months, or more than about nine months, or more than about ten months, or more than about 11 months, or more than about one year, or month than about two years, or more than about three years, or more than about 4 years or more than about 5 years, or more than about 10 years, previously.

By "therapeutic agent", we include one or more therapeutic agent selected from the list comprising of: rituximab, rituximab biosimilars, ofatumumab, obinutuzumab, alemtuzumab, ocrelizumab, galiximab, tositumomab, ibritumomab, a CD20 antibody, a CD40 antibody, a CD19 antibody, a CD37 antibody, a CD52 antibody, chlorambucil, cyclophosphamide, hyperfractionated cyclophosphamide, fludarabine, oxaliplatin, ibrutinib, a nucleoside analogue, an alkylator, bendamustine, bortezomib, lenalidomide, vincristine, doxorubicin (also known as adriamycin), prednisone, idarubicin, melphalan, cladribine, cytarabine, dexamethasone, methotrexate, mesna, gemcitabine, temsirolimus, mitoxantrone, cisplatin, thalidomide, etoposide, procarbazine, flavopiridol, enzastaurin, bleomycin, vinblastine, anthracycline, ifosfamide, carboplatin, methylprednisolone and dacarbazine; and/or one or more therapeutic agent combination selected from the list comprising of: fludarabine and cyclophosphamide (FC); cyclophosphamide, vincristine, doxorubicin, liposomal doxorubicin and prednisone (CHOP); cyclophosphamide, vincristine and prednisone (COP—also known as CVP); rituximab, cyclophosphamide, vincristine and prednisone (R—COP—also known as R—CVP); idarubicin and fludarabine; melphalan, chlorambucil and prednisone (MCP); rituximab and chlorambucil; rituximab, cyclophosphamide, vincristine, doxorubicin and prednisone (R—CHOP); rituximab, fludarabine and cyclophosphamide (R—FC); mesna, ifosfamide, mitoxantrone and etoposide; mesna, ifosfamide, mitoxantrone, etoposide and rituximab; lenalidomide and rituximab; rituximab and cladribine; rituximab, melphalan, chlorambucil and prednisone (R-MCP); cytarabine, cyclophosphamide, vincristine, doxorubicin and prednisone; hyperfractionated cyclophosphamide, vincristine, doxorubicin and dexamethasone (hyper-CVAD); rituximab, cyclophosphamide, vincristine, doxorubicin and dexamethasone (R-hyper-CVAD); ifosfamide, carboplatin and etoposide (ICE); ifosfamide, carboplatin, etoposide and rituximab; gemcitabine, dexamethasone and carboplatin; gemcitabine, dexamethasone, carboplatin and rituximab; gemcitabine and oxaliplatin; gemcitabine, oxaliplatin and rituximab; methotrexate and cytarabine; bortezomib and gemcitabine; rituximab and bortezomib; fludarabine, cyclophosphamide and mitoxantrone (FCM); rituximab, fludarabine, cyclophosphamide and mitoxantrone (R-FCM—also known as FCMR); rituximab and fludarabine; dexamethasone and gemcitabine; dexamethasone, gemcitabine and cisplatin; dexamethasone, gemcitabine, cisplatin and rituximab; dexamethasone, fludarabine, mitoxantrone and dexamethasone (RFND); thalidomide and rituximab; prednisone, etoposide, procarbazine and cyclophosphamide (PEP-C); rituximab, thalidomide, prednisone, etoposide, procarbazine and cyclophosphamide; bendamustine and rituximab (BR); rituximab, cyclophosphamide, doxorubicin, vincristine, etoposide and prednisone (R-CHOEP—also known as EPOCH-R); adriamycin, bleomycin, vinblastine and dacarbazine (ABVD); bleomycin, etoposide, adriamycin, cyclophosphamide, vincristine, procarbazine and prednisone (BEACOPP); cyclophosphamide, vincristine, procarbazine and prednisone (COPP); cyclophosphamide, etoposide, prednisone and procarbazine (CEPP); rituximab, cyclophosphamide, etoposide, prednisone and procarbazine (RCEPP); rituximab, cyclophosphamide, liposomal doxorubicin, vincristine and prednisone (RCDOP); rituximab, cyclophosphamide, mitoxantrone, vincristine and prednisone (RCNOP); rituximab, cyclophosphamide, etoposide, vincristine and prednisone; dexamethasone, cisplatin, cytarabine and rituximab (DHAP); etoposide, methylprednisolone, cytarabine, cisplatin and rituximab (ESHAP); and, chlorambucil, vinblastine, procarbazine and prednisone (ChlVPP).

In addition to the therapeutic agents outlined above, the person skilled in medicine would understand the other types and combinations of therapeutic agents that could be used to treat cancer, and/or relapsed cancer, and/or refractory cancer; examples of which can be found in the Agency for Healthcare Research and Quality Guideline Summary NGC-9392 September 2012, Agency for Healthcare Research and Quality Guideline Summary NGC-9278 2012, McKay et al., 2012, British Journal of Haematology: 12046, Hallek et al., 2008, Blood, 111: 5446-5456, Wang et al., 2013, N. Engl. J. Med., 369(6): 507-516, Byrd et al., N. Engl. J. Med., 369(1): 32-42, and NCCN Guidelines on Non-Hodgkin's Lymphomas Version 1.2014.

By "received cancer treatment and not responded", we include that after having received cancer treatment the subject does not exhibit a reduction in the severity of cancer symptoms, and/or the subject does not exhibit a reduction in the number of cancer symptoms, and/or that the subject does not have an improved cancer prognosis, and/or the subject does not exhibit a reduction in the diagnostic markers of cancer.

By "cancer progressed in the subject", we include that during cancer treatment the subject exhibits an increase in the severity of cancer symptoms, and/or the subject exhibits an increase in the number of cancer symptoms, and/or that the subject has a worse cancer prognosis, and/or the subject exhibit an increase in the diagnostic markers of cancer.

By "exhibit", we include that the subject displays a cancer symptom and/or a cancer diagnostic marker, and/or the cancer symptom and/or a cancer diagnostic marker can be measured, and/or assessed, and/or quantified.

It would be readily apparent to the person skilled in medicine what the cancer symptoms and cancer diagnostic markers would be and how to measure and/or assess and/or quantify whether there is a reduction or increase in the severity of the cancer symptoms, or a reduction or increase in the cancer diagnostic markers; as well as how those cancer symptoms and/or cancer diagnostic markers could be used to form a prognosis for the cancer.

Cancer treatments are often administered as a course of treatment, which is to say that the therapeutic agent is administered over a period of time. The length of time of the course of treatment will depend on a number of factors, which could include the type of therapeutic agent being administered, the type of cancer being treated, the severity of the cancer being treated, and the age and health of the subject, amongst others reasons.

By "during the treatment", we include that the subject is currently receiving a course of treatment, and/or receiving a therapeutic agent, and/or receiving a course of a therapeutic agent.

Preferably, the invention provides a composition, or a use, or a method, or a kit, wherein the subject is characterized as having not responded if the subject has previously been treated for cancer, but achieves less than partial remission.

Remission is a well-known term in the art of cancer medicine which relates to the assessment of the reduction in cancer in a subject. Partial remission is also a well-known term in the art of cancer medicine which relates to a stage in remission where the cancer in a subject as measured using a particular cancer symptom and/or cancer diagnostic marker is 50% reduced compared to the level of that particular cancer symptom and/or cancer diagnostic marker before treatment. In some situations, for a subject to be classified as having partial remission that reduction in the cancer symptom and/or cancer diagnostic marker must be maintained over a particular length of time. It would be clear to a person skilled in medicine whether a subject is in remission for cancer, and what stage in the remission the subject is at.

By "achieves less than partial remission", we include that the cancer symptom or cancer diagnostic marker has been assessed and/or measured and/or quantified based on a reduction in the severity of cancer symptoms, and/or a reduction in the number of cancer symptoms, and/or an improved cancer prognosis, and/or a reduction in the cancer diagnostic markers; and is less than 50% reduced compared to the cancer symptom or cancer diagnostic marker before treatment.

We also include that the assessment and/or measurement and/or quantification of whether the subject achieves less than partial remission is based on a comparison between the cancer symptom and/or cancer diagnostic marker following the cessation of treatment and the cancer symptom and/or cancer diagnostic marker before the treatment has begun, and/or the cancer symptom and/or cancer diagnostic marker during treatment. It is also included that assessment and/or measurement and/or quantification may occur at least one time, or at least two times, or at least three times, or at least four times, or at least five times, or at least six times, or at least seven times, or at least eight times, or at least nine times, or at least ten times, or at least 15 times, or at least 20 times before a subject is said to have achieved less than partial remission.

We further include that a subject achieves less than partial remission if the reduction in the cancer symptom and/or cancer diagnostic marker following the cessation of treatment is less than about 1%, or is less than about 5%, or is less than about 10%, or less than about 15%, or less than about 20%, or less than about 25%, or less than about 30%, or less than about 35%, or less than about 40%, or less than about 45%, or less than about 50% compared to the cancer symptom and/or cancer diagnostic marker before the treatment has begun, and/or the cancer symptom and/or cancer diagnostic marker during treatment.

Preferably, the invention provides a composition, or a use, or a method, or a kit, wherein the relapsed cancer is characterized as being a relapsed cancer if the subject has previously been treated for cancer and has previously responded to the treatment, and subsequently relapsed.

By "previously been treated for cancer", we include that the subject has previously been treated with a therapeutic agent, but that that treatment has ceased. Therefore, we include that the subject has previously been treated for cancer if the cessation of treatment with a therapeutic agent occurred at least about one day, or at least about two days, or at least about three days, or at least about four days, or at least about five days, or at least about six days, or more than about one week, or more than about two weeks, or more than about three weeks, or more than about one month, or more than about two months, or more than about three months, or more than about four months, or more than about five months, or more than about six months, or more than about seven months, or more than about eight months, or more than about nine months, or more than about ten months, or more than about 11 months, or more than about one year, or more than about two years, or more than about three years, or more than about 4 years, or more than about 5 years, or more than about 10 years, previously.

It would be clear to a person skilled in medicine whether a patient has responded to treatment.

By "previously responded to the treatment", we include that following the cessation of treatment there an assessed and/or measured and/or quantified reduction in the severity of cancer symptoms, and/or a reduction in the number of cancer symptoms, and/or an improved cancer prognosis, and/or a reduction in the cancer diagnostic markers.

Relapsed is a well-known term in the art of cancer medicine which relates to a cancer of a subject worsening following that cancer of the subject having previously responded to treatment. It would be clear to a person skilled in medicine when a cancer had relapsed.

By "subsequently relapsed", we include the subject exhibits an increase in the severity of cancer symptoms, and/or the subject exhibits an increase in the number of cancer symptoms, and/or that the subject has a worse cancer prognosis, and/or the subject exhibit an increase in the cancer diagnostic markers after the subject has previously responded to treatment.

Preferably, the invention provides a composition, or a use, or a method, or a kit, wherein the subject is characterized as having subsequently relapsed, if the subject (i) achieves at least a partial remission following treatment and/or if the subject achieves at least a complete remission following treatment, but (ii) the cancer progressed in the subject after the cessation of the treatment.

By "complete remission following treatment", we include that after the cessation of treatment there are no detectable cancer symptoms and/or cancer diagnostic markers.

We also include that in some cases the complete remission following treatment is if the cancer symptoms and/or cancer diagnostic markers are not detectable for at least about one day, or at least about two days, or at least about three days, or at least about four days, or at least about five days, or at least about six days, or more than about one week, or more than about two weeks, or more than about three weeks, or more than about one month, or more than about two months, or more than about three months, or more than about four months, or more than about five months, or more than about six months, or more than about seven months, or more than about eight months, or more than about nine months, or more than about ten months, or more than about 11 months, or more than about one year, or more than about two years, or more than about three years, or more than about 4 years, or more than about 5 years, or more than about 10 years, or about 20 years, or about 30 years, or about 40 years, or about 50 years following the cessation of treatment. Most particularly, we include that in some case the complete remission following treatment is if the cancer symptoms and/or cancer diagnostic markers are not detectable more than about six months following the cessation of treatment.

Preferably, the invention provides a composition, or a use, or a method, or a kit, wherein the subject subsequently relapsed more than about 1 month following the cessation of treatment.

Preferably, the invention provides a composition, or a use, or a method, or a kit, wherein the subject subsequently relapsed more than about 1 month, or more than about 2 months, or more than about 3 months, or more than about 4 months, or more than about 5 months, or more than about 6 months, or more than about 7 months, or more than about 8 months, or more than about 9 months, or more than about 10 months, or more than about 11 months, or more than about 12 months, or more than about 2 years, or more than about 3 years, or more than about 4 years, or more than about 5 years, or more than about 6 years, or more than about 7 years, or more than about 8 years, or more than about 9 years, or more than about 10 years following the cessation of treatment. Most preferably, wherein the subject subsequently relapsed more than about 6 months following the cessation of treatment.

Preferably, the invention provides a composition, or a use, or a method, or a kit, wherein the subject exhibits the characteristics of a relapsed cancer at least one time, or at least two times, or at least three times, or at least four times, or at least five times, or at least six times, or at least seven times, or at least eight times, or at least nine times, or at least ten times.

By "exhibits the characteristics of a relapsed cancer", we include that the subject has previously been treated for cancer and has previously responded to the treatment, and subsequently relapsed.

It is thought that a cancer may relapse because it has developed a resistance to the treatment that had previously been used to treat that cancer in the subject. Therefore, a subject with a relapsed cancer is often treated using a different therapeutic agent to the therapeutic agent previously used to treat the cancer in that subject. Accordingly, in the embodiment mentioned immediately above, we include that each subsequent time the subject exhibits the characteristics of a relapsed cancer then the subject is treated with a different therapeutic agent to the therapeutic agent that the subject has previously been treated with, and/or the subject is treated with the same therapeutic agent to the therapeutic agent that the subject has previously been treated with.

Preferably, the invention provides a composition, or a use, or a method, or a kit, wherein the treatment is an antibody treatment, for example, the antibody molecule as defined in (i) of earlier embodiments, which was administered in the absence of the agent as defined in (ii) of the earlier embodiments.

By "administered in the absence", we include that the antibody molecule as defined in (i) was administered a period of time after and/or before the agent as defined in (ii). Accordingly, by "period of time" we include that antibody molecule as defined in (i) was administered more than one hour, or more than two hours, or more than three hours, or more than six hours, or more than 12 hours, or more than 18 hours, or more than 24 hours, or more than two days, or more than three days, or more than four days, or more than five days, or more than six days, or more than seven days, or more than two weeks, or more than three weeks, or more than four weeks, or more than five weeks, or more than six weeks, or more than seven weeks, or more than eight weeks, or more than three months, or more than four months, or more than five months, or more than six months, or more than seven months, or more than eight months, or more than nine months, or more than ten months, or more than 11 months, or more than 12 months, or more than 1 year, or more than two years, or more than three years, or more than four years, or more than five years, or more than ten years, or more than 20 years before and/or after before the agent as defined in (ii).

Preferably, the invention provides a composition, or a use, or a method, or a kit, wherein the treatment comprises one or more therapeutic agent.

Preferably, the invention provides a composition, or a use, or a method, or a kit, wherein the target cell comprises an elevated level of FcγRIIb expression.

It would be known to the person skilled in molecular biology and cellular biology what an elevated level of FcγRIIb expression would be, and how the expression could be measured. For example, in addition to the methods of measuring FcγRIIb expression mentioned above, FcγRIIb expression levels can be measured by immunohistochemistry of tumor biopsies. A person skilled in the art would understand that there are multiple techniques and methodologies for determining FcγRIIb expression levels.

By "target cell comprises an elevated level of FcγRIIb expression", we include that the target cell comprises an elevated level of FcγRIIb protein and/or that the target cell comprises an elevated level of FcγRIIb mRNA compared to a control, as described below.

Preferably, the invention provides a composition, or a use, or a method, or a kit, wherein elevated FcγRIIb expression on the target cell is determined relative to a control.

A suitable control would be one that has a normal level of FcγRIIb expression. Selecting the correct control and defining the normal level of FcγRIIb expression might depend on a number of variables, such as the subject, the type of target cell type in the subject, and the type of cancer. It would be apparent to the skilled person in molecular biology or cell biology what an appropriate control and a normal level of FcγRIIb expression would be.

By "control", we include that the control is a control cell, and/or the control is information from a database of FcγRIIb expression levels. We also include that the control cell is a different cell-type to the target cell, and/or is the same cell-type to the target cell. We further include that the control cell is from a control individual, and that that control individual may be the subject, and/or an individual other than the subject.

Preferably, the invention provides a composition, or a use, or a method, or a kit, wherein the control comprises control cells of a control individual with a non-refractory cancer and/or a non-relapsed cancer.

By "control individual with a non-refractory cancer and/or a non-relapsed cancer", we include that that control individual has a cancer that is not a relapsed cancer and/or a refractory cancer. We also include that that control individual has previously been treated at least once with a therapeutic agent.

Preferably, the invention provides a composition, or a use, or a method, or a kit, wherein the elevated FcγRIIb expression is at least 2-fold higher in the target cell of the subject when compared to the control.

We also include that the elevated FcγRIIb expression is about 10 fold higher, or about 20 fold higher, or about 30 fold higher, or about 40 fold higher, or about 50 fold higher, or about 60 fold higher, or about 70 fold higher, or about 80 fold higher, or about 90 fold higher, or about 100 fold higher, or about 200 fold higher, or about 300 fold higher, or about 400 fold higher, or about 500 fold higher, or about 600 fold higher, or about 700 fold higher, or about 800 fold higher, or about 900 fold higher, or about 1000 fold higher in the target cell compared to the control.

Preferably, the invention provides a composition, or a use, or a method, or a kit, wherein the target cell is a cancer cell.

A cancer cell is a cell that exhibits the characteristics of cancer, which is to say it exhibits one or more cancer diagnostic markers. It would be clear to a person skilled in cell biology and oncology whether the target cell is a cancer cell.

Preferably, the invention provides a composition, or a use, or a method, or a kit, wherein the target cell is a B cell.

B cells (otherwise known a B lymphocytes) are a type of cell of the adaptive immune response, which are distinguished from other cells of the immune system by the presence of B cell receptors on the cell surface.

By "B cell", we include plasma B cells (also known a effector B cells), and/or memory B cells, and/or B-1 cells, and/or B-2 cells, and/or marginal-zone B cells, and/or follicular B cells, and/or regulatory B cells, and/or naïve B cells.

Preferably, the invention provides a composition, or a use, or a method, or a kit, wherein the relapsed cancer, and/or the refractory cancer, and/or the cancer cell, and/or the same cancer-type, and/or the cancer is selected from the group comprising of: non-Hodgkin lymphoma; follicular lymphoma; diffuse large B cell lymphoma; mantle cell lymphoma; chronic lymphocytic leukaemia; small lymphocytic lymphoma.

Non-Hodgkin lymphoma (NHL) is the collective name for a group of different lymphomas, which includes: follicular cell lymphoma, mantle cell lymphoma, splenic marginal zone lymphoma, MALT lymphoma, Lymphoplasmacytic NHL (also known as Waldenstrom's macroglobulinemia), small lymphocytic lymphoma, chronic lymphocytic leukaemia, diffuse large B cell lymphoma, diffused mixed cell lymphoma, Burkitt's lymphoma, anaplastic large cell lymphoma, and diffuse mixed cell lymphoma, amongst others.

Each one of the above described cancers is well-known, and the symptoms and cancer diagnostic markers are well described, as are the therapeutic agents used to treat those cancers. Accordingly, the symptoms, cancer diagnostic markers, and therapeutic agents used to treat non-Hodgkin lymphoma, follicular lymphoma, diffuse large B cell lymphoma, mantle cell lymphoma, chronic lymphocytic leukaemia, and small lymphocytic lymphoma would be known to those skilled in medicine.

Preferably, the invention provides a composition, or a use, or a method, or a kit, wherein the subject having not responded, and/or partial remission in a subject, and/or complete remission in a subject, and/or cancer having progressed in a subject is determined by measuring one or more from the group comprising:

(i) a lymphocyte count; and/or
(ii) a neutrophil count; and/or
(iii) a platelet count; and/or
(iv) a hemoglobin count; and/or
(v) a percentage of tumour cells; and/or
(vi) a percentage of bone marrow lymphocytes; and/or
(vii) a percentage of circulating lymphocytes; and/or
(viii) the presence and/or absence of biomarkers on lymphocytes; and/or
(ix) cancer staging; and/or
(x) histological examination; and/or
(xi) bone marrow examination; and/or
(xii) cytogenetic examination; and/or
(xiii) lymph node evaluation; and/or
(xiv) physical symptoms; and/or
(xv) a reduction of cancer cells in the spleen.

It will be appreciated that (i), (ii), (iii), (iv), (v), (vi), (vii), (viii), (ix), (x), (xi), (xii), (xiii) and (xv) relate to "cancer diagnostic markers"; and that (xiv) relates to "cancer symptoms".

Through the decades of research and innovation in the field of oncology, the "cancer diagnostic markers" and "cancer symptoms" of a large number of cancers is well characterized, as are the methods of measuring and assessing cancer diagnostic markers and cancer symptoms. Accordingly, those skilled in oncology would appreciate how each of the above points relates to a particular cancer and, based on the measurement or assessment of a particular cancer diagnostic markers or cancer symptoms, it would be readily apparent to skilled individuals whether a subject has not responded to treatment, or whether the subject is in partial remission, or whether the subject is in complete remission, or whether the cancer has progressed in a subject; examples of which can be found in McKay et al., 2012, British Journal of Haematology: 12046, Hallek et al., 2008, Blood, 111: 5446-5456 and NCCN Guidelines on Non-Hodgkin's Lymphomas Version 1.2014.

The assessment of a number of the diagnostic cancer markers relies (such as "a lymphocyte count", "a neutrophil count", "a platelet count", "a hemoglobin count", "a percentage of atypical cells", "a percentage of bone marrow lymphocytes", and "a percentage of circulating lymphocytes") rely on the quantification of cells and molecules within the subject. The assays for quantifying those cells and molecules are well known in the art.

By "tumour cells" we include neoplastic cells, and/or neoplastic cells that are CD19+, CD5+ and CD23+.

A number of biomarkers can be indicative of certain types of cancer. For example, chronic lymphocytic leukaemia cells co-express CD5, CD19, CD20 and CD23. However, the levels of CD20 and CD79b is lower if compared to normal B cells.

By "presence and/or absence of biomarkers on lymphocytes" we include that the term "presence" includes an increased amount of the biomarker when compared to a control B cell, or detectable biomarker, and an absence includes a reduced amount of the biomarker when compared to a control B cell, or no detectable biomarker. We also include that the control B cell can be from a "control individual". We further include that presence and/or absence of biomarkers on lymphocytes includes the presence of CD5, and/or CD19, and/or CD20, and/or CD23, and/or cyclin D1, and/or BCL2, and/or FMC6, and/or CD3, and/or CD10 and/or BCL6, and/or CD21, and/or CD45, and/or Ki-67, and/or IRF4/MUM1, and/or MYC, and/or CD30, and/or CD138, and/or EBER-ISH, and/or ALK, and/or HHV8, and/or kappa/lambda, and/or CD79b, and/or the absence of CD20, and/or CD79b, and/or CD10, and/or CD23, and/or BCL6.

Clinical definitions of the diagnosis, prognosis and progression of a large number of cancers rely on certain classifications known as staging. Those staging systems act to collate a number of different cancer diagnostic markers and cancer symptoms to provide a summary of the diagnosis, and/or prognosis, and/or progression of the cancer. It would be known to the person skilled in oncology how to assess the diagnosis, and/or prognosis, and/or progression of the cancer using a staging system, and which cancer diagnostic markers and cancer symptoms should be used to do so.

By "cancer staging", we include the Rai staging, which includes stage 0, stage I, stage II, stage III and stage IV, and/or the Binet staging, which includes stage A, stage B and stage C, and/or the Ann Arbour staging, which includes stage I, stage II, stage III and stage IV.

It is known that cancer can cause abnormalities in the morphology of cells. These abnormalities often reproducibly occur in certain cancers, which means that examining these changes in morphology (otherwise known as histological examination) can be used in the diagnosis or prognosis of cancer. Techniques for visualizing samples to examine the morphology of cells, and preparing samples for visualization, are well known in the art; for example, light microscopy or confocal microscopy.

By "histological examination", we include the presence of small, mature lymphocyte, and/or the presence of small, mature lymphocytes with a narrow border of cytoplasm, the presence of small, mature lymphocytes with a dense nucleus lacking discernible nucleoli, and/or the presence of small, mature lymphocytes with a narrow border of cytoplasm, and with a dense nucleus lacking discernible nucleoli, and/or the presence of atypical cells, and/or cleaved cells, and/or prolymphocytes.

It is well known that cancer is a result of mutations in the DNA of the cell, which can lead to the cell avoiding cell death or uncontrollably proliferating. Therefore, examining these mutations (also known as cytogenetic examination) can be a useful tool for assessing the diagnosis and/or prognosis of a cancer. An example of this is the deletion of the chromosomal location 13q14.1 which is characteristic of chronic lymphocytic leukaemia. Techniques for examining mutations in cells are well known in the art; for example, fluorescence in situ hybridization (FISH).

By "cytogenetic examination", we include the examination of the DNA in a cell, and, in particular the chromosomes. Cytogenetic examination can be used to identify changes in DNA which may be associated with the presence of a refractory cancer and/or relapsed cancer. Such may include: deletions in the long arm of chromosome 13, and/or the deletion of chromosomal location 13q14.1, and/or trisomy of chromosome 12, and/or deletions in the long arm of chromosome 12, and/or deletions in the long arm of chromosome 11, and/or the deletion of 11q, and/or deletions in the long arm of chromosome 6, and/or the deletion of 6q, and/or deletions in the short arm of chromosome 17, and/or the deletion of 17p, and/or the t(11:14) translocation, and/or the (q13:q32) translocation, and/or antigen gene receptor rearrangements, and/or BCL2 rearrangements, and/or BCL6 rearrangements, and/or t(14:18) translocations, and/or t(11:14) translocations, and/or (q13:q32) translocations, and/or (3:v) translocations, and/or (8:14) translocations, and/or (8:v) translocations, and/or t(11:14) and (q13:q32) translocations.

It is known that subjects with cancer exhibit certain physical symptoms, which are often as a result of the burden of the cancer on the body. Those symptoms often reoccur in the same cancer, and so can be characteristic of the diagnosis, and/or prognosis, and/or progression of the disease. A person skilled in medicine would understand which physical symptoms are associated with which cancers, and how assessing those physical systems can correlate to the diagnosis, and/or prognosis, and/or progression of the disease By "physical symptoms", we include hepatomegaly, and/or splenomegaly.

By "subject having not responded", we include that the measurement and/or assessment of points (i), and/or (ii), and/or (iii), and/or (iv), and/or (v), and/or (vi), and/or (vii), and/or (viii), and/or (ix), and/or (x), and/or (xi), and/or (xii), and/or (xiii), and/or (xiv) and/or (xv) in the embodiment immediately above is unchanged, or if a change has occurred it is negligible, in the subject when compared between before treatment and following the cessation of treatment, and/or when compared between during treatment and following the cessation of treatment, and/or during treatment.

By "partial remission in a subject", we include that for "lymphocyte count" there is an at least 50% decrease in the lymphocyte count following the cessation of treatment compared to before treatment and/or during treatment, and/or for "lymph node evaluation" an at least 50% decrease in the size of one or more lymph node following the cessation of treatment compared to before treatment and/or during treatment, and/or no additional enlarged lymph nodes, and/or for "physical symptoms" an at least 50% decrease in the size the spleen (in relation to splenomegaly) following the cessation of treatment compared to before treatment and/or during treatment, and/or an at least 50% decrease in the size the liver (in relation to hepatomegaly) following the cessation of treatment compared to before treatment and/or during treatment, and/or for "neutrophil count" no more than 1500 cells/µl, and/or for "platelet count" there is no more than 100,000 platelets/µl, and/or there is an at least 50% decrease in the number of neutrophils count following the cessation of treatment compared to before treatment and/or during treatment, and/or for "hemoglobin count" there is no more than 11 g/dL, and/or there is an at least 50% decrease in the amount of hemoglobin following the cessation of treatment compared to before treatment and/or during treatment.

By "complete remission in a subject", we include that for "lymphocytes count" there is a cell count of at the most 4000 cells/µl, and/or for "lymph node evaluation" the lymph nodes are at the most 1.5 cm in diameter, and/or for "physical symptoms" there is no detectable hepatomegaly, and/or no detectable splenomegaly, and/or for "neutrophil count" no more than 1500 cells/µl, and/or for "platelet count" there is no more than 100,000 platelets/µl, and/or for "hemoglobin count" there is no more than 11 g/dL.

By "cancer having progressed in a subject", we include that for "lymphocytes count" there is an at least 50% increase in the number of lymphocyte count following the cessation of treatment compared to before treatment and/or during treatment, and/or at least more than 5000 cells/µl, and/or for "lymph node evaluation" there is an enlargement of lymph nodes to a diameter of at least 1.5 cm, and/or an at least 50% increase in the size of the lymph nodes following the cessation of treatment compared to before treatment and/or during treatment, and/or for "physical symptoms" there is the appearance of hepatomegaly, and/or there is the appearance of splenomegaly, and/or an at least 50% increase in the size the spleen (in relation to splenomegaly) following the cessation of treatment compared to before treatment and/or during treatment, and/or an at least 50% increase in the size the liver (in relation to hepatomegaly) following the cessation of treatment compared to before treatment and/or during treatment, and/or for "hemoglobin count" the hemoglobin levels decrease by more than 20 g/L, and/or the hemoglobin levels decrease to less than 100 g/L, for "platelet count" there is an at least 50% decrease in the number of neutrophils count following the cessation of treatment compared to before treatment and/or during treatment, and/or there is at the most 100,000 platelets/µl.

Preferably, the invention provides a composition, or a use, or a method, or a kit, wherein the agent comprises: a polypeptide; or an anticalin; or a peptide; or an antibody; or a chimeric antibody; or a single chain antibody; or an aptamer; or a darpin; or a Fab, or a F(ab')$_2$, or a Fv, or a ScFv or a dAb antibody fragment; or an IgG2 antibody; or an IgG4 antibody; or a chimeric molecule of IgG2 and IgG4; or an antibody variant comprising a N297Q mutation; or a DANA variant antibody; or a small molecule; or a natural product; or an affibody; or a peptidomimetic; or a nucleic acid; or a peptide nucleic acid molecule; or a lipid; or a carbohydrate; or a protein based on a modular framework including ankyrin repeat proteins, or armadillo repeat proteins, or leucine rich proteins, or tetratricopeptide repeat proteins, or a Designed Ankyrin Repeat Proteins (DARPins).

Preferably, the invention provides a composition, or a use, or a method, or a kit, wherein the agent as defined in (ii) is one or more antibody molecule that specifically binds FcγRIIb.

Preferably, the invention provides a composition, or a use, or a method, or a kit, wherein the agent as defined in (ii) is one or more antibody molecule which does not include a domain capable of recruiting an effector cell.

The immune system comprises a number of different cell types which each have a different role in producing, aiding or maintaining an immune response. In order to undertake its role in immunity, a cell of the immune system will often react to stimuli which will often lead to that cell being mobilized to a particular bodily location or target (such as a cell which possess the signal). One class of cell of the immune system is an effector cell; the identity and roles of which would be well known to a person skilled in immunology.

By "effector cell" we include, an effector T cell, and/or an effector B cell (also known as plasma cells), and/or an effector memory T cell, and/or an effector memory CD4$^+$ T cell, and/or an effector memory CD8$^+$ T cell.

By "domain capable of recruiting an effector cell", we include an epitope and/or antigen on the antibody molecule which will mobilize an effector cell to the location of the antibody molecule. We also include that the domain capable of recruiting an effector cell may be the Fc domain of the antibody molecule, and/or an antigen and/or epitope on the Fc domain of the antibody molecule.

Preferably, the invention provides a composition, or a use, or a method, or a kit, wherein the agent as defined in (ii) is one or more antibody molecules which are monoclonal antibody molecules, and/or polyclonal antibody molecules, and/or bi-specific antibody molecules.

As outlined above, different types and forms of antibody are included in the invention, and would be known to the person skilled in immunology. It is well known that antibodies used for therapeutic purposes are often modified with additional components which modify the properties of the antibody molecule.

Accordingly, we include that the antibody molecule of the invention (for example, a monoclonal antibody molecule, and/or polyclonal antibody molecule, and/or bi-specific antibody molecule) comprises a detectable moiety and/or a cytotoxic moiety.

By "detectable moiety", we include one or more from the group comprising of: an enzyme; a radioactive atom; a fluorescent moiety; a chemiluminescent moiety; a bioluminescent moiety. The detectable moiety allows the antibody molecule to be visualised in vitro, and/or in vivo, and/or ex vivo.

By "cytotoxic moiety", we include a radioactive moiety, and/or enzyme, wherein the enzyme is a caspase, and/or toxin, wherein the toxin is a bacterial toxin or a venom; wherein the cytotoxic moiety is capable of inducing cell lysis.

We further include that the antibody molecule may be in an isolated form and/or purified form, and/or may be PEGylated.

In the following embodiments, the SEQ ID NOs refer to the sequences indicated in clones below.

As discussed above, the CDRs of an antibody bind to the antibody target. The assignment of amino acids to each CDR described herein is in accordance with the definitions according to Kabat E A et al. 1991, In "Sequences of Proteins of Immulogical Interest" Fifth Edition, NIH Publication No. 91-3242, pp xv-xvii.

As the skilled person would be aware, other methods also exist for assigning amino acids to each CDR. For example, the International ImMunoGeneTics information system (IMGT®) (http://www.imgt.org/ and Lefranc and Lefranc "The Immunoglobulin FactsBook" published by Academic Press, 2001).

It is appreciated that molecules containing three or fewer CDR regions (in some cases, even just a single CDR or a part thereof) are capable of retaining the antigen-binding activity of the antibody from which the CDR(s) are derived. For example, in Gao et al., 1994, J. Biol. Chem., 269:

32389-93 it is described that a whole VL chain (including all three CDRs) has a high affinity for its substrate.

Molecules containing two CDR regions are described, for example, by Vaughan & Sollazzo 2001, Combinatorial Chemistry & High Throughput Screening, 4: 417-430. On page 418 (right column—3 Our Strategy for Design) a minibody including only the H1 and H2 CDR hypervariable regions interspersed within framework regions is described. The minibody is described as being capable of binding to a target. Pessi et al., 1993, Nature, 362: 367-9 and Bianchi et al., 1994, J. Mol. Biol., 236: 649-59 are referenced by Vaughan & Sollazzo and describe the H1 and H2 minibody and its properties in more detail. In Qiu et al., 2007, Nature Biotechnology, 25:921-9 it is demonstrated that a molecule consisting of two linked CDRs are capable of binding antigen. Quiocho 1993, Nature, 362: 293-4 provides a summary of "minibody" technology. Ladner 2007, Nature Biotechnology, 25:875-7 comments that molecules containing two CDRs are capable of retaining antigen-binding activity.

Molecules containing a single CDR region are described, for example, in Laune et al., 1997, JBC, 272: 30937-44, in which it is demonstrated that a range of hexapeptides derived from a CDR display antigen-binding activity and it is noted that synthetic peptides of a complete, single, CDR display strong binding activity. In Monnet et al., 1999, JBC, 274: 3789-96 it is shown that a range of 12-mer peptides and associated framework regions have antigen-binding activity and it is commented on that a CDR3-like peptide alone is capable of binding antigen. In Heap et al., 2005, J. Gen. Viral., 86: 1791-1800 it is reported that a "micro-antibody" (a molecule containing a single CDR) is capable of binding antigen and it is shown that a cyclic peptide from an anti-HIV antibody has antigen-binding activity and function. In Nicaise et al., 2004, Protein Science, 13:1882-91 it is shown that a single CDR can confer antigen-binding activity and affinity for its lysozyme antigen.

Thus, molecules having three or fewer CDRs are capable of retaining the antigen binding properties of the antibodies for which they are derived.

Preferably, the invention provides a composition, or a use, or a method, or a kit, wherein the agent comprises a variable heavy chain (VH) comprising the following CDRs:
(i) SEQ ID NO: 51 and SEQ ID NO: 52 and SEQ ID NO: 53; or
(ii) SEQ ID NO: 57 and SEQ ID NO: 58 and SEQ ID NO: 59; or
(iii) SEQ ID NO: 63 and SEQ ID NO: 64 and SEQ ID NO: 65; or
(iv) SEQ ID NO: 69 and SEQ ID NO: 70 and SEQ ID NO: 71; or
(v) SEQ ID NO: 75 and SEQ ID NO: 76 and SEQ ID NO: 77; or
(vi) SEQ ID NO: 81 and SEQ ID NO: 82 and SEQ ID NO: 83; or
(vii) SEQ ID NO: 87 and SEQ ID NO: 88 and SEQ ID NO: 89; or
(viii) SEQ ID NO: 93 and SEQ ID NO: 94 and SEQ ID NO: 95; or
(ix) SEQ ID NO: 99 and SEQ ID NO: 100 and SEQ ID NO: 101; or
(x) SEQ ID NO: 105 and SEQ ID NO: 106 and SEQ ID NO: 107; or
(xi) SEQ ID NO: 111 and SEQ ID NO: 112 and SEQ ID NO: 113; or
(xii) SEQ ID NO: 117 and SEQ ID NO: 118 and SEQ ID NO: 119; or
(xiii) SEQ ID NO: 123 and SEQ ID NO: 124 and SEQ ID NO: 125; or
(xiv) SEQ ID NO: 129 and SEQ ID NO: 130 and SEQ ID NO: 131; or
(xv) SEQ ID NO: 135 and SEQ ID NO: 136 and SEQ ID NO: 137; or
(xvi) SEQ ID NO: 141 and SEQ ID NO: 142 and SEQ ID NO: 143; or
(xvii) SEQ ID NO: 147 and SEQ ID NO: 148 and SEQ ID NO: 149; or
(xviii) SEQ ID NO: 153 and SEQ ID NO: 154 and SEQ ID NO: 155; or
(xix) SEQ ID NO: 159 and SEQ ID NO: 160 and SEQ ID NO: 161; or
(xx) SEQ ID NO: 165 and SEQ ID NO: 166 and SEQ ID NO: 167; or
(xxi) SEQ ID NO: 171 and SEQ ID NO: 172 and SEQ ID NO: 173; or
(xxii) SEQ ID NO: 177 and SEQ ID NO: 178 and SEQ ID NO: 179; or
(xxiii) SEQ ID NO: 183 and SEQ ID NO: 184 and SEQ ID NO: 185; or
(xxiv) SEQ ID NO: 189 and SEQ ID NO: 190 and SEQ ID NO: 191.

Preferably, the invention provides a composition, or a use, or a method, or a kit, wherein the agent comprises a variable light chain (VL) comprising the following CDRs:
(i) SEQ ID NO: 54 and SEQ ID NO: 55 and SEQ ID NO: 56; or
(ii) SEQ ID NO: 60 and SEQ ID NO: 61 and SEQ ID NO: 62; or
(iii) SEQ ID NO: 66 and SEQ ID NO: 67 and SEQ ID NO: 68; or
(iv) SEQ ID NO: 72 and SEQ ID NO: 73 and SEQ ID NO: 74; or
(v) SEQ ID NO: 78 and SEQ ID NO: 79 and SEQ ID NO: 80; or
(vi) SEQ ID NO: 84 and SEQ ID NO: 85 and SEQ ID NO: 86; or
(vii) SEQ ID NO: 90 and SEQ ID NO: 91 and SEQ ID NO: 92; or
(viii) SEQ ID NO: 96 and SEQ ID NO: 97 and SEQ ID NO: 98; or
(ix) SEQ ID NO: 102 and SEQ ID NO: 103 and SEQ ID NO: 104; or
(x) SEQ ID NO: 108 and SEQ ID NO: 109 and SEQ ID NO: 110; or
(xi) SEQ ID NO: 114 and SEQ ID NO: 115 and SEQ ID NO: 116; or
(xii) SEQ ID NO: 120 and SEQ ID NO: 121 and SEQ ID NO: 122; or
(xiii) SEQ ID NO: 126 and SEQ ID NO: 127 and SEQ ID NO: 128; or
(xiv) SEQ ID NO: 132 and SEQ ID NO: 133 and SEQ ID NO: 134; or
(xv) SEQ ID NO: 138 and SEQ ID NO: 139 and SEQ ID NO: 140; or
(xvi) SEQ ID NO: 144 and SEQ ID NO: 145 and SEQ ID NO: 146; or
(xvii) SEQ ID NO: 150 and SEQ ID NO: 151 and SEQ ID NO: 152; or
(xviii) SEQ ID NO: 156 and SEQ ID NO: 157 and SEQ ID NO: 158; or
(xix) SEQ ID NO: 162 and SEQ ID NO: 163 and SEQ ID NO: 164; or
(xx) SEQ ID NO: 168 and SEQ ID NO: 169 and SEQ ID NO: 170; or (xxi) SEQ ID NO: 174 and SEQ ID NO: 175 and SEQ ID NO: 176; or
(xxii) SEQ ID NO: 180 and SEQ ID NO: 181 and SEQ ID NO: 182; or
(xxiii) SEQ ID NO: 186 and SEQ ID NO: 187 and SEQ ID NO: 188; or
(xxiv) SEQ ID NO: 192 and SEQ ID NO: 193 and SEQ ID NO: 194.

Preferably, the invention provides a composition, or a use, or a method, or a kit, wherein the agent comprises a variable heavy chain (VH) amino acid sequence selected from the group consisting of: SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; and SEQ ID NO: 26.

Preferably, the invention provides a composition, or a use, or a method, or a kit, wherein the agent comprises a variable light chain (VL) amino acid sequence selected from the group consisting of: SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; and SEQ ID NO: 50.

Preferably, the invention provides a composition, or a use, or a method, or a kit, wherein the agent comprises the following CDR amino acid sequences:
(i) SEQ ID NO: 51 and SEQ ID NO: 52 and SEQ ID NO: 53 and SEQ ID NO: 54 and SEQ ID NO: 55 and SEQ ID NO: 56; or
(ii) SEQ ID NO: 57 and SEQ ID NO: 58 and SEQ ID NO: 59 and SEQ ID NO: 60 and SEQ ID NO: 61 and SEQ ID NO: 62; or
(iii) SEQ ID NO: 63 and SEQ ID NO: 64 and SEQ ID NO: 65 and SEQ ID NO: 66 and SEQ ID NO: 67 and SEQ ID NO: 68; or
(iv) SEQ ID NO: 69 and SEQ ID NO: 70 and SEQ ID NO: 71 and SEQ ID NO: 72 and SEQ ID NO: 73 and SEQ ID NO: 74; or
(v) SEQ ID NO: 75 and SEQ ID NO: 76 and SEQ ID NO: 77 and SEQ ID NO: 78 and SEQ ID NO: 79 and SEQ ID NO: 80; or SEQ ID NO: 81 and SEQ ID NO: 82 and SEQ ID NO: 83 and SEQ ID NO: 84 and SEQ ID NO: 85 and SEQ ID NO: 86; or
(vii) SEQ ID NO: 87 and SEQ ID NO: 88 and SEQ ID NO: 89 and SEQ ID NO: 90 and SEQ ID NO: 91 and SEQ ID NO: 92; or
(viii) SEQ ID NO: 93 and SEQ ID NO: 94 and SEQ ID NO: 95 and SEQ ID NO: 96 and SEQ ID NO: 97 and SEQ ID NO: 98; or
(ix) SEQ ID NO: 99 and SEQ ID NO: 100 and SEQ ID NO: 101 and SEQ ID NO: 102 and SEQ ID NO: 103 and SEQ ID NO: 104; or
(x) SEQ ID NO: 105 and SEQ ID NO: 106 and SEQ ID NO: 107 and SEQ ID NO: 108 and SEQ ID NO: 109 and SEQ ID NO: 110; or
(xi) SEQ ID NO: 111 and SEQ ID NO: 112 and SEQ ID NO: 113 and SEQ ID NO: 114 and SEQ ID NO: 115 and SEQ ID NO: 116; or
(xii) SEQ ID NO: 117 and SEQ ID NO: 118 and SEQ ID NO: 119 and SEQ ID NO: 120 and SEQ ID NO: 121 and SEQ ID NO: 122; or
(xiii) SEQ ID NO: 123 and SEQ ID NO: 124 and SEQ ID NO: 125 and SEQ ID NO: 126 and SEQ ID NO: 127 and SEQ ID NO: 128; or
(xiv) SEQ ID NO: 129 and SEQ ID NO: 130 and SEQ ID NO: 131 and SEQ ID NO: 132 and SEQ ID NO: 133 and SEQ ID NO: 134; or
(xv) SEQ ID NO: 135 and SEQ ID NO: 136 and SEQ ID NO: 137 and SEQ ID NO: 138 and SEQ ID NO: 139 and SEQ ID NO: 140; or
(xvi) SEQ ID NO: 141 and SEQ ID NO: 142 and SEQ ID NO: 143 and SEQ ID NO: 144 and SEQ ID NO: 145 and SEQ ID NO: 146; or
(xvii) SEQ ID NO: 147 and SEQ ID NO: 148 and SEQ ID NO: 149 and SEQ ID NO: 150 and SEQ ID NO: 151 and SEQ ID NO: 152; or
(xviii) SEQ ID NO: 153 and SEQ ID NO: 154 and SEQ ID NO: 155 and SEQ ID NO: 156 and SEQ ID NO: 157 and SEQ ID NO: 158; or
(xix) SEQ ID NO: 159 and SEQ ID NO: 160 and SEQ ID NO: 161 and SEQ ID NO: 162 and SEQ ID NO: 163 and SEQ ID NO: 164; or
(xx) SEQ ID NO: 165 and SEQ ID NO: 166 and SEQ ID NO: 167 and SEQ ID NO: 168 and SEQ ID NO: 169 and SEQ ID NO: 170; or
(xxi) SEQ ID NO: 171 and SEQ ID NO: 172 and SEQ ID NO: 173 and SEQ ID NO: 174 and SEQ ID NO: 175 and SEQ ID NO: 176; or
(xxii) SEQ ID NO: 177 and SEQ ID NO: 178 and SEQ ID NO: 179 and SEQ ID NO: 180 and SEQ ID NO: 181 and SEQ ID NO: 182; or
(xxiii) SEQ ID NO: 183 and SEQ ID NO: 184 and SEQ ID NO: 185 and SEQ ID NO: 186 and SEQ ID NO: 187 and SEQ ID NO: 188; or
(xxiv) SEQ ID NO: 189 and SEQ ID NO: 190 and SEQ ID NO: 191 and SEQ ID NO: 192 and SEQ ID NO: 193 and SEQ ID NO: 194.

Preferably, the invention provides a composition, or a use, or a method, or a kit, wherein the agent comprises the following amino acid sequences:
(i) SEQ ID NO: 3 and SEQ ID NO: 27; or
(ii) SEQ IS NO: 4 and SEQ ID NO: 28; or
(iii) SEQ IS NO: 5 and SEQ ID NO: 29; or
(iv) SEQ ID NO: 6 and SEQ ID NO: 30; or
(v) SEQ ID NO: 7 and SEQ ID NO: 31; or
(vi) SEQ ID NO: 8 and SEQ ID NO: 32; or
(vii) SEQ ID NO: 9 and SEQ ID NO: 33; or
(viii) SEQ ID NO: 10 and SEQ ID NO: 34; or
(ix) SEQ ID NO: 11 and SEQ ID NO: 35; or
(x) SEQ ID NO: 12 and SEQ ID NO: 36; or
(xi) SEQ ID NO: 13 and SEQ ID NO: 37; or
(xii) SEQ ID NO: 14 and SEQ ID NO: 38; or
(xiii) SEQ ID NO: 15 and SEQ ID NO: 39; or
(xiv) SEQ ID NO: 16 and SEQ ID NO: 40; or
(xv) SEQ ID NO: 17 and SEQ ID NO: 41; or
(xvi) SEQ ID NO: 18 and SEQ ID NO: 42; or
(xvii) SEQ ID NO: 19 and SEQ ID NO: 43; or
(xviii) SEQ ID NO: 20 and SEQ ID NO: 44; or
(xix) SEQ ID NO: 21 and SEQ ID NO: 45; or
(xx) SEQ ID NO: 22 and SEQ ID NO: 46; or
(xxi) SEQ ID NO: 23 and SEQ ID NO: 47; or
(xxii) SEQ ID NO: 24 and SEQ ID NO: 48; or
(xxiii) SEQ ID NO: 25 and SEQ ID NO: 49; or
(xxiv) SEQ ID NO: 26 and SEQ ID NO: 50.

The agents of the invention may also comprise the constant regions (CH) and (CL) of SEQ ID NO 1 and SEQ ID NO 2.

In a further embodiment, the agent is capable of competing with the agents of the invention described herein, for example agents comprising the amino acid sequences set out in the embodiments above (for example SEQ ID NOs: 1-194), for preventing or reducing FcγRIIb binding to the Fc domain of the antibody molecule.

By "capable of competing" for preventing or reducing FcγRIIb binding to the Fc domain of the antibody molecule with an agent (such as an antigen molecule) as defined herein we mean that the tested agent is capable of inhibiting or otherwise interfering, at least in part, with the binding of an agent as defined herein to FcγRIIb and preventing or reducing FcγRIIb binding to the Fc domain of the antibody molecule.

For example, the agent may be capable of inhibiting the binding of an agent described herein by at least about 10%; for example at least about 20%, or at least about 30%, at least about 40%, at least about 50%, at least about 60%, at least about 70%, at least about 80%, at least about 90%, at least about 95%, at least about 100% and/or inhibiting the ability of the agent to prevent or reduce FcγRIIb binding to the Fc domain of the antibody molecule by at least about 10%; for example at least about 20%, at least about 30%, at least about 40%, at least about 50%, at least about 60%, at least about 70%, at least about 80%, at least about 90%, at least about 95%, or at least about 100%.

Competitive binding may be determined by methods well known to those skilled in the art, such as Enzyme-linked immunosorbent assay (ELISA).

ELISA assays can be used to evaluate epitope-modifying or blocking antibodies. Additional methods suitable for identifying competing antibodies are disclosed in *Antibodies: A Laboratory Manual*, Harlow & Lane, which is incorporated herein by reference (for example, see pages 567 to 569, 574 to 576, 583 and 590 to 612, 1988, CSHL, NY, ISBN 0-87969-314-2).

The agents of the invention may comprise the following constant regions (CH and CL):

```
IgG1-CH
                                           [SEQ ID NO: 1]
ASTKGPSVFPLAPSSKSTSGGTAALGCLVKDYFPEPVTVSWNSGALTSGV

HTFPAVLQSSGLYSLSSWTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRWSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHEALHNHYTQKSLSLSPGK

I-CL
                                           [SEQ ID NO: 2]
QPKAAPSVTLFPPSSEELQANKATLVCLISDFYPGAVTVAWKADSSPVKA
GVETTTPSKQSNNKYAASSYLSLTPEQWKSHRSYSCQVTHEGSTVEKTVA
PTECS
```

The agents of the invention may comprise one or more sequences of the following clones:

```
Antibody clone: 1A01
1A01-VH
                                           [SEQ ID NO: 3]
EVQLLESGGGLVQPGGSLRLSCAASGFTFSDYYMNWIRQTPGKGLEWVSLIGWDGGS

TYYADSVKGRFTISRDNSENTLYLQMNSLRAEDTAVYYCARAYSGYELDYWGQGTLVT

VSS

1A01-VL
                                           [SEQ ID NO: 27]
QSVLTQPPSASGTPGQRVTISCSGSSSNIGNNAVNWYQQLPGTAPKLLIYDNNNRPSG

VPDRFSGSKSGTSASLAISGLRSEDEADYYCAAWDDSLNASIFGGGTKLTVLG

CDR regions
                                           [SEQ ID NO: 51]
CDRH1: DYYMN
                                           [SEQ ID NO: 52]
CDRH2: LIGWDGGSTYYADSVKG
                                           [SEQ ID NO: 53]
CDRH3: AYSGYELDY
                                           [SEQ ID NO: 54]
CDRL1: SGSSSNIGNNAVN
                                           [SEQ ID NO: 55]
CDRL2: DNNNRPS
                                           [SEQ ID NO: 56]
CDRL3: AAWDDSLNASI Antibody clone: 1B07
                                           [SEQ ID NO: 4]
EVQLLESGGGLVQPGGSLRLSCAASGFTFSSYGMHWVRQAPGKGLEWVAFTRYDGS

NKYYADSVRGRFTISRDNSKNTLYLQMNSLRAEDTAVYYCARENIDAFDVWGQGTLVT

VSS
```

```
1B07-VL
                                                       [SEQ ID NO: 28]
QSVLTQPPSASGTPGQRVTISCSGSSSNIGNNAVNWYQQLPGTAPKLLIYDNQQRPSG

VPDRFSGSKSGTSASLAISGLRSEDEADYYCEAWDDRLFGPVFGGGTKLTVLG

CDR regions
                                                       [SEQ ID NO: 57]
CDRH1: SYGMH
                                                       [SEQ ID NO: 58]
CDRH2: FTRYDGSNKYYADSVRG
                                                       [SEQ ID NO: 59]
CDRH3: ENIDAFDV
                                                       [SEQ ID NO: 60]
CDRL1: SGSSSNIGNNAVN
                                                       [SEQ ID NO: 61]
CDRL2: DNQQRPS
                                                       [SEQ ID NO: 62]
CDRL3: WDDRLFGPV Antibody clone: 1C04
1C04-VH
                                                       [SEQ ID NO: 5]
EVQLLESGGGLVQPGGSLRLSCAASGFTFSSYAMSWVRQAPGKGLEWVSSISDSGAG

RYYADSVEGRFTISRDNSKNTLYLQMNSLRAEDTAVYYCARTHDSGELLDAFDIWGQG

TLVTVSS

1C04-VL
                                                       [SEQ ID NO: 29]
QSVLTQPPSASGTPGQRVTISCSGSSSNIGSNHVLWYQQLPGTAPKLLIYGNSNRPSG

VPDRFSGSKSGTSASLAISGLRSEDEADYYCAAWDDSLNGWVFGGGTKLTVLG

CDR regions
                                                       [SEQ ID NO: 63]
CDRH1: SYAMS
                                                       [SEQ ID NO: 64]
CDRH2: SISDSGAGRYYADSVEG
                                                       [SEQ ID NO: 65]
CDRH3: THDSGELLDAFDI
                                                       [SEQ ID NO: 66]
CDRL1: SGSSSNIGSNHVL
                                                       [SEQ ID NO: 67]
CDRL2: GNSNRPS
                                                       [SEQ ID NO: 68]
CDRL3: AAWDDSLNGWV Antibody clone: 1E05
1E05-VH
                                                       [SEQ ID NO: 6]
EVQLLESGGGLVQPGGSLRLSCAASGFTFSTYAMNWVRQVPGKGLEWVAVISYDGSN

KNYVDSVKGRFTISRDNSKNTLYLQMNSLRAEDTAVYYCARNFDNSGYAIPDAFDIWG

QGTLVTVSS

1E05-VL
                                                       [SEQ ID NO: 30]
QSVLTQPPSASGTPGQRVTISCTGSSSNIGAGYDVHWYQQLPGTAPKLLIYDNNSRPS

GVPDRFSGSKSGTSASLAISGLRSEDEADYYCAAWDDSLGGPVFGGGTKLTVLG

CDR regions
                                                       [SEQ ID NO: 69]
CDRH1: TYAMN
                                                       [SEQ ID NO: 70]
CDRH2: VISYDGSNKNYVDSVKG
                                                       [SEQ ID NO: 71]
CDRH3: NFDNSGYAIPDAFDI
```

-continued

```
CDRL1: TGSSSNIGAGYDVH                                    [SEQ ID NO: 72]

[SEQ ID NO: 73]
CDRL2: DNNSRPS
                                                         [SEQ ID NO: 74]
CDRL3: AAWDDSLGGPV

Antibody clone: 2A09
2A09-VH
                                                         [SEQ ID NO: 7]
EVQLLESGGGLVQPGGSLRLSCAASGFTFSNAWMSWVRQAPGKGLEWVAYISRDADI

THYPASVKGRFTISRDNSKNTLYLQMNSLRAEDTAVYYCTIGFDYAGDDAFDIWGQT

LVTVSS

2A09-VL
                                                         [SEQ ID NO: 31]
QSVLTQPPSASGTPGQRVTISCSGSSSNIGSNAVNWYQQLPGTAPKLLIYGNSDRPSG

VPDRFSGSKSGTSASLAISGLRSEDEADYYCAAWDDSLNGRWVFGGGTKLTVLG

CDR regions
                                                         [SEQ ID NO: 75]
CDRH1: NAWMS
                                                         [SEQ ID NO: 76]
CDRH2: YISRDADITHYPASVKG
                                                         [SEQ ID NO: 77]
CDRH3: GFDYAGDDAFDI
                                                         [SEQ ID NO: 78]
CDRL1: SGSSSNIGSNAVN
                                                         [SEQ ID NO: 79]
CDRL2: GNSDRPS
                                                         [SEQ ID NO: 80]
CDRL3: AAWDDSLNGRWV Antibody clone: 2B08
2B08-VH
                                                         [SEQ ID NO: 8]
EVQLLESGGGLVQPGGSLRLSCAASGFTFSDYYMSWVRQAPGKGLEWVALIGHDGNN

KYYLDSLEGRFTISRDNSKNTLYQMNSLRAEDTAVYYCARATDSGYDLLYWGQTLV

TVSS

2B08-VL
                                                         [SEQ ID NO: 32]
QSVLTQPPSASGTPGQRVTISCSGSSSVIGNNAVNWYQQLPGTAPKLLIYYDDLLPSGV

PDRFSGSKSGTSASLAISGLRSEDEADYYCTTWDDSLSGVVFGGGTKLTVLG

CDR regions
                                                         [SEQ ID NO: 81]
CDRH1: DYYMS
                                                         [SEQ ID NO: 82]
CDRH2: LIGHDGNNKYYLDSLEG
                                                         [SEQ ID NO: 83]
CDRH3: ATDSGYDLLY
                                                         [SEQ ID NO: 84]
CDRL1: SGSSSNIGNNAVN
                                                         [SEQ ID NO: 85]
CDRL2: YDDLLPS
                                                         [SEQ ID NO: 86]
CDRL3: TTWDDSLSGVV
```

```
Anitbody clone: 2E08
2E08-VH
                                                            [SEQ ID NO: 9]
EVQLLESGGGLVQPGGSLRLSCAASGFTFSDYYMSWIRQAPGKGLEWVSAIGFSDDNT

YYADSVKGRFTISRDNSKNTLYLQMNSLRAEDTAVYYCAGGDGSGWSFWGQGTLVTV

SS

2E08-VL
                                                           [SEQ ID NO: 33]
WSVLTQPPSASGTPGQRVTISCSGSSSNIGNNAVNWYQQLPGTAPKLLIYDNNKRPSG

VPDRFSGSKSGTSASLAISGLRSEDEADYYCATWDDSLRGWVFGGGTKLTVLG

CDR regions
                                                           [SEQ ID NO: 87]
CDRH1: DYYMS
                                                           [SEQ ID NO: 88]
CDRH2: AIGFSDDNTYYADSVKG
                                                           [SEQ ID NO: 89]
CDRH3: GDGSGWSF
                                                           [SEQ ID NO: 90]
CDRL1: SGSSSNIGNNAVN
                                                           [SEQ ID NO: 91]
CDRL2: DNNKRPS
                                                           [SEQ ID NO: 92]
CDRL3: ATWDDSLRGWV Antibody clone: 5C04
5C04-VH
                                                           [SEQ ID NO: 10]
EVQLLESGGGLVQPGGSLRLSCAASGFTFSNYGMHWVRQAPGKGLEWVAVISYDGSN

KYYADSVKGRFTISRDNSKNTLYLQMNSLRAEDTAVYYCAREWRDAFDIWGQGTLVTV

SS

5C04-VL
                                                           [SEQ ID NO: 34]
QSVLTQPPSASGTPGQRVTISCTGSSSNIGAGYDVHWYQQLPGTAPKLLIYSDNQRPS

GVPDRFSGSKSGTSASLAISGLRSEDEADYYCAAWDDSLSGSWVFGGGTKLTVLG

CDR regions
                                                           [SEQ ID NO: 93]
CDRH1: NYGMH
                                                           [SEQ ID NO: 94]
CDRH2: VISYDGSNKYYADSVKG
                                                           [SEQ ID NO: 95]
CDRH3: WRDAFDI
                                                           [SEQ ID NO: 96]
CDRL1: TGSSSNIGAGYDVH
                                                           [SEQ ID NO: 97]
CDRL2: SDNQRPS
                                                           [SEQ ID NO: 98]
CDRL3: AAWDDSLSGSWV Antibody clone: 5C05
5C05-VH
                                                           [SEQ ID NO: 11]
EVQLLESGGGLVQPGGSLRLSCAASGFTFSTYGMHWVRQAPGKGLEWVAVISYDGSN

KYYADSVKGRFTISRDNSKNTLYLQMNSLRAEDTAVYYCARENFDAGDVWGQGTLVTV

SS
```

-continued

5C05-VL
[SEQ ID NO: 35]
QSVLTQPPSASGTPGQRVTISC TGSSSNIGAGYDVH WYQQLPGTAPKLLIY SNSQRPS

GVPDRFSGSKSGTSASLAISGLRSEDEADYYC AAWDDSLNGQVV FGGGTKLTVLG

CDR regions
[SEQ ID NO: 99]
CDRH1: TYGMH
[SEQ ID NO: 100]
CDRH2: VISYDGSNKYYADSVKG
[SEQ ID NO: 101]
CDRH3: ENFDAFDV
[SEQ ID NO: 102]
CDRL1: TGSSSNIGAGYDVH
[SEQ ID NO: 103]
CDRL2: SNSQRPS
[SEQ ID NO: 104]
CDRL3: AAWDDSLNGQVV Antibody clone: 5D07
5D07-VH
[SEQ ID NO: 12]
EVQLLESGGGLVQPGGSLRLSCAASGFTFS TYGMH WVRQAPGKGLEWVA VIAYDGSK

KDYADSVKG RFTISRDNSKNTLYLQMNSLRAEDTAVYYCAR EYRDAFDI WGQGTLVTV

SS

5D07-VL
[SEQ ID NO: 36]
QSVLTQPPSASGTPGQRVTISC TGSSSNIGAGYDVH WYQQLPGTAPKLLIY GNSNRPS

GVPDRFSGSKSGTTASLAISGLRSEDEADYYC AAWDDSVSGWM FGGGTKLTVLG

CDR regions
[SEQ ID NO: 105]
CDRH1: TYGMH
[SEQ ID NO: 106]
CDRH2: VIAYDGSKKDYADSVKG
[SEQ ID NO: 107]
CDRH3: EYRDAFDI
[SEQ ID NO: 108]
CDRL1: TGSSSNIGAGYDVH
[SEQ ID NO: 109]
CDRL2: GNSNRPS
[SEQ ID NO: 110]
CDRL3: AAWDDSVSGWM Antibody clone: 5E12
[SEQ ID NO: 13]
EVQLLESGGGLVQPGGSLRLSCAASGFTFS SYGMH WVRQAPGKGLEWVA VISYDGIN

KDYADSMKG RFTISRDNSKNTLYLQMNSLRAEDTAVYYCAR ERKDAGDI WGQGTLVTV

SS

5E12-VL
[SEQ ID NO: 37]
QSVLTQPPSASGTPGQRVTISC TGSSSNIGAGYDVH WYQQLPGTAPKLLIY SNNQRPS

GVPDRFSGSKSGTSASLAISGLRSEDEADYYC ATWDDSLNGLV FGGGTKLTVLG

CDR regions
[SEQ ID NO: 111]
CDRH1: SYGMH
[SEQ ID NO: 112]
CDRH2: VISYDGINKDYADSMKG
[SEQ ID NO: 113]
CDRH3: ERKDAFDI -continued

CDRL1: TGSSSNIGAGYDVH [SEQ ID NO: 114]

CDRL2: SNNQRPS [SEQ ID NO: 115]

CDRL3: ATWDDSLNGLV [SEQ ID NO: 116]

Antibody clone: 5G08
5G08-VH
[SEQ ID NO: 14]
EVQLLESGGGLVQPGGSLRLSCAASGFTFN NYGMH WVRQAPGKGLEWVA VISYDGSN RYYADSVKG RFTMSRDNSKNTLYLQMNSLRAEDTAVYYCAR DRWNGMDV WGQGTLVTVSS 5G08-VL
[SEQ ID NO: 38]
QSVLTQPPSASGTPGQRVTISC SGSSSNIGAGYDVH WYQQLPGTAPKLLIY ANNQRPS GVPDRFSGSKSGTSASLAISGLRSEDEADYYC AAWDDSLNGPWV FGGGTKLTVLG CDR regions
CDRH1: NYGMH [SEQ ID NO: 117]

CDRH2: VISYDGSNRYYADSVKG [SEQ ID NO: 118]

CDRH3: DRWNGMDV [SEQ ID NO: 119]

CDRL1: SGSSSNIGAGYDVH [SEQ ID NO: 120]

CDRL2: ANNQRPS [SEQ ID NO: 121]

CDRL3: AAWDDSLNGPWV [SEQ ID NO: 122]

Antibody clone: 5H06
5H06-VH
[SEQ ID NO: 15]
EVQLLESGGGLVQPGGSLRLSCAASGFTFS SYGMH WVRQAPGKGLEWVA VISYDGSD TAYADSVKG RFTISRDNSKNTLYLQMNSLRAEDTAVYYCAR DHSVIGAFDI WGQGTLVTVSS 5H06-VL
[SEQ ID NO: 39]
QSVLTQPPSASGTPGQRVTISC SGSSSNIGSNTVN WYQQLPGTAPKLLIY DNNKRPS GVPDRFSGSKSGTSASLAISGLRSEDEADYYC SSYAGSNNVV FGGGTKLTVLG CDR regions
CDRH1: SYGMH [SEQ ID NO: 123]

CDRH2: VISYDGSDTAYADSVKG [SEQ ID NO: 124]

CDRH3: DHSVIGAFDI [SEQ ID NO: 125]

CDRL1: SGSSSNIGSNTVN [SEQ ID NO: 126]

CDRL2: DNNKRPS [SEQ ID NO: 127]

CDRL3: SSYAGSNNVV [SEQ ID NO: 128]

-continued

```
Antibody clone: 6A09
6A09-VH
                                                [SEQ ID NO: 16]
EVQLLESGGGLVQPGGSLRLSCAASGFTFSSYGMHWVRQAPGKGLEWVAVTSYDGN

TKYYANSVKGRFTISRDNSKNTLYLQMNSLRAEDTAVYYCAREDCGGDCFDYWGQGT

LVTVSS

6A09-VL
                                                [SEQ ID NO: 40]
QSVLTQPPSASGTPGQRVTISCTGSSSNIGAGYDVHWYQQLPGTAPKLLIYGNSNRPS

GVPDRFSGSKSGTSASLAISGLRSEDEADYYCAAWDDSLNEGVFGGGTKLTVLG

CDR regions
                                                [SEQ ID NO: 129]
CDRH1: SYGMH
                                                [SEQ ID NO: 130]
VTSYDGNTKYYANSVKG
                                                [SEQ ID NO: 131]
CDRH3: EDCGGDCFDY
                                                [SEQ ID NO: 132]
CDRL1: TGSSSNIGAGYDVH
                                                [SEQ ID NO: 133]
CDRL2: GNSNRPS
                                                [SEQ ID NO: 134]
CDRL3: AAWDDSLNEGV Antibody clone: 6B01
6B01-VH
                                                [SEQ ID NO: 17]
EVQLLESGGGLVQPGGSLRLSCAASGFTFSNYGMHWVRQAPGKGLEWVAVISYDGSN

KYYADSVKGRFTISRDNSKNTLYLQMNSLRAEDTAVYYCARDQLGEAFDIWGQGTLVT

VSS

6B01-VL
                                                [SEQ ID NO: 41]
QSVLTQPPSASGTPGQRVTISCTGSSSNIGAGYDVHWYQQLPGTAPKLLIYDNNKRPS

GVPDRFSGSKSGTSASLAISGLRSEDEADYYCATWDDSLSGPVFGGGTKLTVLG

CDR regions
                                                [SEQ ID NO: 135]
CDRH1: NYGMH
                                                [SEQ ID NO: 136]
CDRH2: VISYDGSNKYYADSVKG
                                                [SEQ ID NO: 137]
CDRH3: DQLGEAFDI
                                                [SEQ ID NO: 138]
CDRL1: TGSSSNIGAGYDVH
                                                [SEQ ID NO: 139]
CDRL2: DNNKRPS
                                                [SEQ ID NO: 140]
CDRL3: ATWDDSLSGPV Antibody clone: 6C11
6C11-VH
                                                [SEQ ID NO: 18]
EVQLLESGGGLVQPGGSLRLSCAASGFTFDDYGMSWVRQAPGKGLEWVSAISGSGSS

TYYADSVKGRFTISRDNSKNTLYLQMNSLRAEDTAVYYCAGGDIDYFDYWGQGTLVTV

SS
```

6C11-VL

[SEQ ID NO: 42]

QSVLTQPPSASGTPGQRVTISCTGSSSNFGAGYDVHWYQQLPGTAPKLLIYENNKRPS

GVPDRFSGSKSGTSASLAISGLRSEDEADYYCAAWDDSLNGPVFGGGTKLTVLG

CDR regions

CDRH1: DYGMS [SEQ ID NO: 141]

CDRH2: AISGSGSSTYYADSVKG [SEQ ID NO: 142]

CDRH3: GDIDYFDY [SEQ ID NO: 143]

CDRL1: TGSSSNFGAGYDVH [SEQ ID NO: 144]

CDRL2: ENNKRPS [SEQ ID NO: 145]

CDRL3: AAWDDSLNGPV [SEQ ID NO: 146]

Antibody clone: 6C12
6C12-VH

[SEQ ID NO: 19]

EVQLLESGGGLVQPGGSLRLSCAASGFTFSSYGMHWVRQAPGKGLEWVAVISYDGSNKYYADSVKGRFTISRDNSKNTLYLQMNSLRAEDTAVYYCARERRDAFDIWGQGTLVTVSS

6C12-VL

[SEQ ID NO: 43]

QSVLTQPPSASGTPGQRVTISCTGSSSNIGAGYDVHWYQQLPGTAPKLLIYSDNQRPS

GVPDRFSGSKSGTSASLAISGLRSEDEADYYCATWDSDTPVFGGGTKLTVLG

CDR regions

CDRH1: SYGMH [SEQ ID NO: 147]

CDRH2: VISYDGSNKYYADSVKG [SEQ ID NO: 148]

CDRH3: ERRDAFDI [SEQ ID NO: 149]

CDRL1: TGSSSNIGAGYDVH [SEQ ID NO: 150]

CDRL2: SDNQRPS [SEQ ID NO: 151]

CDRL3: ATWDSDTPV [SEQ ID NO: 152]

Antibody clone: 6D01

6D01-VH

[SEQ ID NO: 20]

EVQLLESGGGLVQPGGSLRLSCAASGFTFSSYGMHWVRQAPGKGLEWVAVISYDGSNKYYADSVKGRFTISRDNSKNTLYLQMNSLRAEDTAMYYCARDHSAAGYFDYWGQGTLVTVSS

6D01-VL

[SEQ ID NO: 44]

QSVLTQPPSASGTPGQRVTISCSGSSSNIGSNTVNWYQQLPGTAPKLLIYGNSIRPSGGPDRFSGSKSGTSASLAISGLRSEDEADYYCASWDDSLSSPVFGGGTKLTVLG

CDR regions

CDRH1: SYGMH [SEQ ID NO: 153]

CDRH2: VISYDGSNKYYADSVKG [SEQ ID NO: 154]

-continued

```
                                               [SEQ ID NO: 155]
CDRH3: DHSAAGYFDY
                                               [SEQ ID NO: 156]
CDRL1: SGSSSNIGSNTVN
                                               [SEQ ID NO: 157]
CDRL2: GNSIRPS
                                               [SEQ ID NO: 158]
CDRL3: ASWDDSLSSPV

Antibody clone: 6G03
6G03-VH
                                               [SEQ ID NO: 21]
EVQLLESGGGLVQPGGSLRLSCAASGFTFGSYGMHWVRQAPGKGLEWVSGISWDSAI

IDYAGSVKGRFTISRDNSKNTLYLQMNSLRAEDTAVYYCAKDEAAAGAFDIWGQGTLVT

VSS

6G03-VL
                                               [SEQ ID NO: 45]
QSVLTQPPSASGTPGQRVTISCTGSSSNIGAGYDVHWYQQLPGTAPKLLIYGNTDRPS

GVPDRFSGSKSGTSASLAISGLRSEDEADYYCAAWDDSLSGPVVFGGGTKLTVLG

CDR regions
                                               [SEQ ID NO: 159]
CDRH1: SYGMH
                                               [SEQ ID NO: 160]
CDRH2: GISWDSAIIDYAGSVKG
                                               [SEQ ID NO: 161]
CDRH3: DEAAAGAFDI
                                               [SEQ ID NO: 162]
CDRL1: TGSSSNIGAGYDVH
                                               [SEQ ID NO: 163]
CDRL2: GNTDRPS
                                               [SEQ ID NO: 164]
CDRL3: AAWDDSLSGPVV Antibody clone: 6G08
6G08-VH
                                               [SEQ ID NO: 22]
EVQLLESGGGLVQPGGSLRLSCAASGFTLSSYGISWVRQAPGKGLEWVSGISGSGGN

TYYADSVKGRFTISRDNSKNTLYLQMNSLRAEDTAVYYCASSVGAYANDAFDIWGQGT

LVTVSS

6G08-VL
                                               [SEQ ID NO: 46]
QSVLTQPPSASGTPGQRVTISCTGSSSNIGAGYDVHWYQQLPGTAPKLLIYGDTNRPS

GVPDRFSGSKSGTSASLAISGLRSEDEADYYCAAWDDSLNGPVFGGGTKLTVLG

CDR regions
                                               [SEQ ID NO: 165]
CDRH1: SYGIS
                                               [SEQ ID NO: 166]
CDRH2: GISGSGGNTYYADSVKG
                                               [SEQ ID NO: 167]
CDRH3: SVGAYANDAFDI
                                               [SEQ ID NO: 168]
CDRL1: TGSSSNIGAGYDVH
                                               [SEQ ID NO: 169]
CDRL2: GDTNRPS
                                               [SEQ ID NO: 170]
CDRL3: AAWDDSLNGPV
```

```
Antibody clone: 6G11
6G11-VH
                                            [SEQ ID NO: 23]
EVQLLESGGGLVQPGGSLRLSCAASGFTFSSYGMHWVRQAPGKGLEWMAVISYDGS

NKYYADSVKGRFTISRDNSKNTLYLQMNSLRAEDTAVYYCARELYDAFDIWGQGTLVTV

SS

6G11-VL
                                            [SEQ ID NO: 47]
QSVLTQPPSASGTPGQRVTISCTGSSSNIGAGYDVHWYQQLPGTAPKLLIYADDHRPS

GVPDRFSGSKSGTSASLAISGLRSEDEADYYCASWDDSQRAVIFGGGTKLTVLG

CDR regions
                                            [SEQ ID NO: 171]
CDRH1: SYGMH
                                            [SEQ ID NO: 172]
CDRH2: VISDGSNKYYADSVKG
                                            [SEQ ID NO: 173]
CDRH3: ELYDAFDI
                                            [SEQ ID NO: 174]
CDRL1: TGSSSNIGAGYDVH
                                            [SEQ ID NO: 175]
CDRL2: ADDHRPS
                                            [SEQ ID NO: 176]
CDRL3: ASWDDSQRAVI Antibody clone: 6H08
6H08-VH
                                            [SEQ ID NO: 24]
EVQLLESGGGLVQPGGSLRLSCAASGFTFNNYGMHWVRQAPGKGLEWVAVISYDGSN

KYYADSVKGRFTISKDNSKNTLYLQMNSLRAEDTAVYYCAREYKDAFDIWGQGTLVTVS

S

6H08-VL
                                            [SEQ ID NO: 48]
QSVLTQPPSASGTPGQRVTISCTGSSSNIGSNTVNWYQQLPGTAPKLLIYDNNKRPSGV

PDRFSGSKSGTSASLAISGLRSEDEADYYCQAWGTGIRVFGGGTKLTVLG

CDR regions
                                            [SEQ ID NO: 177]
CDRH1: NYGMH
                                            [SEQ ID NO: 178]
CDRH2: VISYDGSNKYYAD SVKG
                                            [SEQ ID NO: 179]
CDRH3: EYKDAFDI
                                            [SEQ ID NO: 180]
CDRL1: TGSSSNIGSNTVN
                                            [SEQ ID NO: 181]
CDRL2: DNNKRPS
                                            [SEQ ID NO: 182]
CDRL3: QAWGTGIRV Antibody clone: 7C07
7C07-VH
                                            [SEQ ID NO: 25]
EVQLLESGGGLVQPGGSLRLSCAASGFTFSSYGMHWVRQAPGKGLEWVAVISYDGSN

KYYADSVKGRFTISRDNSQNTLYLQMNSLRAEDTAVYYCAREFGYIILDYWGQGTLVTV

SS
```

```
7C07-VL
                                                            [SEQ ID NO: 49]
QSVLTQPPSASGTPGQRVTISCSGSSSNIGSNTVNWYQQLPGTAPKLLIYRDYERPSGV

PDRFSGSKSGTSASLAISGLRSEDEADYYCMAWDDSLSGVVFGGGTKLTVLG

CDR regions
                                                            [SEQ ID NO: 183]
CDRH1: SYGMH
                                                            [SEQ ID NO: 184]
CDRH2: VISYDGSNKYYADSVKG
                                                            [SEQ ID NO: 185]
CDRH3: EFGYIILDY
                                                            [SEQ ID NO: 186]
CDRL1: SGSSSNIGSNTVN
                                                            [SEQ ID NO: 187]
CDRL2: RDYERPS
                                                            [SEQ ID NO: 188]
CDRL3: MAWDDSLSGVV Antibody clone: 4B02
4B02-VH
                                                            [SEQ ID NO: 26]
EVQLLESGGGLVQPGGSLRLSCAASGFTFSNHGMHWVRQAPGKGLEWVAVISYDGTN

KYYADSVRGRFTISRDNSKNTLYLQMNSLRAEDTAVYYCARETWDAGDVWGQGTLVT

VSS

4B02-VL
                                                            [SEQ ID NO: 50]
QSVLTQPPSASGTPGQRVTISCSGSSSNIGSNNANWYQQLPGTAPKLLIYDNNKRPSG

VPDRFSGSKSGTSASLAISGLRSEDEADYYCQAWDSSTVVFGGGTKLTVLG

CDR regions
                                                            [SEQ ID NO: 189]
CDRH1: NHGMH
                                                            [SEQ ID NO: 190]
CDRH2: VISYDGTNKYYADSVRG
                                                            [SEQ ID NO: 191]
CDRH3: ETWDAFDV
                                                            [SEQ ID NO: 192]
CDRL1: SGSSSNIGSNNAN
                                                            [SEQ ID NO: 193]
CDRL2: DNNKRPS
                                                            [SEQ ID NO: 194]
CDRL3: QAWDSSTVV
```

Preferably, the invention provides a composition, or a use, or a method, or a kit, wherein the agent is an agent capable of competing with the agents as defined in in earlier embodiments for preventing or reducing FcγRIIb binding to the Fc domain of the antibody molecule.

Preferably, the invention provides a composition, or a use, or a method, or a kit, wherein the agent prevents or reduces FcγRIIb signalling.

Fc receptors can modulate cell behaviour through cell signalling. It would be known to the person skilled in cell biology what downstream cell signalling modulators are activated and/or deactivated by FcγRIIb signalling, and what the effects activating and/or deactivating those cell signalling modulators would have on the cell.

By "the agent prevents or reduces FcγRIIb signalling", we include that FcγRIIb signalling is prevented or reduced when FcγRIIb is bound to an Fc domain, and/or that FcγRIIb signalling is prevented or reduced when FcγRIIb is not bound to an Fc domain.

Preferably, the invention provides a composition, or a use, or a method, or a kit, wherein the agent prevents or reduces internalization of the antibody molecule by the target cell.

Preferably, the invention provides a composition, or a use, or a method, or a kit, wherein the cell surface antigen is selected from the group comprising of: CD19: or a portion thereof; CD20: or a portion thereof; CD40: or a portion thereof; CD52: or a portion thereof; Thy-1 (i.e. CD90, Cluster of Differentiation 90 (Biofactors. 2009 May-June; 35(3):258-65)): or a portion thereof; Ly-6 (i.e. Lymphocyte Antigen 6 (Mol Biol Rep. 2009 April; 36(4):697-703)): or a portion thereof; CD59 (i.e. Complement regulatory protein (Mol Immunol. 2007 January; 44(I-3):73-81)): or a portion thereof; Fas (i.e. FS7-associated cell surface antigen, CD95, APO-1 or TNFRSF6 (Adv Exp Med Biol. 2009; 647:64-93)): or a portion thereof; EGFR (i.e. Epidermal Growth Factor Receptor (FEBS J. 2010 January; 277(2):301-8)): or a portion thereof; Her2 (i.e. Human epidermal growth factor receptor 2 (Clin Breast Cancer. 2008 October; 8(5): 392-401)): or a portion thereof; CXCR4 (i.e. Chemokine Receptor 4 (Biochim Biophys Acta. 2007 April; 1768(4):952-63)): or a portion thereof; HLA Molecules (i.e. Human Leukocyte Antigen molecules (Korean J Lab Med. 2010 June; 30(3): 203)): or a portion thereof; GM1 (i.e. ganglioside, monosialotetrahexosylganglioside (J Lipid Res. 2010 September; 51(9):2731-8)): or a portion thereof; CD22 (i.e. Cheson (2008) NEJM 359(6): 613-26): or a portion thereof; CD23 (Cheson, 2008): or a portion thereof; CD80 (Cheson, 2008): or a portion thereof; CD74 (Cheson, 2008): or a portion thereof; DRD (Cheson, 2008): or a portion thereof.

Preferably, the invention provides a composition, or a use, or a method, or a kit, wherein the antibody molecule as defined in (i) specifically binds to CD20.

Preferably, the invention provides a composition, or a use, or a method, or a kit, wherein the antibody molecule as defined in (i) is a Type I CD20 antibody.

Preferably, the invention provides a composition, or a use, or a method, or a kit, wherein the antibody molecule as defined in (i) is a Type II CD20 antibody.

There are two types of CD20 antibody molecules, which were first defined by the inventors as falling into different groupings in 2003 (Cragg et al., 2003. Complement-mediated lysis by anti-CD20 mAb correlates with segregation into lipid rafts. Blood 101:1045-1052 and Chan, et al., 2003. CD20-induced lymphoma cell death is independent of both caspases and its redistribution into triton X-100 insoluble membrane rafts. Cancer Res 63:5480-5489) and then subsequently defined as Type I and II antibody molecule in 2004 (Cragg and Glennie 2004. Antibody specificity controls in vivo effector mechanisms of anti-CD20 reagents. Blood 103:2738-2743). Initially the basis for this was that anti-CD20 mAb fall into two distinct types of reagents based on their ability to eradicate lymphoma xenografts: type I (e.g. rituximab and 1F5) utilize complement; and type II (e.g. BI), do not. Both types of antibody molecule gave excellent prolongation of survival, but depleting complement activity, by administering CVF, considerably diminished the potency of rituximab and 1F5, but had no effect on the activity of BI. These results clearly showed that different CD20 antibody molecules operate different effector mechanisms in vivo. Furthermore, they are in complete accord with previous work showing that rituximab and 1F5 are able to activate complement efficiently as a result of translocating CD20 to lipid rafts in the target cell membrane, something that BI-type antibody molecule cannot do (Cragg et al., 2003. Complement-mediated lysis by anti-CD20 mAb correlates with segregation into lipid rafts. Blood 101:1045-1052). There is an excellent correlation with the ability of the antibody molecule to engage complement and induce CD20 to move into lipid rafts (Cragg et al., 2003. Complement-mediated lysis by anti-CD20 mAb correlates with segregation into lipid rafts. Blood 101:1045-1052 and Cragg, and Glennie 2004. Antibody specificity controls in vivo effector mechanisms of anti-CD20 reagents. Blood 103:2738-2743). Therefore Type I and II nature can be defined by their ability to move CD20 into lipid rafts. This can be determined as indicated below. There is also a correlation with Type II antibody molecule being able to elicit more potent homotypic adhesion and direct cell death but these could not be used alone to define a Type I or II antibody molecule (unlike the Tx-100 raft assays; see below).

Therefore, various anti-CD20 antibody molecules be classified as type I (e.g. rituximab an ofatumumab) or type II (e.g. tositumomab (BI), GA101 and 11B8) according to their ability to redistribute CD20 in the plasma membrane and their activity in various effector assays (Weng and Levy 2009. Genetic polymorphism of the inhibitory IgG Fc receptor FcgammaRIIb is not associated with clinical outcome in patients with follicular lymphoma treated with rituximab. Leuk Lymphoma 50:723-727., Chan et al., 2003. CD20-induced lymphoma cell death is independent of both caspases and its redistribution into triton X-100 insoluble membrane rafts. Cancer Res 63:5480-5489 and Cragg and Glennie2004. Antibody specificity controls in vivo effector mechanisms of anti-CD20 reagents. Blood 103:2738-2743). Type I (e.g. rituximab, ofatumumab) anti-CD20 antibody molecules induce CD20 to redistribute into large detergent resistant microdomains (rafts), whereas type II (tositumomab-like) anti-CD20 monoclonal antibodies do not (Beer et al., 2010. Seminars in Haematology 47(2):pp 107-114).

As discussed above, anti-CD20 antibody molecules can be designated as Type I or Type II by virtue of whether they redistribute CD20 into lipid rafts. This is done by the Tx-100 insolubility assay or by sucrose density gradient separation and western blotting. Both methods are described in Cragg et al Blood 2003 as follows:

1. Assessment of Raft Associated Antigen by Triton X-100 Insolubility

As a rapid assessment of antigen presence in raft microdomains, we utilised a flow cytometry method based on Triton X-100 insolubility at low temperatures. In brief, cells were washed in RPMI/1% BSA and resuspended at $2.5 \times 10^6$/ml. Cells were then incubated with 10 µg/ml of an FITC conjugated mAb for 15 minutes at 37° C., washed in cold PBS/1% BSA/20 mM sodium azide, and then the sample divided in half. One half was maintained on ice to allow calculation of 100% surface antigen levels, whilst the other was treated with 0.5% Triton X-100 for 15 minutes on ice to determine the proportion of antigens remaining in the insoluble raft fraction. Cells were then maintained at 4° C. throughout the remainder of the assay, washed once in PBS/BSA/azide, resuspended and assessed by flow cytometry as detailed above. Similar results were obtained using indirect methods of detection. To determine the constitutive level of raft association of target antigens, cells were first treated with 0.5% Triton X-100 for 15 minutes on ice and washed in PBS/BSA/azide prior to binding of FITC-labeled mAb. To assess whether more antigen could be moved into the Triton X-100 insoluble fraction by additional cross-linking, cells were incubated with FITC-mAb as before, washed and then divided into four. Two of these samples were incubated with goat anti-mouse Ig F(ab')2 fragments for 15 minutes on ice. After washing, one of the cross-linked and one of the non-cross-linked samples were lysed in Triton X-100 and washed as detailed above prior to flow cytometry.

2. Sucrose Density Gradient Separation and Western Blotting—Preparation of Lipid Raft Fractions and Western Blotting Monoclonal Ab (1 µg/$10^6$ cells) was added to cells at 37° C. Following 20 minutes incubation, cells were pelleted and lysed in ice-cold 1.0% Triton X-100 in MES-buffered saline (25 mM MES, pH 6.5, 150 mM NaCl, 1 mM phenylmethylsulfonyl fluoride, 5 ug/ml aprotinin, 5 µg/ml leupeptin, 10 mM EDTA). Lipid raft fractions were then prepared by sucrose density gradient centrifugation. Briefly, lysates were mixed with an equal volume of 80% sucrose in lysis buffer, overlaid with a discontinuous 5-30% sucrose density gradient and then centrifuged at 200,000×g for 16 h. Fractions (0.5 ml) were collected and analysed by Western blotting. 15 ml aliquots of each fraction were diluted 1:1 in 2× loading buffer, heated to 95° C. for 5 min and separated on 15% SDS-PAGE gels, before transfer onto PVDF membranes and incubated with primary antibody (for example mouse anti-CD20, clone 7D1 to detect CD20 or anti-Lyn rabbit polysera; Serotec, UK to identify the raft fractions), followed by HRP-conjugated secondary antibody (Amersham Biosciences UK Ltd). Blots were visualised using ECL+plus (Amersham Biosciences UK Ltd).

Anti-CD20 antibody molecules can require the A×P motif in the large loop of CD20 (Ofatumumab and other Genmab antibodies do not). However, (Niederfellner, G et al. 2011. Blood 118, 358-367) indicates Type II antibody molecules bind to a slightly different region of the CD20 loop compared to Type I.

Preferably, the invention provides a composition, or a use, or a method, or a kit, wherein the Type I CD20 antibody is rituximab, or a rituximab biosimilar, or ofatumumab.

Preferably, the invention provides a composition, or a use, or a method, or a kit, wherein the Type II CD20 antibody is obinutuzumab, or tositumomab.

Preferably, the invention provides a composition, or a use, or a method, or a kit, wherein the antibody molecule as defined in (i) is a CD52 antibody.

Preferably, the invention provides a composition, or a use, or a method, or a kit, wherein the CD52 antibody is alemtuzumab.

Preferably, the invention provides a composition, or a kit, wherein the composition or kit comprises one or more therapeutic agent.

Preferably, the invention provides a use, wherein the composition further comprises one or more therapeutic agent.

Preferably, the invention provides a method, wherein the subject is further administered with one or more therapeutic agent.

Preferably, the invention provides a composition, or a use, or a method, or a kit, wherein the subject has refractory cancer or relapsed cancer, or the subject has refractory cancer and relapsed cancer.

Preferably, the invention provides a composition, or a use, or a method, or a kit, wherein the subject has refractory chronic lymphocytic leukaemia or relapsed chronic lymphocytic leukaemia, or the subject has refractory chronic lymphocytic leukaemia and relapsed chronic lymphocytic leukaemia.

Preferably, the invention provides a composition, or a use, or a method, or a kit, substantially as described and/or claimed herein with reference to the description, and/or examples, and/or accompanying drawings.

The listing or discussion in this specification of an apparently prior-published document should not necessarily be taken as an acknowledgement that the document is part of the state of the art or is common general knowledge.

Preferred, non-limiting examples which embody certain aspects of the invention will now be described, with reference to the following figures:

FIG. 1. Generation and characterization of mAb capable of distinguishing hFcγRIIB and hFcγRIIA. (A) scFv clones were screened for specific binding to hFcγRIIB or and hFcγRIIA. Yellow dots represent clones specific for hFcγRIIB that were chosen for conversion to full-length IgG. (B) Binding analysis of hFcγRIIB mAb. A hFcγRIIB mAb was assessed for binding to hFcγRIIB-transfected cells (red-line) or hFcγRIIA-transfected cells (blue line). The same mAb was assessed for binding to hFcγRIIB-transfected cells in the presence on IC (3 nM, green-line), indicating that the mAb is capable of competing out IC binding to hFcγRIIB-expressing cells. The figure shows data from one representative hFcγRIIB clone. (C) Binding profile of the generated mAb on PBMC populations determined by flow cytometry. hFcγRIIA specific mAb displayed strong binding to monocytes and neutrophils whereas hFcγRIIB specific mAbs primarily bound to B cells, with the exception of 6A09 which also bound to monocytes and neutrophils and so is likely dual-specific for hFcγRIIA and B. (D) Dose-dependent binding of mAbs to B cells. mAbs were added at 0.1, 1 or 10 µg/ml and the intensity of staining determined by flow cytometry. (E) Affinity of hFcγRIIB mAb. A selection of hFcγRIIB specific mAb (7C07, 5C04, 5C05) were assessed for their binding to various concentrations of hFcγRIIB fusion protein (0 (red), 0.16 (green), 0.8 (blue), 4 (pink), 20 (turquoise), and 100 (brown) nM) by surface plasmon resonance. The sensograms show typical binding responses for each mAb. The KD values were calculated from the 1:1 binding model (see Table 2).

FIG. 1(2/2). Therapeutic effects of hFcγRII mAb (AT10) and generation of specific mAbs capable of distinguishing hFcγRIIB and hFcγRIIA. (Top) SCID mice (5/group) xenografted with Daudi cells (s.c.) were treated (i.p.) as indicated by arrows. Mean tumor weights plotted±SEM and analyzed using unpaired t test; p values compare rituximab (Rit) alone vs. Rit+AT10-treated groups (**p≤0.005). Representative data (n=2). (Bottom) hFcγRIIB mAb binding to hFcγRIIB— (red-line) or hFcγRIIA-transfected cells (blue-line) and mAb-dependent inhibition of IC binding to hFcγRIIB-transfected cells (green-line). See also FIGS. 7 and 8 and Table 6.

Figure 2:
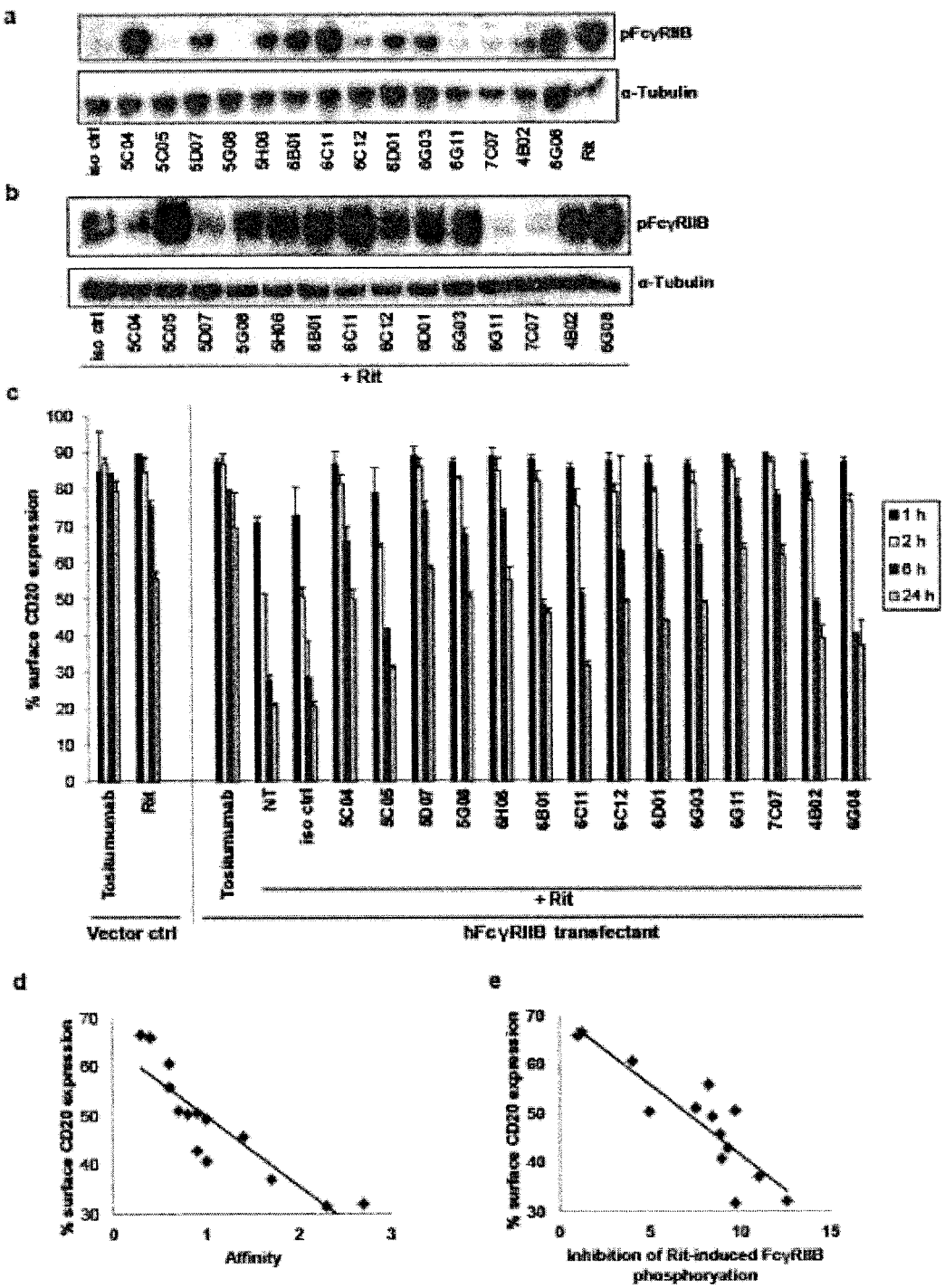

FIG. 2. hFcγRIIB mAbs are capable of blocking rituximab (Rit) engagement with FcγRIIB on the surface of target cells. (A) Ability of hFcγRIIB specific mAb to elicit hFcγRIIB ITIM phosphorylation. Raji cells were treated with N297Q hFcγRIIB specific mAb (10 µg/ml) at 37° C. for 30 minutes before being lysed and assessed by immunoblotting for the phosphorylation status of hFcγRIIB (pFcγRIIB). hIgG1 isotype control (iso ctrl) and Rit were used as negative and positive controls, respectively. α-Tubulin was probed as a loading control. (B) Ability of hFcγRIIB specific mAb to block hFcγRIIB ITIM phosphorylation induced by Rit. Raji cells were pre-treated with N297Q hFcγRIIB mAb (10 µg/ml) for 10 minutes before addition of 10 µg/ml Rit at 37° C. for 30 minutes. Treated cells were lysed, and assessed by immunoblotting for pFcγγRIIB and α-Tubulin, as above. Representative blots of at least 3 independent experiments shown. (C) Ability of hFcγRIIB specific mAb to block internalization induced by Rit. Vector ctrl or hFcγRIIB-transfected Ramos cells were treated with WT or N297Q variants of hFcγRIIB mAb (10 µg/ml) and AF488-labeled Rit (5 µg/ml) for the indicated time-points at 37° C. Internalization of Rit was determined using a quenching assay and is expressed as the % of surface CD20 expression. AF488-labeled tositumomab was used as negative control as it does not significantly internalize following engagement of CD20.[22] The mean±SD of 3 independent experiments is shown. (D) Ability of the panel of mAb to block Rit internalization (shown in C) was correlated with their relative ranked affinities ($R^2$=0.78). (E) Ability of the panel of mAb to block Rit internalization (shown in C) was correlated with their ability to block Rit-induced phosphorylation of hFcγRIIB (B), as assessed by Image J densitometry software ($R^2$=0.79).

FIG. 3. hFcγRIIB mAb 6G11 has potent cytotoxic activity in vitro and is capable of blocking Rit engagement with hFcγRIIB on the surface of target CLL cells. (A) IHC analysis of hFcγRIIB mAb 7C07 and 6G11 assessed on a range of frozen tissues. 6G11 showed very specific binding to cells in human spleen with virtually absent background staining to non-lymphocytic cells, and little-to-no staining on splenic tissue from cynomolgus monkey or mouse, while 7C07 showed binding both to lymphocytes as expected but also to endothelial linings of both human and cynomolgus monkey tissue. (B-E) Cytotoxic ability of 6G11 in assays measuring ADCC (B), PCD (C) and ADCP (D) on primary patient CLL cells. CLL cells were opsonized with 6G11 (10 μg/ml); Rit (10 μg/ml) was added as a positive control in each assay. Each dot represents mean of triplicate samples from one CLL patient. (E) ADCC assay using effector cells carrying the high or low affinity hFcγRIIIA allelic variants (158F and V, respectively). 6G11 was more potent at inducing ADCC compared to Rit in both cases. The figure shows mean±SD from three independent experiments using three different CLL donors. (F) Ability of 6G11 to impair Rit internalization from the surface of CLL cells. Six CLL samples were treated with WT (left panel) or N297Q (right panel) mAb, iso ctrl or 6G11 (10-20 μg/ml) and AF488-labeled Rit (5 μg/ml) at 37° C. for up to 6 hours. Internalization of Rit was assessed as above with % surface CD20 expression presented. (G) Ability of 6G11 to remain at the surface of CLL cells. Six CLL samples were treated with WT or N297Q 6G11 (10 μg/ml) for up to 6 hours and hFcγRIIB surface expression was quantified indirectly by staining with anti-hF(a')$_2$-PE. Values were normalized to staining performed on ice at time 0 and expressed as % surface hFcγRIIB expression. Data are expressed as box and Whiskers plots; p values compare groups as indicated ($*p \leq 0.05$). (H and I) Augmentation of ADCP with 6G11. CFSE-labeled CLL cells were opsonized with Rit in combination with N297Q iso ctrl or 6G11 for 3 hours in culture, washed and added to MDMs at 5:1 ratio. Following co-culture, CD206-APC staining was used to identify MDMs, and results were analyzed by flow cytometry. Representative dot plots are shown in (H) and the % of double-positive events calculated as the proportion of MDMs that have phagocytosed CFSE$^{+ve}$ CLL cells shown in (I). (J) Augmentation of ADCC with 6G11. CLL cells were opsonized with Rit in combination with N297Q iso ctrl or 6G11 for 3 hours and then co-cultured with NK cells. Each dot represents the mean of triplicates from one primary CLL sample. Data analyzed through paired t test (B, C, D, E, I and J) t test; p values compare groups as indicated ($*p \leq 0.05$, $p \leq 0.005$, $**p \leq 0.0001$).

Figures 4H, 4I:
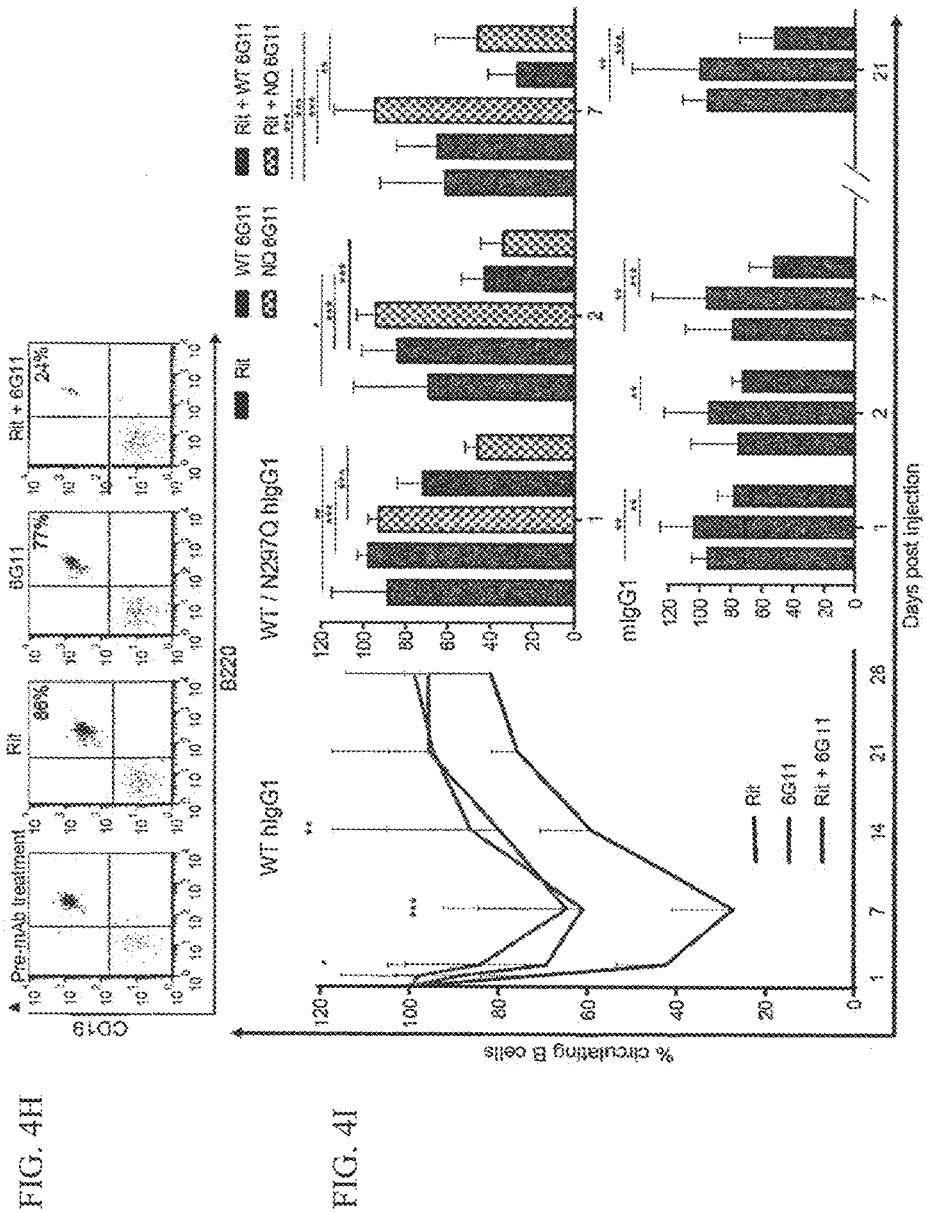

FIG. 4. hFcγRIIB mAb 6G11 is active in vivo and potentiates CD20 mAb depletion of B cells. (A and B) Ability of 6G11 to delete hFcγRIIB$^{+ve}$ target cells in vivo. hFcγRIIB$^{+/-}$×mFcγRII$^{-/-}$ target and mFcγRII$^{-/-}$ non-target C57BL/6 splenocytes labeled with high or low levels of CFSE, respectively, were adoptive transferred (i.v.) into WT or γKO C57BL/6 mice. 24 hours later, mice received the indicated WT or N297Q 6G11 mAbs (i.v.); and 16 hours later circulating (A) or splenic (B) cells were analyzed to determine the target to non-target ratio remaining. Data were normalized to give a ctrl (NT) Target:Non-target ratio of 1.0. Each dot depicts a result from an individual mouse, with the mean ratios indicated by the horizontal line (±SEM). Data are combined from at least 2 independent experiments. (C-E) Ability of 6G11 to augment the capacity of Rit to delete target cells in vivo. (C) hCD20$^{+/-}$×hFcγRIIB$^{+/-}$× mFcγRII$^{-/-}$ target and mFcγRII$^{-/-}$ non-target C57BL/6 splenocytes labeled with high or low levels of CFSE, respectively, were injected (i.v.) into WT C57BL/6 recipient mice, as above. 24 hours later, mice received the indicated mAbs alone or in combination (5-10 μg; i.v.); and 16 hours later spleens were analyzed to determine the target to non-target ratio and normalized, as above. Data are combined from at least 3 independent experiments. (D) CFSE$^{+ve}$ hCD20$^{+/-}$× hFcγRIIB$^{+/-}$×mFcγRII$^{-/-}$ target and mFcγRII$^{-/-}$ non-target C57BL/6 splenocytes were injected (i.v.) into hFcγRIIB$^{+/-}$× mFcγRII$^{-/-}$ C57BL/6 recipient mice, as above. On day 1 and 2, mice received WT 6G11 (500 μg; i.v./i.p.) followed by Rit (5-50 μg; i.v.) on day 2; and 16 hours later spleens were analyzed to determine the target to non-target ratio and normalized as above. Data are combined from at least 3 independent experiments. (E) hCD20$^{+/-}$×hFcγRIIB$^{+/-}$× mFcγRII$^{-/-}$ C57BL/6 mice received either Rit or 6G11 (500 μg) or 250 μg of each mAb in combination i.v. on day 0 and the number of circulating B cells was assessed over time, as indicated. Bars indicate means±SEM of the % of circulating B cells in up to 12 mice/group from at least 2 independent experiments, normalized to pre-treatment levels. Two way ANOVA statistical testing was performed to compare treatment groups; p values compare groups as indicated ($p \leq 0.01$, $*p \leq 0.001$) (F-G) Ability of 6G11 to augment the capacity of GA101$_{gly}$ to delete target cells in vivo. CFSE$^{+ve}$ hCD20$^{+/-}$×hFcγRIIB$^{+/-}$×mFcγRII$^{-/-}$ target and mFcγRII$^{-/-}$ non-target C57BL/6 splenocytes were injected (i.v.) into WT recipient mice, and subsequently treated on day 1 with GA101$_{gly}$ or 6G11 alone or in combination (0.2 μg; i.v.), and 16 hours later spleens were analyzed to determine the target to non-target ratio, and expressed as detailed above. Data are combined from 3 independent experiments. (G) CFSE$^{+ve}$ hCD20$^{+/-}$×hFcγRIIB$^{+/-}$× mFcγRII$^{-/-}$ target and mFcγRII$^{-/-}$ non-target C57BL/6 splenocytes were injected (i.v.) into hFcγRIIB$^{+/-}$×mFcγRII$^{-/-}$ recipient mice, and subsequently treated on day 1 and 2 with either WT iso ctrl or 6G11 (500 μg; i.p.), followed by GA101$_{gly}$ (1 μg; i.v.) on day 2, and 16 hours later spleens were analyzed to determine the target to non-target ratio, and expressed as detailed above. One way ANOVA statistical testing was performed to compare treatment groups with NT/iso ctrl or CD20 mAb/6G11 alone-treated groups (A-D and F-G); p values compare groups as indicated ($*p \leq 0.05$, $p \leq 0.01$, $*p \leq 0.001$).

FIG. 4(2/2). hFcγRIIB mAb 6G11 is active in vivo and potentiates CD20 mAb depletion of B cells. hCD20$^{+/-}$× hFcγRIIB$^{+/-}$×mFcγRII$^{-/-}$ mice received either Rit±WT or N297Q 6G11 (20 mg/kg) or 10 mg/kg of each mAb in combination on day 0 and the number of circulating B cells assessed over time. (Top) Representative dot plots analyzing circulatory B cells indicating pre-treatment and day 2 post mAb injection. Numbers in the upper right quadrants indicate % B cells compared to pre-treatment levels. (Bottom) Left graph indicating depletion of circulating B cells with Rit±WT 6G11; top right graph indicates depletion of circulating B cells with Rit±WT or N297Q 6G11; lower right graph indicates depletion of circulating B cells with Rit (m2a; 4 mg/kg)±6G11 (mIgG1; 20 mg/kg). Means+SD of % circulating B cells post treatment, normalized to pre-treatment levels, shown; up to 12 mice/group combined from at least 2 independent experiments. Two-way ANOVA performed. See also FIG. 15.

FIG. 5. hFcγRIIB mAb 6G11 potentiates Rit depletion of patient CLL cells in vivo. (A-B) Primary patient CLL cells engraft into NOD/SCID mice and form distinct proliferative clusters in the spleen, similar to what is observed in humans. Mice were irradiated prior to i.v. inoculation with 6-10×10$^7$ primary patient CLL cells. 4-5 days after injection, the spleens were taken, sections prepared and stained for the presence of (A) hCD19 (red) or Ki67 (green) and assessed by immunofluorescence or (B) hCD20 and Ki67 and assessed by IHC. (C) Anti-tumor activity of Rit, 6G11 or the combination in mice injected with human CLL cells. NOD/SCID mice were inoculated with primary human CLL cells as above, 4-5 days after inoculation, mice were treated with 1-10 mg/kg of either hCD20 mAb, hFcγRII mAb or both. Mice received a second injection 2-3 days later and were sacrificed 2-3 days after last treatment with the % of human CLL cells remaining in the spleen enumerated and normalized to the proportion present after treatment with the isotype control mAb. CLL samples from 10 different patients were assessed in this way. Each dot represents one mouse. (D and E) The proportion of complete responders (D), i.e., mice with no CLL cells detected in spleens, and objective responders, i.e., mice with ≥75% reduction in CLL cells (E) was then calculated from the data presented above in (C). (F-G) Response of refractive patient CLL cells to treatment in vivo. CLL cells from patients, previously designated as refractory (n=4; see Table 4) were inoculated, treated and assessed as in (C-E). (F) Indicates the raw data with dots representing individual mice and (G) indicates the frequency of objective responders in Rit-refractory patients. One way ANOVA analysis was performed to compare treatment groups; p values compare groups as indicated (*p≤0.05, p≤0.01, *p≤0.001).

FIG. 5(2/2). hFcγRIIB mAb 6G11 potentiates therapeutic mAb depletion of normal and malignant target cells in vivo. (A-B) The spleen of a NOD/SCID mouse engrafted with primary patient CLL cells was assessed by immunofluorescence (A) or by IHC (B); ctrl, no primary mAb. (C) Mice xenografted with human CLL cells (n=11 patients) were treated with 1-10 mg/kg of hCD20 mAb (Rit), hFcγRIIB mAb (6G11), or both and % CLL cells remaining in the spleen enumerated and normalized to the proportion after treatment with iso ctrl. (D) Mice xenografted with CLL cells from patients previously designated as refractory (n=4) were treated and assessed as in (C). (E) CFSE$^+$ hCD20$^{+/-}$×hFcγRIIB$^{+/-}$×mFcγRII$^{-/-}$ (target) and mFcγRII$^{-/-}$ (non-target) splenocytes were injected (i.v.) into WT mice and treated with GA101$_{gly}$ or 6G11 alone or in combination (0.008 mg/kg) and assessed for deletion in the spleen as before. Data combined from 2-3 independent experiments. (F) CFSE$^+$ hCD20$^{+/-}$×hFcγRIIB$^{+/-}$×mFcγRII$^{-/-}$ (target) and mFcγRII$^{-/-}$ (non-target) splenocytes were injected into hFcγRIIB$^{+/-}$×mFcγRII$^{-/-}$ recipient mice and treated with either WT iso ctrl or 6G11 (20 mg/kg), followed by GA101$_{gly}$ (0.04 mg/kg) and analyzed as in (E). (G) Mice engrafted with CLL cells (n=4) were treated with GA101 (0.2 mg/kg), 6G11 (1 mg/kg), or both and assessed as in (C). (H) Mice engrafted with CLL cells (n=3) were treated with alemtuzumab (Alem; 1 mg/kg), 6G11 (1 mg/kg) or both and assessed as in (C). (C-D and G-H) Pie charts represent the number of NR (black), OR (blue) and CR (green) primary patient CLL-bearing mice following mAb therapy, as defined in Table 1. (C—H) Each dot depicts an individual mouse, with mean ratios indicated by the horizontal line. (E and F) Data analyzed using one-way ANOVA and (C-D and G-H) a permutation statistical test. See also FIGS. 16 and 17 and Tables 8 and 4.

Figure 6:
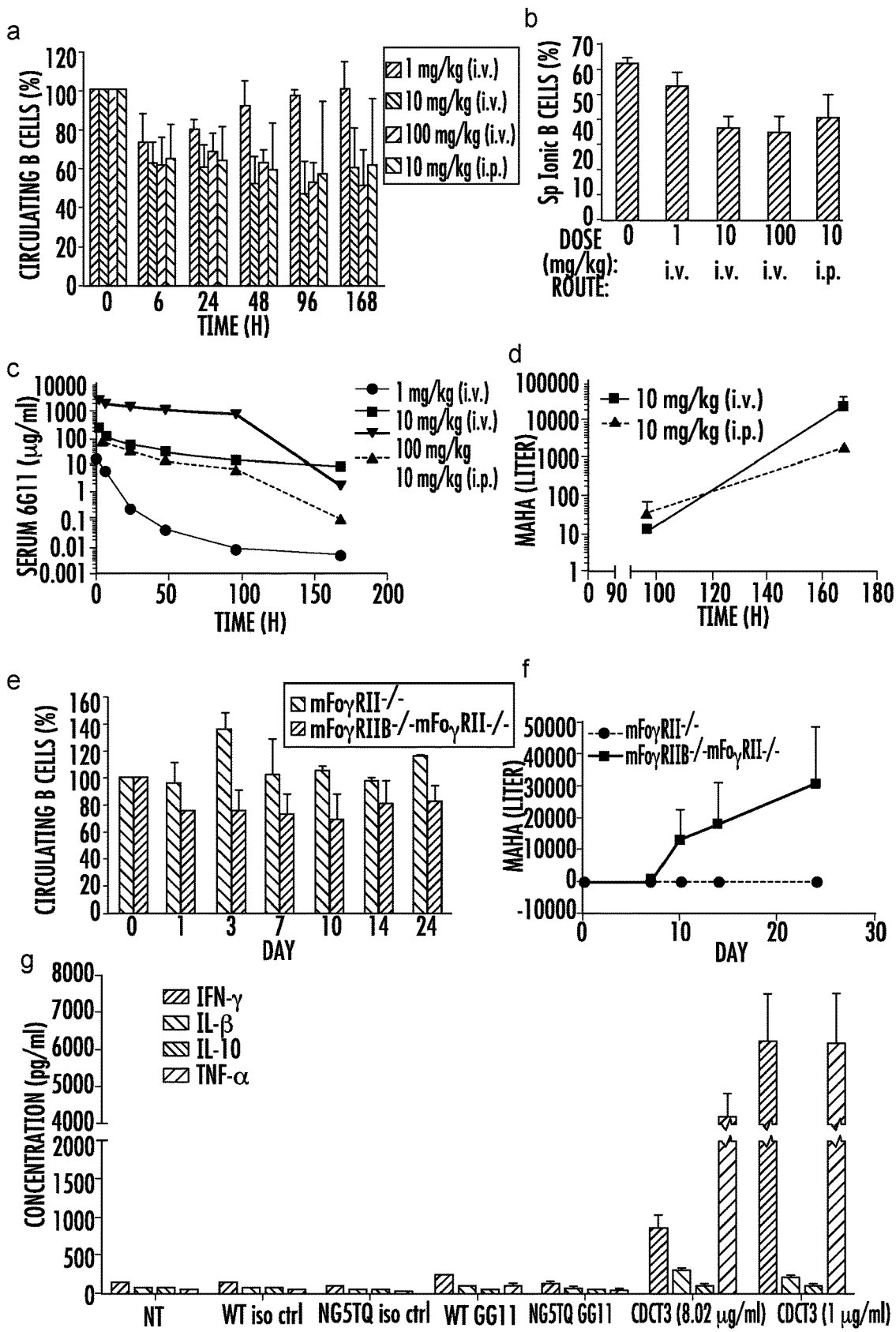
Figure 6:
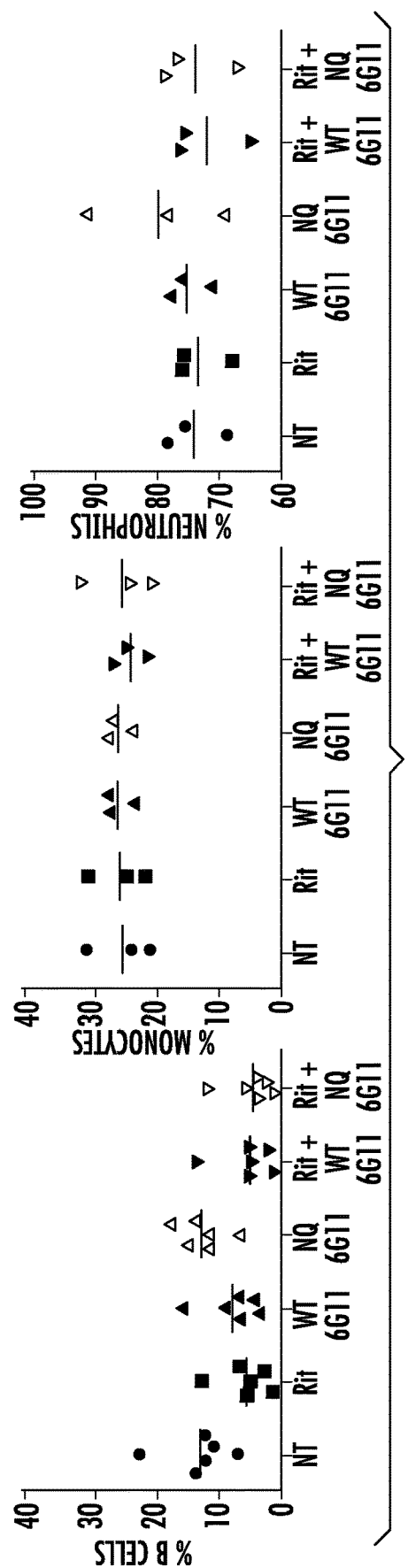
Figure 17C:
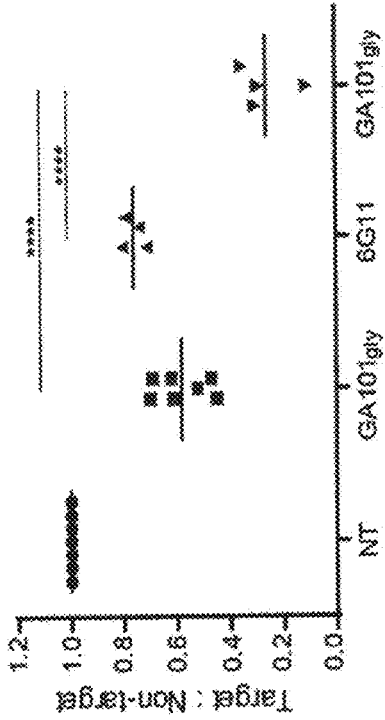
Figure 17D:
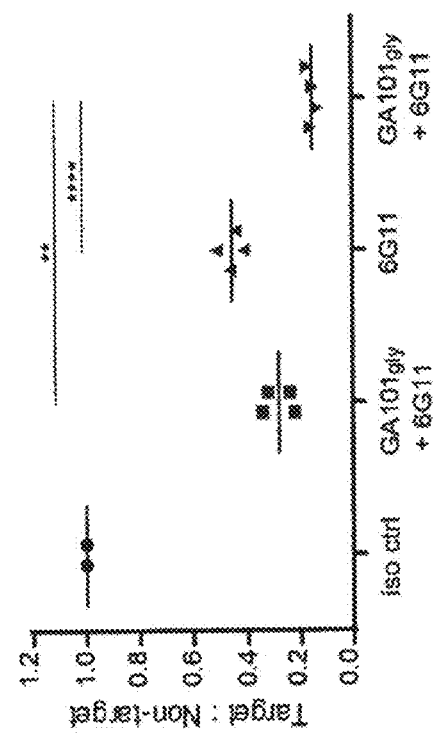
Figure 17A:
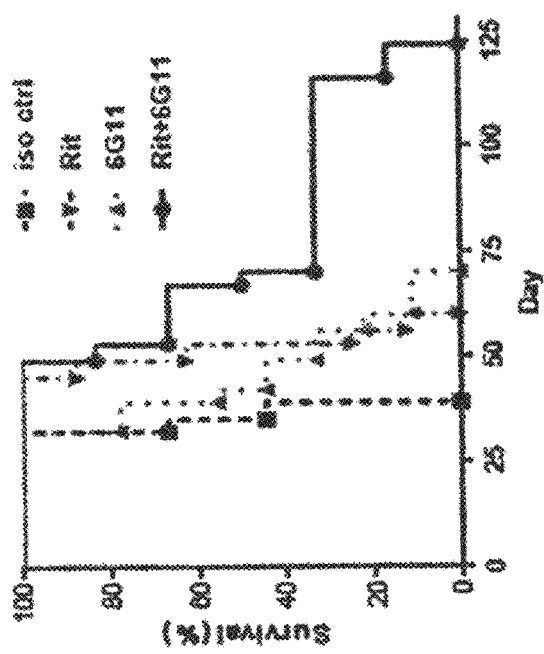

FIG. 6. hFcγRIIB mAb 6G11 is tolerated and does not result in toxicity in preclinical in vivo and in vitro systems. (A-D) In vivo efficacy and half-life of 6G11 following a single administration (FIG. 17A). Age- and sex-matched hFcγRIIB$^{+/-}$×mFcγRII$^{-/-}$ mice (6-7 mice/group) were injected with indicated concentrations of WT 6G11 mAb (i.v. or i.p.). (A) The % of circulatory B cells were assessed over time up to day 7 by flow cytometry. (B) On day 7 the mice were sacrificed and the number of B cells in the spleen (expressed as the % of splenic lymphocytes) quantified by flow cytometry. (C) Serum 6G11 mAb concentrations and (D) MAHA titers over the 7 day period were assessed by MSD (mean+SEM), as described in the Materials and Methods section. (E-F) Invivo efficacy and half-life of 6G11 following multiple administrations. Age- and sex-matched hFcγRIIB Tg×mFcγRII$^{-/-}$ mice (6 mice/group) or mFcγRII$^{-/-}$ mice (3 mice/group) were injected with 10 mg/kg WT 6G11 mAb i.v. on day 0, followed by i.p. injections of the same dose on days 3, 7 and 10. Mice were sacrificed 10 days later (day 24) and organs assessed for toxicity (FIG. 17C). (E) Blood was sampled over time and circulating B cells were quantified by flow cytometry (mean+SD). (F) MAHA titers against 6G11 mAb were assessed as in (D) (mean+SEM). (G) In vitro cytokine response using high density pre-cultured human PBMCs. Human PBMCs were pre-cultured at 1×10$^7$/ml for 48 hours prior to the addition of PBS (NT) or 10 μg/ml WT or N297Q variants of the iso ctrl or 6G11 for 48 hours. Supernatants were harvested and concentrations of IFN-γ, IL-6, IL-10 and TNF-α assessed by MSD. CD3 mAb (OKT3) was used as a positive control at optimal and sub-optimal concentrations (1 and 0.02 μg/ml, respectively). Data are representative of 3 independent experiments using PBMCs from 3 independent healthy donors (mean±SEM).

FIG. 6(2/2). hFcγRIIB mAb 6G11 is well tolerated and does not result in toxicity. In vitro whole blood depletion assay to assess potency of Rit±WT or N297Q 6G11 in depleting hFcγRIIB$^+$ blood B cells (Left graph), monocytes (Middle graph) or neutrophils (Right graph). Mean values shown (horizontal lines) with each dot representing an individual donor. See also FIGS. 14, 18 and 19 and Table 7.

Figure 7:
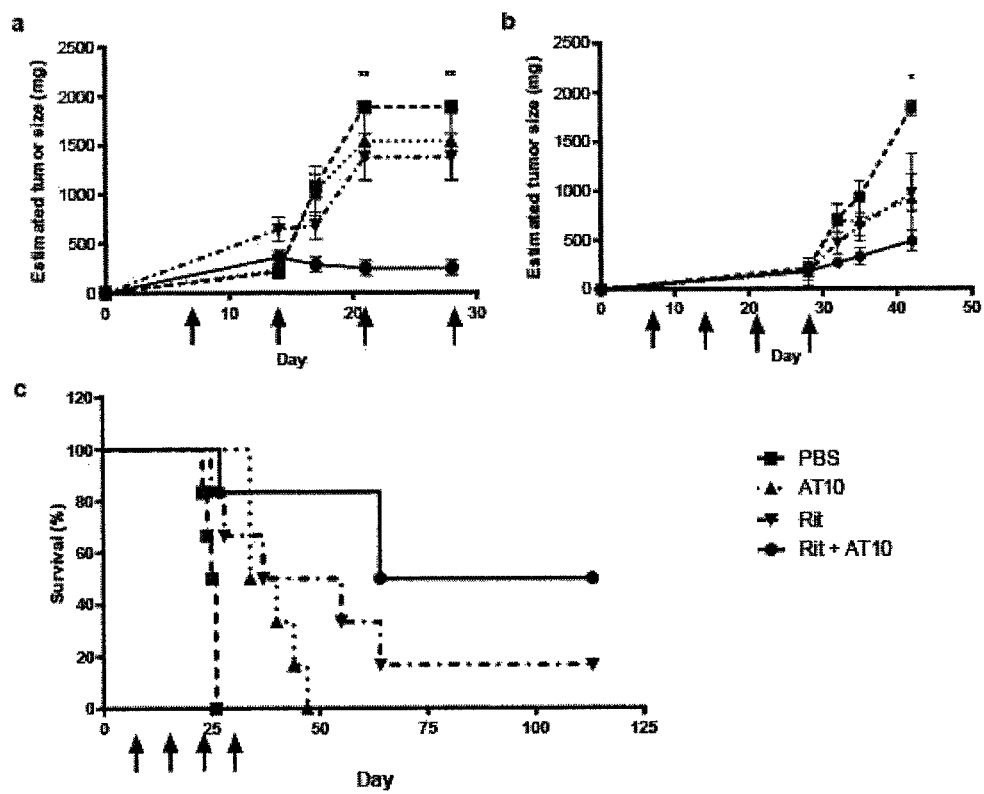

FIG. 7. hFcγRII mAb (AT10) potentiates clearance of malignant B cells by Rit in vivo. (A) 5×10$^6$ Daudi or (B) Raji cells mixed in Matrigel at 1:1 ratio were injected (s.c.) into the flanks of SCID mice (up to 5 mice/group). Tumour-bearing mice were subsequently injected (i.p.) with the indicated mAb on a weekly basis starting on day 7, up to 4 times, as indicated on the X axis (arrow). Tumour growth was monitored over time and estimated using the following equation: [Weight=(length×width$^2$)/2]. Mean tumor volumes are plotted±SE of measurement. Representative data from 2 independent experiments are shown. (C) 2.5×10$^6$ Raji cells were injected (i.v.) into SCID mice (6 mice/group). As above, tumour-bearing mice were subsequently injected (i.p.) with indicated mAb on a weekly basis starting on day 7, up to 4 times. Mice were monitored over time and sacrificed upon the development of signs of terminal tumour development. Data were analyzed using an unpaired t test; p values compare groups as indicated (*p≤0.05, **p≤0.005).

FIG. 8. Generated clones are highly specific for hFcγRIIB. (A) Alignment of the hFcγRIIA amino acid (aa) sequence (top) compared to the highly homologous hFcγRIIB protein (bottom). Differences are highlighted in red, with the IgG binding site indicated. (B-D) hFcγRIIB-specific mAbs were incubated with PBMCs and then assessed for binding to CD14$^{+ve}$ monocytes, (B) CD19$^{+ve}$ B cells (C) or CD3$^{+ve}$ T cells (D) by flow cytometry. A high and dose-dependent binding to CD19$^{+ve}$ B cells in the blood (C) was observed for all clones except 2B08 and 2E08; whereas the converse was true for binding to CD14$^{+ve}$ monocytes (B). Clone 6A09 showed cross-reactivity towards both monocytes and B cells. (D) None of the mAbs stained CD3$^{+ve}$ T cells.

Figure 9:
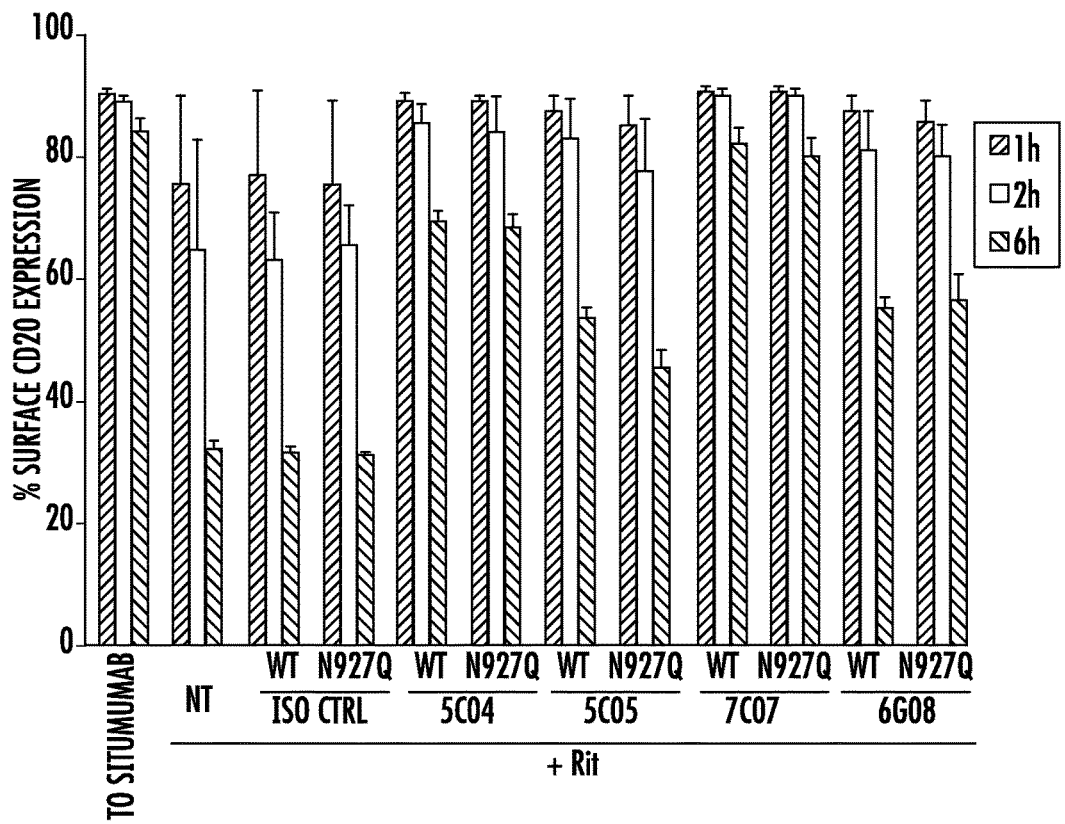

FIG. 9. Both WT and N297Q variants of hFcγRIIB mAbs are equally capable of blocking Rit internalization from the surface of target cells. (A-B) Ability of WT and/or N297Q (NQ) hFcγRIIB specific mAbs (clones 6G11 and 6G08) to elicit hFcγRIIB ITIM phosphorylation (pFcγRIIB) on isolated human tonsil B cells (A) and primary peripheral blood monocytes (B), respectively. α-Tubulin, GAPDH and hFcγRIIB were used as loading controls, as indicated; representative blots shown. (C) hFcγRIIB-transfected Ramos cells were treated with WT or N297Q variants (10 μg/ml) of a selection of hFcγRIIB mAb (representing a selection of antagonists and agonists) or isotype controls (iso ctrl) and AF488-labeled Rit (Rit; 5 µg/ml) for the indicated time-points at 37° C. Internalization of Rit was determined using a quenching assay and expressed as the percentage of surface CD20 expression. AF488-labeled tositumomab was used as negative control as it does not significantly internalize following engagement of CD20.[22] The mean+SD of 3 independent experiments is shown.

Figure 10:
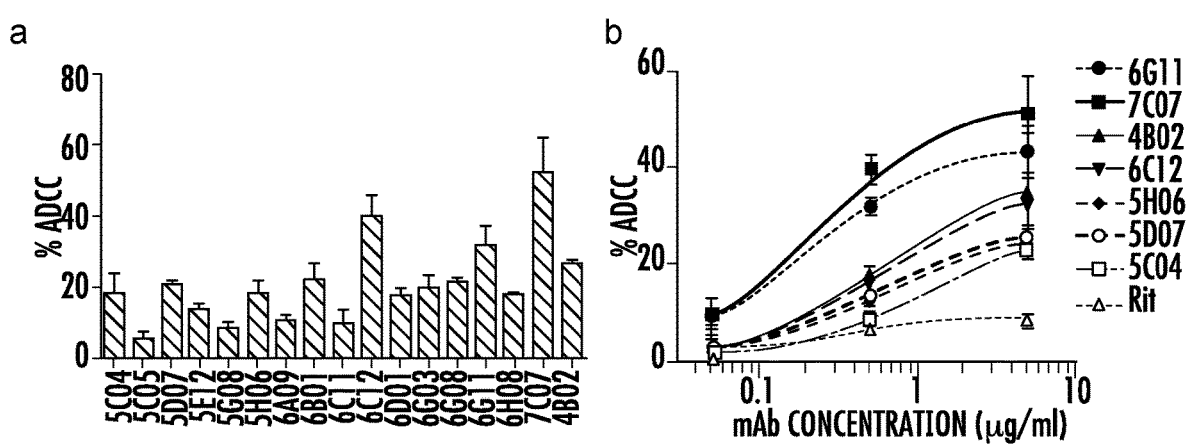

FIG. 10. ADCC activity of hFcγRIIB mAb in vitro. (A) Raji cells pre-opsonized with hFcγRIIB mAb were co-cultured with NK cells purified from peripheral blood of healthy donors and ADDC activity assessed as described in the Materials and Methods section. The figure shows the mean of 4 independent experiments+SD. (B) Based on results in A, seven hFcγRIIB specific mAbs were further tested for their ADCC activity over a range of concentrations. Rit (Rit) was included as a positive control. All hFcγRIIB mAb were shown to perform more favorably than Rit, with 7C07 and 6G11 being the best performing mAb, even at lower concentrations. One representative experiment of 2 shown; data points represent mean+SD from triplicate samples.

Figure 11:
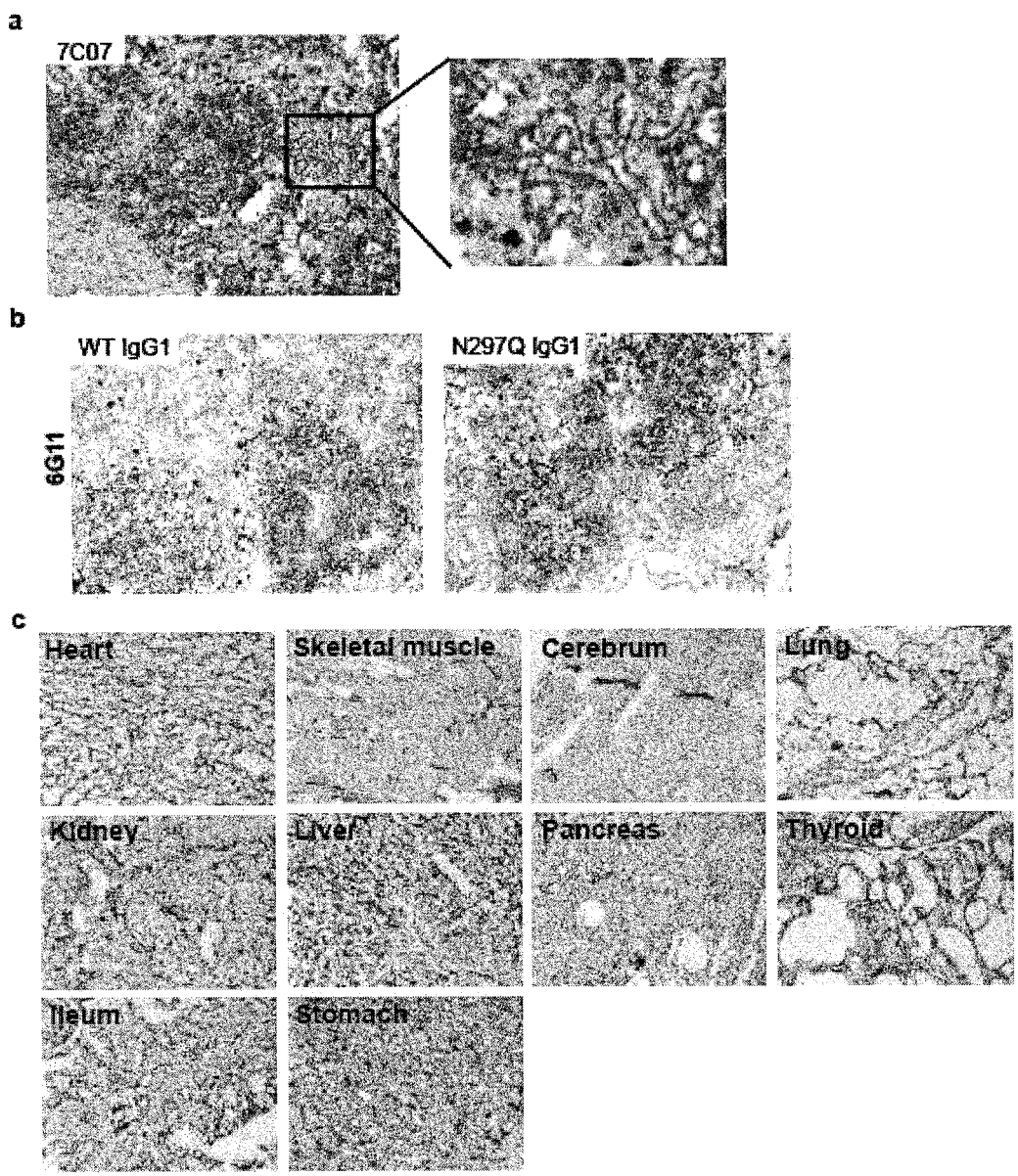

FIG. 11. IHC of human tissues stained with WT or N297Q hFcγRIIB mAbs. WT or N297Q variants of 7C07 or 6G11 were added to fresh frozen sections taken from a variety of tissues. Tissue reactivity was detected using Tyramide Signal Amplification (TSA; PerkinElmer) amplification without hydrogen peroxide block. (A) 7C07 staining of human spleen. 7C07 was shown to non-specifically stain the sinusoids and blood vessels. (B) WT or N297Q variants of 6G11 were added to human spleen sections and assessed for binding as detailed above. Both formats were shown to equally stain small lymphocyte cells in this tissue. (C) Staining of 6G11 (1 µg/ml) followed by TSA detection on cryopreserved cross-sections from a variety of human tissues, as indicated on the sections. No reactivity was observed.

Figure 12:
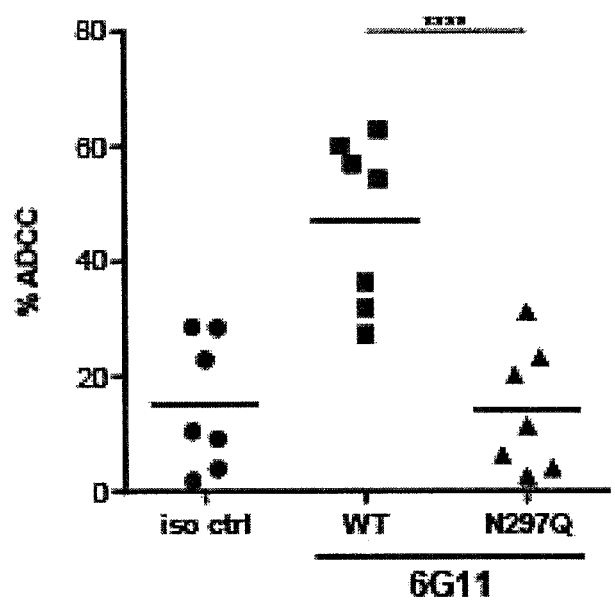

FIG. 12. Aglycosylated N297Q 6011 variant is devoid of intrinsic Fc-dependent effector activity and fails to induces ADDC in vitro. Primary human CLL cells were opsonized with WT or N297Q versions of 6G11 or a WT hIgG1 isotype control (10 µg/ml) and then co-cultured with NK92 cells and ADDC activity assessed as described in the Materials and Methods section. Unlike WT 6G11, the N297Q 6G11 mAb had no intrinsic Fc mediated effector function as illustrated by ADCC efficacy comparable to the iso ctrl-opsonized target cells. Each dot represents one CLL patient; **** p≤0.0001 as assessed by paired student's t test.

Figure 13:
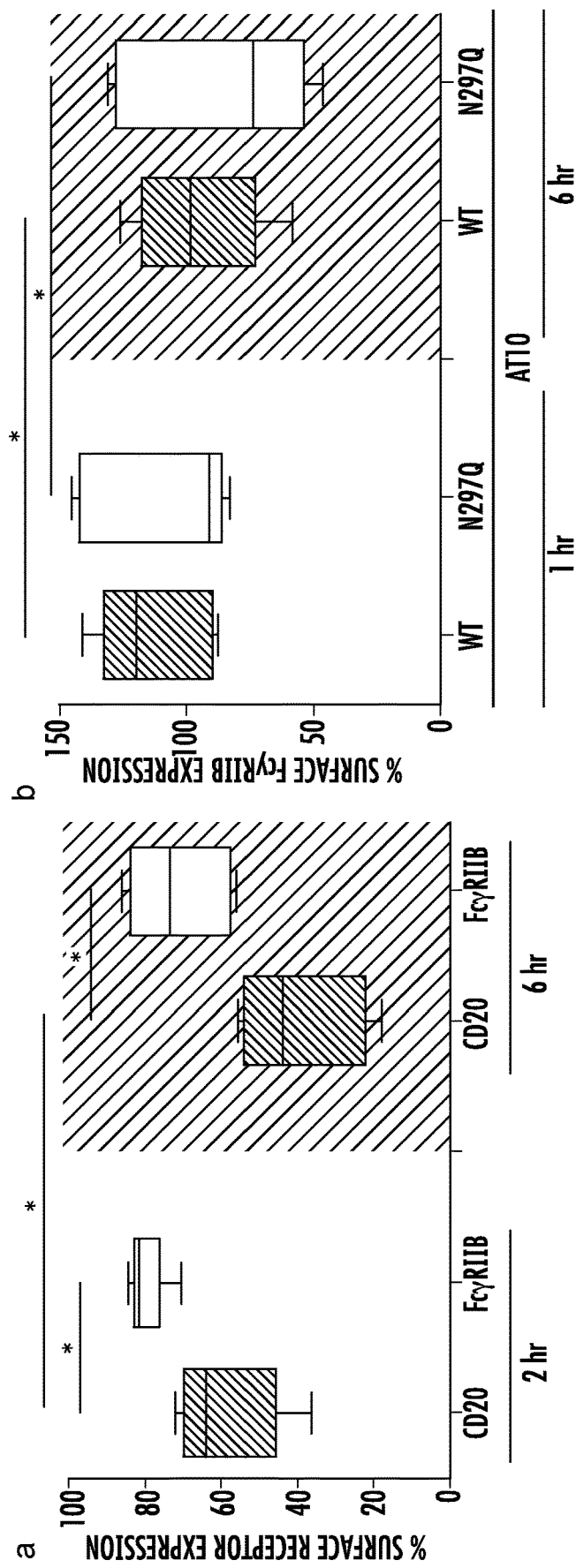

FIG. 13. hFcγRIIB is more resistant to mAb-induced internalization than CD20 on primary human CLL cells. Six CLL samples were treated with either 5 µg/ml AF488-labeled Rit (grey bars) or AF488-labeled WT 6G11 (white bars) at 37° C. for 2 or 6 hours before assessment of internalization as before; % surface CD20 or hFcγRIIB expression is presented. (B) Six CLL samples were treated with WT or N297Q AT10 (10 µg/ml) for 1-6 hours and hFcγRIIB surface expression was quantified indirectly by staining with anti-hF(ab')$_2$—PE. Values were normalized to staining performed on ice at time 0 and expressed as % surface hFcγRIIB expression. Data are expressed as box and Whiskers plots Wilcoxon test was performed to compare treatment groups; p values compare groups as indicated (*p≤0.05).

FIG. 14. Generation and characterization of hFcγRIIB mice. (A) Full length hFcγRIIB2 was amplified from Raji cells and ligated with the native hFcγRIIB promoter isolated from the same cells through overlapping PCR to generate the construct indicated. (B) Expression of hFcγRIIB Tg was assessed by PCR amplification in positive and negative mouse lines. (C) Mice were generated, backcrossed and circulatory blood was phenotyped by staining with CD19-PE and hFcγRII (AT10)-FITC mAb and assessed by flow cytometry. (D) Expression activatory and inhibitory mFcγRII and/or hFcγRIIB receptors were investigated on BMDMs generated from indicated mouse strains, using specific in-house generated mAbs (Tutt et al, manuscript in preparation). The data indicate a lack of compensatory changes in the profile of activatory and inhibitory mFcγR in the presence of the human transgene. (E) Expression of mFcγRII or hFcγRIIB were assessed on CD19$^{-ve}$ CD11b$^{+ve}$ NK1.1$^{-ve}$ Ly6G$^{+ve}$ neutrophils from the spleens of the indicated WT or hFcγRIIB$^{+/-}$×mFcγRII$^{-/-}$ mice, respectively. Representative dot plots of 3 independent experiments shown. As expected, mFcγRII but not hFcγRIIB is expressed on the neutrophils. (F) Frozen sections from WT or hFcγRIIB$^{+/-}$×mFcγRII$^{-/-}$ mouse spleens were analysed by immunofluorescence and expression of hFcγRIIB Tg was assessed and compared to endogenous mFcγRII receptor using the indicated markers (AT130-2 and AT10 mAb, respectively; red); B cell (B220; top panel (green)) and macrophage (F4/80; bottom panel (green)).

FIG. 14(4/5). Generation and characterization of hFcγRIIB Tg mice and assessment of PK, PD, MABEL and CRS-inducing properties of 6G11 mAb. Related to FIG. 14. (D) The gating strategy for immunophenotyping mouse leukocyte subsets (Rose et al, 2012). (E) Expression of mFcγRII or hFcγRIIB were assessed on circulating (blood) and splenic B cells, monocytes/macrophages and neutrophils of the indicated WT or hFcγRIIB$^{+/-}$×mFcγRII$^{-/-}$ mice and human blood, respectively. Representative dot plots of at least 3 independent experiments shown.

FIG. 14(5/5). Generation and characterization of hFcγRIIB Tg mice and assessment of PK, PD, MABEL and CRS-inducing properties of 6G11 mAb. Related to FIG. 14. (F) Assessment of hFcγRIIB expression on circulating (blood) and splenic leukocyte subsets of hFcγRIIB$^{+/-}$× mFcγRII$^{-/-}$ mice and on healthy human leukocytes as well as CLL patients and B cell lines shown, as indicated. Mean±SD shown; each dot represents a single donor/sample. (Middle panel) Frozen sections from WT or hFcγRIIB$^{+/-}$×mFcγRII$^{-/-}$ mouse spleens were analyzed by immunofluorescence and expression of hFcγRIIB Tg was assessed and compared to the endogenous mFcγRII using the indicated markers (AT130-2 and AT10 mAbs, respectively; red); B cell (B220; top panel (green)) and macrophage (F4/80; bottom panel (green)). (Bottom panel) Assessment of hFcγRIIB expression on CD31$^+$ endothelial cells in hFcγRIIB$^{+/-}$×mFcγRII$^{-/-}$ mouse liver.

Figure 15:
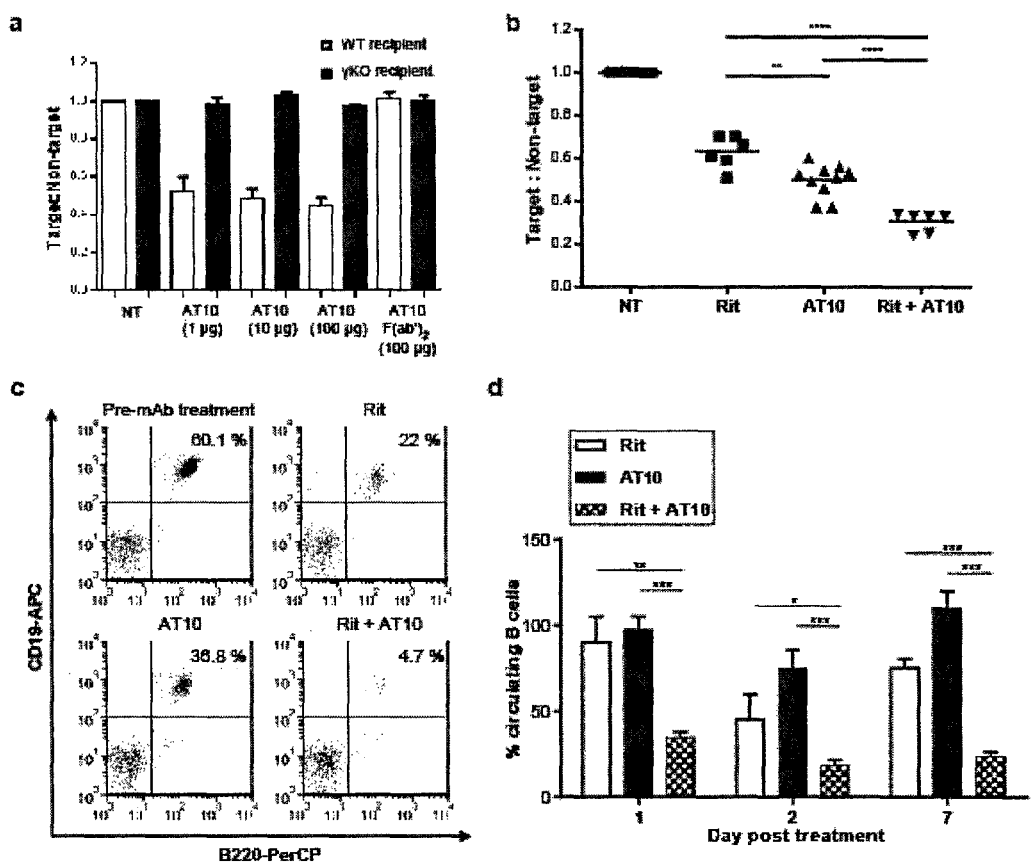

FIG. 15. hFcγRII mAb AT10 is active in vivo and potentiates Rit depletion of B cells. (A) hFcγRIIB$^{+/-}$×mFcγRII$^{-/-}$ target and mFcγRII$^{-/-}$ non-target C57BL/6 splenocytes labeled with high or low levels of CFSE, respectively, were adoptive transferred (i.v.) into WT or γKO C57BL/6 recipient mice. 24 hours later, mice received the indicated WT or F(ab)$_2$ fragments of the hFcγRII mAb AT10 (i.v.; mIgG1); and 16 hours later splenic cells analyzed to determine the target to non-target ratio remaining. Data were normalized to give a ctrl (NT) Target:Non-target ratio of 1.0. Each dot depicts a result from an individual mouse, with the mean ratios indicated by the horizontal line. Data are combined from 4-6 mice/group from at least 2 independent experiments. (B) hCD20$^{+/-}$×hFcγRIIB$^{+/-}$×mFcγRII$^{-/-}$ target and mFcγRII$^{-/-}$ non-target C57BL/6 splenocytes labeled with high or low levels of CFSE, respectively, were injected (i.v.)

into WT C57BL/6 recipient mice. 24 hours later, mice received the indicated mAbs alone or in combination (10 μg; i.v.); and 16 hours later spleens were analyzed to determine the target to non-target ratio as above. Data are combined from at least 3 independent experiments. (C and D) Systemic depletion of B cells using Rit and AT10, alone or in combination. hCD20$^{+/-}$×hFcγRIIB$^{+/-}$×mFcγRII$^{-/-}$ C57BL/6 mice received either 500 μg Rit (Rit, hIgG1), AT10 (mIgG1) or 250 μg of each mAb in combination (i.v.) on day 0 and the number of circulating B cells was assessed over time by flow cytometry. (C) Representative flow cytometry dotplots analyzing circulatory B cells indicating pre-treatment and day 2 post mAb injection. (D) Bars indicate means±SEM of circulating B cell numbers on indicated days post mAb injection; ≥6 mice/group from 2 independent experiments, normalized to pre-treatment circulating blood B cells (expressed as % circulating B cells). One way (B) and Two way ANOVA (D) statistical testing were performed to compare treatment groups; p values compare groups as indicated (*p≤0.05, p≤0.01 and *p≤0.001).

Figure 16:
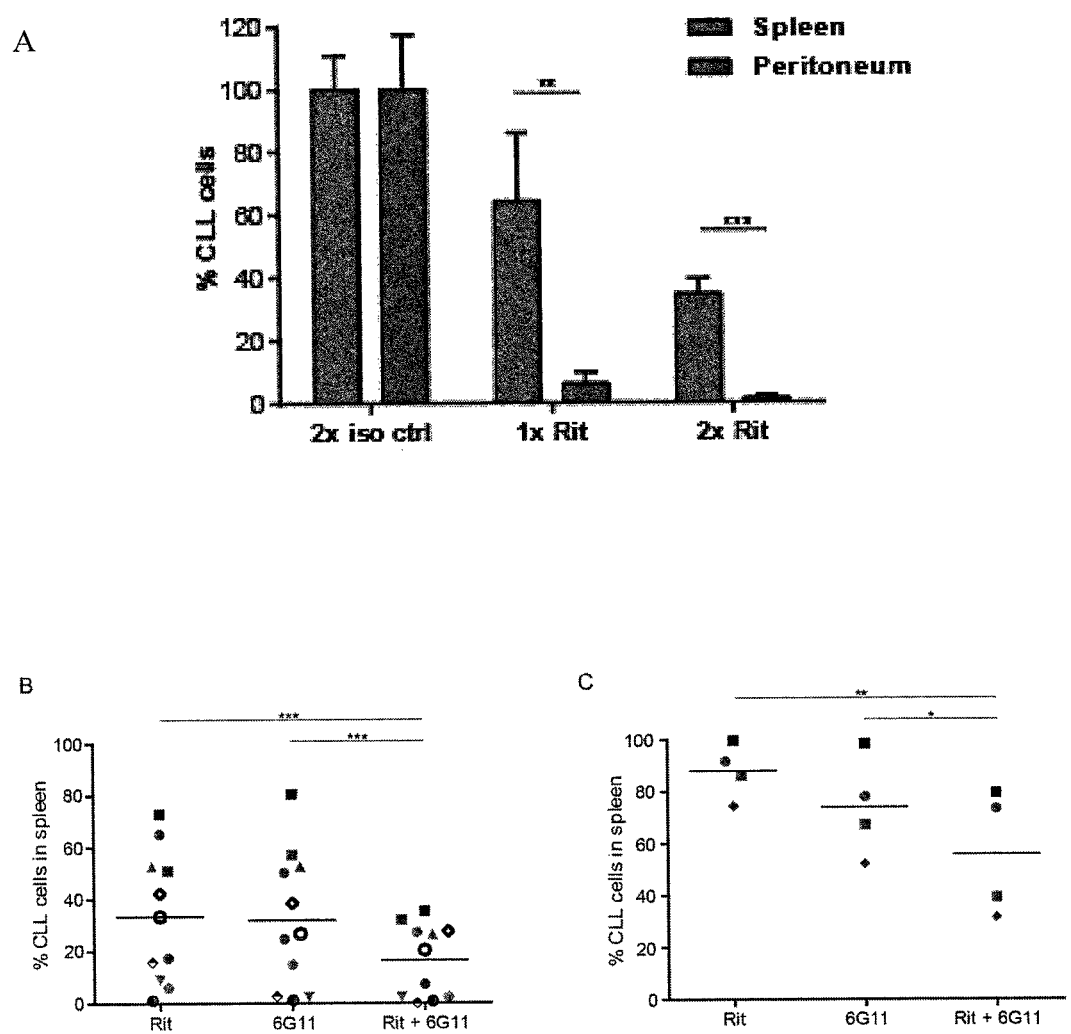

FIG. 16. CLL cells are protected from Rit-dependent depletion by interaction with stromal cells.

(A) 6-10×10$^7$ primary patient CLL cells were transferred i.v. and i.p simultaneously into immunodeficient NOD/SCID mice. 4-5 days after injection mice were treated with 1 or 2 doses of Rit (Rit) or an isotype control at 10 mg/kg. 2 days later, mice were sacrificed and the number of remaining CLL cells in the spleen and peritoneum assessed by flow cytometry, before normalizing to the samples receiving the isotype control. The data show that the CLL cells in the peritoneum were efficiently deleted (dashed bars) with a single dose of mAb whereas Rit-induced depletion from the spleen (filled bars) was incomplete even following two doses of Rit. The figure shows the mean of 3-5 mice/group+SEM. Data analyzed through t test; p values compare groups as indicated (p≤0.01, **p≤0.001).

(B) Anti-tumor activity of Rit, 6G11 or the combination in mice xenografted with human CLL cells. Mice were treated with 1-10 mg/kg of either hCD20 mAb (Rit), hFcγRIIB mAb (6G11) or both and % CLL cells remaining in the spleen enumerated and normalized to the proportion after treatment with the iso ctrl. Mean values from each independent experiment shown, with each patient color-coded (n=11 patients).

(C) CLL cells from patients previously designated as refractory (n=4; see Table S4) were xenografted, treated and assessed as in (B). Data were analyzed using paired one-way ANOVA test.

FIG. 17. hFcγRIIB mAb 6G11 potentiates Rit depletion of mantle cell lymphoma (MCL) cells in vivo. (A) NOD/SCID mice were inoculated (s.c.) with 10×10$^6$ Jeko-1 MCL cells, and streated when tumors reached 4×4 mm with a combination of 6G11, Rit (Rit) or a combination of both. Mice were monitored over time and sacrificed upon the development of signs of terminal tumour development. Data were analyzed using an unpaired t test (*p≤0.05 and *** p≤0.001). (B) NOD/SCID mice were irradiated and then inoculated with 6-7×10$^6$ primary human MCL cells. 4-5 days after inoculation, mice were treated with 1 mg/kg of either Rit (Rit), 6G11 or both. Mice received a second injection 2-3 days later and were sacrificed 2-3 days later with the % of human MCL cells remaining in the spleen enumerated. The data clearly show the capacity of both mAbs and particularly the combination to delete the primary human MCL cells. One way ANOVA test was performed to compare treatment groups; p values compare groups as indicated (*p≤0.05, *** p≤0.001).

(C and D) Ability of 6G11 to augment the capacity of the type II hCD20 mAb GA101$_{gly}$ to delete target cells in vivo. (C) CFSE$^+$ hCD20$^{+/-}$×hFcγRIIB$^{+/-}$×mFcγRII$^{-/-}$ (target) and mFcγRII$^{-/-}$ (non-target) splenocytes were adoptively transferred (i.v.) into WT mice and treated with GA101$_{gly}$ or 6G11 alone or in combination (0.008 mg/kg) and blood assessed as before. Data combined from 2-3 independent experiments. (D) CFSE$^+$ hCD20$^{+/-}$×hFcγRIIB$^{+/-}$× mFcγRII$^{-/-}$ (target) and mFcγRII$^{-/-}$ (non-target) splenocytes were adoptively transferred (i.v.) into hFcγRIIB$^{+/-}$× mFcγRII$^{-/-}$ recipient mice and treated with either iso ctrl or 6G11 (20 mg/kg), followed by GA101$_{gly}$ (0.04 mg/kg) and blood analyzed as before. Each dot depicts a result from an individual mouse, with mean ratios indicated by the horizontal lines. (B, C, F and G) Data analyzed using one-way ANOVA test (*p≤0.05, p≤0.01, *p≤0.001 and ****p≤0.0001).

Figure 18:
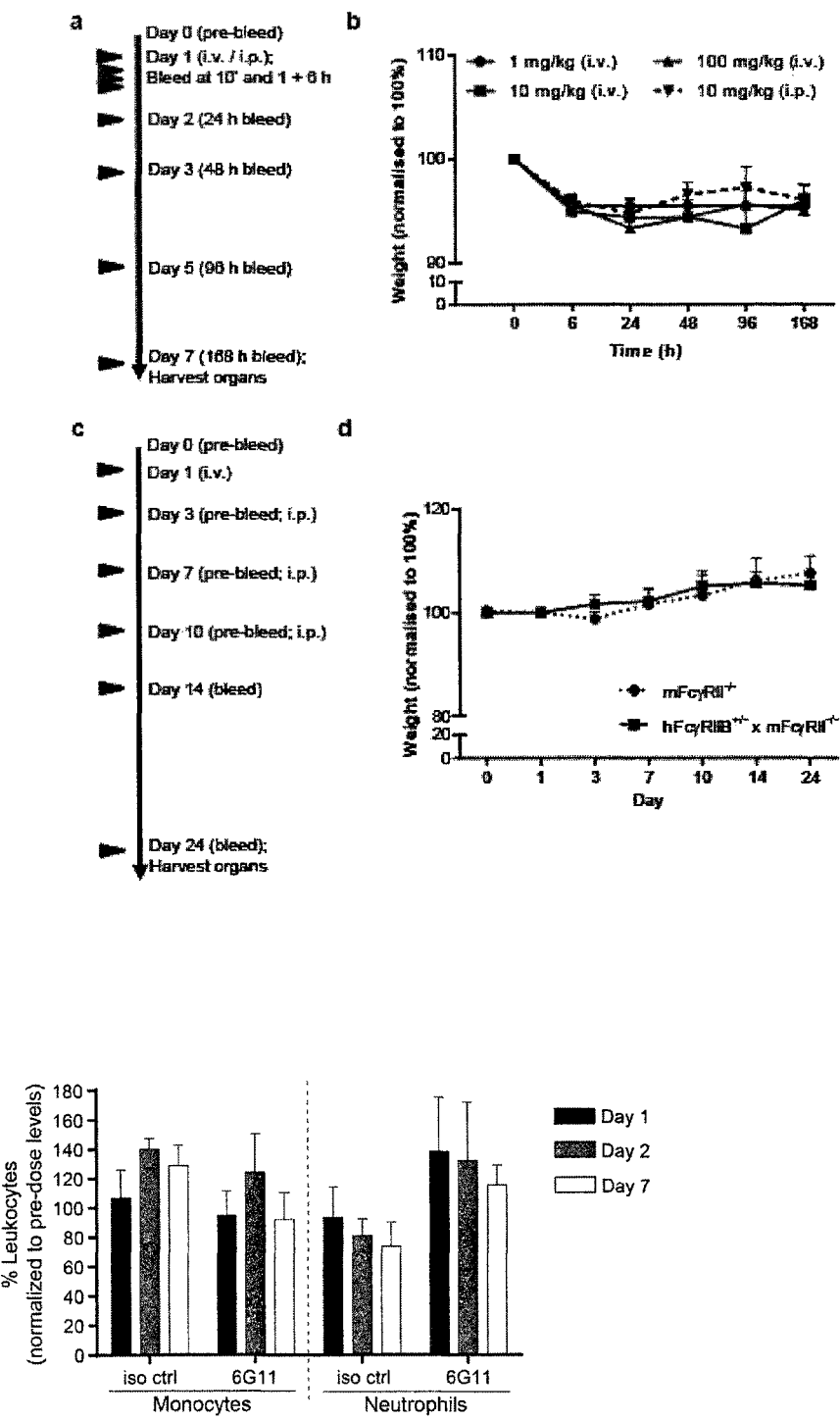

FIG. 18. Assessing PK, PD and MABEL properties of 6G11 in vivo. (A and B) Age- and sex-matched hFcγRIIB$^{+/-}$×mFcγRII$^{-/-}$ mice (6-7 mice/group) were injected with 1-100 mg/kg WT 6G11 mAb (i.v. or i.p.) and sampled, as indicted in the schematic diagram (A). Mice were sacrificed on day 7 of experiment and the organs assessed for signs of toxicity. (B) Mouse weights were assessed over time up to day 7 (168 hours) post mAb injection (normalized to 100% of the day 0 weight and then expressed as the means+SEM for each group). (C and D) Age- and sex-matched hFcγRIIB Tg×mFcγRII$^{-/-}$ mice (6 mice/group) or mFcγRII$^{-/-}$ mice (3 mice/group) were injected with 10 mg/kg WT 6G11 (i.v.) on day 0, followed by i.p. injection of the same doses of mAb on day 3, 7 and 10, as indicated in the schematic diagram (C). Mice were sacrificed on day 24 of the experiment and the organs assessed for signs of toxicity. (D) Mouse weights were measured throughout the experiment and assessed as detailed in (B).

(Bottom panel) Assessment of circulating monocytes and neutrophils depletion by WT 6G11 (20 mg/kg) in hFcγRIIB$^{+/-}$×mFcγRII$^{-/-}$ mice (4 mice/group; mean+SD).

Figure 19:

FIG. 19. In vitro whole blood and diluted blood (20% v/v) cytokine release assays. (A) Fresh or (B) 5× diluted (in serum-free CTL medium) heparinised blood from 3 healthy volunteers was treated with 10 μg/ml of the indicated mAb for 24 hours at 37° C., before supernatants were harvested for subsequent analysis. Cytokines (IL-1β, IL-2, IL-6, IL-8, TNF-α and IFN-γ) were quantified by MSD. Each dot is indicative of an individual donor (n=3).

EXAMPLES

Example 1: Experimental Data

Summary

Therapeutic antibodies have transformed cancer therapy, unlocking new mechanisms of action by engaging the immune system. Unfortunately, cures rarely occur and patients display either intrinsic or acquired resistance. Here, we demonstrate the therapeutic potential of targeting and blocking human (h) FcγRIIB, a receptor implicated in immune cell desensitization and tumor cell resistance to antibody drugs. FcγRIIB-blocking antibodies prevented internalization of the CD20-specific antibody rituximab thereby maximizing cell surface accessibility and immune effector cell mediated antitumor activity in vitro and in vivo. In fully syngeneic hFcγRIIB Tg mouse models, hFcγRIIB mAb potentiated rituximab B cell depletion. In a mouse model assessing depletion of human Chronic Lymphocytic Leukemia (CLL) tumor cells from resistance-prone stromal compartments, co-administration with rituximab improved objective and complete responses, including experiments with CLL cells from relapsed/refractory patients. A lead candidate hFcγRIIB-specific antibody, 6G11, was shown to have good on-target immunoreactivity, favorable pharmacokinetics and no adverse effects in-vivo with additive/synergistic activity in combination with rituximab. These data support the further clinical development of this hFcγRIIB-specific mAb for the immunotherapy of B-cell lymphoproliferative disorders.

INTRODUCTION

Biological therapies in general and monoclonal antibodies (mAb) in particular, are an ever-expanding class of therapeutics.[1] They have revolutionized cancer therapy and have become the standard of care alongside conventional chemotherapy for several malignancies. For over a decade we have known that much of the activity of therapeutic mAb is governed by their interaction with Fc gamma receptors (FcγR). Specifically, it is the relative expression level, affinity and activity of the FcγR which explains much of the therapeutic activity of IgG (reviewed in[2,3]). Much less is known of mechanisms underlying intrinsic or acquired resistance to antibody drugs. While 'don't-eat-me' signals such as CD47 have been shown to limit antibody mediated effector cell anti-cancer activity[4], evidence of their clinical importance is still at an early stage. With an increasing number of antibody therapies being developed for treatment of several types of cancer, there is an emerging need to understand cancer cell resistance to these therapies, and develop drugs to overcome them.

Since several anti-cancer mAb depend on engaging antibody-dependent immune cell-mediated anti-tumor mechanisms for preclinical[5-8] and clinical efficacy[9-11], there is a particular need to understand and prevent resistance mechanisms to these common antibody effector mechanisms.

The human (h) CD20 specific mAb rituximab was the first to be approved for cancer immunotherapy, and as such has been widely administered to patients with CD20 expressing B cell cancers including follicular lymphoma (FL), diffuse large cell B cell lymphoma (DLBCL), chronic lymphocytic leukemia (CLL), and mantle cell lymphoma (MCL) (reviewed in[12]). Interestingly, while rituximab is efficacious in FL and DLBCL where it improves overall survival, only modest responses are seen in CLL and MCL. Furthermore, even within rituximab-responsive lymphomas some individuals show resistance on first treatment or become resistant to rituximab-containing combination therapy, making it an ideal system in which to study mAb resistance mechanisms.

A recent study demonstrated that the inhibitory Fc gamma receptor IIB (FcγRIIB/CD32B) promotes rituximab internalization from target B cells[32,33]. As the main IgG binding immune receptor expressed on B cells, FcγRIIB appears to act by 'sucking in' rituximab from the B cell surface, effectively muting all mAb-dependent immune cell anti-cancer mechanisms ([13] and manuscript in preparation). In contrast, so-called type II anti-CD20 mAbs such as the recently approved obinutuzumab (GA101) are not as sensitive to this process, perhaps due to their inability to redistribute CD20 into lipid rafts (Cragg et al., 2003; Lim et al., 2011). FcγRIIB-mediated rituximab internalization correlated with clinical responsiveness and followed the order CLL>MCL>FL and DLBCL[32,33]. In keeping with a role for FcγRIIB in Ab resistance, a retrospective analysis of MCL patients treated with rituximab immunochemotherapy demonstrated greater survival amongst patients with FcγRIIB-negative compared with FcγRIIB-positive tumor biopsies.[13] Similarly poor responses were observed in FL patients expressing high levels of with FcγRIIB receiving rituximab monotherapy ([14] and manuscript submitted).

The following Example describes the development of antibodies to hFcγRIIB, capable of blocking rituximab internalization and investigate their therapeutic potential in vitro and in vivo. Transgenic (Tg) mice co-expressing hCD20 and hFcγRIIB in a human cell type- and tissue-specific manner were generated and used in proof-of-concept studies, and to assess PK/PD and toxicological parameters. The effect of hFcγRIIb mAbs, used alone or in combination with rituximab or other CD20 mAbs, in preventing or overcoming resistance was then assessed in these and other unique mouse models where human CLL cells (maintaining the phenotype of patients i.e. rituximab-responsive or relapsed/refractory), could be studied in vivo in relevant resistance-prone tissue compartments comprising human stromal cells.

Material and Methods

Animals and Cells

Human (h) CD20 Tg, γ-chain$^{-/-}$ and mouse (m) FcγRIIB$^{-/-}$ mice have been described previously (Beers et al., 2008) with genotypes confirmed by PCR and/or flow cytometry. Mice were bred and maintained in local facilities in accordance with home office guidelines. Animal experiments were cleared through local ethical committees and were performed under Home Office licenses PPL30/1269 and M90-11. Human (h) CD20 Tg, γ-chain$^{-/-}$ and FcγRIIB$^{-/-}$ mice have been described previously[15] with genotypes confirmed by PCR and/or flow cytometry. Ten to twelve week-old female BALB/c and C57BL/6 mice were supplied by Harlan UK Limited (Blackthorn, Oxon, UK), and maintained in local animal facilities. CB-17 SCID mice were purchased from Charles River and then bred and maintained in local animal facilities. For xenograft studies with primary tumor cells (see below), 6-8 week-old female NOD SCID mice were supplied by Taconic (Bomholt, Denmark) and maintained in local facilities.

Clinical Samples

Ethical approval for the use of clinical samples was obtained by the Southampton University Hospitals NHS Trust from the Southampton and South West Hampshire Research Ethics Committee or by the Ethics Committee of Skåne University Hospital. Informed consent was provided in accordance with the Declaration of Helsinki. Samples were released from the Human Tissue Authority licensed University of Southampton, Cancer Science Unit Tissue Bank or obtained through the Department of Hematology and Department of Oncology at, Skånes University Hospital, Lund. CLL and MCL samples were assessed as single cell suspensions that had been isolated, Ficoll purified and cryopreserved for subsequent analysis or used fresh in xenograft studies.

Cell Culture

Cell culture was performed in supplemented RPMI (RPMI containing 2 mM glutamine, 1 mM pyruvate, 100 IU/ml penicillin and streptomycin and 10% FCS [Myoclone]) (GIBCO BRL, Paisley, Scotland). Mouse splenic B cells were purified by negative selection using MACS B cell isolation kits (Miltenyi Biotec, UK) and cultured in the same media. Cell-lines were obtained from ECACC and maintained in antibiotic-free supplemented RPMI medium. Normal human peripheral B cells were purified by negative selection using MACS B-cell isolation kits (Miltenyi Biotec, UK).

Generation of Monocyte-Derived Macrophages (MDM) and Bone Marrow Derived Macrophages (BMDM)

Human MDMs were differentiated from peripheral blood obtained either from the National Blood Service, Southampton General Hospital (Southampton, UK) or from the blood centres in the hospital of Halmstad or Skåne University Hospital (Sweden). Briefly adherent $CD14^+$ monocytes were cultured in RPMI containing penicillin (100 U/mL), streptomycin (100 µg/mL), 10% FCS and 25-100 ng/mL endotoxin-low recombinant human macrophage-colony stimulating factor (M-CSF; R & D Systems, US or produced in-house), as previously described.[16] Half of the medium was replaced with fresh M-CSF every 2 days until harvest. On day 7-10 of culture, MDMs were harvested following a short incubation with cold PBS.

BMDMs were generated from cells isolated from the bone marrow of the femur and tibia of mice, as previously reported.[17] Briefly, bone marrow cells were cultured in RPMI 1640 (Life Technologies Invitrogen, Paisley, U.K.) enriched with 10% FCS, 2 mM glutamine and 1 mM pyruvate, penicillin and streptomycin (each at 100 µg/ml), and 20% L929 cell-conditioned medium (containing M-CSF). Cells were cultured at 37° C., 5% CO2 for 10-14 days prior to use. Macrophage differentiation was routinely confirmed by morphological examination and/or flow cytometry for CD11b and F4/80 expression.

Antibodies and Reagents mAb were typically produced from the culture supernatant of hybridoma or stably transfected CHO-k1 cells. IgG was purified on Protein A with purity assessed by electrophoresis (Beckman EP system; Beckman) and lack of aggregation confirmed by HPLC. $F(ab')_2$ fragments were produced as described previously.[18] The hFcγRII mAb AT10 was previously described.[19] Rituximab was gifted by Southampton General Hospital oncology pharmacy or purchased from the University hospital Pharmacy in Lund, Sweden. Antibodies against phosphorylated hFcγRIIB (Clone EP926Y) (Origene, US), and α-tubulin (Cell Signaling, US) were used for immunoblotting. AF647 labeled IgG1, anti-CD3-PE, anti-CD19-perCp-Cy5.5 and anti-CD56-AF488 (BD Biosciences) were used to label PBMCs. For PBMC immunophenotyping, FcγRIIB mAb labelled with PE using zenon labelling kit (Molecular Probes) was used in conjunction with anti-CD3-FITC, anti-CD19-PerCP-Cy5.5 and anti-CD56-APC.

Flow Cytometry

Fluorescently conjugated mAb were purchased from BD Biosciences, eBiosciences, AbD Serotec or made in-house. Flow cytometry was as described previously[20] with samples assessed on a FACScan, FACSCalibur or FACSCanto II with data analyzed with CellQuest Pro or FACSDiva (all BD Biosciences).

Generation of hFcγRIIB mAb hFcγRIIB mAb were identified by screening the n-CoDeR® scFv phage display library. The extra cellular domain of hFcγRIIB and hFcγRIIA were fused to mIgG3-Fc (hFcγRIIA/B-Fc) to use as targets and non-targets, respectively and were produced in transiently transfected HEK293 cells followed by purification on protein A. Three consecutive selections were performed. Pre-selection occurred prior to selection 1 and was performed against coated mouse IgG3K and biotinylated hFcγRIIA-Fc loaded on Streptavidin Dynabeads. Binding phages were eluted by trypsin digestion and amplified on plates using standard procedures. The amplified phages from selection 1 were used for selection against hFcγRIIB coated to etched polystyrene balls (Polysciences, US). Pre-selection for selection 2 was performed against excess coated Streptavidin. Selection 3 was performed as a limiting dilution selection, e.g., using biotinylated hFcγRIIB in different concentrations. hFcγRIIA was used as competitor in all selections. Phagemids from selection 3 were converted to scFv producing format and used in subsequent screening assays where specific binding to soluble or cell bound antigens as well as inhibition of immune complex binding was assessed. Three different commercial antibodies against hFcγRII (MCA1075XZ, AbD Serotec; MAB1330, R & D Systems; AF1330, R & D Systems) were used for the evaluation of recombinant and cell surface bound FcγRIIB. For evaluation of cell surface bound FcγRIIB by flow cytometry and fluorescence microarray technology (FMAT), mouse anti-hFcγRII-APC (BD Pharmingen) was also used. In all experiments corresponding isotype controls were included as negative controls. For evaluation of cell-bound antigens, CHO-k1 cells were co-transfected with either FcγRIIA-pIRO or FcγRIIB-pIRO together with pIRESpuro using FuGENE (Roche). Pyromycin (InvivoGen) at 10 µg/ml was used for selection of transfected cells. Individual clones obtained through limiting dilution were then stained with hFcγRII antibody (BD Biosciences) and the corresponding isotype control followed by flow cytometry and FMAT analysis to select the highest expressing clones, which were used in further experiments. For primary screening of scFv, FcγRIIA and FcγRIIB transfected CHO-k1 cell were seeded into FMAT plates. E. coli expressed scFv were added followed by deglycosylated mouse anti-HIS antibody (R & D Systems) and deglycosylated anti-mouse-Cy5 (GE Healthcare). Stained cells were detected using the 8200 detection system (Applied Biosystems). Positive clones from the primary screening were re-expressed and re-tested once more for binding to the FcγRIIA and FcγRIIB transfected cells. ScFv clones that specifically bound FcγRIIA or FcγRIIB and inhibited IC binding were sequenced over CDR H1, H2 and H3 using standard procedures to identify unique clones. Unique clones were purified on Ni-NTA spin columns (GE Healthcare) after periplasma preparation with lysosyme (Sigma) from a 10 ml expression preparation in E. coli. In total 17 unique clones were converted to WT and N297Q hIgG1 variants. VH and VL were PCR amplified and inserted into expression vectors containing the heavy- and light-chain constant regions of the antibody, respectively Thereafter, HEK 293EBNA cells (Life Technologies) adapted to growth in suspension were transfected using PEI and the cell-suspension was then allowed to incubate under agitation for 4 hours at 37° C. before dilution with feed-solution (Ultra-PepSoy, Sheffield Bio-Science) and harvesting 6 days post-transfection The harvested culture media was sterile-filtered and applied to a column packed with MabSelect (GE Healthcare) connected to an ÄKTA Purifier system. The column was washed with loading buffer and eluted with a low-pH buffer. The eluted antibody was sterile-filtered and dialyzed to an appropriate formulation buffer using a Spectra/Por Dialysis Membrane 4 (Spectrum Laboratories Inc). After dialysis the material was sterile-filtered and stored at 4° C. Purified IgG was then assessed for binding to transfected CHO-k1 cells as well as cell-lines and PBMCs natively expressing FcγRIIB.

Blockade of Immune Complex (IC) Binding

ICs were formed by mixing hIgG1 specific for FITC with FITC-BSA-biotin or FITC-BSA at a 10:1 molar ratio. The mixture was pre-incubated for 1 hour at room temperature before usage. Supernatants (10 µl) of E. coli expressed ScFv clones that specifically bound FcγRIIA and FcγRIIB were added to FcγRIIA and FcγRIIB expressing CHO-k1 cells and left to bind for 1 hour. ICs were added at 3 nM. Bound IC was detected using Strep Alexa Fluor (AF)-647 (Life Technologies, UK) followed by flow cytometry and blocking was quantified as loss of AF674 signal.

Antibody-Dependent Cellular Phagocytosis (ADCP) and Cellular Cytotoxicity (ADCC)

Phagocytosis assays (ADCP) were performed largely as detailed previously.[23] After maturation into macrophages, the cells were harvested using either ice-cold PBS or Accutase (Sigma) or trypsin/EDTA (Life Technologies, UK) and re-plated at $5\times10^4$ cells/well in 96-well plates and incubated for 2-4 hours or overnight at 37° C. Subsequently, the CLL cells were labeled with 5 μM carboxyfluorescein succinimidyl ester (CFSE, Molecular Probes) for 15 minutes at 37° C. After washing, the CLL cells were incubated with the opsonizing mAb(s) at 10 μg/ml for 30 minutes and thereafter added to the macrophage cultures at a ratio of 5:1. After 1 hour, cells were collected using scraping and stained with APC-labeled CD206 (BD Biosciences) or hFcγRIII mAb (3G8, in-house) for 15 minutes on ice to distinguish the MDMs. Cells were harvested and analyzed by flow cytometry with a minimum of 5000 macrophages collected. The percentage of cells that stained double positive was determined as a measure of phagocytic potential. Confirmation of phagocytosis was routinely provided by confocal microscopy.[23]

ADCC assays were performed in two ways: using either primary $CD56^{+ve}$ NK cells MACS-isolated (Miltenyi Biotec, Germany) from the peripheral blood of healthy volunteers; or an NK-92 cell line stably transfected to express the CD16-158V allele together with GFP (purchased from Conkwest, San Diego, CA).[24] In assays using primary NK cell effectors, target cells were pre-incubated with mAb at 1-10 μg/ml for 30 minutes prior to mixing with NK cells. The cells were incubated for 3-4 hours in RPMI 1640+ GlutaAMX medium (Life Technologies) containing 10 mM HEPES buffer, 1 mM sodium Pyruvate and 10% FBS (all Gibco) at a 20:1 effector:target cell ratio. Lysis was measured using CellaTOX kit (Cell Technology Inc) according to the manufacturer's instruction and the resulting bioluminescence was read in a Victor$^2$V luminometer. When the NK cell line was used, NK cells were incubated with targets at a 1:1 to 5:1 excess for 4 hours and lysis was determined by flow cytometry. Briefly, at the end of the incubation, the cell suspension was incubated with 9 nM SYTOX Red dead cell stain (Life Technologies) for 20 minutes in the dark and the cells were then assayed by flow cytometry.

For investigations of how inhibition of internalization affects ADCP and ADCC, the CLL cells were allowed to incubate with rituximab alone or in combination with an isotype control or N297Q mutated variant of 6G11 for 3-4 hours prior to co-culture with effectors to allow time for antibody internalization.

Internalization Assay and AF488 Labeling mAb were labeled with AF488 according to the manufacturer's instructions (Life Technologies, UK). To determine internalization, a quenching assay was performed as detailed previously.[23] In brief, cell samples ($2-4\times10^5$ cells/well) were incubated with AF488 labeled mAb (5 μg/ml), for the given time, washed, resuspended and incubated at 4° C. for 30 minutes in the presence or absence of anti-AF488 quenching antibody (Life Technologies, UK). Samples were then assessed by flow cytometry. Results are represented as % surface accessible mAb, which is inversely proportional to the amount of mAb internalized.

Western Blotting

Western blotting was performed as described previously.[26] Briefly, $2.5-5\times10^6$ cells were treated, washed and lysed in onyx buffer containing a cocktail of protease and phosphatase inhibitors. Samples were then separated by SDS PAGE and proteins transferred immediately onto PVDF membrane. Membranes were blocked with 5% non-fat dried milk, incubated with the appropriately diluted primary antibodies, washed and then incubated with horseradish peroxidase-conjugated anti-rabbit or anti-mouse IgG (Sigma Aldrich, UK). The bands were visualized by incubation with enhanced chemiluminescence (ECL; GE Healthcare, UK) and exposure to light-sensitive film (Hyperfilm ECL; GE Healthcare, UK). Densitometry was performed using the Image J software as per manufacturer's instructions.

Immunotherapy In Vivo

Adoptive transfer assay: As detailed previously (Beers et al., 2010b), $\sim2\times10^7$ splenocytes/ml were stained as targets or non-targets with 5 μM and 0.5 μM CFSE, respectively, washed, combined in a 1:1 ratio and injected on i.v. into recipient mice ($\sim5\times10^6$ cells/mouse). Mice were then injected i.v. and/or i.p. on day 1 and/or 2 and culled 1 day later to examine blood and splenic leukocytes using flow cytometry.

Adoptive Transfer.

Adoptive transfer assays were performed largely as detailed previously.[27] Briefly, $\sim2\times10^7$ splenocytes/ml from the relevant C57BL/6 mice were stained as targets (T) or non-targets (NT) with 5 μM and 0.5 μM CFSE, respectively for 10 minutes at room temperature, washed, combined in a 1:1 NT:T ratio and injected on day −1 intravenously (i.v.) into recipient mice ($\sim5\times10^6$ splenocytes/mouse). Mice were then injected i.v. with mAb on day 0, and culled 1 day later to examine their blood and splenocytes for NT and T cells. In some adoptive experiments, recipient mice were then injected with mAb on day 0 and day 1 (via i.v. and/or i.p. routes), and culled 1 day later to examine their blood and splenocytes for NT and T cells. The B cell population was identified by FSC—H and SSC—H parameters and CD19 positivity using flow cytometry.

B Cell Deletion:

For systemic B cell depletion assays, mice of varying genotypes were given a single dose of hCD20, hFcγRII or both mAb i.v. (250-500 μg) and then the proportion of B cells remaining in the blood or organs assessed by flow cytometry or immunohistochemistry (IHC) over time, as before.[27]

Primary Human Xenograft Models:

Blood samples from CLL or MCL patients in leukemic phase were collected and used for xenograft studies within 24 hours of collection. Briefly, the PBMCs were isolated using Ficoll Paque PLUS and after thorough washing the cells were resuspended in sterile PBS at $3-5\times10^8$ cells/ml. Mice were irradiated with 1Gy 1-5 hours prior to i.v. injection with 200 μl cell suspension corresponding to $6-10\times10^7$ cells/mouse. At day 4-5 after cell injection, the mice were treated with 1-10 mg/kg of either hCD20 mAb, hFcγRII mAb or both. Mice received a second injection 2-3 days later and were sacrificed 2-3 days later. Spleens were isolated, divided in two with one half frozen in OCT and the other rendered into a single cell suspension. Thereafter, red blood cells were lysed using lysis buffer (Gibco) before incubation with cell surface staining mAbs for 30 minutes on ice. Human cells were identified and quantified as hCD45 positive and leukemic cells through hCD5 and hCD19 staining (BD Biosciences).

In Vivo Leukocyte Depletion

Systemic depletion of mouse peripheral blood leukocytes were assessed over time by flow cytometry following injection of hFcγRIIB$^{+/-}$×mFcγRII$^{-/-}$ C57BL/6 mice with either 20 mg/kg of isotype control or WT 6G11 (i.v.). Leukocyte subset levels were normalized to pre-dose levels and expressed as %.

In Vivo PD, PK and Immunogenicity

Serum concentrations of 6G11 (PK) and MAHA were determined using ECL immunoassays. 6G11 mAb was detected in mouse serum using biotinylated-anti-6G11 polyclonal goat sera and Streptavidin-Sulfo Tag (Meso Scale Diagnostics, US). Quantification of mAb levels in serum was performed by comparison with a known standard curve generated for 6G11. 6G11 PK parameters (Cmax, Tmax, AUC, CL(F), Vz(F), Vss and t½) were evaluated with a non-compartmental model using the software application Phoenix™ WinNonlin v.6.2 (Pharsight Corp, CA, US). Cmax and Tmax were obtained directly from the serum concentration-time profile.

A qualitative and semi-quantitative ECL immunoassay was used to detect the presence of MAHA directed to 6G11 in mouse serum. Samples were diluted in assay buffer with biotin and Sulfo-Tag labelled 6G11. Following incubation, samples were transferred to a pre-blocked streptavidin plate. The signal was assessed using MSD based technology, with the luminescence signal proportional to the level of anti-6G11 present in the sample. Affinity purified goat anti-6G11 serum was utilized for preparation of the positive control samples.

In Vivo Pharmacodynamics (PD), Pharmacokinetics (PK), Minimum Anticipated Biological Effect Level (MABEL) and Immunogenicity Studies Single dose PD, PK and MABEL: Age- and sex-matched hFcγRIIB$^{+/-}$×mFcγRII$^{-/-}$ mice were injected with a single dose of 1, 10 or 100 mg/kg of WT 6G11, examining both i.v. and i.p. routes of administration at the 10 mg/kg dose (FIG. 17A). Serial blood samples were taken immediately post injection and up to 168 hours before termination. Animals were examined throughout for any signs of distress, weight loss, toxicity or pathology. Depletion of hFcγRIIB$^{+ve}$ B cells (PD) and other parameters (e.g., 6G11 PK and mouse anti-human antibodies [MAHA]) were investigated, as follows.

Repeated Dose Immunogenicity:

Age- and sex-matched hFcγRIIB$^{+/-}$×mFcγRII$^{-/-}$ mice and mFcγRII$^{-/-}$ control mice were injected with multiple shots of 10 mg/kg WT 6G11, as indicated in FIG. 17C, over a 10 day period (an initial i.v. administration followed by 3 doses delivered i.p.). Pre-dose blood samples were analyzed for circulatory B cells (CD19$^{+ve}$ and B220$^{+ve}$) by flow cytometry. Animals were examined throughout and 14 days later as above. Serum concentrations of 6G11 (PK) and MAHA were determined, as follows.

6G11 PK Analysis:

An ECL immunoassay was used to determine 6G11 concentrations in mouse serum. Sheep anti-hIgG (the Binding Site) or goat anti-hλ (AbD Serotec) (in the presence of Rituximab) were coated on a 96-well MSD plate and then blocked using 0.45% Fish gelatin. 6G11 mAb was detected by subsequent additions of biotinylated-anti-6G11 polyclonal goat sera and Streptavidin-Sulfo Tag (Meso Scale Diagnostics, MSD), allowing any unbound material to be washed away. Read buffer T (MSD) containing tripropylamine was added and the sTag associated with 6G11 produced a chemiluminescent signal when an electrical voltage was applied. Quantification of mAb levels in serum was performed by comparison with a known standard curve generated for 6G11.

6G11 PK was evaluated with a non-compartmental model using the software application Phoenix™ WinNonlin v.6.2 (Pharsight Corp, Mountain View, CA, US). PK parameter estimates, including Cmax, Tmax, AUC, CL(F), Vz(F), Vss and t1/2 were determined. Cmax and Tmax were obtained directly from the serum concentration-time profile (Table 3).

In Vitro Whole Blood Depletion Assay

Fresh heparinized human blood was diluted 5× in CTL medium (Cell Technology Limited, Germany), and seeded in 96-well plates with either 20 µg/ml Rit and/or WT or N297Q 6G11; or left NT for 24 hours before cells were harvested and stained with anti-human CD3-PerCP-Cy5.5/FITC, CD19-PE, CD14-APC and CD66b-FITC mAbs to identify T cells, B cells, monocytes and neutrophils for flow cytometry, respectively. Ratio of leukocyte subsets relative to CD3$^+$ cells was calculated.

TABLE 3

| Dose group | | t½ (day) | Vz (mL/kg) | Vss (mL/kg) | CL (mL/day/kg) | AUC (day * µg/mL) | Cmax (µg/mL) | Tmax (hr) |
|---|---|---|---|---|---|---|---|---|
| 10 mg/kg IV | Geom mean | | 88.8 | 82.5 | 48.5 | 206 | 201000 | 0.166 |
| N = 6 | Stdev | 0.607 | 14.2 | 15.1 | 36.2 | 106 | 55800 | |
| | CV (%) | | 16.0 | 18.3 | 74.6 | 51.3 | 27.8 | |
| | Harm mean | 1.08 | | | | | | |
| | CV(%) | 56.0 | | | | | | |
| 10 mg/kg IP | Geom mean | | 107 | | 29.0 | 344 | 117000 | 3.83 |
| N = 4 | Stdev | 0.65 | 7.52 | | 6.10 | 72.0 | 13300 | 2.50 |
| | CV (%) | | 7.04 | | 21.0 | 20.9 | 11.4 | 65.2 |
| | Harm mean | 2.49 | | | | | | |
| | CV(%) | 26.0 | | | | | | |
| 100 mg/kg IV | Geom mean | | 53.7 | 54.6 | 12.2 | 7770 | 2350000 | 0.224 |
| N = 6 | Stdev | 0.925 | 16.0 | 16.2 | 1.12 | 638 | 402000 | 0.340 |
| | CV (%) | | 29.7 | 29.6 | 9.16 | 8.21 | 17.2 | 152 |
| | Harm mean | 3.09 | | | | | | |
| | CV(%) | 29.9 | | | | | | |

Immunogenicity Assay (MAHA):

A qualitative and semi-quantitative ECL immunoassay was used to detect the presence of MAHA directed to WT hIgG1 6G11 in mouse serum. Samples were diluted in assay buffer with Biotin and Sulfo-Tag labelled 6G11. Following incubation, samples were transferred to a pre-blocked streptavidin plate. Read buffer T (MSD) containing tripropylamine was added and the signal assessed using MSD based technology, with the luminescence signal proportional to the level of anti-6G11 present in the sample. Affinity purified goat anti-6G11 sera was utilized for preparation of the positive control samples.

In Vitro Cytokine Release Assay

PBMCs were purified by Lymphoprep (Axis-Shield, Oslo, Norway) density centrifugation. Cells were pre-incubated at high density culture[28] ($1×10^7$/ml) for 48 hours in serum-free CTL medium (Cell Technology Limited, Germany) in a 24-well plate at a high density (1.5 ml/well). Cells were subsequently washed, resuspended in serum-free CTL medium ($1×10^6$/ml) and seeded in a 96 well plate (100 μl/well) that were pre-coated with 0.02 or 1 μg/ml OKT3 or left untreated (NT). WT and N297Q variants of hFcγRIIB mAb (clone 6G11) or isotype-matched control mAbs (hIgG1) were added at a concentration of 10 μg/ml and cells incubated for a further 48 hours. Cytokines (IL-6, -10, IFN-γ and TNF-α) were quantified in treated PBMC supernatants by MSD V-Plex assay (Meso Scale Discovery, Rockville, USA) according to the manufacturer's instructions.

Immunohistochemistry (IHC)

IHC staining of human and other animal tissues was performed as follows. Organs from various sources were harvested, frozen and then sectioned prior to immunostaining with 6G11 and 7C07 clones. Tissue reactivity was detected using Tyramide Signal Amplification (TSA; PerkinElmer) amplification without hydrogen peroxide block. Antigen negative tissues were included to identify any non-hFcγRIIB specific binding.

Statistical Analysis

To compare differences between experimental groups in vitro, two-tailed t-test analysis was performed. To assess survival differences between experimental groups in vivo, Kaplan Meier curves were produced and analyzed by Log rank testing. For in vivo experiments containing more than two groups, two-way or one-way ANOVA were used. For differences in objective or complete response in vivo Chi-square tests were used. Statistical analysis was performed using GraphPadPrism software (version 5 for Windows).

Generation of Transgenic Mice Expressing hFcγRIIB and hCD20

The hFcγRIIB2 transgene was constructed from Raji genomic DNA and cDNA by overlapping PCR reactions using primers targeting different exon and intron junctions. The expression cassette includes the hFcγRIIB promoter[22] exon 1/2, intron 2-3 and exons 3-7 (2.4 kb) and was initially cloned into pcDNA3 (Invitrogen) via NotI and XbaI sites and ligated to the BGH polyA sequence of the vector. The construct (including the polyA sequence) was 3517 bp long and was further subcloned into vector pBC-SK (Stratagene) via NotI and SmaI sites. Functional expression of the construct was confirmed in transiently transfected IIA1.6 cells by flow cytometry using AT10-FITC. The purified expression cassette lacking vector sequences was microinjected into the male pronuclei of FVB/N zygotes. Tg mice were screened by either PCR (amplifying exons 3-7 of the cDNA fragment from genomic DNA extracted from ear tips) or flow cytometry of peripheral blood using AT10-FITC. Resulting Tg-positive founders were backcrossed to C57BL/6 or BALB/c mice for >10 generations. hFcγRIIB Tg mice lacking the corresponding mouse receptor were produced by intercrossing with the mouse FcγRIIB$^{-/-}$ mice. The resulting mice were then intercrossed with hCD20 Tg mice to generate hCD20×hFcγRIIB$^{+/-}$×mFcγRIIB$^{-/-}$ progeny.

Surface Plasmon Resonance

A BIAcore T100 analyzer (GE Healthcare, UK) was used to determine the binding affinity of the hFcγRIIB mAb, as described elsewhere.[25] mAb were immobilized onto a CM5 sensorchip (GE Healthcare, UK), using standard amine coupling according to the manufacturer's instructions. Soluble hFcγRIIB (0.16-100 nM; R & D Systems, UK) was injected for 5 minutes and dissociation monitored for 10 minutes. Background binding to the control flow cell was monitored and subtracted automatically. The $K_D$ values were calculated from the 1:1 binding model using the BIAcore T100 Evaluation software.

Immunotherapy In Vivo

Subcutaneous cell line xenograft tumor model: SCID mice (3-6 mice/group) were injected subcutaneously with $5×10^6$ Daudi or Raji cells in growth factor reduced Matrigel Matrix (BD Biosciences, UK) on day 0, and subsequently treated with therapeutic mAb weekly on day 7, 14, 21 and 28. NOD.SCID mice were injected subcutaneously with $10×10^6$ Jeko-1 cells on day 0. Tumor growth was monitored and when tumors reached 4×4 mm, mice were randomized and treated with therapeutic mAb at 10 mg/kg twice weekly. Tumor growth was monitored over time using calipers and tumor size was estimated using the following equation:

$$[Weight=(length×width^2)/2]$$

Intravenous Cell Line Xenograft Model:

SCID mice (6/group) were injected i.v. with the $2.5×10^6$ Raji cells (BD Biosciences, UK) on day 0, and subsequently treated with therapeutic mAb weakly up to 4 times on day 7, 14, 21 and 28. Tumor growth was monitored regularly by examining mice for any signs of paralysis.

In Vitro Cytokine Release Assay

Fresh or 5× diluted (in serum-free CTL medium) heparinised blood was cultured in 96-well plates (U bottom) and treated with 10 μg/ml mAb for 24 hours at 37° C., before supernatants were harvested for subsequent analysis. Cytokines (IL-1β, -2, -4, -6, -10, IFN-γ and TNF-α) were quantified in treated whole or diluted blood supernatants by MSD V-Plex assay (Meso Scale Discovery, Rockville, USA) according to the manufacturer's instructions.

Fluorescence Microscopy

Tissues for sectioning were frozen in OCT media (RA Lamb, Thermo Shandon) placed in isopentane on a bed of dry ice. 10 μm frozen sections were fixed in acetone, blocked with 5% normal goat serum and incubated with mAb to hFcγRII/CD32 (clone AT10, generated in house), mFcγRII/CD32 (clone AT130-2, generated in house[29]) B cells (rat anti-mouse CD45R/B220; BD Pharmingen, UK), follicular dendritic cells (rat anti-mouse FDC; BD Pharmingen, UK) and macrophages (rat anti-mouse F4/80; AbD Serotec, UK) followed by DyLight594-conjugated goat anti-hIgG (Abcam, Cambridge, UK) and AF488-conjugated goat anti-rat IgG (Life Technologies, UK). Sections were mounted in Vectashield (Vector Laboratories, UK) and images collected using a CKX41 inverted microscope reflected fluorescence system equipped with a CC12 colour camera running under Cell B software, using a Plan Achromat 10×0.25 objective lens (all Olympus, UK). RGB image files (TIFF) were transferred to Adobe Photoshop (CS6) and red/green image overlays were contrast-stretched to use the whole grey scale.

Neutrophil Staining Protocol

Blood samples or spleens were taken from age and sex matched C57BL/6, mFcγRII−/− and mFcγRII−/−× hFcγRIIb+/− mice. Spleens were homogenised by passing through a 100 μm cell strainer (BD) then washed in complete RPMI and resuspended in 5 ml PBS, 200 μl cell suspension was used per tube for Flow cytometry. Samples were stained with 10 μg/ml anti-mouse FcγRII (AT130-2 F(ab')2-FITC), anti-human FcγRII (AT10 F(ab')$_2$-FITC) or irrelevant control (3G8 F(ab')$_2$-FITC) (all produced and labelled in-house) plus the following: anti-mouse CD19 (1D3-PE, in-house), anti-mouse NK1.1 (PK136-AlexaFluor 647), anti-mouse CD11b (M1/70-Pacific Blue), anti-mouse CD11c (N418-PE-Cy7), anti-mouse Ly-6-G (1A8-APC-Cy7), anti-mouse Ly-6C (HK1.4-PerCP-Cy5.5; all BioLegend unless otherwise stated). Cells were stained for 30 minutes at 4° C. then 1 ml erythrocyte lysis buffer added (AbD Serotec, UK), cells were centrifuged then washed once and analysed on a FACs Canto. Debris and CD11c$^{high}$ cells were excluded, neutrophils were CD19− CD11b+ NK1.1− Ly-6G+.

Results

Generation and Characterization of mAbs Specific for the Fc Binding Domain of hFcγRIIB It has recently been reported that resistance to rituximab, a type I CD20 mAb, in some lymphoma patients could be explained, in part, by its internalization from the tumor and that the expression of the inhibitory FcγRIIB/CD32B on the target B cell surface promotes this process.[13-23] Consistent with this hypothesis, in vivo co-administration of AT10 with rituximab resulted in additive/synergistic anti-tumor responses in two different lymphoma xenograft models where hCD20 and hFcγRIIB are co-expressed on the tumors (FIG. 7).

The extracellular domain of hFcγRIIB is ~98% homologous to the extracellular domain of hFcγRIIA, a key activatory FcγR (FIG. 8A). Since these two receptors mediate opposing functions, it is critical for a therapeutic antibody to be highly specific for hFcγRIIB. AT10 does not fulfill this criterion since it binds to both hFcγRIIA and hFcγRIIB with similar affinity.[19] Additionally it is of murine origin (IgG1), limiting its translational potential. To generate hFcγRIIB specific antibodies with therapeutic potential in humans, we used our proprietary human antibody phage-display library n-CoDeR®,[30] panning for binding to hFcγRIIB and against binding to hFcγRIIA (or vice versa) to generate monospecific reagents (FIG. 1). The resultant mAb were assessed for their ability to selectively bind FcγRIIB (FIG. 1A) and block immune complex (IC) binding to hFcγRIIB, but not hFcγRIIA (FIG. 1B). Screening for binding to individual human PBMC subsets (neutrophils, monocytes, B cells, T cells and NK cells), isolated B cells (FIGS. 1C and D; FIG. 8B-D), malignant human B cell lines or splenocytes from Tg mice (hFcγRIIB+/−×mFcγRII−/−; data not shown), demonstrated the high specificity of the antibodies for either hFcγRIIB or hFcγRIIA. The relative affinities of these mAb for hFcγRIIB were determined by ELISA (Table 1) with a subset assessed by surface plasmon resonance showing KD for binding to hFcγRIIB in the range 2×10⁻⁶-2×10⁻⁸ M (FIG. 1E and Table 2). Based on the above findings, 14 highly specific hFcγRIIB mAb were identified and validated. Although the fine specificity for each mAb has not been defined, they all block IC binding and do not cross-react with FcγRIIA, strongly indicating they bind around the IgG binding cleft, where a high concentration of residues differing between FcγRIIA and B occur (FIGS. 7 and 8).

TABLE 1 hFcγRIIA and hFcγRIIB mAb EC50 data

| Clone Name | EC50 FcγRIIA$^{+ve}$ CHO | EC50 FcγRIIB$^{+ve}$ CHO | EC50 FcγRIIA | EC50 FcγRIIB |
|---|---|---|---|---|
| iso ctrl | nb | nb | nb | nb |
| 1A01 | 0.4 | nm | 0.2 | |
| 1B07 | 0.3 | nb | 0.3 | |
| 1C04 | 0.3 | nb | 1.5 | |
| 1E05 | 0.5 | nb | 0.7 | |
| 2A09 | 0.6 | nb | 0.6 | |
| 2B08 | 0.6 | nm | 2.0 | |
| 2E08 | 0.3 | nm | 1.3 | |
| 5C04 | nm | 0.4 | | 0.8 |
| 5C05 | nb | 1.7 | | 2.7 |
| 5D07 | nm | 0.4 | | 0.6 |
| 5E12 | nb | 1.0 | | 3.4 |
| 5G08 | nb | 0.7 | | 0.7 |
| 5H06 | nm | 0.4 | | 0.6 |
| 6A09 | nm | 1.4 | | 3.7 |
| 6B01 | nm | 0.5 | | 1.4 |
| 6C11 | nb | 0.5 | | 2.3 |
| 6C12 | nb | 0.3 | | 1.0 |
| 6D01 | nm | 0.3 | | 0.9 |
| 6G03 | nb | 0.4 | | 0.9 |
| 6G08 | nb | 0.6 | | 1.7 |
| 7C07 | nm | 0.3 | | 0.3 |
| 4B02 | nb | 0.6 | | 1.0 |
| 6G11 | nm | 0.3 | | 0.4 |
| 6H08 | nb | 1.4 | | 3.6 |

TABLE 2

Biacore affinity and avidity data for selected hFcγRIIB mAb clones

| FcγRIIB clone | $K_A$ (1/MS) | $K_D$ (1/s) | $K_D$ (M) |
|---|---|---|---|
| 7C07 | 9.13 × 10⁵ | 0.01851 | 2.39 × 10⁻⁸ |
| 6G11 | 6.9 × 10⁶ | 0.1819 | 2.64 × 10⁻⁸ |
| 5C04 | 3.24 × 10⁵ | 0.04808 | 1.42 × 10⁻⁷ |
| 6G08 | 4.72 × 10⁵ | 0.3365 | 7.13 × 10⁻⁷ |
| 5C05 | 801.6 | 0.001769 | 5.45 × 10⁻⁷ |

Antagonistic hFcγRIIB mAb Block Rituximab Internalization

Incubation of hFcγRIIB+ve B cells with rituximab induces inhibitory signaling through hFcγRIIB, and is associated with phosphorylation of the hFcγRIIB cytoplasmic ITIM motif.[31-33] We speculated, based on the immune inhibitory function of this receptor, that mAb capable of preventing both CD20 internalization and blocking hFcγRIIB activation/phosphorylation would be of therapeutic interest. We therefore screened the 14 hFcγRIIB specific mAb for their ability to regulate FcγRIIB phosphorylation in non-Hodgkins lymphoma Raji B cells. In order to assess antibody-mediated effects in a variable domain dependent manner, we engineered antibody variants carrying the N297Q mutation in their constant region that cannot bind to FcγR through their constant Fc domain (see below). 34 Short-term treatment (30 minutes) of Raji cells with the hFcγRIIB mAb resulted in two different responses; mAb that induced high levels of phosphorylation of the hFcγRIIB ITIM (e.g., clones 5C04 and 6G08) and those that had little or no effect such as clones 6G11 and 7C07 (FIG. 2A). Similar observations were seen with primary CLL cells, tonsils, and monocytes (FIGS. 9B and 9C, and data not shown). These data demonstrate that hFcγRIIB mAb, capable of blocking immune-complex binding to hFcγRIIB without activating this receptor, were successfully generated.

Next, we investigated whether the hFcγRIIB mAb could block the interaction between hFcγRIIB and rituximab and prevent the resultant rituximab internalization. Some mAb such as 6G08 remained agonistic, stimulating receptor phosphorylation. In contrast, two mAb (6G11 and 7C07) referred hereon as antagonistic were able to almost completely prevent the FcγRIIB phosphorylation induced after rituximab binding on Raji and primary CLL cells (FIG. 2B and data not shown) much like AT10.[32]. Using a flow cytometric quenching assay[23], we determined the same mAb were able to efficiently block internalization of rituximab from the surface of hFcγRIIB-transfected Ramos cells (FIG. 2C). Notably, the lack of internalization in the presence of these mAb was similar to that seen with the type II mAb, tositumomab, and Ramos cells lacking hFcγRIIB (FIG. 2C). Both WT and N297Q variants had equivalent activity in this assay, indicating an antibody variable domain (Fv)-dependent effect (FIG. 9) and demonstrating that antagonistic effects were retained in the WT hIgG1 format. Subsequent analysis revealed that the ability of the mAb panel to block rituximab internalization was directly related to their relative affinity for hFcγRIIB; $R^2=0.78$ (FIG. 2D), which was in turn correlated to their relative ranked ability to block phosphorylation of hFcγRIIB after rituximab stimulation; $R^2=0.79$ (FIG. 2E). Thus, high affinity antagonistic hFcγRIIB mAb prevented hFcγRIIB-mediated removal of rituximab from the target cell surface.

Antagonistic hFcγRIIB mAb Induce Fc:FcγR-Dependent Cytotoxicity and Block Rituximab Internalization, Thereby Eliciting Potent Anti-Tumor Activity In Vitro The finding that the antagonistic effects of some mAb were retained in the WT hIgG1 format, which productively engages with activatory FcγR-expressing immune cells, suggested that these mAb might have intrinsic Fc:FcγR-dependent anti-tumor activity. We therefore screened our hFcγRIIB mAb for such effects. Incubation of opsonized target Raji cells with primary NK cells demonstrated that the antagonistic mAb 7C07 and 6G11 also had the highest cytotoxic activity, greater than that elicited by rituximab itself (FIGS. 10A and B). Having established that these two clones had the highest affinity, strongest activity in blocking rituximab internalization and in eliciting ADCC, we next assessed their binding to a panel of human and animal tissues known to express FcγR. Both clone 7C07 and 6G11 specifically stained lymphocytes in human spleen and tonsils (FIG. 3A and data not shown). Neither 7C07 nor 6G11 reacted with lymphocytes in cynomolgus monkeys, rats, rabbits or mice indicating that these mAb are not cross-reactive for FcγRIIB in other species (FIG. 3A and data not shown). However, clone 7C07, but not 6G11 also stained the sinusoids of spleen and lymph node tissues from humans, and other species, indicating an undesired cross-reactivity (FIG. 3A and FIG. 11A). WT and N297Q mAb were shown to stain equivalently (FIG. 11B), and no additional unanticipated cross-reactivity was observed on other human tissues (FIG. 11C). Based on this reactivity profile, clone 6G11 was selected as our lead clinical candidate.

The intrinsic cytotoxic activity of 6G11 was further explored in ADCC, PCD and ADCP assays, using a broad panel of primary patient CLL samples. Substantial activity was demonstrated in each assay at a level significantly greater than that observed with rituximab (FIG. 3B-D). Furthermore, 6G11 was more efficacious in inducing cell death compared to rituximab in assays with NK cell effectors expressing either the high or low affinity variants of hFcγRIIIA (158 V or F, respectively) (FIG. 3E).

Subsequently, we examined the ability of 6G11 to prevent the internalization of rituximab from the surface of CLL cells. Both WT and N297Q variants of 6G11 (itself devoid of intrinsic Fc-dependent effector activity; FIG. 12) were able to significantly prevent rituximab internalization (FIG. 3F). Interestingly, unlike CD20, and as previously reported[17] engagement of hFcγRIIB on the surface of CLL cells by either WT or N297Q hIgG1 mAb (6G11 or AT10) did not result in high levels of hFcγRIIB internalization when assessed directly or indirectly (FIG. 3G and FIGS. 13A and B).

Figures 3H, 3I, 3J:
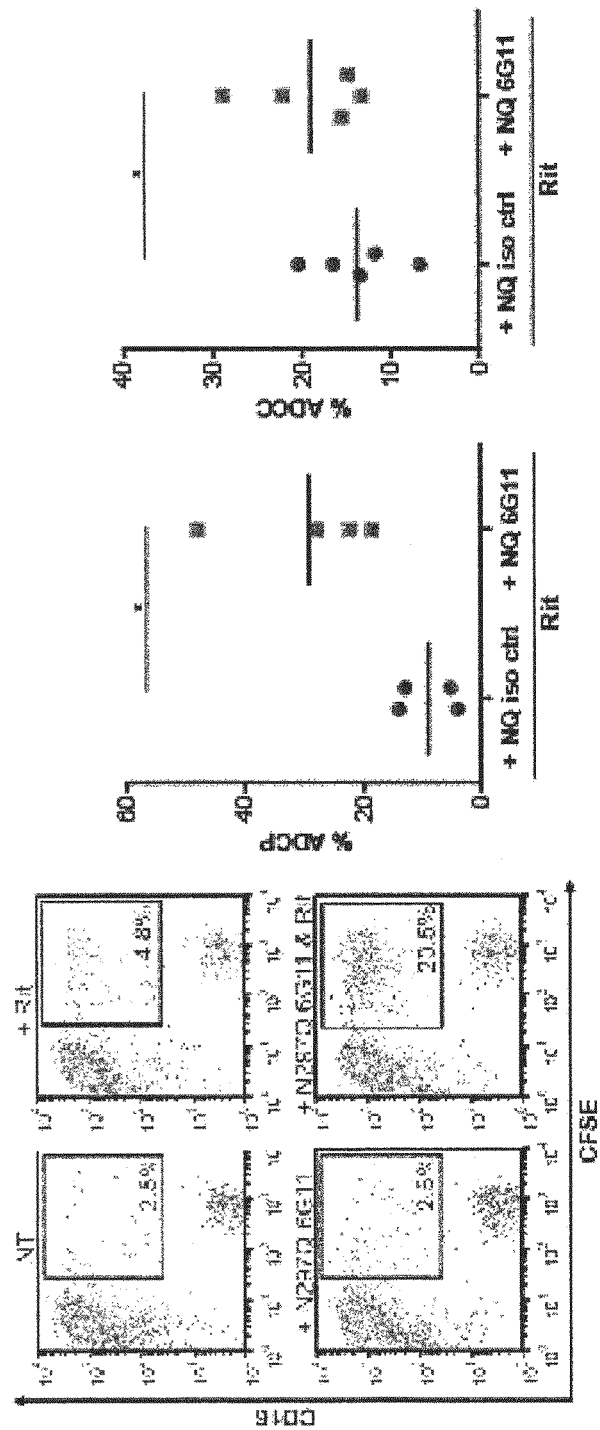

To address whether 6G11 could also enhance the cytotoxic activity of rituximab by preventing its internalization we co-incubated primary CLL cells with rituximab and an N297Q variant of 6G11 and assessed MDM ADCP and NK cell ADCC. Strikingly, N297Q 6G11 was shown to substantially promote the ability of MDM to engulf rituximab-opsonized CLL cells compared to rituximab alone (FIGS. 3H and I). Similar increases in activity were seen in ADCC assays with NK cells (FIG. 3J). NK cells do not express FcγRIIB, confirming that any augmentation evoked by the hFcγRIIB mAb arises from effects on the target cells due to their inhibition of rituximab internalization. These data confirm that blocking hFcγRIIB on the surface of B cell targets inhibits internalization of the mAb:Ag:hFcγRIIB complex, and augments their ability to be targeted for deletion by effector cells.

Taken together, these observations suggested that 6G11 can elicit anti-tumor activity through dual mechanisms— intrinsic cytotoxic activity and potentiation of rituximab activity through prevention of its removal from the cell surface.

6G11 has Intrinsic B Cell Depleting Activity and Potentiates Depletion with Rituximab in Immune Competent hCD20$^{+ve}$ hFcγRIIb$^{+ve}$ Tg Mice As discussed above, hFcγRIIB is expressed on both target B cells, where it mediates the undesirable removal of rituximab from the cell surface, and on key immune effector cells such as macrophages where it functions to dampen anti-cancer antibody responses.[5-7,35] To understand the impact of targeting hFcγRIIB systemically on relevant hFcγRIIB-expressing cell-types, we generated mice expressing the hFcγRIIB gene under the control of the hFcγRIIB promoter (FIGS. 14A and B). The expression and distribution of hFcγRIIB in the Tg mouse closely resembles that in human tissues being strongly expressed on B lymphocytes, BMDM and monocytes but not on neutrophils unlike mFcγRII (FIGS. 14C-F and not shown). Furthermore, equivalent expression was maintained in the mFcγRII$^{-/-}$ background allowing us to study the effect of hFcγRIIB in the absence of complications from the endogenous mouse inhibitory FcγR. Importantly, the antagonistic activity of 6G11 was retained in these mice (FIG. 14(5/5). In addition, hFcγRIIB expression on endothelial cells was lower than that in WT mice and more similar to that in humans (FIG. 14(5/5).

To ascertain the safety of 6G11 treatment in vivo we performed a dose-escalation study treating cohorts of hFcγRIIB$^{+/-}$×mFcγRII$^{-/-}$ mice with 1, 10 or 100 mg/kg 6G11 (FIG. 18). None of the treated mice suffered adverse events such as acute effects, distress or weight loss (FIG. 18). Tissue examination at day 7 failed to indicate any gross toxicity in the organs (kidney, brain, spleen, liver, lungs). Substantial depletion of hFcγRIIB$^+$ B cells was observed both in the blood (FIG. 6A) and spleen (FIG. 6B) at doses above 1 mg/kg, with equivalent activity in the 10 and 100 mg/kg groups. 6G11 is a fully human mAb easily detected in the sera of mice but inherently immunogenic and so we concurrently assessed its half-life and evidence of mouse anti-human antibody (MAHA) responses. At doses >1 mg/kg, target-mediated clearance that affects the PK profile was overcome, with little or no effect of target binding in the 10 and 100 mg/kg groups (FIG. 6C). However, within 7 days significant MAHA was observed resulting in rapid mAb clearance (FIG. 6D). Based upon the time-points prior to the advent of significant MAHA, we estimate the mAb half-life to be in the region of 2-4 days for the 10 and 100 mg/kg doses (FIG. 6C, D and Table 7).

We also performed a repeat dosing study to better mimic how 6G11 might be delivered clinically, administering it 4 times throughout a 24-day period (FIG. 18) with mice examined as before. Depletion of circulating B cells was observed in hFcγRIIB$^{+/-}$×mFcγRII$^{-/-}$ but not the mFcγRII$^{-/-}$ control group injected with multiple doses (10 mg/kg) of 6G11 (FIG. 6E). Likewise, mice did not suffer weight loss (FIG. 18) or adverse events and no signs of gross toxicity were observed (data not shown). As before, substantial MAHA responses were observed in hFcγRIIB$^{+/-}$×mFcγRII$^{-/-}$ mice within 1 week and contributed to rapid loss of 6G11 from the serum (FIG. 6F). In contrast, no MAHA was detected in the mFcγRII$^{-/-}$ control group, indicating a co-dependence on xenogeneic mAb and surface antigen being required for MAHA induction (FIG. 6F).

To explore if hFcγRIIB$^+$ cells other than B cells might be deleted after 6G11 treatment, whole blood depletion assays with human blood (FIG. 6(2/2)) and in vivo experiments with the hFcγRIIB Tg mice (Figure S4N) were performed. B cells but not monocytes or neutrophils were deleted by WT 6G11 IgG1 but not N297Q 6G11. The same lack of depletion of monocytes and neutrophils was seen in combination with rituximab (FIG. 6(2/2)). Next, we used a recently developed in vitro cytokine release syndrome (CRS) assay (CRA) (Hussain et al., 2015) to assess the potential impact of 6G11 on human peripheral blood mononuclear cells (PBMCs) rendered sensitive to stimulation through high density culture (Romer et al., 2011) and able to detect substantial levels of IFN-γ, TNF-α and/or IL-8 following addition of several mAb specificities (CD3, CD28 or CD52) previously highlighted as eliciting CRS. Application of WT or N297Q 6G11 for 48 hr did not result in substantial cytokine release, unlike with 500× lower doses of CD3 mAb (FIG. 6). Similar results were obtained using a whole or diluted blood CRA (FIG. 19).

Collectively, these data demonstrated no adverse effects and indicated a therapeutically relevant PK profile for 6G11 mAb, supporting efficacy studies.

6G11 has Intrinsic Activity and Potentiates Depletion with Rituximab in Immune-Competent Mice The depleting potential of targeting hFcγRIIB, alone or in combination with rituximab was assessed using both hIgG1 6G11 and mIgG1 AT10. First, in short-term adoptive transfer assays[23], where CFSE$^{+ve}$ hFcγRIIB$^{+/-}$×mFcγRII$^{-/-}$ splenocytes were injected into WT recipients and consequently treated with 6G11 (FIGS. 4A and B), or AT10 (FIG. 15A) transferred cells were observed to be efficiently depleted from the circulation and spleen. Interestingly, administration of as low as 1 µg mAb was sufficient to elicit ~50% B cell depletion. Depletion was wholly dependent upon Fc:activatory FcγR interaction as activity was lost with F(ab')$_2$ fragments and N297Q variants; hFcγRIIB$^{+ve}$ targets were also not deleted in γ chain$^{-/-}$ mice, lacking activatory FcγRs (FIGS. 4A and B and FIG. 15A). These data confirm that antagonistic hFcγRII mAbs are capable of deleting target cells in vivo, dependent upon the interaction with activatory FcγRs on immune effector cells as indicated previously.[36]

To extend our analysis to combination therapy with rituximab, hCD20$^{+/-15,37}$×hFcγRIIB$^{+/-}$×mFcγRII$^{-/-}$ mice were generated by inter-crossing. Combination of rituximab and 6G11 (or AT10) resulted in higher depletion of hCD20$^{+/-}$×hFcγRIIB$^{+/-}$×mFcγRII$^{-/-}$ B cells compared to either mAb alone in short-term assays transferring targets into WT recipients (FIG. 4C and FIG. 15B, respectively). Similarly, adoptively transferred hCD20$^{+/-}$×hFcγRIIB$^{+/-}$×mFcγRII$^{-/-}$ B cells were more significantly depleted by combining rituximab with 6G11 in hFcγRIIB$^{+/-}$×mFcγRII$^{-/-}$ recipient mice (expressing the hFcγRIIB also on the effector cells) (FIG. 4D).

We next investigated the effect of the combination on circulatory B cells in the hCD20$^{+/-}$×hFcγRIIB$^{+/-}$×mFcγRII$^{-/-}$ mouse model. As before the combination resulted in significantly higher depletion of circulating B cells compared to monotherapy (FIG. 4E and FIGS. 15C and D), demonstrating this capacity for the first time in a fully syngeneic system in which hFcγRIIB is expressed on both the target and effector cells. The effect of combining rituximab and WT hIgG1 6G11 (or AT10) was greater than that expected for additive activity (FIGS. 4(2/2) and 15, respectively), as judged from the responses observed with the individual mAbs applied singly at two-fold higher doses.

To assess whether intrinsic (B cell depleting) versus extrinsic (rituximab boosting) effects of 6G11 were more important for this activity, we used N297Q 6G11 in the hCD20$^{+/-}$×hFcγRIIB$^{+/-}$×mFcγRII$^{-/-}$ mice and show that while N297Q 6G11 alone is inactive in deletion, it significantly boosts rituximab deletion of B cells (FIG. 4(2/2). Similar results were seen with mIgG1 6G11. As expected and observed with AT10 (FIG. 15), mIgG1 6G11 displayed poor single agent depleting activity in hCD20$^{+/-}$×hFcγRIIB$^{+/-}$×mFcγRII$^{-/-}$ mice (Hamaguchi et al., 2006), but similar to N297Q hIgG1 6G11, was able to significantly boost a murine IgG2a version of rituximab in its ability to deplete B cells (FIG. 15). Moreover, owing to its mouse Fc, it is not actively cleared by MAHAs, facilitating longer-term assessment of the combination therapy. These data show the long-term beneficial effect of antagonizing hFcγRIIB-function for enhancing rituximab's depleting activity in vivo.

Together, these studies confirmed a dual mechanism of action in vivo for 6G11, involving intrinsic anti-tumor function coupled to the potentiation of rituximab anti-tumor activity through the prevention of internalization.

6G11 Enhances Type II hCD20 mAb-Mediated Depletion of B Cells In Vivo

In order to investigate whether 6G11 was also effective in combination with type II hCD20 mAb, which are not internalized to the same extent as type I CD20 mAbs[13,23,33], and which were recently approved for use in CLL, we performed experiments in the adoptive transfer model. As for rituximab, both GA101$_{gly}$ (glycosylated obinutuzumab) and 6G11 monotherapy resulted in modest depletion of splenic and circulating target CFSE$^{+ve}$ hCD20$^{+/-}$×hFcγRIIB$^{+/-}$×mFcγRII$^{-/-}$ B cells, whereas the combination therapy significantly enhanced depletion of both splenic and circulating target cells in the recipient WT and hFcγRIIB$^{+/-}$×mFcγRII$^{-/-}$ mice (FIGS. 4F and G; and data not shown). These data suggest that 6G11 would be also effective in combination with other direct B cell targeting mAbs.

6G11 Boosts Rituximab-Mediated Depletion of Primary CLL Cells and Improves Objective and Complete Anti-Tumor Responses In Vivo Although rituximab has been employed successfully to improve the treatment of several B cell malignancies, it has limited activity in controlling CLL. Despite initial peripheral depletion in the blood, effective tumor de-bulking from the secondary lymphoid tissues and so-called proliferation centers is less successful. Therefore, to better assess the anti-tumor activity of 6G11 against CLL cells, we developed an animal model wherein primary human CLL cells home to secondary lymphoid organs (spleen and bone marrow), and proliferate in clusters alongside supportive human T cells, thereby closely mimicking the situation in the human disease (FIGS. 5A and B). In this model, rituximab is effective at depleting CLL cells residing in the peritoneal cavity, but it is incompletely effective at depleting CLL cells in the proliferation centers present in the spleen (FIG. 16).

When mice engrafted with primary CLL cells were treated with either rituximab or 6G11 alone, significant reductions in tumor mass were seen in the spleens compared to animals treated with an isotype control mAb (FIG. 5C). Treatment with a combination of rituximab and 6G11 resulted in even higher depletion rates (FIG. 5C). Moreover, when these data were assessed according to the criteria of response rates, the numbers of partial and complete responders following combinatorial therapy were significantly higher than isotype control-treated mice or monotherapies (FIGS. 5D and 5E, respectively).

Additionally, the numbers of objective—(OR; defined as >75% reduction of CLL cells in the spleen) and complete-responders (CR; defined as <0.1% CLL cells in the spleen) following combination therapy were significantly higher than isotype control-treated mice or monotherapies (FIGS. 5 and 5(2/2), and Table 5). These data demonstrate the increased efficacy of the rituximab/6G11 combination therapy against primary CLL cells in vivo.

We then examined the ability of 6G11 to treat mice engrafted with CLL cells isolated from rituximab, ofatumumab (hCD20 mAb) and/or alemtuzumab (hCD52 mAb)-refractory patients (Table 4). The xenografted mice were treated with either 6G11 or rituximab as monotherapy, or with the two mAbs in combination. As expected, treatment with rituximab alone was inefficient (FIGS. 5 and 5(2/2) and Table 8) and >95% of mice failed to generate OR. In contrast, 6G11 alone showed significant CLL cell depletion, but failed to improve OR (FIGS. 5 and 5(2/2) and Table 5). Remarkably, however, co-administration of rituximab with 6G11 resulted in robust depletion (FIGS. 5 and 5(2/2), and Table 8) with >25% OR (Table 5). These data suggest that, in addition to boosting rituximab activity in responder patients, 6G11 may be active against treatment-refractory CLL cells.

Combination Therapy with Rituximab and 6G11 Overcomes Refractory CLL Cells In Vivo Thereafter, we examined the ability of 6G11 to treat mice engrafted with CLL cells isolated from rituximab and/or alemtuzumab (hCD52 mAb)-refractory patients in the presence or absence of rituximab (Table 4). As expected, depletion of the cells with rituximab alone was inefficient, but this was significantly improved in the presence of 6G11 (FIG. 5F). Moreover, a higher number of mice engrafted with the refractory CLL cells receiving the combinational therapy achieved partial responses with the combination (FIG. 5G). These data provide encouragement that 6G11 can boost rituximab efficacy in both rituximab-sensitive and -refractory patient groups.

TABLE 4

Information regarding patient info, previous treatment and responses of patients clinically defined as Rituximab refractory. This is compared to relative responses in the in vivo model where the number of CLL cells in the spleen of isotype control treated mice is set to 100% + SD.

| | | Relative responses to in vivo treatment, % | | | |
|---|---|---|---|---|---|
| Previous treatments | Additional information | Cntrl | Rit | 6G11 | Rit + 6G11 |
| Year 1: FCx2 - no response<br>Year 3: FC + Alemtuzumab x3 followed by BR -no response<br>Year 5: DHAPx1 - no response<br>Year 6-7: irradiation | Female<br>Age 44<br>diagnosed 7 years prior to sampling<br>WBC 234 at time of sampling | 100 ± 15 | 92 ± 21 | 78 ± 18 | 73 ± 14 |
| Year 2: FCR x3 with initial response, progression within 7 months<br>Year 3: BR - progression during treatment<br>Year 3: Ofatumumab - no response<br>Year 3: Diseased | Female<br>Age 71<br>diagnosed 3 years prior to sampling<br>13q and monosomi 12<br>WBC 50 at time of sampling<br>Sample acquired between BR and Ofatumumab treatment | 100 ± 21 | 100 ± 28 | 98 ± 31 | 79 ± 18 |

TABLE 4-continued

Information regarding patient info, previous treatment and responses of patients clinically defined as Rituximab refractory. This is compared to relative responses in the in vivo model where the number of CLL cells in the spleen of isotype control treated mice is set to 100% + SD.

| | | Relative responses to in vivo treatment, % | | | |
|---|---|---|---|---|---|
| Previous treatments | Additional information | Cntrl | Rit | 6G11 | Rit + 6G11 |
| Year 1-2: Klorambucil<br>Year 3: F +<br>Alemtuzumab - response<br>but progression within<br>ca 1 year.<br>Year 5: FCR x2 -<br>response but<br>progression within ca 1<br>year<br>Year 7: BR x4 - response<br>but progression within 7<br>months<br>Year 8: BR - partial<br>response<br>Year 9: Diseased | Female<br>Age 66<br>diagnosed 8<br>years prior to<br>sampling<br>FISH normal<br>(13q, 11q,<br>17p, +12)<br>WBC 359 at<br>time of sampling<br>(September 2013)<br>Sample<br>acquired before<br>last BR<br>treatment year 8 | 100 ± 36 | 74 ± 35 | 52 ± 16 | 31 ± 10 |
| Year 2: Steroid pulses +<br>Alemtuzumab - partial<br>but short remission<br>Year 3: Ofatumumab -<br>weak initial response<br>progression within 3<br>months<br>Year 4: Diseased | Male<br>Age 70<br>diagnosed 3<br>years prior to<br>sampling<br>50% chr 12<br>trisomi<br>WBC 77 at time<br>of sampling<br>Sample during<br>progression<br>after<br>Ofatumumab<br>treatment | 100 ± 38 | 88 ± 56 | 73 ± 49 | 55 ± 26 |

Figure 17B:
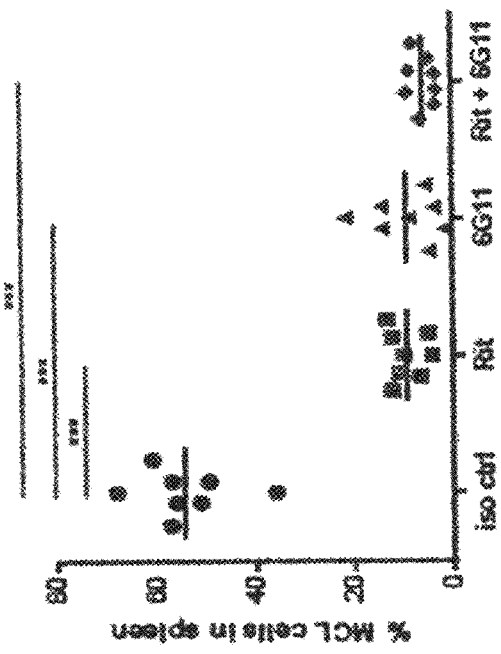

Combination Therapy with Rituximab and 6G11 has Activity In Vivo Against Primary MCL Cells To evaluate the ability of 6G11 to target other types of malignant B cells, we used immunodeficient mouse models engrafted with Jeko MCL cells or freshly isolated primary MCL cells (FIGS. 17A and B, respectively). When mice were engrafted with Jeko MCL cells, monotherapy with either 6G11 or rituximab did not result in long-term survival, whereas the combination was effective in curing ~30% of mice out to 100 days. Similarly, as with primary CLL cells, primary MCL cells responded favorably to the combination therapy (FIG. 17B).

6G11 is Well-Tolerated, has Therapeutically Relevant Pharmacokinetics In Vivo and does not Result in a Cytokine Storm In Vitro Next, to ascertain the safety of the 6G11 mAb treatment we performed a dose escalation study treating cohorts of hFcγRIIB$^{+/-}$xmFcγRII$^{-/-}$ mice with a single shot of 1, 10 or 100 mg/kg of 6G11, examining both i.v. and i.p. routes of administration at the 10 mg/kg dose (FIG. 18A). None of the treated mice suffered adverse events such as acute effects, distress or weight loss (FIG. 17B). Tissue examination at day 7 failed to indicate any gross toxicity in the organs (kidney, brain, spleen, liver, lungs) (data not shown). Depletion of hFcγRIIB$^{+ve}$ B cells was observed both in the blood (FIG. 6A) and spleen (FIG. 6B), at doses above 1 mg/kg, with equivalent activity in the 10 and 100 mg/kg groups indicating efficacy. 6G11 is a fully human mAb easily detected in the sera of mice but inherently immunogenic and so we concurrently assessed its half-life and evidence of mouse anti-human antibody (MAHA) responses (FIGS. 6C and D). These data indicate that at doses above 1 mg/kg, target mediated clearance that affects the PK profile is overcome, with little-to-no effect of target binding seen in the 10 and 100 mg/kg groups. However, within 7 days significant MAHA was observed (increasing by 4 orders of magnitude from day 4 to 7 in the 10 mg/kg i.v. group; FIG. 6D) resulting in rapid clearance of the mAb. Based upon the first 4 days post-administration prior to the advent of significant MAHA, we estimate the antibody ½ life to be in the region of 2-4 days for the 10 and 100 mg/kg doses (FIGS. 6C and D and Table 3).

We also performed a repeat dose study to mimic better how 6G11 might be delivered clinically, administering it over a 10 day period (an initial i.v. administration followed by 3 doses delivered i.p.; FIG. 17C) with animals examined throughout and 14 days later (24 days in total of receiving mAb) for any signs of distress, weight loss, toxicity or pathology. As before, depletion of circulating B cells was observed in hFcγRIIB$^{+/-}$xmFcγRII$^{-/-}$ but not the mFcγRII$^{-/-}$ control group injected with multiple (10 mg/kg) doses of 6G11 (FIG. 6E). Likewise, mice did not suffer weight loss (FIG. 17B), did not appear to suffer adverse events and no signs of gross toxicity were observed (FIG. 17D; and data not shown). As before, substantial MAHA responses were observed in hFcγRIIB$^{+/-}$xmFcγRII$^{-/-}$ mice within 1 week and contributed to rapid loss of 6G11 from the serum (FIG. 6F). Interestingly, no MAHA was detected in the mFcγRII$^{-/-}$ control group, indicating that the presence of surface antigen is required for MAHA induction (FIG. 6F).

Finally, we used a recently developed in vitro cytokine release syndrome (CRS) assay to assess the potential impact of 6G11 on human PBMCs rendered sensitive to stimulation through high density culture.[28] This assay system is able to detect substantial levels of IFN-γ, TNF-α and/or IL-8 following addition of several mAb specificities (CD3, CD28 or CD52) previously highlighted as eliciting CRS (FIG. 6F and manuscript in preparation). Application of WT or N297Q 6G11 in this assay for 48 hours did not result in substantial cytokine release, unlike with 500 times lower doses of CD3 mAb (FIG. 6G). Similar results were obtained using a whole blood cytokine assay (FIG. 18), which together indicate a good safety profile for 6G11 prior to investigation in humans.

6G11 Enhances Therapeutic Activity of Other Clinically-Relevant Antibodies In Vivo Recent observations indicate that FcγRIIB-dependent internalization may underlie resistance to several clinically relevant antibodies besides rituximab (Vaughan et al., 2014); (Pallasch et al., 2014). We therefore examined combining 6G11 with the recently approved hCD20 mAb obinutuzumab (GA101), and the clinically well-validated hCD52 specific mAb alemtuzumab. The specificity of obinutuzumab for hCD20 allowed us to study effects in the syngeneic mouse model. Both GA101 and 6G11 monotherapy resulted in modest depletion of splenic and circulating B cells, whereas the combination significantly enhanced depletion in WT (FIG. 5(2/2) and hFcγRIIB[+/−]× mFcγRII[−/−] mice (FIGS. 6F and S6G). Combining 6G11 with GA101 significantly improved splenic tumor cell depletion in the CLL-patient xenograft mouse model (FIG. 5(2/2) and Tables 5 and 8). While alemtuzumab's specificity for hCD52 precluded studies in the syngeneic hCD20 model, there was a significant improvement in therapeutic activity when 6G11 and alemtuzumab were combined in the CLL-mouse model, with >90% of combination-treated mice developing CR (FIG. 5(2/2) and Tables 5 and 8).

These data provide evidence that 6G11 may overcome mAb drug-resistance for multiple targets.

TABLE 5

Responses to mAb treatment in primary CLL-patient xanografts

| Therapeutic mAb (samples) | Treatment No. of CLL Samples | Isotype ctrl, % (n/N) | | | Therapeutic mAb, % (n/N) | | |
|---|---|---|---|---|---|---|---|
| | | NR | OR | CR | NR | OR | CR |
| Rituximab (all-comers) | 11 | 94 (61/65) | 4.5 (3/65) | 1.5 (1/65) | 58 (37/64) | 30[a] (19/64) | 12[a] (8/64) |
| Rituximab (refractory) | 4 | 100 (21/21) | 0 | 0 | 95.5 (21/22) | 4.5 (1/22) | 0 |
| GA101 (all-comers) | 3 | 100 (20/20) | 0 | 0 | 30 (6/20) | 70[c] (14/20) | 0 |
| GA101 (resistant) | 1 | 80 (4/5) | 20 (1/5) | 0 | 80 (4/5) | 20 (1/5) | 0 |
| Alemtuzumab (all-comers) | 3 | 100 (15/15) | 0 | 0 | 0 | 47[b] (7/15) | 53[b] (8/15) |

| Therapeutic mAb (samples) | 6G11 (hFcγRIIB), % (n/N) | | | Thereapeutic mAb + 6G11, % (n/N) | | |
|---|---|---|---|---|---|---|
| | NR | OR | CR | NR | OR | CR |
| Rituximab (all-comers) | 52 (35/67) | 33[a] (22/67) | 15[c] (10/67) | 26 (17/66) | 42[a,d,f] (28/66) | 32[a,e,f] (21/66) |
| Rituximab (refractory) | 95.5 (21/22) | 4.5 (1/22) | 0 | 74 (14/19) | 26[c] (5/19) | 0 |
| GA101 (all-comers) | 50 (10/20) | 50[e] (10/20) | 0 | 20 (4/20) | 75[a] (15/20) | 5 (1/20) |
| GA101 (resistant) | 100 (5/5) | 0 | 0 | 40 (2/5) | 60 (3/5) | 0 |
| Alemtuzumab (all-comers) | 7 (1/14) | 99[a] (13/14) | 0 | 0 | 7 (1/15) | 93[a,d,e] (14/15) |

All-comers, primary CLL samples with no indication of prior resistance;
resistant, primary CLL samples with prior demonstration of rituximab resistance;
NR, non-responder (no CLL cell depletion);
OR, objective responder (≥75% reduction in CLL cells);
CR, complete responder (≤0.1% CLL cells).
[a] $p \leq 0.001$ vs isotype control.
[b] $p \leq 0.05$ vs isotype control.
[c] $p \leq 0.01$ vs isotype control.
[d] $p \leq 0.001$ vs therapeutic mAb.
[e] $p \leq 0.05$ vs therapeutic mAb.
[f] $p \leq 0.01$ vs therapeutic mAb.

TABLE 6 related to FIG. 1. Affinity measurements of hFcγRIIA and hFcγRIIB mAbs as assessed by ELISA and/or SPR.

| Clone Name | EC50 FcγRIIA+ CHO | EC50 FcγRIIB+ CHO | EC50 FcγRIIA | EC50 FcγRIIB | $K_A$ (1/MS) | $K_D$ (1/s) | $K_D$ (M) |
|---|---|---|---|---|---|---|---|
| iso ctrl | nb[a] | Nb | nb | nb | | | |
| 1A01 | 0.4 | Nm | 0.2 | | | | |
| 1B07 | 0.3 | Nb | 0.3 | | | | |
| 1C04 | 0.3 | Nb | 1.5 | | | | |
| 1E05 | 0.5 | Nb | 0.7 | | | | |
| 2A09 | 0.6 | Nb | 0.6 | | | | |
| 2B08 | 0.6 | Nm | 2.0 | | | | |

TABLE 6-continued related to FIG. 1. Affinity measurements of hFcγRIIA and hFcγRIIB mAbs as assessed by ELISA and/or SPR.

| Clone Name | EC50 FcγRIIA+ CHO | EC50 FcγRIIB+ CHO | EC50 FcγRIIA | EC50 FcγRIIB | $K_A$ (1/MS) | $K_D$ (1/s) | $K_D$ (M) |
|---|---|---|---|---|---|---|---|
| 2E08 | 0.3 | Nm | 1.3 | | | | |
| 5C04 | nm[b] | 0.4 | | 0.8 | $3.24 \times 10^5$ | 0.04808 | $1.42 \times 10^{-7}$ |
| 5C05 | nb | 1.7 | | 2.7 | 801.6 | 0.001769 | $5.45 \times 10^{-7}$ |
| 5D07 | nm | 0.4 | | 0.6 | | | |
| 5E12 | nb | 1.0 | | 3.4 | | | |
| 5G08 | nb | 0.7 | | 0.7 | $4.72 \times 10^5$ | 0.3365 | $7.13 \times 10^{-7}$ |
| 5H06 | nm | 0.4 | | 0.6 | | | |
| 6A09 | nm | 1.4 | | 3.7 | | | |
| 6B01 | nm | 0.5 | | 1.4 | | | |
| 6C11 | nb | 0.5 | | 2.3 | | | |
| 6C12 | nb | 0.3 | | 1.0 | | | |
| 6D01 | nm | 0.3 | | 0.9 | | | |
| 6G03 | nb | 0.4 | | 0.9 | | | |
| 6G08 | nb | 0.6 | | 1.7 | | | |
| 7C07 | nm | 0.3 | | 0.3 | $9.13 \times 10^5$ | 0.01851 | $2.39 \times 10^{-8}$ |
| 4B02 | nb | 0.6 | | 1.0 | | | |
| 6G11 | nm | 0.3 | | 0.4 | $6.9 \times 10^6$ | 0.1819 | $2.64 \times 10^{-8}$ |
| 6H08 | nb | 1.4 | | 3.6 | | | |

[a]nb: no binding.
[b]nm: not measured.

TABLE 7 related to FIG. 14. Pharmacokinetics (PK) parameter estimates of WT 6G11 mAb in hFcγRIIB+/− × mFcγRII−/− mice.

| Dose group | | $t\frac{1}{2}$ (day)[a] | Vz (ml/kg)[b] | Vss (ml/kg)[c] | CL (ml/day/kg)[d] | AUC (day * μg/ml)[e] | Cmax (μg/ml)[f] | Tmax (hour)[g] |
|---|---|---|---|---|---|---|---|---|
| 10 mg/kg (i.v.) | Geom mean | | 88.8 | 82.5 | 48.5 | 206 | 201000 | 0.166 |
| n = 6 | Stdev | 0.607 | 14.2 | 15.1 | 36.2 | 106 | 55800 | |
| | CV (%) | | 16.0 | 18.3 | 74.6 | 51.3 | 27.8 | |
| | Harm mean | 1.08 | | | | | | |
| | CV (%) | 56.0 | | | | | | |
| 10 mg/kg (i.p.) | Geom mean | | 107 | | 29.0 | 344 | 117000 | 3.83 |
| n = 4 | Stdev | 0.65 | 7.52 | | 6.10 | 72.0 | 13300 | 2.50 |
| | CV (%) | | 7.04 | | 21.0 | 20.9 | 11.4 | 65.2 |
| | Harm mean | 2.49 | | | | | | |
| | CV (%) | 26.0 | | | | | | |
| 100 mg/kg (i.v.) | Geom mean | | 53.7 | 54.6 | 12.2 | 7770 | 2350000 | 0.224 |
| n = 6 | Stdev | 0.925 | 16.0 | 16.2 | 1.12 | 638 | 402000 | 0.340 |
| | CV (%) | | 29.7 | 29.6 | 9.16 | 8.21 | 17.2 | 152 |
| | Harm mean | 3.09 | | | | | | |
| | CV (%) | 29.9 | | | | | | |

[a]mAb half-life.
[b]Volume of distribution associated with terminal phase.
[c]Volume of distribution at steady state (steady state, the state of equilibrium obtained at the end of a certain number of administrations).
[d]Clearance; the volume of plasma cleared (i.e., no longer containing any of the drug concerned) per unit time.
[e]Area under the curve; corresponds to the integral of the plasma concentration of the drug versus an interval of definite time.
[f]The peak plasma concentration of a drug after administration.
[g]The time it takes to reach Cmax.

TABLE 8 related to FIGS. 5 and 5(2/2). Detailed p values analyzed using a permutation statistical test for comparisons of different mAb treatments in the in vivo patient-derived xenograft models.

| All-comer CLL patient xenografts | | | | | | | | |
|---|---|---|---|---|---|---|---|---|
| | iso ctrl | Rit | 6G11 | Rit + 6G11 | Alem | Alem + 6G11 | GA101 | GA101 + 6G11 |
| iso ctrl | NA | $10^{-9}$ | $10^{-9}$ | $10^{-9}$ | $1.8 \times 10^{-5}$ | $1.8 \times 10^{-5}$ | $2.5 \times 10^{-7}$ | $2.2 \times 10^{-8}$ |
| Rit | $10^{-9}$ | NA | 0.23 | $2.6 \times 10^{-8}$ | NA | NA | NA | NA |
| 6G11 | $10^{-9}$ | 0.23 | NA | $2.4 \times 10^{-6}$ | $3.7 \times 10^{-5}$ | $3.5 \times 10^{-5}$ | 0.15 | $1.8 \times 10^{-5}$ |
| Alem | $1.8 \times 10^{-5}$ | NA | $3.7 \times 10^{-5}$ | NA | NA | $2.9 \times 10^{-4}$ | NA | NA |
| GA101 | $2.5 \times 10^{-7}$ | NA | 0.15 | NA | NA | NA | NA | 0.0095 |

| Rituximab-refractoty CLL patient xenografts | | | | |
|---|---|---|---|---|
| | iso ctrl | Rit | 6G11 | Rit + 6G11 |
| iso ctrl | NA | 0.10 | 0.040 | $8.7 \times 10^{-6}$ |
| Rit | 0.10 | NA | 0.28 | 0.0025 |
| 6G11 | 0.040 | 0.28 | NA | 0.01 |

| MCL patient xenografts | | | | |
|---|---|---|---|---|
| | iso ctrl | Rit | 6G11 | Rit + 6G11 |
| iso ctrl | NA | $8.6 \times 10^{-4}$ | $8.6 \times 10^{-4}$ | $8.6 \times 10^{-4}$ |
| Rit | $8.6 \times 10^{-4}$ | NA | 0.57 | 0.033 |
| 6G11 | $8.6 \times 10^{-4}$ | 0.57 | NA | 0.12 |

NA: not applicable.

Discussion

Cancer cells are highly proliferative, inherently genomic unstable and have a high propensity for mutation. These facets provide the perfect environment for cellular evolution under selection from conventional anti-cancer drugs, where genetically distinct, treatment resistant clones emerge leading to treatment failure. This capacity is clearly evident in the resistance mechanisms that develop against DNA damaging chemotherapy and small molecule inhibitors which target distinct signaling pathways, such as imatinib, erlotinib and ibrutinib.[39-43] Such mechanisms involve mutations in targeted receptors or compensatory changes in downstream signaling proteins.[44] Others involve multi-drug resistance mechanisms achieved through upregulation of drug efflux pumps (reviewed in[45]). The failure of conventional and targeted small molecule inhibitors has led to the search for means to overcome these modes of resistance and also alternative therapies, including those that engage the immune system.

Monoclonal antibodies (mAb) have to date been the most successful exponent of this approach, with Abs in hematological disorders leading the field. B cell cancers represent the clinically best-studied type of cancer with respect to antibody therapy. Since the approval of rituximab in 1997, and with the recent approval of second (ofatumumab) and third (obinutuzumab) generation hCD20 mAbs, these agents have become an important mainstay in the armamentarium to treat B cell cancers. However, it is clear that mAb immunotherapy is also susceptible to both intrinsic and acquired resistance. It is now well-established that tumors influence their surrounding microenvironment by subverting stromal and myeloid cells to support their survival and growth.[46] At least two mechanisms of resistance relevant to mAb therapy are precipitated by the inhibitory FcγRIIB (reviewed in[47]). In addition to the inhibitory effect on effector cells indicated by Clynes[5], it has recently been shown that rituximab and other type I hCD20 mAb engage hFcγRIIB by bipolar antibody bridging on the B cell surface, resulting in internalization of the mAb:CD20:FcγRIIB complex[13,23,48], thereby limiting its ability to engage critical Fc-dependent effector functions ([23] and Tipton et al. unpublished). Here, this Example describes the generation of fully human hFcγRIIb mAb that are able to block both of these resistance mechanisms and are thus able to unleash the full potential of other therapeutic mAb and help overcome resistance to antibody therapy in vivo.

Strikingly, co-administration of hFcγRIIB mAb did not only improve objective and complete responses of mice grafted with CLL cells from rituximab-responding patients, but importantly they also overcame the mAb treatment-resistant phenotype of CLL cells from relapsed/refractory patients resistant to rituximab or the hCD52-targeting mAb, alemtuzumab.

A role for tumor cell FcγRIIB was recently proposed in resistance to hCD52 mAb therapy in select microenvironments (Pallasch et al., 2014). hFcγRIIB was found upregulated in alemtuzumab-resistant bone marrow leukemic B cells compared with more susceptible splenic compartments, and shRNA-mediated knock-down of hFcγRIIB in these improved hCD52 mAb therapy in otherwise resistant tissue. These findings are consistent with the observations made in our CLL model. Whereas CLL cells in susceptible peritoneal compartments were readily depleted by hCD20 mAb, depletion in resistant microenvironments required blocking of tumor FcγRIIB. Consistent with high FcγRIIB expression underlying decreased mAb activity in resistant tissue compartments, FcγRIIB-blocking enhanced alemtuzumab and also type II hCD20 mAb in our CLL model. We previously showed that type II hCD20 mAbs only internalize efficiently in the presence of high levels of FcγRIIB (Vaughan et al., 2014). Collectively, these observations demonstrate that FcγRIIB-mediated resistance is relevant to several different clinically approved antibodies, indicating a broad therapeutic potential for combination with hFcγRIIB mAb.

It has previously been shown that type I CD20 mAbs show a much greater tendency to internalize into targeted tumor cells than type II[13,23,33], with the latter only internalized efficiently in the presence of high levels of FcγRIIB.[33] The finding here that the B cell depleting activity of type II CD20 antibodies appears to be similarly improved by co-treatment with 6G11 in vivo is therefore intriguing. Hemann and co-workers recently indicated a role for tumor cell FcγRIIB in resistance to hCD52 mAb therapy in select microenvironments.[49] FcγRIIB was found to be upregulated in alemtuzumab-resistant bone marrow compared with more susceptible splenic compartments, and siRNA-mediated knock-down of FcγRIIB in leukemic cells improved hCD52 mAb therapeutic effects in otherwise resistant tissue. These findings are consistent with the observations made with our CLL model. Whereas solitary CLL cells in susceptible splenic compartments were readily depleted by hCD20 mAb treatment, depletion of clustered proliferating CLL cells in resistant microenvironments required blocking of tumor FcγRIIB. Importantly, these observations (herein and[33]) demonstrate that FcγRIIB-mediated resistance is relevant to several different clinically approved antibodies and validated targets, indicating a broad therapeutic potential for combination with hFcγRIIB mAb.

Resistance to antibody therapy is observed in several types of cancer. Among B cell cancers, CLL and MCL are less well treated with hCD20 mAb-containing regimens compared with FL and DLBCL, indicating intrinsic resistance mechanisms in the former. Furthermore, individual patients with FL and DLBCL show inherent resistance to hCD20 mAb therapy, and a proportion of all B cell cancer patients initially responsive to antibody-containing immune therapy develop resistance and no longer benefit from treatment. Previous observations ([32,14] and unpublished data) indicate that FcγRIIB-mediated antibody internalization might be a common mechanism underlying resistance in these different B cell cancers and individuals. Herein, we present findings that co-administration with hFcγRIIB mAbs boosts rituximab antitumor activity against both CLL and MCL tumor cells in vivo, consistent with the observation that FcγRIIB-mediated antibody internalization is a therapeutically relevant resistance mechanism common to different B cell cancers.

This Example further demonstrates that hFcγRIIB mAb have intrinsic anti-tumor activity. Veri et al. previously developed hFcγRIIB-specific mAb but did not examine their activity against cancer targets in vivo.[50] Rankin et al. subsequently showed that targeting hFcγRIIB on malignant human B cells could be efficacious as a monotherapy. However, this study[36] used immunodeficient xenograft systems, where owing to the lack of Ab cross-reactivity with the mouse receptor, the target antigen was expressed only on the tumor, but not on critical immune effector cells, precluding assessment of the net effects of hFcγRIIB mAb. In the current work, using two different mAb clones, one fully human derived from phage-display and one murine derived through conventional hybridoma technology, we demonstrate in immunocompetent syngeneic mouse models where hFcγRIIB is expressed on both the target B cells and effectors that antagonistic hFcγRIIB antibodies have intrinsic antitumor activity. Importantly, using double Tg mice expressing both hCD20 and hFcγRIIB, we further demonstrate that mAb blocking of hFcγRIIB-mediated internalization boosts rituximab therapeutic activity when both targets are expressed in immunocompetent hosts in a cell- and tissue-specific manner analogous to that in man. Intriguingly, there was a particularly pronounced and apparent synergistic effect of co-administrating antagonistic hFcγRIIB mAbs and CD20 mAbs (rituximab or obinutuzumab) in this setting. It is tempting to speculate that enhanced activity resulted from mAb blocking of hFcγRIIB's immune suppressive function in effector cells, much as has been observed following genetic deletion of hFcγRIIB in similar immune competent models.[6,7] Regardless, and consistent with releasing FcγRIIB-mediated inhibition and preventing rituximab internalization (rather than direct targeting) being the principal mechanism of hFcγRIIB mAb boosting of rituximab therapeutic activity, we found that B cell deletion was less efficient with AT10 compared with 6G11 alone (perhaps due to the difference in isotype), but that the combination of AT10 and rituximab was equally effective in augmenting rituximab activity. Of note, it has long been appreciated that CLL is sub-optimally treated with rituximab[51] and other Type I anti-CD20 mAb[52,53] with higher doses being required. Coupled to our previous data[13] our new results indicate that combination therapy with hFcγRIIB mAb may not only be a way of preventing resistance but perhaps also a way of decreasing the dose of hCD20 mAb required in these cases.

At least three distinct mechanisms may thus contribute to the overall in vivo therapeutic activity of 6G11: intrinsic cytotoxicity; prevention of therapeutic mAb internalization; and neutralization of FcγRIIB-inhibitory signaling in immune cells. Several observations suggest that blocking receptor internalization and inhibitory signaling are the most critical for overcoming drug resistance. Firstly, there was a pronounced and apparently synergistic effect when antagonistic hFcγRIIB and hCD20 mAbs were co-administrated to the mice where hFcγRIIB is expressed on both target and effector cells. Secondly, we found that whereas B cell deletion was inefficient with AT10 alone, the combination of AT10 and rituximab was effective in augmenting rituximab activity. Most definitively, our data with N297Q hIgG1 6G11, which lacks the ability to engage activatory FcγR and has no direct cytotoxic capacity, confirms that blocking FcγRIIB activity is the key mechanism behind the efficacy of this approach. This provides evidence that function-blocking mAbs to FcγRIIB can recapitulate the enhanced anti-cancer mAb responses observed following genetic deletion of FcγRIIB (Clynes et al., 2000). However, here we have not explored directly the relative importance of antagonizing FcγRIIB function on the target versus immune effector cells for activity; these studies form the basis of our ongoing endeavors.

Of note, it has long been appreciated that CLL is sub-optimally treated with rituximab (O'Brien et al., 2001) and ofatumumab (Coiffier et al., 2008; Coiffier et al., 2006) with higher doses being required. Coupled to our previous data our current results indicate that combination therapy with hFcγRIIB mAb may not only be a way of preventing resistance, but perhaps also of decreasing the dose or shortening duration of hCD20 mAb therapy.

In addition to affording significant activity, a therapeutic mAb must also be tolerable and have therapeutically relevant pharmacokinetics (PK). The very high specificity of 6G11 for hFcγRIIB, with its lack of binding to the 98% homologous human hFcγRIIA, and negligible cross-reactivity with animal species commonly used for toxicological studies, prompted us to investigate safety parameters and PK/PD in Tg mice expressing human hFcγRIIB at levels and on cell-types and tissues similar to man. These studies indicated that 6G11 was well-tolerated and animals showed no signs of distress, weight loss, toxicity or pathology. Dose-titration experiments demonstrated that doses of 10 mg/kg or greater sufficed to saturate hFcγRIIB in vivo, yielded equivalent B cell depletion, and were able to maintain long-term blockade or removal of the receptor. In contrast, a dose of 1 mg/kg was sub-optimal, was cleared rapidly and did not appreciably delete splenic B cells. At doses above receptor saturation, terminal half-life of 6G11 was estimated at 2-4 days in the mouse. Although the lack of cross-reactivity with non-human primate species precluded interspecies scaling, these figures indicate a therapeutically relevant PK profile typical for a hIgG1 mAb with a half-life in the order of weeks in man.

Interestingly, in both human blood and in vivo in hFcγRIIB Tg mice, 6G11-treatment resulted in specific deletion of B cells. Although monocytes in both systems express hFcγRIIB, they were not substantially deleted. Current evidence suggests that macrophages and/or monocytes are the key effector cells responsible for mAb therapy (Beers et al., 2010); (Biburger et al., 2011; Gul et al., 2014) and so our data indicate that the key effectors are not deleted by hFcγRIIB mAb.

We previously explored an equivalent panel of anti-mouse FcγRII specific mAb mAb[25] and observed that they had limited therapeutic benefit due to their rapid consumption in vivo, predominantly by the non-tumor cells of the host.[17] Importantly, similar rates of internalization were not seen on human target cells, at least in vitro, in agreement with earlier studies.[36] Here, we extended these observations and demonstrated that the same was seen on primary human CLL samples and that in mice expressing hFcγRIIB Tg, rapid and extensive mAb consumption was not observed. These data confirm our earlier supposition that mouse and human inhibitory FcγRII(B) have different properties in relation to their capacity for internalization and to function as an antigenic sink, and suggest that hFcγRIIB mAb such as 6G11 will work effectively in humans.

Collectively, this Example demonstrates in vivo proof-of-concept that hFcγRIIB mAbs overcome the intrinsic and acquired resistance of tumor cells to mAb drugs; overcoming relapsed/refractory CLL cells. Our data support the clinical development of hFcγRIIB mAbs for therapy of FcγRIIB-expressing B cell cancers.

These data support the clinical development of hFcγRIIB mAbs for therapy of FcγRIIB-expressing B cell cancers. Furthermore, analogous to the spread of CD20 mAbs into other diseases there is evidence to suggest their utility in other therapeutic settings such as autoimmunity where FcγRIIB-expressing targets may be amenable to manipulation, for example in systemic light-chain amyloidosis where the target PCs express high levels of FcγRIIB (Zhou et al., 2008) and rheumatoid arthritis where B cell activation might be reduced through agonism of FcγRIIB (Baerenwaldt et al., 2011; Mauri and Jury, 2010).

REFERENCES

1. Reichert, J. M. & Dhimolea, E. The future of antibodies as cancer drugs. *Drug Discov Today* 17, 954-963 (2012).
2. Nimmerjahn, F. & Ravetch, J. V. FcgammaRs in health and disease. *Curr Top Microbiol Immunol* 350, 105-125 (2011).
3. Nimmerjahn, F. & Ravetch, J. V. Fcgamma receptors as regulators of immune responses. *Nature reviews* 8, 34-47 (2008).
4. Chao, M. P., et al. Anti-CD47 antibody synergizes with rituximab to promote phagocytosis and eradicate non-Hodgkin lymphoma. *Cell* 142, 699-713 (2010).
5. Clynes, R. A., Towers, T. L., Presta, L. G. & Ravetch, J. V. Inhibitory Fc receptors modulate in vivo cytoxicity against tumor targets. *Nature medicine* 6, 443-446 (2000).
6. Minard-Colin, V., et al. Lymphoma depletion during CD20 immunotherapy in mice is mediated by macrophage FcgammaRI, FcgammaRIII, and FcgammaRIV. *Blood* 112, 1205-1213 (2008).
7. Hamaguchi, Y., Xiu, Y., Komura, K., Nimmerjahn, F. & Tedder, T. F. Antibody isotype-specific engagement of Fcgamma receptors regulates B lymphocyte depletion during CD20 immunotherapy. *The Journal of experimental medicine* 203, 743-753 (2006).
8. Beers, S. A., et al. Antigenic modulation limits the efficacy of anti-CD20 antibodies: implications for antibody selection. *Blood* 115, 5191-5201 (2010).
9. Dyer, M. J., Hale, G., Hayhoe, F. G. & Waldmann, H. Effects of CAMPATH-1 antibodies in vivo in patients with lymphoid malignancies: influence of antibody isotype. *Blood* 73, 1431-1439 (1989).
10. Weng, W. K. & Levy, R. Two immunoglobulin G fragment C receptor polymorphisms independently predict response to rituximab in patients with follicular lymphoma. *J Clin Oncol* 21, 3940-3947 (2003).
11. Cartron, G., et al. Therapeutic activity of humanized anti-CD20 monoclonal antibody and polymorphism in IgG Fc receptor FcgammaRIIIa gene. *Blood* 99, 754-758 (2002).
12. Lim, S. H., et al. Anti-CD20 monoclonal antibodies: historical and future perspectives. *Haematologica* 95, 135-143 (2010).
13. Lim, S. H., et al. Fc gamma receptor IIb on target B cells promotes rituximab internalization and reduces clinical efficacy. *Blood* (2011).
14. Lee, C. A. K., Margaret; Cogliatti, Sergio; Crowe, Susanne; Cragg, Mark S; Schmitz, Shu-Fang H; Ghielmini, Michele and Peter W Johnson. Expression of Inhibitory Fc Receptor (FcgRIIB) Is a Marker of Poor Response to Rituximab Monotherapy in Follicular Lymphoma (FL). *ASH abstract* 50396 (2012).
15. Beers, S. A., et al. Type II (tositumomab) anti-CD20 monoclonal antibody out performs type I (rituximab-like) reagents in B-cell depletion regardless of complement activation. *Blood* 112, 4170-4177 (2008).
16. Roghanian, A., et al. Filament-associated TSGA10 protein is expressed in professional antigen presenting cells and interacts with vimentin. *Cellular immunology* 265, 120-126 (2010).
17. Williams, E. L., et al. Immunotherapy Targeting Inhibitory Fcgamma Receptor IIB (CD32b) in the Mouse Is Limited by Monoclonal Antibody Consumption and Receptor Internalization. *J Immunol* 191, 4130-4140 (2013).
18. Glennie, M. J., McBride, H. M., Worth, A. T. & Stevenson, G. T. Preparation and performance of bispecific F(ab' gamma)2 antibody containing thioether-linked Fab' gamma fragments. *J Immunol* 139, 2367-2375 (1987).
19. Greenman, J., et al. Characterization of a new monoclonal anti-Fc gamma RII antibody, AT10, and its incorporation into a bispecific F(ab')2 derivative for recruitment of cytotoxic effectors. *Mol Immunol* 28, 1243-1254 (1991).
20. Tutt, A. L., et al. Monoclonal antibody therapy of B cell lymphoma: signaling activity on tumor cells appears more important than recruitment of effectors. *J Immunol* 161, 3176-3185 (1998).
21. Olsson, N., et al. Proteomic analysis and discovery using affinity proteomics and mass spectrometry. *Mol Cell Proteomics* 10, M110 003962 (2011).
22. Nishimura, T., et al. Characterization of the human Fc gamma RIIB gene promoter: human zinc-finger proteins (ZNF140 and ZNF91) that bind to different regions function as transcription repressors. *Int Immunol* 13, 1075-1084 (2001).
23. Beers, S. A., et al. Antigenic modulation limits the efficacy of anti-CD20 antibodies: implications for antibody selection. *Blood* 115, 5191-5201 (2010).
24. Binyamin, L., et al. Blocking NK cell inhibitory self-recognition promotes antibody-dependent cellular cytotoxicity in a model of anti-lymphoma therapy. *J Immunol* 180, 6392-6401 (2008).
25. Williams, E. L., et al. Development and characterisation of monoclonal antibodies specific for the murine inhibitory FcgammaRIIB (CD32B). *European journal of immunology* (2012).
26. Walshe, C. A., et al. Induction of cytosolic calcium flux by CD20 is dependent upon B Cell antigen receptor signaling. *The Journal of biological chemistry* 283, 16971-16984 (2008).
27. Beers, S. A., Chan, C. H., French, R. R., Cragg, M. S. & Glennie, M. J. CD20 as a target for therapeutic type I and II monoclonal antibodies. *Semin Hematol* 47, 107-114 (2010).
28. Romer, P. S., et al. Preculture of PBMCs at high cell density increases sensitivity of T-cell responses, revealing cytokine release by CD28 superagonist TGN1412. *Blood* 118, 6772-6782 (2011).
29. Williams, E. L., et al. Development and characterisation of monoclonal antibodies specific for the murine inhibitory FcgammaRIIB (CD32B). *European journal of immunology* 42, 2109-2120 (2012).
30. Hallborn, J. & Carlsson, R. Automated screening procedure for high-throughput generation of antibody fragments. *Biotechniques Suppl*, 30-37 (2002).
31. Cragg M S, A. A., O'Brien L, Tutt A, Chan H T C, Anderson V A, Glennie M J. Opposing properties of CD20 mAb. in *Leukocyte Typing VII* 95-97 (Oxford University Press, Oxford, 2002).
32. Lim, S. H., et al. Fc gamma receptor IIb on target B cells promotes rituximab internalization and reduces clinical efficacy. *Blood* 118, 2530-2540 (2011).
33. Vaughan, A. T., et al. Inhibitory FcgammaRIIb (CD32b) becomes activated by therapeutic mAb in both cis and trans and drives internalization according to antibody specificity. *Blood* 123, 669-677 (2014).
34. Tao, M. H. & Morrison, S. L. Studies of aglycosylated chimeric mouse-human IgG. Role of carbohydrate in the structure and effector functions mediated by the human IgG constant region. *J Immunol* 143, 2595-2601 (1989).
35. Montalvao, F., et al. The mechanism of anti-CD20-mediated B cell depletion revealed by intravital imaging. *The Journal of clinical investigation* (2013).
36. Rankin, C. T., et al. CD32B, the human inhibitory Fc-gamma receptor IIB, as a target for monoclonal antibody therapy of B-cell lymphoma. *Blood* 108, 2384-2391 (2006).
37. Hu, C. Y., et al. Treatment with CD20-specific antibody prevents and reverses autoimmune diabetes in mice. *The Journal of clinical investigation* 117, 3857-3867 (2007).
38. Rossi, D., et al. Clinical impact of small TP53 mutated subclones in chronic lymphocytic leukemia. *Blood* (2014).
39. Zhang, J., Yang, P. L. & Gray, N. S. Targeting cancer with small molecule kinase inhibitors. *Nat Rev Cancer* 9, 28-39 (2009).
40. Pao, W., et al. Acquired resistance of lung adenocarcinomas to gefitinib or erlotinib is associated with a second mutation in the EGFR kinase domain. *PLoS Med* 2, e73 (2005).
41. Yun, C. H., et al. The T790M mutation in EGFR kinase causes drug resistance by increasing the affinity for ATP. *Proceedings of the National Academy of Sciences of the United States of America* 105, 2070-2075 (2008).
42. Shah, N. P., et al. Multiple BCR-ABL kinase domain mutations confer polyclonal resistance to the tyrosine kinase inhibitor imatinib (STI571) in chronic phase and blast crisis chronic myeloid leukemia. *Cancer Cell* 2, 117-125 (2002).
43. Corbin, A. S., Buchdunger, E., Pascal, F. & Druker, B. J. Analysis of the structural basis of specificity of inhibition of the Abl kinase by STI571. *The Journal of biological chemistry* 277, 32214-32219 (2002).
44. Engelman, J. A., et al. MET amplification leads to gefitinib resistance in lung cancer by activating ERBB3 signaling. *Science* (New York, N.Y. 316, 1039-1043 (2007).
45. Cragg, M. S., Harris, C., Strasser, A. & Scott, C. L. Unleashing the power of inhibitors of oncogenic kinases through BH3 mimetics. *Nat Rev Cancer* 9, 321-326 (2009).
46. Hanahan, D. & Weinberg, R. A. Hallmarks of cancer: the next generation. *Cell* 144, 646-674 (2011).
47. Williams, E. L., et al. Overcoming resistance to therapeutic antibodies by targeting Fc Receptors. Resistance to Immunotherapeutic Antibodies in Cancer: Strategies to Overcome Resistance. *Pubs*. Springer In Press (2013).
48. Vaughan, A. T., et al. Inhibitory FcγRIIb (CD32b) becomes activated by therapeutic mAb in both cis and trans and drives internalization according to antibody specificity. *Blood* (2013).
49. Pallasch, C. P., et al. Sensitizing protective tumor microenvironments to antibody-mediated therapy. *Cell* 156, 590-602 (2014).
50. Veri, M. C., et al. Monoclonal antibodies capable of discriminating the human inhibitory Fcgamma-receptor IIB (CD32B) from the activating Fcgamma-receptor IIA (CD32A): biochemical, biological and functional characterization. *Immunology* 121, 392-404 (2007).
51. O'Brien, S. M., et al. Rituximab dose-escalation trial in chronic lymphocytic leukemia. *J Clin Oncol* 19, 2165-2170 (2001).
52. Coiffier, B., et al. Safety and efficacy of ofatumumab, a fully human monoclonal anti-CD20 antibody, in patients with relapsed or refractory B-cell chronic lymphocytic leukemia: a phase 1-2 study. *Blood* 111, 1094-1100 (2008).
53. Coiffier, B., et al. Significant Correlation between Survival Endpoints and Exposure to Ofatumumab (HuMax-CD20) in Chronic Lymphocytic Leukemia. *ASH Annual Meeting Abstracts* 108, 2842-(2006).

54. Shawn Rose, Alexander Misharin, Harris Perlman, 2012, A novel Ly6c/Ly6G-based strategy to analyse the mouse splenic myeloid compartment, *Cytometry Part A* 81(4): 343-50
55. Beers, S. A., French, R. R., Chan, H. T., Lim, S. H., Jarrett, T. C., Vidal, R. M., Wijayaweera, S. S., Dixon, S. V., Kim, H., Cox, K. L., et al. (2010). Antigenic modulation limits the efficacy of anti-CD20 antibodies: implications for antibody selection. *Blood* 115, 5191-5201.
56. Biburger, M., Aschermann, S., Schwab, I., Lux, A., Albert, H., Danzer, H., Woigk, M., Dudziak, D., and Nimmerjahn, F. (2011). Monocyte subsets responsible for immunoglobulin G-dependent effector functions in vivo. *Immunity* 35, 932-944.
57. Coiffier, B., Lepretre, S., Pedersen, L. M., Gadeberg, O., Fredriksen, H., van Oers, M. H., Wooldridge, J., Kloczko, J., Holowiecki, J., Hellmann, A., et al. (2008). Safety and efficacy of ofatumumab, a fully human monoclonal anti-CD20 antibody, in patients with relapsed or refractory B-cell chronic lymphocytic leukemia: a phase 1-2 study. *Blood* 111, 1094-1100.
58. Coiffier, B., Tilly, H., Pedersen, L. M., Plesner, T., Frederiksen, H., van Oers, M. H. J., Wooldridge, J., Kloczko, J. S., Holowiecki, J., Hellmann, A., et al. (2006). Significant Correlation between Survival Endpoints and Exposure to Ofatumumab (HuMax-CD20) in Chronic Lymphocytic Leukemia. *ASH Annual Meeting Abstracts* 108, 2842-.
59. Cragg, M. S., Morgan, S. M., Chan, H. T., Morgan, B. P., Filatov, A. V., Johnson, P. W., French, R. R., and Glennie, M. J. (2003). Complement-mediated lysis by anti-CD20 mAb correlates with segregation into lipid rafts. *Blood* 101, 1045-1052.
60. Gul, N., Babes, L., Siegmund, K., Korthouwer, R., Bogels, M., Braster, R., Vidarsson, G., Ten Hagen, T. L., Kubes, P., and van Egmond, M. (2014). Macrophages eliminate circulating tumor cells after monoclonal antibody therapy. *The Journal of clinical investigation* 124, 812-823.
61. Hamaguchi, Y., Xiu, Y., Komura, K., Nimmerjahn, F., and Tedder, T. F. (2006). Antibody isotype-specific engagement of Fcgamma receptors regulates B lymphocyte depletion during CD20 immunotherapy. *The Journal of experimental medicine* 203, 743-753.
62. Hussain, K., Hargreaves, C. E., Roghanian, A., Oldham, R. J., Chan, H. T., Mockridge, C. I., Chowdhury, F., Frendeus, B., Harper, K. S., Strefford, J. C., et al. (2015). Upregulation of FcgammaRIIb on monocytes is necessary to promote the superagonist activity of TGN1412. *Blood* 125, 102-110.
63. Lim, S. H., Vaughan, A. T., Ashton-Key, M., Williams, E. L., Dixon, S. V., Chan, H. T., Beers, S. A., French, R. R., Cox, K. L., Davies, A. J., et al. (2011). Fc gamma receptor IIb on target B cells promotes rituximab internalization and reduces clinical efficacy. *Blood* 118, 2530-2540.
64. O'Brien, S. M., Kantarjian, H., Thomas, D. A., Giles, F. J., Freireich, E. J., Cortes, J., Lerner, S., and Keating, M. J. (2001). Rituximab dose-escalation trial in chronic lymphocytic leukemia. *J Clin Oncol* 19, 2165-2170.
65. Pallasch, C. P., Leskov, I., Braun, C. J., Vorholt, D., Drake, A., Soto-Feliciano, Y. M., Bent, E. H., Schwamb, J., Iliopoulou, B., Kutsch, N., et al. (2014). Sensitizing protective tumor microenvironments to antibody-mediated therapy. *Cell* 156, 590-602.
66. Romer, P. S., Berr, S., Avota, E., Na, S. Y., Battaglia, M., ten Berge, I., Einsele, H., and Hunig, T. (2011). Preculture of PBMCs at high cell density increases sensitivity of T-cell responses, revealing cytokine release by CD28 superagonist TGN1412. *Blood* 118, 6772-6782.
67. Vaughan, A. T., Iriyama, C., Beers, S. A., Chan, C. H., Lim, S. H., Williams, E. L., Shah, V., Roghanian, A., Frendeus, B., Glennie, M. J., and Cragg, M. S. (2014). Inhibitory FcgammaRIIb (CD32b) becomes activated by therapeutic mAb in both cis and trans and drives internalization according to antibody specificity. *Blood* 123, 669-677.

Example 2—Exemplary Pharmaceutical Formulations

Whilst it is possible for a composition, and/or antibody, and/or agent, and/or medicament of the invention to be administered alone, it is preferable to present it as a pharmaceutical formulation, together with one or more acceptable carriers. The carrier(s) must be "acceptable" in the sense of being compatible with the composition, and/or antibody, and/or agent, and/or medicament of the invention and not deleterious to the recipients thereof. Typically, the carriers will be water or saline which will be sterile and pyrogen-free.

The following examples illustrate medicaments and pharmaceutical compositions according to the invention in which the active ingredient is an antibody molecule and/or agent of the invention.

Example A: Tablet

| Active ingredient | 100 mg |
|---|---|
| Lactose | 200 mg |
| Starch | 50 mg |
| Polyvinylpyrrolidone | 5 mg |
| Magnesium stearate | 4 mg |
| | 359 mg |

Tablets are prepared from the foregoing ingredients by wet granulation followed by compression.

Example B: Ophthalmic Solution

| Active ingredient | 0.5 g |
|---|---|
| Sodium chloride, analytical grade | 0.9 g |
| Thiomersal | 0.001 g |
| Purified water to | 100 ml |
| pH adjusted to | 7.5 |

Example C: Tablet Formulations

The following formulations A and B are prepared by wet granulation of the ingredients with a solution of povidone, followed by addition of magnesium stearate and compression.

Formulation A

| | mg/tablet | mg/tablet |
|---|---|---|
| (a) Active ingredient | 250 | 250 |
| (b) Lactose B.P. | 210 | 26 |
| (c) Povidone B.P. | 15 | 9 |

-continued

|  | mg/tablet | mg/tablet |
|---|---|---|
| (d) Sodium Starch Glycolate | 20 | 12 |
| (e) Magnesium Stearate | 5 | 3 |
|  | 500 | 300 |

Formulation B

|  | mg/tablet | mg/tablet |
|---|---|---|
| (a) Active ingredient | 250 | 250 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
|  | 500 | 300 |

Formulation C

|  | mg/tablet |
|---|---|
| Active ingredient | 100 |
| Lactose | 200 |
| Starch | 50 |
| Povidone | 5 |
| Magnesium stearate | 4 |
|  | 359 |

The following formulations, D and E, are prepared by direct compression of the admixed ingredients. The lactose used in formulation E is of the direction compression type.

Formulation D

|  | mg/capsule |
|---|---|
| Active Ingredient | 250 |
| Pregelatinised Starch NF15 | 150 |
|  | 400 |

Formulation E

|  | mg/capsule |
|---|---|
| Active Ingredient | 250 |
| Lactose | 150 |
| Avicel ® | 100 |
|  | 500 |

Formulation F (Controlled Release Formulation)

The formulation is prepared by wet granulation of the ingredients (below) with a solution of povidone followed by the addition of magnesium stearate and compression.

|  | mg/tablet |
|---|---|
| (a) Active Ingredient | 500 |
| (b) Hydroxypropylmethylcellulose (Methocel K4M Premium) ® | 112 |

-continued

|  | mg/tablet |
|---|---|
| (c) Lactose B.P. | 53 |
| (d) Povidone B.P.C. | 28 |
| (e) Magnesium Stearate | 7 |
|  | 700 |

Drug release takes place over a period of about 6-8 hours and was complete after 12 hours.

Example D: Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

|  | mg/capsule |
|---|---|
| (a) Active ingredient | 250 |
| (b) Lactose B.P. | 143 |
| (c) Sodium Starch Glycolate | 25 |
| (d) Magnesium Stearate | 2 |
|  | 420 |

Formulation C

|  | mg/capsule |
|---|---|
| (a) Active ingredient | 250 |
| (b) Macrogol 4000 BP | 350 |
|  | 600 |

Capsules are prepared by melting the Macrogol 4000 BP, dispersing the active ingredient in the melt and filling the melt into a two-part hard gelatin capsule.

Formulation D

|  | mg/capsule |
|---|---|
| Active ingredient | 250 |
| Lecithin | 100 |
| Arachis Oil | 100 |
|  | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
|---|---|
| (a) Active ingredient | 250 |
| (b) Microcrystalline Cellulose | 125 |

-continued

|  | mg/capsule |
|---|---|
| (c) Lactose BP | 125 |
| (d) Ethyl Cellulose | 13 |
|  | 513 |

Example E: Injectable Formulation

| Active ingredient | 0.200 g |
|---|---|

Sterile, pyrogen free phosphate buffer (pH7.0) to 10 ml

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example F: Intramuscular Injection

| Active ingredient | 0.20 g |
|---|---|
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G: Syrup Suspension

| Active ingredient | 0.2500 g |
|---|---|
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H: Suppository

|  | mg/suppository |
|---|---|
| Active ingredient (63 μm)* | 250 |
| Hard Fat, BP (Witepsol H15 - Dynamit Nobel) | 1770 |
|  | 2020 |

*The active ingredient is used as a powder wherein at least 90% of the particles are of 63 μm diameter or less.

One fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I: Pessaries

|  | mg/pessary |
|---|---|
| Active ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

The invention claimed is:

1. A method of treating relapsed B-cell cancer in a subject, the method comprising administering:
   (i) a first antibody molecule selected from the group consisting of rituximab and obinutuzumab; in combination with
   (ii) a second antibody molecule that prevents or reduces FcγRIIb present on the target B-cell from binding to the Fc domain of the first antibody molecule, and prevents or reduces internalization of the first antibody molecule into the target B-cell wherein the second antibody molecule specifically binds FcγRIIb, wherein the second antibody molecule is an antibody; a chimeric antibody; a single chain antibody; a Fab, F(ab')$_2$, a Fv, a ScFv or a dAb antibody fragment;
   an IgG2 antibody; an IgG4 antibody; a chimeric molecule of IgG2 and IgG4; an antibody variant comprising a N297Q mutation; or a DANA variant antibody; and wherein the second antibody comprises the following CDR amino acid sequences: SEQ ID NO: 171 and SEQ ID NO: 172 and SEQ ID NO: 173 and SEQ ID NO: 174 and SEQ ID NO: 175 and SEQ ID NO: 176;
   wherein that the subject is selected on the basis that the subject has relapsed B-cell cancer, wherein the relapsed B-cell cancer is resistant to treatment with the first antibody molecule, wherein the subject has previously been treated with the first antibody molecule and has previously responded to the treatment, and subsequently relapsed, and that the subject has target B-cells that express FcγRIIb, and wherein the B-cell cancer is selected from the group consisting of non-Hodgkin lymphoma (NHL) and chronic lymphocytic leukaemia (CLL).

2. The method of claim 1, wherein the second antibody molecule is one or more antibody molecules that do not include a domain capable of recruiting an effector cell; and/or are monoclonal antibody molecules, and/or polyclonal antibody molecules, and/or bi-specific antibody molecules.

3. The method of claim 1, wherein the second antibody molecule comprises the following amino acid sequences: SEQ ID NO: 23 and SEQ ID NO: 47.

4. The method of claim 1, wherein the second antibody molecule prevents or reduces FcγRIIb signaling or internalization of the first antibody molecule by the target B-cell.

5. The method of claim 1, wherein the subject is characterized as having not responded if the subject has previously been treated for B-cell cancer, but achieves less than partial remission; and the subject is characterized as having subsequently relapsed, if the subject:
   (i) achieves at least a partial remission following treatment and/or if the subject achieves at least a complete remission following treatment, but;
   (ii) the B-cell cancer progressed in the subject after the cessation of the treatment.

6. The method of claim 1, wherein the non-Hodgkin lymphoma (NHL) is selected from the group consisting of: follicular lymphoma (FL); diffuse large B-cell lymphoma (DLBCL); mantle cell lymphoma (MCL); and small lymphocytic lymphoma (SLL).

7. The method of claim 1, wherein the second antibody molecule does not include a domain capable of recruiting an effector cell.

8. The method of claim 1, wherein the subject has refractory chronic lymphocytic leukaemia or relapsed chronic lymphocytic leukaemia, or the subject has refractory chronic lymphocytic leukaemia and relapsed chronic lymphocytic leukaemia.

9. The method of claim 1, wherein the Non-Hodgkin Lymphoma (NHL) is selected from the group consisting of: follicular lymphoma (FL) and mantle cell lymphoma (MCL).

10. The method of claim 9, wherein the NHL is mantle cell lymphoma (MCL).

11. The method of claim 1, wherein the first antibody molecule is rituximab.

12. The method of claim 1, wherein the first antibody molecule is obinutuzumab.

13. The method of claim 1, wherein the target B-cell, as determined relative to a control, comprises an elevated level of FcγRIIb expression, the control comprising control cells of a control individual with a non-refractory cancer and/or a non-relapsed cancer.

14. The method of claim 13, wherein the elevated FcγRIIb expression in the target B-cell is at least two-fold higher in the target B-cell of the subject when compared to the control.

* * * * *